(12) United States Patent
Hummel et al.

(10) Patent No.: US 12,116,581 B2
(45) Date of Patent: Oct. 15, 2024

(54) TARGETED TRANSCRIPTIONAL REGULATION USING SYNTHETIC TRANSCRIPTION FACTORS

(71) Applicant: KWS SAAT SE & CO. KGaA, Einbeck (DE)

(72) Inventors: Aaron Hummel, Hillsborough, NC (US); Mathias Labs, Frontenac, MO (US)

(73) Assignee: KWS SAAT SE & CO. KGaA, Einbeck (DE)

( * ) Notice: Subject to any disclaimer, the term of this patent is extended or adjusted under 35 U.S.C. 154(b) by 82 days.

(21) Appl. No.: 16/955,954

(22) PCT Filed: Dec. 21, 2018

(86) PCT No.: PCT/EP2018/086700
§ 371 (c)(1),
(2) Date: Jun. 19, 2020

(87) PCT Pub. No.: WO2019/122381
PCT Pub. Date: Jun. 27, 2019

(65) Prior Publication Data
US 2020/0332307 A1 Oct. 22, 2020

Related U.S. Application Data

(60) Provisional application No. 62/738,568, filed on Sep. 28, 2018, provisional application No. 62/609,508, filed on Dec. 22, 2017.

(51) Int. Cl.
*C12N 15/82* (2006.01)
*A01H 1/08* (2006.01)

(52) U.S. Cl.
CPC ........... *C12N 15/8213* (2013.01); *A01H 1/08* (2013.01); *C12N 15/8217* (2013.01)

(58) Field of Classification Search
CPC .................................................. C12N 15/82
See application file for complete search history.

(56) References Cited

U.S. PATENT DOCUMENTS

| 7,256,322 | B2 | 8/2007 | Lowe et al. |
| 2013/0254935 | A1 | 9/2013 | Gordon-Kamm et al. |

FOREIGN PATENT DOCUMENTS

| WO | 2005063990 A2 | 7/2005 |
| WO | 2011/082310 A2 | 7/2011 |
| WO | 2015/044199 A1 | 4/2015 |
| WO | 2016/021973 A1 | 2/2016 |
| WO | 2017/070598 A1 | 4/2017 |
| WO | 2017/074547 A1 | 5/2017 |
| WO | 2018/147343 A1 | 8/2018 |
| WO | 2018/212361 A1 | 11/2018 |

OTHER PUBLICATIONS

Park et al RNA-Guided transcriptional activation via CRISPR/dCas9 mimics overexpression phenotypes in Arabidopsis 2017 PLOS One pp. 1-13 (Year: 2017).*
Lowe et al The Plant Cell 28:1998-2015, provided by Applicant (Year: 1998).*
International Search Report and Written Opinion issued in International Application No. PCT/EP2018/086725 dated Jul. 8, 2019.
Lowder et al., "Robust Trascriptional Activation in Plants Using Multiplexed CRISPR-Act2.0 and mTALE-Act Systems", Molecular Plant, vol. 11, No. 2, 2018, p. 245-256.
Li et al, "A potent Cas9-derived gene activator for plant and mammalian cells", Nature Plants, Nature Publishing Group UK, London, vol. 3, No. 12, 2017, p. 930-936.
Liu et al., "Engineering cell signaling using tunable CRISPR-Cpf1-based transcription factors", Nature Communications, 2017, 8(1): 2095.
Tak et al., "Inducible and multiplex gene regulation using CRISPR-CPf1-based transcription factors", Nature Methods, vol. 14, No. 12, 2017, p. 1163-1166.
Tang et al., "A CRISPR-CPf1 system for efficient genome editing and transcriptional repression in plants", Nature Plants, vol. 3, No. 3, 2017, p. 1-5.
Altpeter et al., "Advancing Crop Transformation in the Era of Genome Editing", The Plant Cell, 2016, vol. 28, pp. 1510-1520.
Eid et al., "CRISPR base editors: genome editing without double-strand breaks", Biochemical Journal, 2018, vol. 475, pp. 1955-1964.
Gaslunas et al., "Cas9-crRNA ribonucleoprotein complex mediates specific DNA cleavage for adaptive immunity in bacteria", PNAS, 2012, vol. 111, pp. E2579-E2586.
Gelvin, "Viral-mediated plant transformation gets a boost", Nature Biotechnology, 2005, vol. 23, No. 6, pp. 684-685.
Jinek et al., "A programmable dual-RNA-guided DNA endonuclease in adaptive bacterial immunity", Science, 2012, vol. 337, pp. 816-821.
Jung et al., "Identification of the transporter responsible for sucrose accumulation in sugar beet taproots", Nature Plants, 2015, vol. 1, Article No. 14001, 7 pages.
Kleinstiver et al., "Engineered CRISPR-Cas9 nucleases with altered PAM specificities", Nature, 2015, 523(7561), pp. 481-485.
Konermann et al., "Genome-scale transcriptional activation by an engineered CRISPR-Cas9 complex", Nature, 2015, vol. 517, pp. 583-588.

(Continued)

*Primary Examiner* — Brent T Page
(74) *Attorney, Agent, or Firm* — Troutman Pepper Hamilton Sanders LLP

(57) ABSTRACT

The present invention relates to the targeted regulation of gene expression and more specifically to synthetic transcription factors (STFs) comprising at least one highly target specific engineered recognition domain and further comprising at least one activation or silencing domain to modulate the expression of a gene of interest, preferably to modulate the transcription of a morphogenic gene of a eukaryote. Further disclosed are methods using the STFs to enhance transformation frequencies, to optimize successful genome editing approaches, to provide haploid or double haploid organisms, and/or to provide compositions suitable for general transformation, but also for breeding purposes.

Figure 1A:
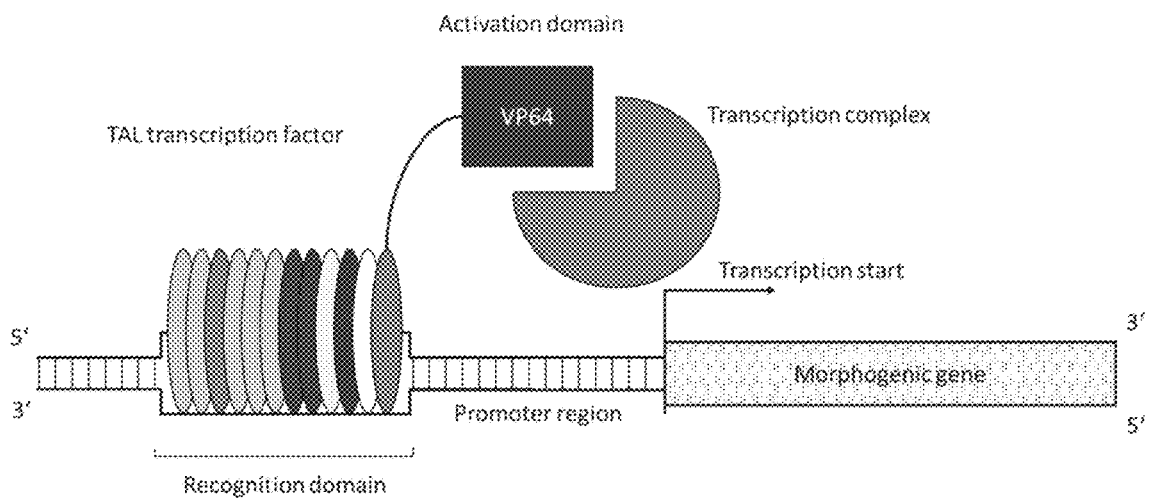

17 Claims, 10 Drawing Sheets
Specification includes a Sequence Listing.

(56) References Cited

OTHER PUBLICATIONS

Lowe et al., "Morphogenic Regulators Baby boom and Wuschel Improve Monocot Transformation", The Plant Cell, 2016, vol. 28, pp. 1998-2015.
Nakka et al., Physiological and molecular characterization of hydroxyphenylpyruvate diogygenase (HPPD)-inhibitor resistance in Palmer Amaranth (*Amaranthus palmeri* S.Wats), Frontiers in Plant Science, 2017, vol. 8, Article 555, 12 pages.
Salesse-Smith et al., "Overexpression of Rubisco subunits with RAF1 increases Rubisco content in maize", Nature Plants, 2018, vol. 4, pp. 802-810.
Shi et al., "Overexpression of ARGOS genes modifies plant sensitivity to ethylene, leading to improved drought tolerance in both Arabidopsis and maize", Plant Physiology, 2015, vol. 169, No. 1, pp. 266-282.
Zhang et al., "Transgenic salt-tolerant tomato plants accumulate salt in follage but not in fruit", Nature Biotechnology, 2001, vol. 19, pp. 765-768.
Bolukbasi et al., "DNA-binding-domain fusions enhance the targeting range and precision of Cas9", Nat Methods, 2015, vol. 12, No. 12, pp. 1150-1156.
Burstein et al., "New CRISPR-Cas systems from uncultivated microbes", Nature, 2017, 542(7640), pp. 237-241.
Chavez et al., "Comparative Analysis of Cas9 Activators Across Multiple Species", Nature Methods, 2016, vol. 13, No. 7, pp. 563-567.
Cheng et al., "Multiplexed activation of endogenous genes by CRISPR-on, an RNA-guided transcriptional activator system," Cell Research, 2013, vol. 23, pp. 1163-1171.
Gao et al., "Engineered Cpf1 variants with altered PAM specificities increase genome targeting range", Nat Biotechnol., 2017, vol. 35, No. 8, pp. 789-792.
International Search Report and Written Opinion issued in International Application No. PCT/EP2018/086700 dated Jun. 18, 2019.
Wu, Miin-Feng, et al., "Auxin-regulated chromatin switch directs acquistion of flower primordium founder fate", Oct. 13, 2015 (Oct. 13, 2015).
Jennifer L. Nemhauser et al., "Plant synthetic biology for molecular engineering of signalling and development", Nature Plants, vol. 2. No. 3, Mar. 2, 2016 (Mar. 2, 2016), p. 16010.
Levi G. Lowder et al, "A CRISPR/Cas9 Toolbox for Multiplexed Plant Genome Editing and Transcriptional Regulation", Plant Physiology, vol. 169, No. 2, Aug. 21, 2015 (Aug. 21, 2015), p. 971-985.
Wusheng Liu et al, "Synthetic TAL effectors for targeted enhancement of transgene expression in plants", Plant Biotechnology Journal, vol. 12, No. 4, May 1, 2014 (May 1, 2014), p. 436-446.
Jeffrey C Miller et al, "A Tale nuclease architecture for efficient genome editing", Nature Biotechnology,vol. 29, No. 2. Dec. 22, 2010 (Dec. 22, 2010), p. 143-148.
Ami M. Kabadi et al, "Engineering synthetic TALE and CRISPR/Cas9 transcription factors for regulating gene expression", Methods, vol. 69, No. 2, Sep. 1, 2014 (Sep. 1, 2014), p. 188-197.
Richard Moore et al, "Transcription Activator-like Effectors: A Toolkit for Synthetic Biology", ACS Synthetic Biology,vol. 3, No. 10, Feb. 13, 2014 (Feb. 13, 2014), p. 708-716.
Yue Xu et al, "Regulation of gene expression by manipulating transcriptional repressor activity using a novel CoSRI technology", Plant Biotechnology Journal,vol. 15, No. 7, Mar. 10, 2017 (Mar. 10, 2017), p. 879-893.
Black Joshua B et al, "Synthetic transcription factors for cell fate reprogramming", Current Opinion in Genetics & Development, Current Biology Ltd, XX.vol. 52, May 24, 2018 (May 24, 2018), p. 13-21.
Gordon-Kamm et al., "Using Morphogenic Genes to Improve Recovery and Regeneration of Transgenic Plants", Plants, vol. 8, No. 2, 2019, p. 38, 19 pages.

\* cited by examiner

FIGURE 3B

```
BBM  TAATCGTTCCTTGACAGGCAACCTGACAGTCAATGGCCGTGACCAAGTATATCAGTCAAGGTGGCCACTTTAGTAGTACAATGT
     361                                                                              450
                   ◄═══════════════ TALE 6 ═══════════════
BBM  ACATCCATGGGCAGATACATCAGGTACTGCATATATGGGCACACATATGACACATGTTTGAGGAAATGAGACAAGTATGTGGAGA
     451                                                                              540
BBM  CTTCCCTAGAAGCAGAAGAAAAGAGAAAAGAAAAAGGAGACACACATATAGTGGTTTCCGTTAAATCATACTACCTCCATTTGTCATC
     541                                                                              630
BBM  ATTAGTACTCTATATATGGGCACATATAGTACTAGTAGTTTCTTGCTAAAAAAAGTTCAGCAATTTCCAACATGTATGCACAAT
     631                                                                              720
BBM  AAACTAATTTTCTTAGAAAGTTATTTCTTAGAAAACCCGGTAATACATCAGGGCTAGTTTGGGAACCCTGGTTCCTAAGGAATTTATTTTCCA
     721                                                                              810
BBM  AAAAAAAAATAGTTATTTCCTGGAAATTAGGAATATAGATTACATAGTAAGTATAGAGTATCGAGTCTCTATAATCATATCATCTC
     811                                                                              900
                                                                          ◄═══ TALE 4
BBM  CATCAGTCTATATAGATTACATAGTAAGTATAGAGTATCGAGTATCTTGGTGTCCAACTATCCTATATATCATCTGGAGTGTACCAGTTGTAT
     901                                                                              990
                                                              ◄═════ TALE 5
BBM  AAATATCTACATCAGTATCAGCAGCTACTGAACATGTGAACAACTATCGAGTATCCTGAATCATTCCTGAACTTGCACTGTCCAAA
     991                                                                              1080
BBM  TGGCTTCTTCCTGATCGTTCCTGAATCATTCTTAAGAGAATCATTCCTGAATCATTGCAAGCCGCTACCATTAGGGACGGAATTCGCACTTCAG
     1081                                                                             1170
                                         ══════ EXON 1 ══════
BBM  ATAATCTACATGGCCAGTCCAGGCTCGGCTTCGTCCGCGCCTCCCCAGACGGGCCGCGGAGGAGGTGCCGGACTCCACGCT
     1171                                                                             1260
```

TARGETED TRANSCRIPTIONAL REGULATION USING SYNTHETIC TRANSCRIPTION FACTORS

CROSS-REFERENCE TO RELATED APPLICATIONS

This application is a U.S. National Phase of International Patent Application No. PCT/EP2018/086700, filed on Dec. 21, 2018, which claims priority to U.S. Provisional Application No. 62/738,568, filed on Sep. 28, 2018 and U.S. Provisional Application No. 62/609,508, filed on Dec. 22, 2017. The entire contents of these applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 9, 2020, is named 245761_000109_SL.txt and is 227,582 bytes in size.

TECHNICAL FIELD

The present invention relates to the targeted regulation of gene expression and more specifically to synthetic transcription factors (STFs) comprising at least one highly target specific engineered recognition domain and further comprising at least one activation or silencing domain to modulate the expression of a gene of interest, preferably to modulate the transcription of a morphogenic gene of a eukaryote. Further disclosed are methods using the STFs to enhance transformation frequencies, to optimize successful genome editing approaches, to provide haploid or double haploid organisms, and/or to provide compositions suitable for general transformation, but also for breeding purposes. These methods and uses either rely on the synergistic interaction of the STF comprising a gene expression modulation domain, e.g. an activation domain or a silencing domain, allowing the reprogramming of a cell and the induction of cell division and/or regeneration simultaneous with transforming said cell or editing the genome of said cell.

BACKGROUND OF THE INVENTION

The ability to efficiently transform and precisely modify genetic material in eukaryotic cells enables a wide range of high value applications in agricultural product development, basic research and other technical fields. Fundamentally, genome engineering or gene editing (GE) provides this capability by introducing predefined genetic variation at specific locations in eukaryotic as well as prokaryotic genomes. Meanwhile, there exists a plethora of methods for transforming different eukaryotic or prokaryotic cells in specific developmental stages. Still, transformation or transfection efficiencies sometimes remain very low for certain cell types or genotypes and highly specific methods fine-tuned for different cells originating from different genotypes have to be established.

Further, the ability not only to modify, but also to specifically modulate, i.e., to activate or inhibit, gene expression in a highly targeted manner has a high value in plant biotechnology.

For example, while transformation of the major monocot crops is currently possible, the process typically remains confined to one or two genotypes per species, often with poor agronomics, and efficiencies that place these methods beyond the reach of agricultural implementation.

In view of the fact that the increase of the global human population will necessitate doubling the world food production in the next few decades and at the same time climate change causes new challenges for plant breeders, there is a great need for optimized crop plants having resistance to biotic and abiotic stress, for example, resistance against emerging plant pathogens or drought resistance. Relying on classical breeding and selection technologies will likely not be effective enough to cope with the dramatically increasing demand and to establish a sustainable supply facing the eco-sociological changes in the future decades. Therefore, new strategies and biotechnological measures have to be developed to establish traits with which plants could better adapt to adverse environmental conditions.

Presently, maize is one of the most important food and feed crop as well as bio-energy source around the world. At the same time, maize has become one of the most important target crops for biotechnological innovation since the establishment of the first transgenic *Bacillus thuringiensis* (Bt) maize products in the mid 1990$^{ies}$. Despite the complexity of the maize genome (in comparison to model plants), there are meanwhile more biotech traits available on the market in maize than in any other crop plants. Transgenic maize production has made tremendous progress since the first successful report using the labor-intensive and time-consuming protoplast transformation method (Rhodes et al., 1988a). Development of microparticle bombardment transformation (Fromm et al., 1990; Gordon-Kamm et al., 1990) and *Agrobacterium*-mediated transformation (Ishida et al., 1996) technologies has made the generation of transgenic maize simpler and more reliable. Highly productive biolistic transformation systems were established in Hi-II with BAR as the selectable marker (Frame et al., 2000), and in the elite inbred line CG00526 with PMI as the selectable marker (Wright et al., 2001). Efficient *Agrobacterium*-mediated transformation systems were reported by using the inbred line A188 (Ishida et al., 1996; Negrotto et al., 2000), Hi-II (Zhao et al., 2001), and A188/Hi-II hybrids (Li et al., 2003). In the last few years, progress in genome engineering technologies has made it possible to make modifications and insert transgenes at specific chromosomal target sites in the maize genome (Shukla et al., 2009; Gao et al., 2010; Liang et al., 2014; for a review: Que et al., Front. Plant. Sci., 2014, 5, 379). Still, none of the above techniques provides reliable and transferable results applicable in different genotypes, let alone in a different plant.

Progress in the plant biotechnological field over the last decades was based on the establishment of transgenic crop plants. Socio-economic and regulatory factors, however, increasingly suggest that the development of non-transgenic plants and plant products becomes more and more important for certain countries and territories.

Morphogenesis usually means the biological process that causes an organism to develop its shape. It is one of three fundamental aspects of developmental biology along with the control of cell growth and cellular differentiation, unified in evolutionary developmental biology. An important class of molecules involved in morphogenesis are transcription factor proteins that determine the fate of cells by interacting with DNA. These can be coded for by master regulatory genes, and either activate or deactivate the transcription of other genes; in turn, these secondary gene products can regulate the expression of still other genes in a regulatory cascade of gene regulatory networks. At the end of this cascade are classes of molecules that control cellular behaviours such as cell migration, or, more generally, their properties, such as cell adhesion or cell motility, cell proliferation and apoptosis.

Recently, the group of Lowe et al. (2016) reported a transformation approach involving overexpression of the maize (*Zea mays*) morphogenic genes Baby boom (BBM) and maize Wuschel (WUS) genes, which produced high transformation frequencies in numerous previously non-transformable maize inbred lines. Lowe et al. found out that overexpression of BBM and WUS in inbred lines which were difficult to transform, resulted in an increase in regeneration capability of transgenic calli. The role of WUS and BBM in plant development was already described earlier (U.S. Pat. No. 7,256,322 B2 or US 2013/0254935 A1).

However, the above and further approaches presently all rely on heterologous overexpression of morphogenic genes e.g. in cellular compartments where such genes are usually not expressed, or on the provision of transgenic crop plants carrying the respective genes stably incorporated in their genomes. Another strategy is the temporally or spatially regulated expression of a target gene, e.g., using inducible and/or tissue-specific promoters. Uncontrolled overexpression, however, can cause phenotypical changes that might affect the fitness and yield efficiency of crop plants making the use of such approaches in agriculture less attractive. There is thus still a great need in identifying new strategies to exploit the functions of endogenous genes, including morphogenic factors, in a targeted way avoiding the need of overexpressing heterologous genes in a cell or cellular system of interest.

Many plant cells have the ability to regenerate a complete organism from only single cells or tissues. This process is usually referred to as totipotency. This process of regeneration of a whole plant seems to be closely related to the process of morphogenesis. The capacity of in vitro cultured plant tissues and cells to undergo morphogenesis, resulting in the formation of discrete organs or even whole plants, has provided opportunities for numerous applications of in vitro plant biology in studies of basic botany, biochemistry, breeding, and development of new crop plants.

Haploids are plants that contain a gametic chromosome number (n). They can originate spontaneously in nature or as a result of various induction techniques. Spontaneous development of haploid plants has been known since 1922, when Blakeslee first described this phenomenon in *Datura stramonium* (Blakeslee et al., 1922); this was subsequently followed by similar reports in *Nicotiana tabacum, Triticum aestivum* and several other species (Forster et al., 2007). However, spontaneous occurrence of haploids is a rare event and therefore of limited practical value.

Haploids produced from diploid species, known as monoploids, contain only one set of chromosomes in the sporophytic phase. They are smaller and exhibit a lower plant vigor compared to donor plants and are sterile due to the inability of their chromosomes to pair during meiosis. In order to propagate them through seed and to include them in breeding programs, their fertility has to be restored with spontaneous or induced chromosome doubling. The obtained doubled or double haploids are homozygous at all loci and can represent a new variety (self-pollinated crops) or parental inbred line for the production of hybrid varieties (cross-pollinated crops). In fact, cross pollinated species often express a high degree of inbreeding depression. For these species, the induction process per se can serve not only as a fast method for the production of homozygous lines but also as a selection tool for the elimination of genotypes expressing strong inbreeding depression. Selection can be expected for traits caused by recessive deleterious genes that are associated with vegetative growth. Therefore, haploid and likewise double haploid plant systems are of great importance for plant breeding strategies, yet little is known about the cross-talk between developmental pathways like morphogenic pathways and a potential influence thereof in the generation of haploid plant systems.

Furthermore, there are severe problems in transforming elite germplasm carrying a highly valuable genotype, as the respective plants or plant parts or in vitro culturable cells derivable from said elite plants are usually highly recalcitrant to transformation and/or transfection. This fact makes the targeted plant development or breeding highly complicated, time-consuming and expensive, as many additional steps of breeding and/or molecular biology have to be applied to successfully transfer an elite event into a genetic background of interest.

It was therefore an aim of the present invention to develop new strategies for the induction of endogenous genes, preferably morphogenic genes, in their natural cellular environment in order to improve the regeneration of crop plants which are otherwise difficult to transform, or even highly recalcitrant to transformation/transfection by known techniques. Furthermore, it was an aim to unify the high precision available with recent gene editing technologies to provide for a tunable and adjustable approach to regulate morphogenic genes, preferably in a transient manner, to allow better transformation and regeneration capabilities in target cells or tissues without unduly influencing the endogenous morphogenesis system of a cell, wherein the approaches should be configured to allow for a genotype-independent increase in transformation/transfection rates.

Based on the exploitation of the artificial regulation of gene expression, mainly transcriptional regulation, it was another aim to provide synthetic transcription factors with silencing capacity with respect to transcriptional control to provide efficient compositions to control transcription and expression of aberrantly expressed genes.

It was a further aim to establish new strategies for providing haploid and double haploid plant cells, cellular systems and whole organisms based on the targeted modification of morphogenic genes to provide a starting material for producing double haploids for a variety of relevant crop plants, said double haploids as completely homozygous lines representing a valuable tool in plant breeding and plant biotechnology.

SUMMARY OF THE INVENTION

The above objectives have been achieved by providing, in a first aspect, a synthetic transcription factor, or a nucleotide sequence encoding the same, comprising at least one recognition domain and at least one gene expression modulation domain, in particular an activation domain, wherein the synthetic transcription factor is configured to modulate the expression of a morphogenic gene in a cellular system.

Further provided is a synthetic transcription factor, wherein the at least one recognition domain is, or is a fragment, of a molecule selected from the group consisting of at least one TAL effector, at least one disarmed CRISPR/nuclease system, at least one Zinc-finger domain, and at least one disarmed homing endonuclease, or any combination thereof.

In another embodiment, there is provided a synthetic transcription factor, wherein the at least one disarmed CRISPR/nuclease system is selected from a CRISPR/dCas9 system, a CRISPR/dCpf1 system, a CRISPR/dCasX system or a CRISPR/dCasY system, or any combination thereof, wherein the at least one disarmed CRISPR/nuclease system comprises at least one guide RNA.

In yet another embodiment, there is provided a synthetic transcription factor, wherein the at least one activation domain is selected from the group consisting of an acidic transcriptional activation domain, preferably, wherein the at least one activation domain is from a TAL effector gene of *Xanthomonas oryzae*, VP16 (SEQ ID NO: 259) or tetrameric VP64 (SEQ ID NO: 260) from Herpes simplex, VPR (SEQ ID NO: 261), SAM (SEQ ID NO: 262; SEQ ID NO: 263), Scaffold (SEQ ID NO: 264; SEQ ID NO: 265), Suntag (SEQ ID NO: 266; SEQ ID NO: 267), P300 (SEQ ID NO: 268), VP160 (SEQ ID NO: 269), or any combination thereof. In a preferred embodiment of the present invention, the activation domain is VP64.

In still another embodiment, there is provided a synthetic transcription factor, wherein the at least one activation domain is located N-terminal and/or C-terminal relative to the at least one recognition domain.

In one embodiment, there is provided a synthetic transcription factor, wherein the morphogenic gene is selected from the group consisting of BBM, WUS, including WUS2, a WOX gene, a WUS or BBM homologue, Lec1, Lec2, WIND1, ESR1, PLT3, PLT5, PLT7, IPT, IPT2, Knotted1, and RKD4.

In a further embodiment, there is provided a synthetic transcription factor, wherein the morphogenic gene comprises a nucleotide sequence selected from the group consisting of (i) a nucleotide sequence set forth in any one of SEQ ID NOs: 199 to 237, (ii) a nucleotide sequence having the coding sequences of the nucleotide sequence set forth in any one of SEQ ID NOs: 199 to 237, (iii) a nucleotide sequence complementary to the nucleotide sequence of (i) or (ii), (iv) a nucleotide sequence having at least 50%, 60%, 70%, 75%, 80%, 85%, 90%, 91%, 92%, 93%, 94%, 95%, 96%, 97%, 98%, or 99% identity, preferably over the whole length, to the nucleotide sequence of (i), (ii) or (iii), (v) a nucleotide sequence hybridzing the nucleotide sequence of (iii) under stringent conditions, (vi) a nucleotide sequence encoding a protein comprising the amino acid sequence set forth in any one of SEQ ID NOs: 238 to 258, (vii) a nucleotide sequence encoding a protein comprising the amino acid sequence at least 50%, 60%, 70%, 75%, 80%, 85%, 90%, 91%, 92%, 93%, 94%, 95%, 96%, 97%, 98%, or 99% identical to a sequence set forth in any one of SEQ ID NOs: 238 to 258, or (viii) a nucleotide sequence encoding a homologue, analogue or orthologue of protein comprising the amino acid sequence set forth in any one of SEQ ID NOs: 238 to 258.

In another embodiment, there is provided a synthetic transcription factor, wherein the synthetic transcription factor is configured to modulate expression, preferably transcription, of the morphogenic gene by binding to a regulation region located at a certain distance in relation to the start codon.

In yet another embodiment, there is provided a synthetic transcription factor, wherein the synthetic transcription factor and/or the at least one recognition domain comprises a sequence set forth in any one of SEQ ID NOs: 1 to 94, or a sequence having at least 85%, 86%, 87%, 88%, 89%, 90%, 91%, 92%, 93%, 94%, 95%, 96%, 97%, 98%, or 99% identity over the whole length of any one of SEQ ID NOs: 1 to 94, or wherein the synthetic transcription factor and/or at least one recognition domain, binds to a regulation region set forth in SEQ ID NOs: 95 to 190 or a sequence having at least 85%, 86%, 87%, 88%, 89%, 90%, 91%, 92%, 93%, 94%, 95%, 96%, 97%, 98%, or 99% identity over the whole length of any one of SEQ ID NOs: 95 to 190.

In a further embodiment, there is provided a synthetic transcription factor, wherein the cellular system is selected from the group consisting of at least one eukaryotic cell or eukaryotic organism, preferably wherein the at least one eukaryotic cell is at least one plant cell, and/or wherein the at least one eukaryotic organism is a plant or a part of a plant.

In one aspect, there is provided a method for increasing the transformation efficiency in a cellular system, wherein the method comprises the steps of: (a) providing a cellular system; (b) introducing into the cellular system at least one synthetic transcription factor, or a nucleotide sequence encoding the same; and (c) introducing into the cellular system at least one nucleotide sequence of interest; (d) optionally: culturing the cellular system under conditions to obtain a transformed progeny of the cellular system; wherein the at least one synthetic transcription factor, or the nucleotide sequence encoding the same, comprises at least one recognition domain and at least one gene expression modulation domain, in particular at least one activation domain, wherein the synthetic transcription factor is configured to modulate the expression, preferably the transcription, of at least one morphogenic gene in the cellular system; and wherein the at least one synthetic transcription factor, or the nucleotide sequence encoding the same, is introduced in parallel to, or sequentially with the introduction of the at least one nucleotide sequence of interest.

In one embodiment, there is provided a method, wherein (a) the at least one synthetic transcription factor, or the sequence encoding the same; and (b) the at least one nucleotide sequence of interest is/are introduced into the cellular system by means independently selected from biological and/or physical means, including transfection, transformation, including transformation by *Agrobacterium* spp., preferably, *Agrobacterium tumefaciens*, a viral vector, biolistic bombardment, transfection using chemical agents, including polyethylene glycol transfection, electro-poration, cell fusion or any combination thereof.

In yet another embodiment, there is provided a method, wherein the at least one recognition domain is, or is a fragment, of a molecule selected from the group consisting of at least one TAL effector, at least one disarmed CRISPR/nuclease system, at least one Zinc-finger domain, and at least one disarmed homing endonuclease, or any combination thereof.

In another embodiment, there is provided a method, wherein the at least one disarmed CRISPR/nuclease system is selected from a CRISPR/dCas9 system, a CRISPR/dCpf1 system, a CRISPR/dCasX system or a CRISPR/dCasY system, or any combination thereof, wherein the at least one disarmed CRISPR/nuclease system comprises at least one guide RNA.

In another embodiment, there is provided a method, wherein the at least one activation domain of the at least one synthetic transcription factor is selected from the group consisting of an acidic transcriptional activation domain, preferably, wherein the at least one activation domain is from a TAL effector gene of *Xanthomonas oryzae*, VP16 or tetrameric VP64 from Herpes simplex, VPR, SAM, Scaffold, Suntag, P300, VP160, or any combination thereof. In a preferred embodiment of the present invention, the activation domain is VP64.

In yet another embodiment, there is provided a method, wherein the at least one activation domain of the at least one synthetic transcription factor is located N-terminal and/or C-terminal relative to the at least one recognition domain of the at least one synthetic transcription factor.

In a further embodiment, there is provided a method, wherein the at least one morphogenic gene is selected from the group consisting of BBM, WUS, including WUS2, a WOX gene, a WUS or BBM homologue, Lec1 Lec2, WIND1, ESR1, PLT3, PLT5, PLT7, IPT, IPT2, Knotted1, and RKD4.

In a further embodiment, there is provided a method, wherein the at least one morphogenic gene comprises a nucleotide sequence selected from the group consisting of (i) a nucleotide sequence set forth in any one of SEQ ID NOs: 199 to 237, (ii) a nucleotide sequence having the coding sequences of the nucleotide sequence set forth in any one of SEQ ID NOs: 199 to 237, (iii) a nucleotide sequence complementary to the nucleotide sequence of (i) or (ii), (iv) a nucleotide sequence having at least 50%, 60%, 70%, 75%, 80%, 85%, 90%, 91%, 92%, 93%, 94%, 95%, 96%, 97%, 98%, or 99% identity, preferably over the whole length, to the the nucleotide sequence of (i), (ii) or (iii), (v) a nucleotide sequence hybridzing the nucleotide sequence of (iii) under stringent conditions, (vi) a nucleotide sequence encoding a protein comprising the amino acid sequence set forth in any one of SEQ ID NOs: 238 to 258, (vii) a nucleotide sequence encoding a protein comprising the amino acid sequence at least 50%, 60%, 70%, 75%, 80%, 85%, 90%, 91%, 92%, 93%, 94%, 95%, 96%, 97%, 98%, or 99% identical to a sequence set forth in any one of SEQ ID NOs: 238 to 258, or (viii) a nucleotide sequence encoding a homologue, analogue or orthologue of protein comprising the amino acid sequence set forth in any one of SEQ ID NOs: 238 to 258.

In another embodiment, there is provided a method, wherein the synthetic transcription factor is configured to modulate expression, preferably transcription, of the morphogenic gene by binding to a regulation region located at a certain distance in relation to the start codon.

In one embodiment, there is provided a method, wherein the synthetic transcription factor and/or the at least one recognition domain comprises a sequence set forth in any one of SEQ ID NOs: 1 to 94, or a sequence having at least 85%, 86%, 87%, 88%, 89%, 90%, 91%, 92%, 93%, 94%, 95%, 96%, 97%, 98%, or 99% identity over the whole length of any one of SEQ ID NOs: 1 to 94, or wherein the synthetic transcription factor and/or at least one recognition domain, binds to a regulation region set forth in SEQ ID NOs: 95 to 190 or a sequence having at least 85%, 86%, 87%, 88%, 89%, 90%, 91%, 92%, 93%, 94%, 95%, 96%, 97%, 98%, or 99% identity over the whole length of any one of SEQ ID NOs: 95 to 190.

In another embodiment, there is provided a method, wherein the cellular system is selected from the group consisting of at least one eukaryotic cell or eukaryotic organism, preferably wherein the at least one eukaryotic cell is at least one plant cell, and/or wherein the at least one eukaryotic organism is a plant or a part of a plant.

In a further aspect, there is provided a method of modifying the genetic material of a cellular system at a predetermined location, wherein the method comprises the following steps: (a) providing a cellular system; (b) introducing at least one synthetic transcription factor, or a sequence encoding the same, into the cellular system, (c) further introducing into the cellular system (i) at least one site-specific nuclease, or a sequence encoding the same, wherein the site-specific nuclease induces a DNA double-strand break at the predetermined location; (ii) optionally: at least one nucleotide sequence of interest, preferably flanked by one or more homology sequence(s) complementary to one or more nucleotide sequence(s) adjacent to the predetermined location in the genetic material of the cellular system; and; (e) optionally: determining the presence of the modification at the predetermined location in the genetic material of the cellular system; and (f) obtaining a cellular system comprising a modification at the predetermined location of the genetic material of the cellular system; wherein the at least one synthetic transcription factor, or the nucleotide sequence encoding the same, comprises at least one recognition domain and at least one activation domain, wherein the at least one synthetic transcription factor is configured to modulate the expression, preferably the transcription, of at least one morphogenic gene in the cellular system; and wherein the at least one synthetic transcription factor, or the nucleotide sequence encoding the same, is introduced in parallel to, or sequentially with the introduction of the at least one site-specific nuclease, or the sequence encoding the same and the optional at least one nucleotide sequence of interest.

In another embodiment of this aspect, there is provided a method, wherein the method further comprises the step of culturing the cellular system under conditions to obtain a genetically modified progeny of the modified cellular system.

In another embodiment of the methods of modifying the genetic material of a cellular system at a predetermined location, there is provided a method, wherein (i) the at least one synthetic transcription factor, or the sequence encoding the same; and (ii) the at least one site-specific nuclease, or the sequence including the same; and optionally (iii) the at least one nucleotide sequence of interest is/are introduced into the cellular system by means independently selected from biological and/or physical means, including transfection, transformation, including transformation by *Agrobacterium* spp. transformation, preferably by *Agrobacterium tumefaciens*, a viral vector, biolistic bombardment, transfection using chemical agents, including polyethylene glycol transfection, electro-poration, cell fusion, or any combination thereof.

In one embodiment, there is provided a method, wherein the at least one recognition domain is, or is a fragment of, a molecule selected from the group consisting of at least one TAL effector, at least one disarmed CRISPR/nuclease system, at least one Zinc-finger domain, and at least one disarmed homing endonuclease, or any combination thereof.

In a further embodiment, there is provided a method, wherein the at least one disarmed CRISPR/nuclease system is selected from a CRISPR/dCas9 system, a CRISPR/dCpf1 system, a CRISPR/dCasX system or a CRISPR/dCasY system, or any combination thereof, wherein the at least one disarmed CRISPR/nuclease system comprises at least one guide RNA.

Further provided is an embodiment of the above methods, wherein the at least one activation domain of the at least one synthetic transcription factor is selected from the group consisting of an acidic transcriptional activation domain, preferably, wherein the at least one activation domain is from a TAL effector gene of *Xanthomonas oryzae*, VP16 or tetrameric VP64 from Herpes simplex, VPR, SAM, Scaffold, Suntag, P300, VP160, or any combination thereof. In a preferred embodiment of the present invention, the activation domain is VP64.

In one embodiment, there is provided a method, wherein the at least one activation domain of the at least one synthetic transcription factor is located N-terminal and/or C-terminal relative to the at least one recognition domain of the at least one synthetic transcription factor.

In a further embodiment, there is provided a method, wherein the at least one morphogenic gene is selected from the group consisting of BBM, WUS, including WUS2, a WOX gene, a WUS or BBM homologue, Lec1 Lec2, WIND1, ESR1, PLT3, PLT5, PLT7, IPT, IPT2, Knotted1, and RKD4.

In a further embodiment, there is provided a method, wherein the at least one morphogenic gene comprises a nucleotide sequence selected from the group consisting of (i) a nucleotide sequence set forth in any one of SEQ ID NOs: 199 to 237, (ii) a nucleotide sequence having the coding sequences of the nucleotide sequence set forth in any one of SEQ ID NOs: 199 to 237, (iii) a nucleotide sequence complementary to the nucleotide sequence of (i) or (ii), (iv) a nucleotide sequence having at least 50%, 60%, 70%, 75%, 80%, 85%, 90%, 91%, 92%, 93%, 94%, 95%, 96%, 97%, 98%, or 99% identity, preferably over the whole length, to the the nucleotide sequence of (i), (ii) or (iii), (v) a nucleotide sequence hybridzing the nucleotide sequence of (iii) under stringent conditions, (vi) a nucleotide sequence encoding a protein comprising the amino acid sequence set forth in any one of SEQ ID NOs: 238 to 258, (vii) a nucleotide sequence encoding a protein comprising the amino acid sequence at least 50%, 60%, 70%, 75%, 80%, 85%, 90%, 91%, 92%, 93%, 94%, 95%, 96%, 97%, 98%, or 99% identical to a sequence set forth in any one of SEQ ID NOs: 238 to 258, or (viii) a nucleotide sequence encoding a homologue, analogue or orthologue of protein comprising the amino acid sequence set forth in any one of SEQ ID NOs: 238 to 258.

In another embodiment, there is provided a method, wherein the synthetic transcription factor is configured to modulate expression, preferably transcription, of the morphogenic gene by binding to a regulation region located at a certain distance in relation to the start codon.

In still another embodiment, there is provided a method, wherein the synthetic transcription factor and/or the at least one recognition domain comprises a sequence set forth in any one of SEQ ID NOs: 1 to 94, or a sequence having at least 85%, 86%, 87%, 88%, 89%, 90%, 91%, 92%, 93%, 94%, 95%, 96%, 97%, 98%, or 99% identity over the whole length of any one of SEQ ID NOs: 1 to 94, or wherein the synthetic transcription factor and/or at least one recognition domain, binds to a regulation region set forth in SEQ ID NOs: 95 to 190, or a sequence having at least 85%, 86%, 87%, 88%, 89%, 90%, 91%, 92%, 93%, 94%, 95%, 96%, 97%, 98%, or 99% identity over the whole length of any one of SEQ ID NOs: 95 to 190.

In a further embodiment, there is provided a method, wherein the cellular system is selected from the group consisting of at least one eukaryotic cell or eukaryotic organism, preferably wherein the at least one eukaryotic cell is at least one plant cell, and/or wherein the at least one eukaryotic organism is a plant or a part of a plant.

In yet a further embodiment, there is provided a method, wherein the one or more nucleotide sequence(s) flanking the at least one nucleotide sequence of interest at the predetermined location is/are at least 85%-100% complementary to the one or more nucleotide sequence(s) adjacent to the predetermined location, upstream and/or downstream from the predetermined location, over the entire length of the respective adjacent region(s).

In another aspect of the present invention, there is provided a method of producing a haploid or double haploid cellular system or organism, wherein the method comprises the following steps: (a) providing a haploid cellular system; (b) introducing into the haploid cellular system at least one synthetic transcription factor, or a nucleotide sequence encoding the same; (c) culturing the haploid cellular system under conditions to obtain at least one haploid or double haploid organism; and (d) optionally, selecting the at least one haploid or double haploid organism obtained in step (c), wherein the at least one synthetic transcription factor, or the nucleotide sequence encoding the same, comprises at least one recognition domain and at least one activation domain, wherein the at least one synthetic transcription factor is configured to modulate the expression, preferably the transcription, of at least one morphogenic gene in the haploid cellular system.

In one embodiment, there is provided a method, wherein the haploid cellular system of step (a) of the above method is a haploid embryo, or wherein the at least one haploid or double haploid organism of step (c) of the above method is obtained through an intermediate step of generating at least one haploid embryo from the haploid cellular system of (b).

In one embodiment, there is provided a method, wherein the at least one synthetic transcription factor, or a sequence encoding the same, is introduced into the haploid cellular system by means independently selected from biological and/or physical means, including transfection, transformation, including transformation by *Agrobacterium* spp. transformation, preferably by *Agrobacterium tumefaciens*, a viral vector, biolistic bombardment, transfection using chemical agents, including polyethylene glycol transfection, electroporation, cell fusion, or any combination thereof.

In a further embodiment, there is provided a method, wherein the at least one recognition domain is or is a fragment of a molecule selected from the group consisting of at least one TAL effector, at least one disarmed CRISPR/nuclease system, at least one Zinc-finger domain, and at least one disarmed homing endonuclease, or any combination thereof.

In yet a further embodiment, there is provided a method, wherein the at least one disarmed CRISPR/nuclease system is selected from a CRISPR/dCas9 system, a CRISPR/dCpf1 system, a CRISPR/dCasX system or a CRISPR/dCasY system, or any combination thereof, wherein the at least one disarmed CRISPR/nuclease system comprises at least one guide RNA.

In another embodiment, there is provided a method, wherein the at least one activation domain of the at least one synthetic transcription factor is selected from the group consisting of an acidic transcriptional activation domain, preferably, wherein the at least one activation domain is from a TAL effector gene of *Xanthomonas oryzae*, VP16 or tetrameric VP64 from Herpes simplex, VPR, SAM, Scaffold, Suntag, P300, VP160, or any combination thereof. In a preferred embodiment of the invention, the actiation domain is VP64.

In a further embodiment, there is provided a method, wherein the at least one activation domain of the at least one synthetic transcription factor is located N-terminal and/or C-terminal relative to the at least one recognition domain of the at least one synthetic transcription factor.

In yet a further embodiment, there is provided a method, wherein the at least one morphogenic gene is selected from the group consisting of BBM, WUS, including WUS2, a WOX gene, a WUS or BBM homologue, Lec1 Lec2, WIND1, ESR1, PLT3, PLT5, PLT7, IPT, IPT2, Knotted1, and RKD4.

In a further embodiment, there is provided a method, wherein the at least one morphogenic gene comprises a nucleotide sequence selected from the group consisting of (i) a nucleotide sequence set forth in any one of SEQ ID NOs: 199 to 237, (ii) a nucleotide sequence having the coding sequences of the nucleotide sequence set forth in any one of SEQ ID NOs: 199 to 237, (iii) a nucleotide sequence complementary to the nucleotide sequence of (i) or (ii), (iv) a nucleotide sequence having at least 50%, 60%, 70%, 75%, 80%, 85%, 90%, 91%, 92%, 93%, 94%, 95%, 96%, 97%, 98%, or 99% identity, preferably over the whole length, to the the nucleotide sequence of (i), (ii) or (iii), (v) a nucleotide sequence hybridzing the nucleotide sequence of (iii) under stringent conditions, (vi) a nucleotide sequence encoding a protein comprising the amino acid sequence set forth in any one of SEQ ID NOs: 238 to 258, (vii) a nucleotide sequence encoding a protein comprising the amino acid sequence at least 50%, 60%, 70%, 75%, 80%, 85%, 90%, 91%, 92%, 93%, 94%, 95%, 96%, 97%, 98%, or 99% identical to a sequence set forth in any one of SEQ ID NOs: 238 to 258, or (viii) a nucleotide sequence encoding a homologue, analogue or orthologue of protein comprising the amino acid sequence set forth in any one of SEQ ID NOs: 238 to 258.

In one embodiment, there is provided a method, wherein the synthetic transcription factor is configured to modulate expression, preferably transcription, of the morphogenic gene by binding to a regulation region located at a certain distance in relation to the start codon.

In a further embodiment, there is provided a method, wherein the synthetic transcription factor and/or the at least one recognition domain comprises a sequence set forth in any one of SEQ ID NOs:1 to 94, or a sequence having at least 85%, 86%, 87%, 88%, 89%, 90%, 91%, 92%, 93%, 94%, 95%, 96%, 97%, 98%, or 99% identity over the whole length of any one of SEQ ID NOs: 1 to 94, or wherein the synthetic transcription factor and/or at least one recognition domain, binds to a regulation region set forth in SEQ ID NOs: 95 to 190, or a sequence having at least 85%, 86%, 87%, 88%, 89%, 90%, 91%, 92%, 93%, 94%, 95%, 96%, 97%, 98%, or 99% identity over the whole length of any one of SEQ ID NOs: 95 to 190.

In yet a further embodiment, there is provided a method, wherein the at least one haploid cellular system is selected from the group consisting of at least one eukaryotic cell or eukaryotic organism, preferably wherein the at least one eukaryotic cell is at least one plant cell, and/or wherein the at least one eukaryotic organism is a plant or a part of a plant.

Further provided is cellular system or a progeny thereof obtained by any one of the methods provided herein.

In another aspect, there is provided a haploid or a double haploid cellular system or organism obtained by any one of the methods provided herein.

In another aspect, there is provided a use of a synthetic transcription factor as provided herein, or a sequence encoding the same, in any of the methods provided herein.

Further aspects and embodiments of the present invention can be derived from the subsequent detailed description, the drawings, the sequence listing as well as the attached set of claims.

BRIEF DESCRIPTION OF THE DRAWINGS AND SEQUENCES

Figure 1B:
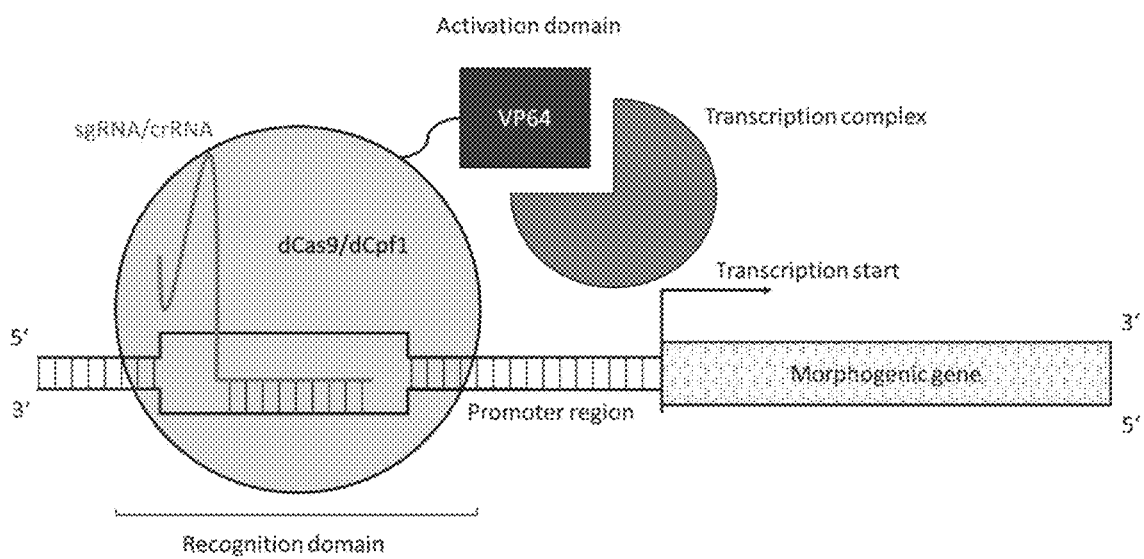

FIG. 1. Illustrative examples of synthetic transcription factors (STFs) for targeted gene activation modification. (A) Targeted gene activation via TAL transcription factor is shown. TAL transcription factors consist of an activation domain (e.g. VP64) fused to the DNA-binding domain of e.g. transcription activator-like effectors (TALEs). (B) Targeted gene activation via the CRISPR/dCas9 and/or CRISPR/dCpf1 transcription system is shown. CRISPR/dCas9 and CRISPR/dCpf1 transcription factor systems comprise a disarmed nuclease (e.g. dCas9 or dCpf1) fused to an activation domain (e.g. VP64). DNA binding is mediated by a guide RNA associated with the disarmed nuclease. Upon binding to the genomic target site in close proximity to the transcription start site of a morphogenic gene of interest the STFs recruit the RNA polymerase II complex (i.e. the transcription complex) via the activation domain to the promoter region of the morphogenic gene where transcription of the gene is initiated.

Figure 2:
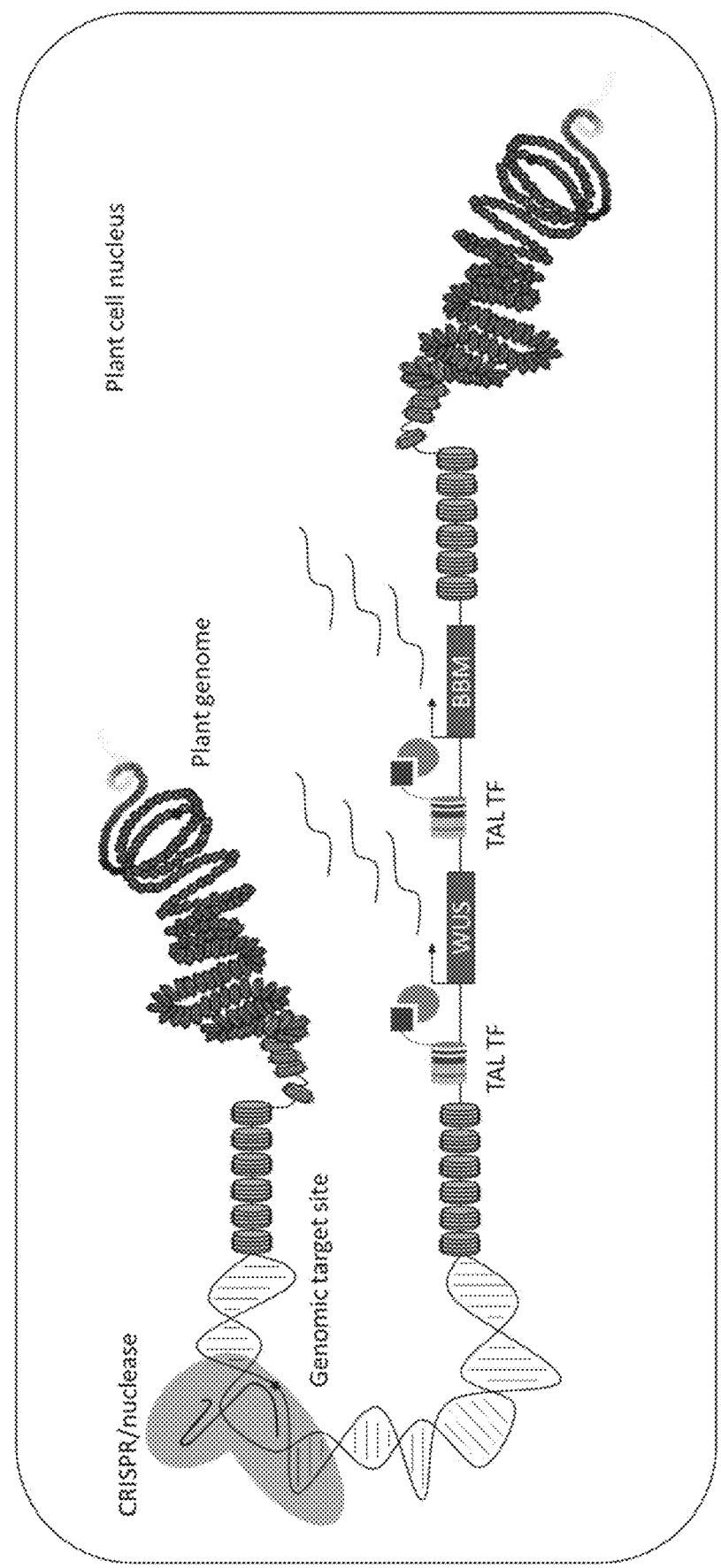

FIG. 2. Schematic depiction of improved gene editing by cotransfection of a gene editing machinery with an exemplary synthetic transcription factors (STFs) specific for morphogenic genes. Modifications such as INDELs or replacement of a target gene with a repair template by a gene editing machinery (e.g. CRSPR/Cpf1 or CRSIPR/Cas9) results in genetically modified plant cell(s). Transient cotransfection of the gene editing machinery with one or more STFs specific for BBM and WUS ensure recovery of the target cell and increase of regeneration of an edited plant.

Figure 3A:
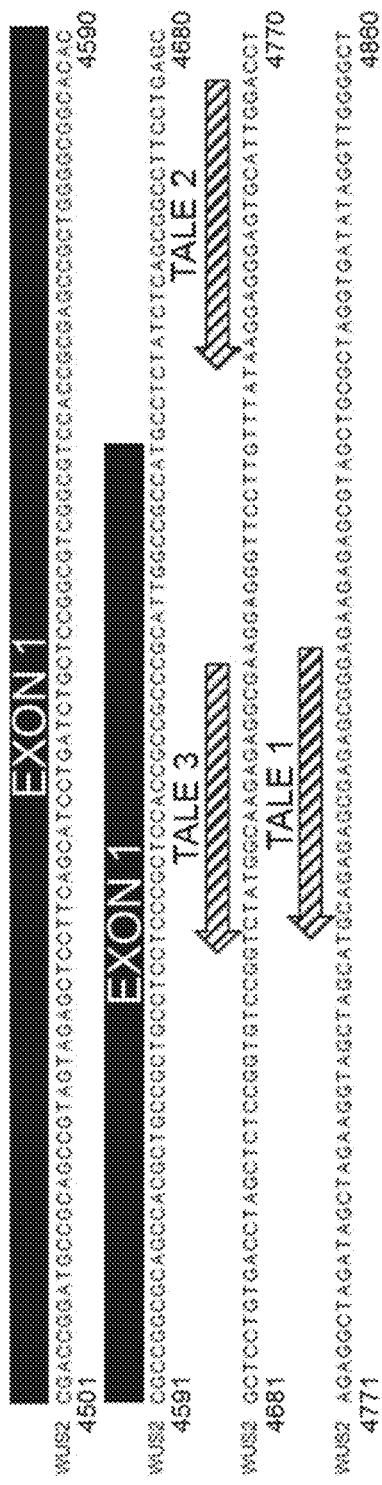

FIG. 3. Design of Tal effector binding sites targeting endogenous Wuschel (WUS) and Babyboom (BBM) genes. The sites were designed with varying distances to the start codon. (A) Binding sites for endogenous WUS (SEQ ID NO: 277) are 18 base pairs in length and further comprise an initial T nucleobase (TALE 1, 2 and 3). (B) Binding sites for endogenous BBM (SEQ ID NO: 278) are 24 base pairs in length and further comprises an initial T nucleobase (TALE 4, 5, and 6, SEQ ID Nos: 270-272).

Figure 4A:
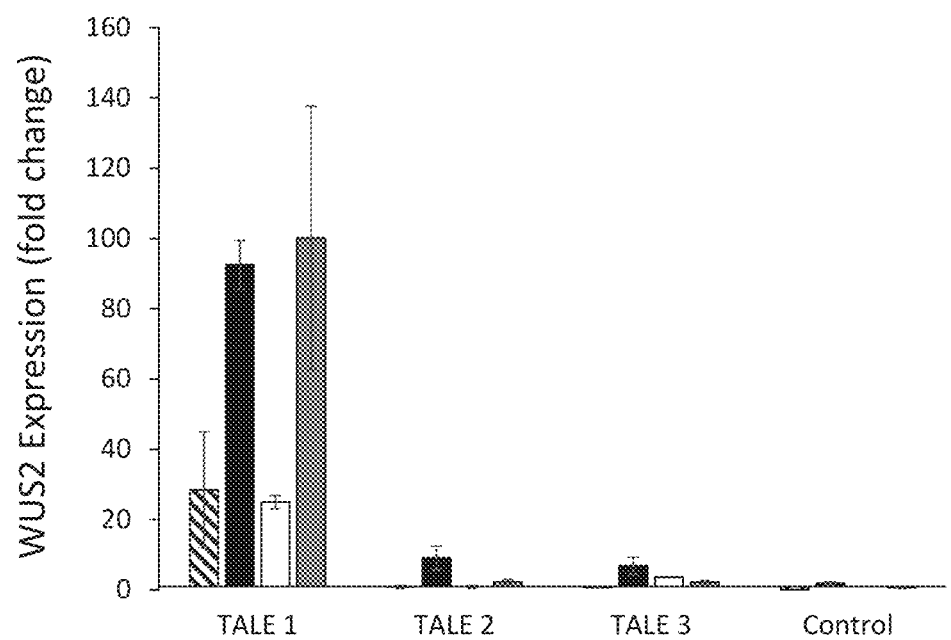
Figure 4B:
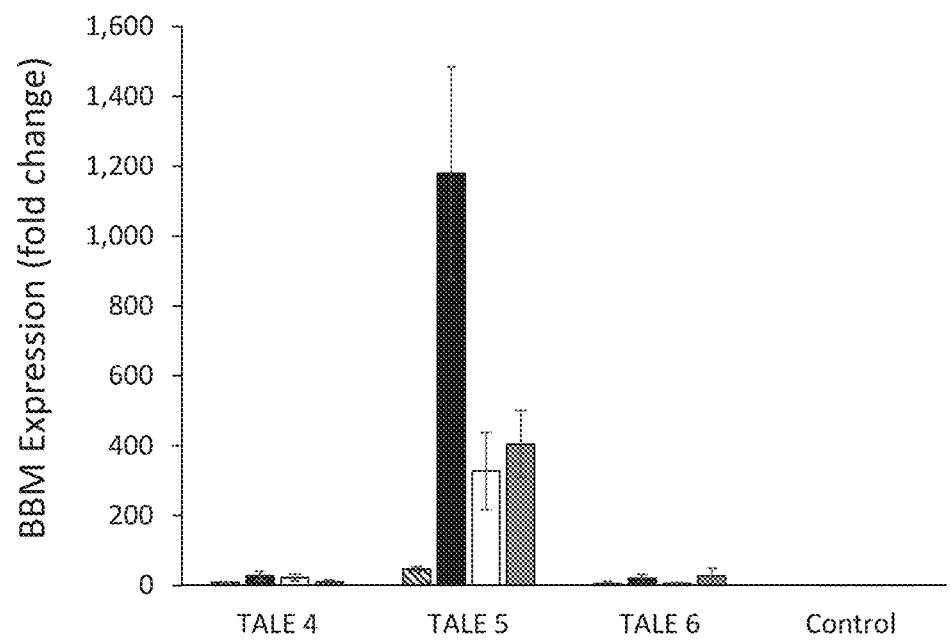

FIG. 4. Transient expression of endogenous WUS and BBM by TALE transcription factors. Induction of gene expression by TAL transcription factors was tested in a maize protoplast assay system. Maize protoplasts were transformed with vector constructs comprising TALE transcription factors targeting WUS or BBM by using a PEG-based transformation system. Experiments were performed in triplicates and repeated four times as biological replicates. After 24 hrs, cDNA was generated from extracted protoplast RNA by using commercially available kits. The expression of endogenpus WUS and BBM was determined by using a SYBR Green qRT-PCR approach. (A) The results indicate that the synthetic transcription factor TALE1 is the strongest inducer for endogenous WUS showing an average fold change of 60 in endogenous WUS gene expression. (B) The results indicate that the synthetic transcription factor TALE5 is the strongest inducer for endogenous BBM showing an average fold change of 490 in endogenous BBM gene expression.

Figure 5:
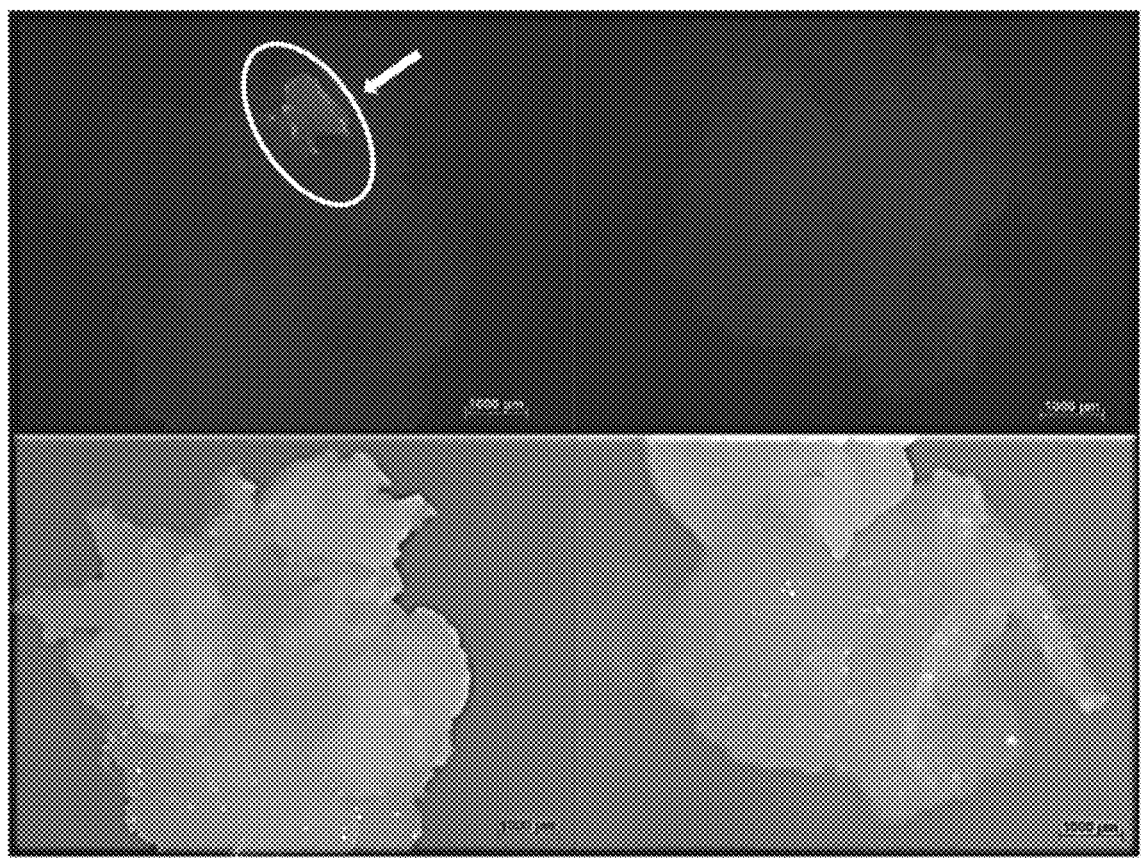

FIG. 5. Evaluation of phenotypic function of endogenous ZmWUS induced by transient TALE transcription factor. In order to evaluate the effect of synthetic transcription factors on regeneration and embryogenesis, callus tissue from corn A188 was transformed by particle bombardment with the fluorescent marker tdTomato (tdT), TALE1 and PLT7. Constructs were delivered to a single cell and induction of cell proliferation was confirmed by fluorescent microscopy upon detection of the red fluorescent signal of tdT (see white circle and arrow).

Figure 6:
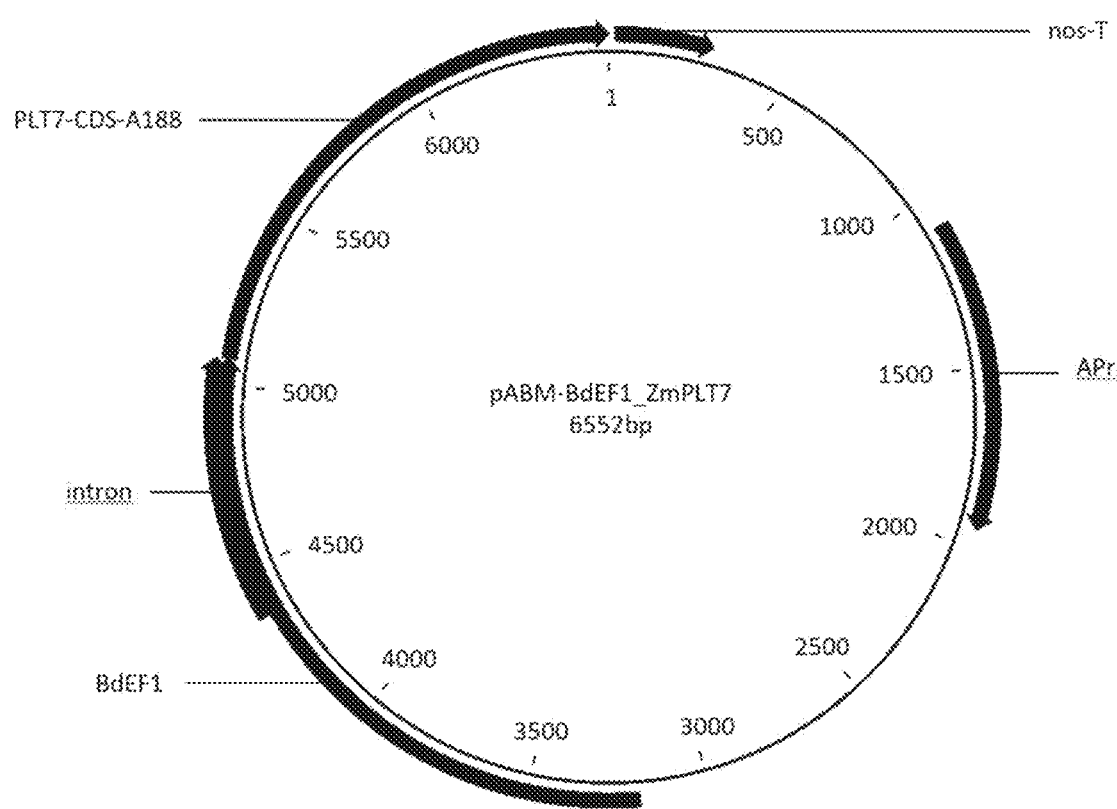

FIG. 6. pABM-BdEF1_ZmPLT7 construct map. Maize PLT7 gene (ZmPLT7) is driven by the strong constitutive EF1 promoter from Brachypodium (BDEF1).

FIG. 7. Effect of the synthetic transcriptional activators in a biolistic maize transformation. The emersion of embryogenic callus was assessed four weeks after bombardment.

Figure 7A:
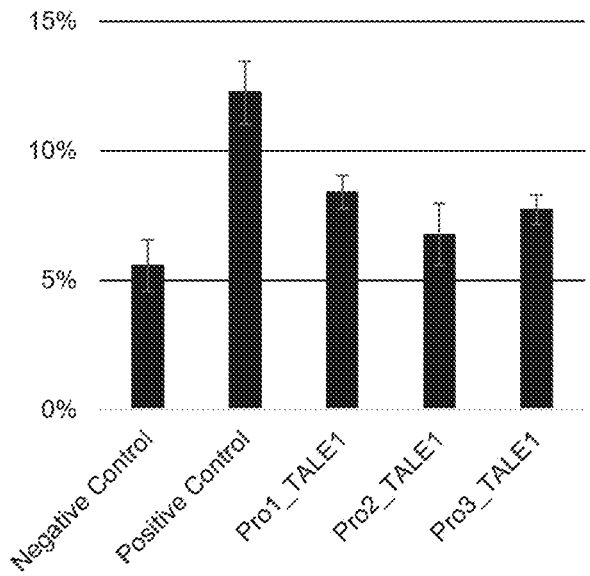
Figure 7B:
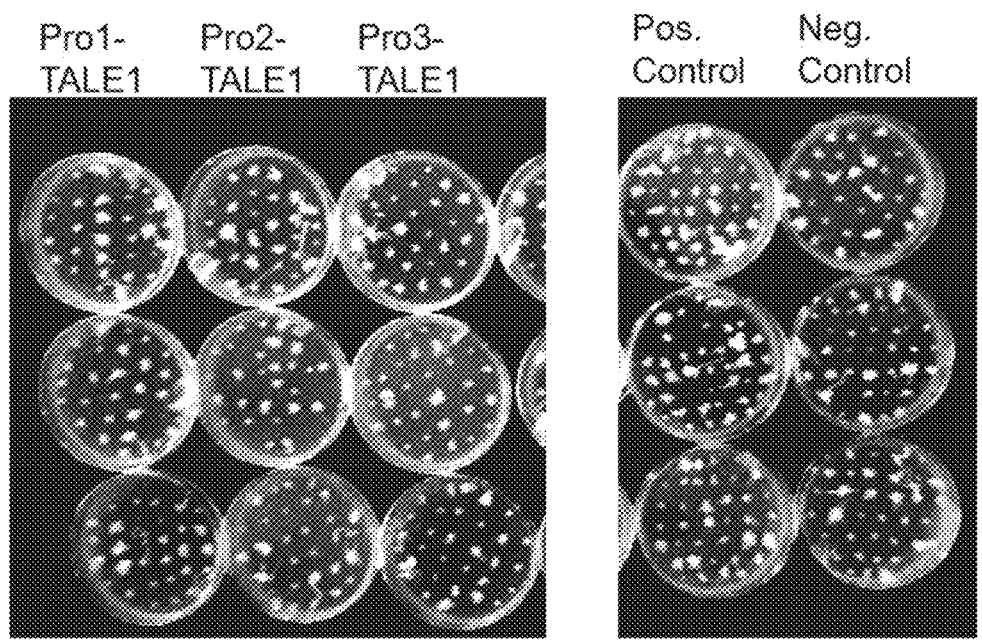

FIG. 7A: About 5.5% of immature embryos showed embryogenic callus when mock-treated. Known morphogenic genes were delivered as a positive control (average 12.4%). Delivery of synthetic transcriptional activators for BBM and WUS2 under different constitutive and tissue specific promoters (Pro1, Pro2, Pro3) showed an increase in embryogenic callus formation. FIG. 7B shows the dishes with the transformed calli of the experiment.

Figure 8:
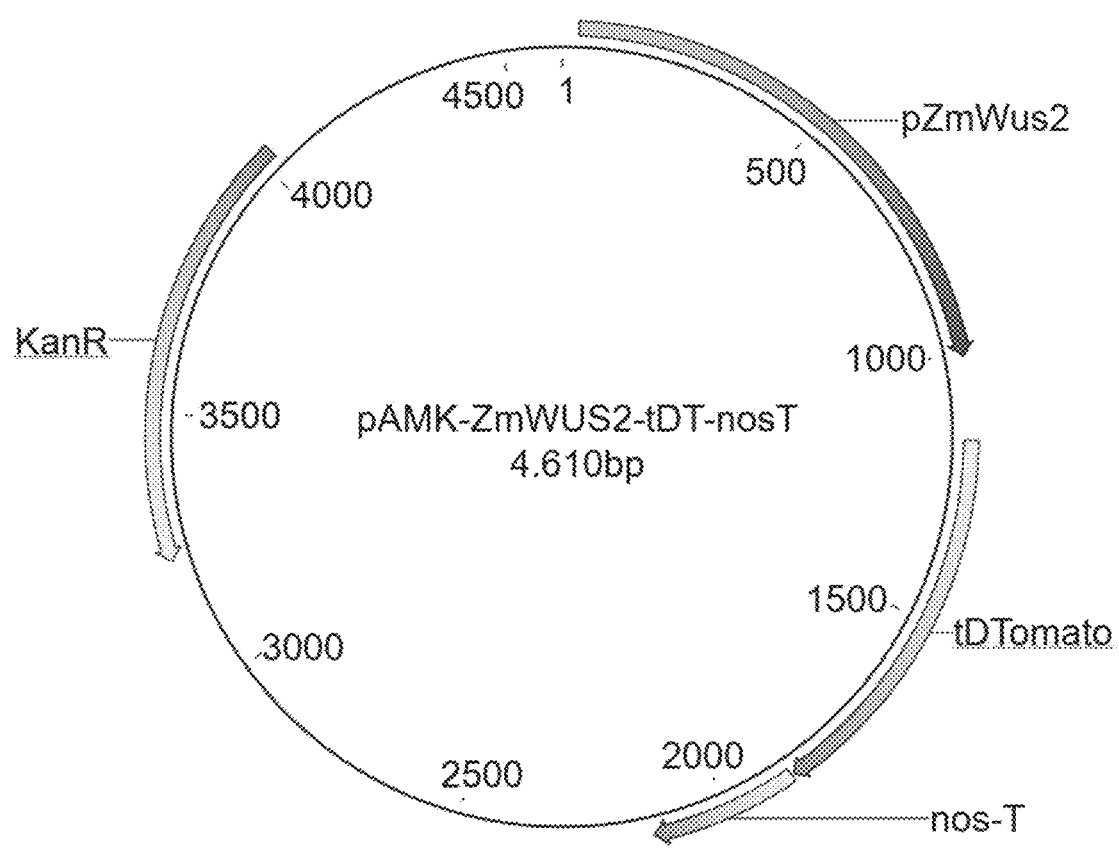

FIG. 8 shows a map of the maize WUS2 (ZmWUS2) promoter report construct pAMK-ZmWUS2-tDT-nosT (SEQ ID NO: 43). tDTomato define the fluorescence tDT report gene, which is driven by maize WUSCHEL2 promoter (pZmWUS2).

Figure 9:
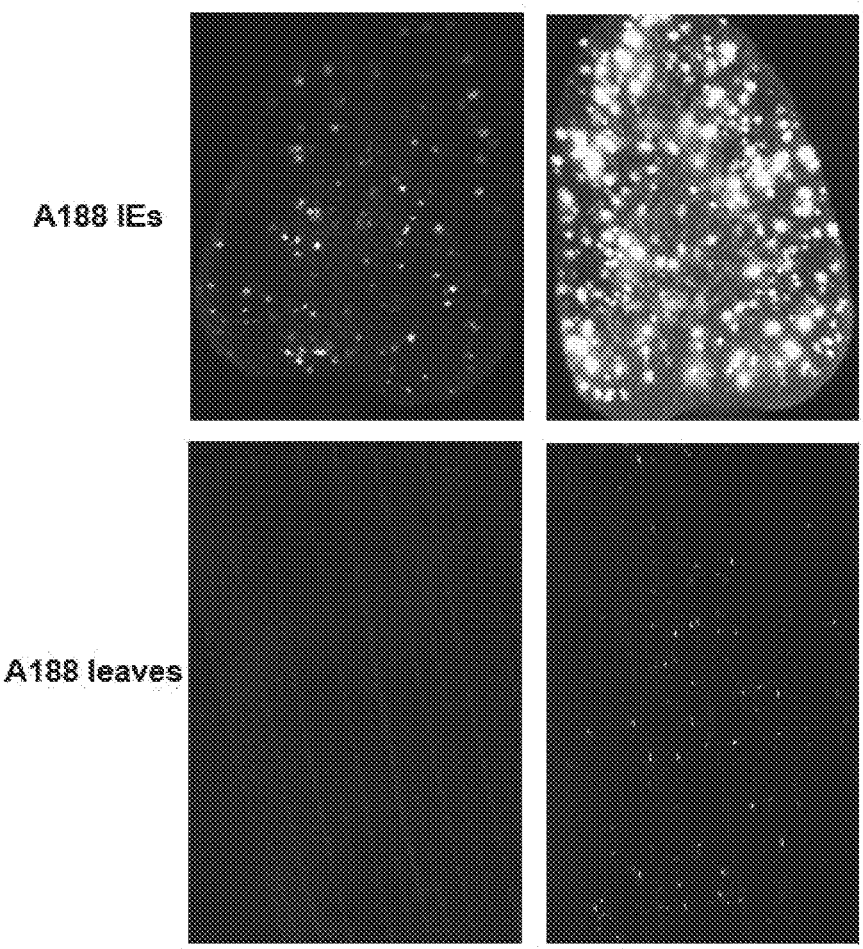

FIG. 9. Induction of ZmWUS2 promoter by synthetic transcriptional activator in leaf and embryo tissue of maize genotype A188. Induction of ZmWUS2 promoter was observed by the expression of the fluorescent protein (tdTomato) (white spots in pictures). The left panels show that the WUS2 promoter does not or only at very low intensity lead to expression of tdTomato in immature embryos (upper panel) and in leaf tissue (lower panel). When co-delivered with the synthetic transcriptional activator TALE1, tdTomato is expressed strongly in immature embryos (right upper panel) and notably in leaves (right lower panel).

TABLE 1

Brief description of sequences disclosed in the sequence listing

| Sequence Identifier [SEQ ID NO]: | description |
|---|---|
| 1-3 | gRNAs of Cas9 targeted to promoter region of BBM from *Zea mays* |
| 4-6 | gRNAs of Cas9 targeted to promoter region of WUS from *Zea mays* |
| 7-9 | crRNAs of Cpf1 targeted to promoter region of BBM from *Zea mays* |
| 10-12 | crRNAs of Cpf1 targeted to promoter region of WUS from *Zea mays* |
| 13-51 | TAL recognition domains targeted to promoter region of BBM from *Zea mays* |
| 52-94 | TAL recognition domains targeted to promoter region of WUS from *Zea mays* |
| 95 | Target promoter region of BBM from *Zea mays* |
| 96 | Target promoter region of WUS from *Zea mays* |
| 97-99 | Target sites of gRNAs of Cas9 in promoter region of BBM from *Zea mays* |
| 100-102 | Target sites of crRNAs of Cpf1 in promoter region of BBM from *Zea mays* |
| 103-105 | Target sites of gRNAs of Cas9 in promoter region of WUS from *Zea mays* |
| 106-108 | Target sites of crRNAs of Cpf1 in promoter region of WUS from *Zea mays* |
| 109-147 | Target sites of TAL effector in promoter region of BBM from *Zea mays* |
| 148-190 | Target sites of TAL effector in promoter region of WUS from *Zea mays* |
| 191-198 | Primers |
| 199-216 | cDNAs of diverse morphogenic genes from various species |
| 217-237 | cDNAs of diverse morphogenic genes from *Zea mays* |
| 238-258 | Proteins encoded by diverse morphogenic genes from *Zea mays* (see SEQ ID Nos: 217-237) |
| 258-269 | Various exemplary nucleotide sequences encoding activation domains or parts thereof |

Definitions

The terms "site-specific DNA modifying enzyme", "sequence-specific DNA modifying enzyme", "gene editing enzyme", "genome editing enzyme", and "genome engineering enzyme" are used interchangeably herein and refer to enzymes or enzyme complexes used to make targeted, specific modification, or targeted, random modification of any genetic or epigenetic information or genome of a living organism at at least one position. The sequence-specific nature of the enzymes means that they can be targeted to edit genes, but also editing of regions other than gene encoding regions of a genome. It further comprises the editing or engineering of the nuclear (if present) as well as other genetic information of a cell. Furthermore, the modification of genetic information comprises the targeted modification of editing, engineering, mutating, or destroying nucleic acid bases contained within nuclear or extranuclear genomes, including either DNA or RNA genomes. It can also include the targeted modification of messages expressed from genomes, such as for example, RNA messages. Such enzymes include, but are not limited to, exonucleases, endonucleases, nickases, helicases, polymerases, ligases, and deaminases including cytidine, adenine, or other base editors. The modification of epigenetic information comprises the targeted modification of methylation, histone modification or of non-coding RNAs possibly causing heritable changes in gene expression.

A "base editor" as used herein refers to a protein or a complex comprising at least one protein or a fragment thereof having the capacity to mediate a targeted base modification, i.e., the conversion of a base of interest resulting in a point mutation of interest. Preferably, the at least one base editor in the context of the present invention comprises at least one nucleic acid recognition domain for targeting the base editor to a specific site of a nucleic acid sequence and at least one nucleic acid editing domain, which performs the conversion of at least one nucleobase at the specific target site. The nucleic acid recognition domain can additionally comprise at least one nucleic acid molecule, e.g., a guide RNA, or any other single- or double-stranded nucleic acid molecule. A "base edit" therefore refers to at least one specific nucleotide carrying a different nucleobase than previously. Based on the above, a "predetermined location" according to the present invention means the location or site in a genomic material in a cellular system, or within a genome of a cell of interest to be modified, where a targeted edit is to be introduced. The base editor may comprise further components besides the nucleic acid recognition domain and the nucleic acid editing domain, such as spacers, localization signals and components inhibiting naturally occurring DNA or RNA repair mechanisms to ensure the desired editing outcome. The term "nucleic acid recognition domain" refers to the component of the base editor, which ensures the site-specificity of the base editor by directing it to a target site within the predetermined location. A nucleic acid recognition domain may be based on a CRISPR system, which specifically recognizes a target sequence within the nucleic acid molecule of the cellular system using a guide RNA (gRNA) or single guide RNA (sgRNA), may be a synthetic fusion of a CRISPR RNA (crRNA) and a trans-activating crRNA (tracrRNA).

A "CRISPR nuclease", as used herein, is any nuclease which has been identified in a naturally occurring CRISPR system, which has subsequently been isolated from its natural context, and which preferably has been modified or combined into a recombinant construct of interest to be suitable as tool for targeted genome engineering. Any CRISPR nuclease can be used and optionally reprogrammed or additionally mutated to be suitable for the various embodiments according to the present invention as long as the original wild-type CRISPR nuclease provides for DNA recognition, i.e., binding properties. Said DNA recognition can be PAM (pro-tospacer adjacent motif) dependent. CRISPR nucleases having optimized and engineered PAM recognition patterns can be used and created for a specific application. The expansion of the PAM recognition code can be suitable to target site-specific effector complexes to a target site of interest, independent of the original PAM specificity of the wild-type CRISPR-based nuclease. CRISPR nucleases also comprise mutants or catalytically active fragments or fusions of a naturally occurring CRISPR effector sequences, or the respective sequences encoding the same. A CRISPR nuclease may in particular also refer to a CRISPR nickase or even a nuclease-deficient variant of a CRISPR polypeptide having endonucleolytic function in its natural environment.

The term "nucleic acid editing domain" refers to the component of the base editor, which initiates the nucleotide conversion to result in the desired edit. The catalytic function of the nucleic acid editing domain may be a cytidine deaminase or an adenine deaminase function.

In general, base editors are composed of at least one nucleic acid recognition domain and at least one nucleic acid editing domain that deaminates cytidine or adenine. Nucleic acid editing domains which deaminate cytidine are able to convert C to T (G to A), and they are called BEs; nucleic acid editing domain which deaminate adenine can convert A to G (T to C), and they are called ABEs.

Base editors usually are composed of cytidine deaminase domain (such as APOBEC1, APOBEC3A, APOBEC3G, PmCDA1, AID), linker (usually XTEN), CRISPR domain (d/nCas9, dCpf1, CasX, CasY, or other suitable domains) and uracil DNA glycosylase inhibitor (UGI). In a modified system, the number of UGI domain or NLS can vary, so does the length of the linker. It can also include other domains such as Gam (e.g. in BE4). There can be variants with amino acid point mutations in the cytidine deaminase domain for different editing window, such as YE-BE3, YEE-BE3 and also mutations in the CRISPR domain for different PAM recognition, such as VQR-BE3, EQR-BE3, VRER-BE3, and SaKKH-BE3. In the BE-PLUS system, the CRISPR domain and cytidine deaminase domain is not expressed as fusion protein but instead linked together using a Suntag system for broadening the editing window. More details on preferred base editors, including cytidine deaminase-based DNA base editors, adenine deaminase-based DNA base editors, can be derived from Eid A et al. (Ayman Eid, Sahar Alshareef and Magdy M. Mahfouz (2018), CRISPR base editors: genome editing without double-strand breaks, Biochemical Journal (2018) 475 1955-1964).

The terms "associated with" or "in association with" according to the present disclosure are to be construed broadly and, therefore, according to present invention imply that a molecule (DNA, RNA, amino acid, comprising naturally occurring and/or synthetic building blocks) is provided in physical association with another molecule, the association being either of covalent or non-covalent nature. For example, a repair template can be associated with a gRNA of a CRISPR nuclease, wherein the association can be of non-covalent nature (complementary base pairing), or the molecules can be physically attached to each other by a covalent bond.

The term "catalytically active fragment" as used herein referring to amino acid sequences denotes the core sequence derived from a given template amino acid sequence, or a nucleic acid sequence encoding the same, comprising all or part of the active site of the template sequence with the proviso that the resulting catalytically active fragment still possesses the activity characterizing the template sequence, for which the active site of the native enzyme or a variant thereof is responsible. Said modifications are suitable to generate less bulky amino acid sequences still having the same activity as a template sequence making the catalytically active fragment a more versatile or more stable tool being sterically less demanding.

A "covalent attachment" or "covalent bond" is a chemical bond that involves the sharing of electron pairs between atoms of the molecules or sequences covalently attached to each other. A "non-covalent" interaction differs from a covalent bond in that it does not involve the sharing of electrons, but rather involves more dispersed variations of electromagnetic interactions between molecules/sequences or within a molecule/sequence. Non-covalent interactions or attachments thus comprise electrostatic interactions, van der Waals forces, π-effects and hydrophobic effects. Of special importance in the context of nucleic acid molecules are hydrogen bonds as electrostatic interaction. A hydrogen bond (H-bond) is a specific type of dipole-dipole interaction that involves the interaction between a partially positive hydrogen atom and a highly electronegative, partially negative oxygen, nitrogen, sulfur, or fluorine atom not covalently bound to said hydrogen atom. Any "association" or "physical association" as used herein thus implies a covalent or non-covalent interaction or attachment. In the case of molecular complexes, e.g. a complex formed by a CRISPR nuclease, a gRNA and a repair template (RT), more covalent and non-covalent interactions can be present for linking and thus associating the different components of a molecular complex of interest.

The terms "CRISPR polypeptide", "CRISPR endonuclease", "CRISPR nuclease", "CRISPR protein", "CRISPR effector" or "CRISPR enzyme" are used interchangeably herein and refer to any naturally occurring or artificial amino acid sequence, or the nucleic acid sequence encoding the same, acting as site-specific DNA nuclease or nickase, wherein the "CRISPR polypeptide" is derived from a CRISPR system of any organism, which can be cloned and used for targeted genome engineering. The terms "CRISPR nuclease" or "CRISPR polypeptide" also comprise mutants or catalytically active fragments or fusions of a naturally occurring CRISPR effector sequences, or the respective sequences encoding the same. A "CRISPR nuclease" or "CRISPR polypeptide" may thus, for example, also refer to a CRISPR nickase or even a nuclease-deficient variant of a CRISPR polypeptide having endonucleolytic function in its natural environment. Preferably, the disclosure of the present invention relies on nuclease-deficient CRISPR nucleases, still possessing their inherent DNA recognition and binding properties assisted by a cognate CRISPR RNA.

Nucleic acid sequences disclosed herein "codon-optimized". "Codon optimization" implies that a DNA or RNA synthetically produced or isolated from a donor organism is adapted to the codon usage of different acceptor organism to improve transcription rates, mRNA processing and/or stability, and/or translation rates, and/or subsequent protein folding of said recombinant nucleic acid in the cell or organism of interest. The skilled person is well aware of the fact that a target nucleic acid can be modified at one position due to the codon degeneracy, whereas this modification will still lead to the same amino acid sequence at that position after translation, which is achieved by codon optimization to take into consideration the species-specific codon usage of a target cell or organism. In turn, nucleic acid sequences as defined herein may have a certain degree of identity to a different sequence, encoding the same protein, but having been codon optimized.

"Complementary" or "complementarity" as used herein describes the relationship between two (c) DNA, two RNA, or between an RNA and a (c) DNA nucleic acid region. Defined by the nucleobases of the DNA or RNA, two nucleic acid regions can hybridize to each other in accordance with the lock-and-key model. To this end the principles of Watson-Crick base pairing have the basis adenine and thymine/uracil as well as guanine and cytosine, respectively, as complementary bases apply. Furthermore, also non-Watson-Crick pairing, like reverse-Watson-Crick, Hoogsteen, reverse-Hoogsteen and Wobble pairing are comprised by the term "complementary" as used herein as long as the respective base pairs can build hydrogen bonding to each other, i.e. two different nucleic acid strands can hybridize to each other based on said complementarity.

As used in the context of the present application, the term "about" can mean +/−10% of the recited value, preferably +/−5% of the recited value. For example, about 100 nucleotides (nt) shall then be understood as a value between 90 and 110 nt, preferably between 95 and 105.

The term "derivative" or "descendant" or "progeny" as used herein in the context of a prokaryotic or a eukaryotic cell, preferably an animal cell and more preferably a plant or plant cell or plant material according to the present disclosure relates to the descendants of such a cell or material which result from natural reproductive propagation including sexual and asexual propagation. It is well known to the person having skill in the art that said propagation can lead to the introduction of mutations into the genome of an organism resulting from natural phenomena which results in a descendant or progeny, which is genomically different to the parental organism or cell, however, still belongs to the same genus/species and possesses mostly the same characteristics as the parental recombinant host cell. Such derivatives or descendants or progeny resulting from natural phenomena during reproduction or regeneration are thus comprised by the term of the present disclosure and can be readily identified by the skilled person when comparing the "derivative" or "descendant" or "progeny" to the respective parent or ancestor. Furthermore, the term "derivative", in the context of a substance or nucleic acid or amino acid molecule and not referring to a replicating cell or organism, can imply a substance or molecule derived from the original substance or molecule by chemical and/or biotechnological means. The resulting derivative will have characteristics allowing the skilled person to clearly define the original or parent molecule the derivative stems from. Furthermore, the derivative might have additional or varying biological functionalities, still a derivative or an "active fragment" of an original molecule will still share at least one biological function of the parent molecule, even though the derivative or active fragment might be shorter/longer than the parent sequence and might comprise certain mutations, deletions or insertions in comparison to the respective parent sequence.

A "eukaryotic cell" as used herein refers to a cell having a true nucleus, a nuclear membrane and organelles belonging to any one of the kingdoms of Protista, Plantae, Fungi, or Animalia. Eukaryotic organisms can comprise monocellular and multicellular organisms. Preferred eukaryotic cells and organisms according to the present invention are plant cells.

As used herein, "fusion" can refer to a protein and/or nucleic acid comprising one or more non-native sequences (e.g., moieties). Any nucleic acid sequence or amino acid sequence according to the present invention can thus be provided in the form of a fusion molecule. A fusion can be at the N-terminal or C-terminal end of the modified protein, or both, or within the molecule as separate domain. For nucleic acid molecules, the fusion molecule can be attached at the 5' or 3' end, or at any suitable position in between. A fusion can be a transcriptional and/or translational fusion. A fusion can comprise one or more of the same non-native sequences. A fusion can comprise one or more of different non-native sequences. A fusion can be a chimera. A fusion can comprise a nucleic acid affinity tag. A fusion can comprise a barcode. A fusion can comprise a peptide affinity tag. A fusion can provide for subcellular localization of the at least one synthetic transcription factor as disclosed herein (e.g., a nuclear localization signal (NLS) for targeting (e.g., a site-specific nuclease) to the nucleus, a mitochondrial localization signal for targeting to the mitochondria, a chloroplast localization signal for targeting to a chloroplast, an endoplasmic reticulum (ER) retention signal, and the like). A fusion can provide a non-native sequence (e.g., affinity tag) that can be used to track or purify. A fusion can be a small molecule such as biotin or a dye such as alexa fluor dyes, Cyanine3 dye, Cyanine5 dye. The fusion can provide for increased or decreased stability. In some embodiments, a fusion can comprise a detectable label, including a moiety that can provide a detectable signal. Suitable detectable labels and/or moieties that can provide a detectable signal can include, but are not limited to, an enzyme, a radioisotope, a member of a specific binding pair; a fluorophore; a fluorescent reporter or fluorescent protein; a quantum dot; and the like. A fusion can comprise a member of a FRET pair, or a fluorophore/quantum dot donor/acceptor pair. A fusion can comprise an enzyme. Suitable enzymes can include, but are not limited to, horse radish peroxidase, luciferase, beta-25 galactosidase, and the like. A fusion can comprise a fluorescent protein. Suitable fluorescent proteins can include, but are not limited to, a green fluorescent protein (GFP), (e.g., a GFP from *Aequoria victoria*, fluorescent proteins from *Anguilla japonica*, or a mutant or derivative thereof), a red fluorescent protein, a yellow fluorescent protein, a yellow-green fluorescent protein (e.g., mNeonGreen derived from a tetrameric fluorescent protein from the cephalochordate *Branchiostoma lanceolatum*) any of a variety of fluorescent and colored proteins. A fusion can comprise a nanoparticle. Suitable nanoparticles can include fluorescent or luminescent nanoparticles, and magnetic nanoparticles, or nanodiamonds, optionally linked to a nanoparticle. Any optical or magnetic property or characteristic of the nanoparticle(s) can be detected. A fusion can comprise a helicase, a nuclease (e.g., FokI), an endonuclease, an exonuclease (e.g., a 5' exonuclease and/or 3' exonuclease), a ligase, a nickase, a nuclease-helicase (e.g., Cas3), a DNA methyltransferase (e.g., Dam), or DNA demethylase, a histone methyltransferase, a histone demethylase, an acetylase (including for example and not limitation, a histone acetylase), a deacetylase (including for example and not limitation, a histone deacetylase), a phosphatase, a kinase, a transcription (co-) activator, a transcription (co-) factor, an RNA polymerase subunit, a transcription repressor, a DNA binding protein, a DNA structuring protein, a long non-coding RNA, a DNA repair protein (e.g., a protein involved in repair of either single- and/or double-stranded breaks, e.g., proteins involved in base excision repair, nucleotide excision repair, mismatch repair, NHEJ, HR, microhomology-mediated end joining (MMEJ), and/or alternative non-homologous end-joining (ANHEJ), such as for example and not limitation, HR regulators and HR complex assembly signals), a marker protein, a reporter protein, a fluorescent protein, a ligand binding protein (e.g., mCherry or a heavy metal binding protein), a signal peptide (e.g., Tat-signal sequence), a targeting protein or peptide, a subcellular localization sequence (e.g., nuclear localization sequence, a chloroplast localization sequence), and/or an antibody epitope, or any combination thereof.

A "gene" as used herein refers to a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

The term "gene expression" or "expression" as used herein refers to the conversion of the information, contained in a gene, into a "gene product". A "gene product" can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

The term "gene activation" or "augmentation/augmenting/activating/upregulating (of) gene expression" refer to any process which results in an increase in production of a gene product. A gene product can be either RNA (including, but not limited to, mRNA, rRNA, tRNA, and structural RNA) or a protein. Accordingly, gene activation includes those processes which increase transcription of a gene and/or translation of an mRNA. Examples of gene activation processes which increase transcription include, but are not limited to, those which facilitate formation of a transcription initiation complex, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes which increase translation include those which increase translational initiation, those which increase translational elongation and those which increase mRNA stability. In general, gene activation comprises any detectable increase in the production of a gene product, preferably an increase in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more.

In contrast, the terms "gene repression" or "inhibition/inhibiting/repressing/silencing/downregulating (of) gene expression" refer to any process which results in a decrease in production of a gene product. A gene product can be either RNA (including, but not limited to, mRNA, rRNA, tRNA, and structural RNA) or protein. Accordingly, gene repression includes those processes which decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes which decrease translation include those which decrease translational initiation, those which decrease translational elongation and those which decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100 fold or any integral value therebetween, more preferably 100-fold or more. Most preferably, gene repression results in complete inhibition of gene expression, such that no gene product is detectable.

The terms "genetic construct" or "recombinant construct", "vector", or "plasmid (vector)" (e.g., in the context of at least one nucleic acid sequence to be introduced into a cellular system) are used herein to refer to a construct comprising, inter alia, plasmids or (plasmid) vectors, cosmids, artificial yeast- or bacterial artificial chromosomes (YACs and BACs), phagemides, bacterial phage based vectors, an expression cassette, isolated single-stranded or double-stranded nucleic acid sequences, comprising DNA and RNA sequences in linear or circular form, or amino acid sequences, viral vectors, including modified viruses, and a combination or a mixture thereof, for introduction or transformation, transfection or transduction into any prokaryotic or eukaryotic target cell, including a plant, plant cell, tissue, organ or material according to the present disclosure. "Recombinant" in the context of a biological material, e.g., a cell or vector, thus implies an artificially produced material. A recombinant construct according to the present disclosure can comprise an effector domain, either in the form of a nucleic acid or an amino acid sequence, wherein an effector domain represents a molecule, which can exert an effect in a target cell and includes a transgene, an single-stranded or double-stranded RNA molecule, including a guide RNA ((s)gRNA), a miRNA or an siRNA, or an amino acid sequences, including, inter alia, an enzyme or a catalytically active fragment thereof, a binding protein, an antibody, a transcription factor, a nuclease, preferably a site specific nuclease, and the like. Furthermore, the recombinant construct can comprise regulatory sequences and/or localization sequences. The recombinant construct can be integrated into a vector, including a plasmid vector, and/or it can be present isolated from a vector structure, for example, in the form of a polypeptide sequence or as a non-vector connected single-stranded or double-stranded nucleic acid. After its introduction, e.g. by transformation or transfection by biological or physical means, the genetic construct can either persist extrachromosomally, i.e. non integrated into the genome of the target cell, for example in the form of a double-stranded or single-stranded DNA, a double-stranded or single-stranded RNA or as an amino acid sequence. Alternatively, the genetic construct, or parts thereof, according to the present disclosure can be stably integrated into the genome of a target cell, including the nuclear genome or further genetic elements of a target cell, including the genome of plastids like mitochondria or chloroplasts. The term plasmid vector as used in this connection refers to a genetic construct originally obtained from a plasmid. A plasmid usually refers to a circular autonomously replicating extrachromosomal element in the form of a double-stranded nucleic acid sequence. In the field of genetic engineering these plasmids are routinely subjected to targeted modifications by inserting, for example, genes encoding a resistance against an antibiotic or an herbicide, a gene encoding a target nucleic acid sequence, a localization sequence, a regulatory sequence, a tag sequence, a marker gene, including an antibiotic marker or a fluorescent marker, a sequence, optionally encoding, a readily identifiable and the like. The structural components of the original plasmid, like the origin of replication, are maintained. According to certain embodiments of the present invention, the localization sequence can comprise a nuclear localization sequence (NLS), a plastid localization sequence, preferably a mitochondrion localization sequence or a chloroplast localization sequence. Said localization sequences are available to the skilled person in the field of plant biotechnology. A variety of plasmid vectors for use in different target cells of interest is commercially available and the modification thereof is known to the skilled person in the respective field.

A "genome" as used herein includes both the genes (the coding regions), the non-coding DNA and, if present, the genetic material of the mitochondria and/or chloroplasts, or the genomic material encoding a virus, or part of a virus. The "genome" or "genetic material" of an organism usually consists of DNA, wherein the genome of a virus may consist of RNA (single-stranded or double-stranded).

The terms "genome editing", "gene editing" and "genome engineering" are used interchangeably herein and refer to strategies and techniques for the targeted, specific modification of any genetic information or genome of a living organism at at least one position. As such, the terms comprise gene editing, but also the editing of regions other than gene encoding regions of a genome. It further comprises the editing or engineering of the nuclear (if present) as well as other genetic information of a cell. Furthermore, the terms "genome editing", "gene editing" and "genome engineering" also comprise an epigenetic editing or engineering, i.e. the targeted modification of, e.g. methylation, histone modification or of non-coding RNAs possibly causing heritable changes in gene expression.

"Germplasm", as used herein, is a term used to describe the genetic resources, or more precisely the DNA of an organism and collections of that material. In breeding technology, the term germplasm is used to indicate the collection of genetic material from which a new plant or plant variety can be created.

The terms "guide RNA", "gRNA", "CRISPR nucleic acid sequence", "single guide RNA", or "sgRNA" are used interchangeably herein and either refer to a synthetic fusion of a CRISPR RNA (crRNA) and a trans-activating crRNA (tracrRNA), or the term refers to a single RNA molecule consisting only of a crRNA and/or a tracrRNA, or the term refers to a gRNA individually comprising a crRNA or a tracrRNA moiety. A tracr and a crRNA moiety, if present as required by the respective CRISPR polypeptide, thus do not necessarily have to be present on one covalently attached RNA molecule, yet they can also be comprised by two individual RNA molecules, which can associate or can be associated by non-covalent or covalent interaction to provide a gRNA according to the present disclosure. In the case of single RNA-guided endonucleases like Cpf1 (see Zetsche et al., 2015), for example, a crRNA as single guide nucleic acid sequence might be sufficient for mediating DNA targeting.

The term "hybridization" as used herein refers to the pairing of complementary nucleic acids, i.e., DNA and/or RNA, using any process by which a strand of nucleic acid joins with a complementary strand through base pairing to form a hybridized complex. Hybridization and the strength of hybridization (i.e., the strength of the association between the nucleic acids) is impacted by such factors as the degree and length of complementarity between the nucleic acids, stringency of the conditions involved, the Tm of the formed hybrid, and the G:C ratio within the nucleic acids. The term hybridized complex refers to a complex formed between two nucleic acid sequences by virtue of the formation of hydrogen bounds between complementary G and C bases and between complementary A and T/U bases. A hybridized complex or a corresponding hybrid construct can be formed between two DNA nucleic acid molecules, between two RNA nucleic acid molecules or between a DNA and an RNA nucleic acid molecule. For all constellations, the nucleic acid molecules can be naturally occurring nucleic acid molecules generated in vitro or in vivo and/or artificial or synthetic nucleic acid molecules. Hybridization as detailed above, e.g., Watson-Crick base pairs, which can form between DNA, RNA and DNA/RNA sequences, are dictated by a specific hydrogen bonding pattern, which thus represents a non-covalent attachment form according to the present invention. In the context of hybridization, the term "stringent hybridization conditions" should be understood to mean those conditions under which a hybridization takes place primarily only between homologous nucleic acid molecules. The term "hybridization conditions" in this respect refers not only to the actual conditions prevailing during actual agglomeration of the nucleic acids, but also to the conditions prevailing during the subsequent washing steps. Examples of stringent hybridization conditions are conditions under which primarily only those nucleic acid molecules that have at least 70%, preferably at least 75%, at least 80%, at least 85%, at least 90%, at least 91%, at least 92%, at least 93%, at least 94%, at least 95%, at least 96%, at least 97%, at least 98%, at least 99%, or at least 99.50% sequence identity undergo hybridization. Stringent hybridization conditions are, for example: 4×SSC at 65° C. and subsequent multiple washes in 0.1×SSC at 65° C. for approximately 1 hour. The term "stringent hybridization conditions" as used herein may also mean: hybridization at 68° C. in 0.25 M sodium phosphate, pH 7.2, 7% SDS, 1 mM EDTA and 1% BSA for 16 hours and subsequently washing twice with 2×SSC and 0.1% SDS at 68° C. Preferably, hybridization takes place under stringent conditions.

The terms "morphogenic" and "morphogenetic" are used interchangeably herein, usually in the context of a gene, wherein the gene product encoded by said gene is involved in morphogenesis, i.e., the biological process that causes an organism to develop its shape. The terms are also used in the context of any factor, including synthetic or naturally occurring transcription factors, directly or indirectly involved in the process of morphogenesis in a cell or organism. Furthermore, the terms are used in the context of the cellular pathways leading to whole plant regeneration.

The terms "nucleotide" and "nucleic acid" with reference to a sequence or a molecule are used interchangeably herein and refer to a single- or double-stranded DNA or RNA of natural or synthetic origin. The term nucleotide sequence is thus used for any DNA or RNA sequence independent of its length, so that the term comprises any nucleotide sequence comprising at least one nucleotide, but also any kind of larger oligonucleotide or polynucleotide. The term(s) thus refer to natural and/or synthetic deoxyribonucleic acids (DNA) and/or ribonucleic acid (RNA) sequences, which can optionally comprise synthetic nucleic acid analoga. A nucleic acid according to the present disclosure can optionally be codon optimized. Codon optimization implies that the codon usage of a DNA or RNA is adapted to that of a cell or organism of interest to improve the transcription rate of said recombinant nucleic acid in the cell or organism of interest. The skilled person is well aware of the fact that a target nucleic acid can be modified at one position due to the codon degeneracy, whereas this modification will still lead to the same amino acid sequence at that position after translation, which is achieved by codon optimization to take into consideration the species-specific codon usage of a target cell or organism. Nucleic acid sequences according to the present application can carry specific codon optimization for the following non limiting list of organisms: *Hordeum vulgare, Sorghum bicolor, Secale cereale, Triticale, Saccharum officinarium, Zea mays, Setaria italic, Oryza sativa, Oryza minuta, Oryza australiensis, Oryza alta, Triticum aestivum, Triticum durum, Hordeum bulbosum, Brachypodium distachyon, Hordeum marinum, Aegilops tauschii, Malus domestica, Beta vulgaris, Helianthus annuus, Daucus glochidiatus, Daucus pusillus, Daucus muricatus, Daucus carota, Eucalyptus grandis, Erythranthe guttata, Genlisea aurea, Nicotiana sylvestris, Nicotiana tabacum, Nicotiana tomentosiformis, Nicotiana benthamiana, Solanum lycopersicum, Solanum tuberosum, Coffea canephora, Vitis vinifera, Cucumis sativus, Morus notabilis, Arabidopsis thaliana, Arabidopsis lyrata, Arabidopsis arenosa, Crucihimalaya himalaica, Crucihimalaya wallichii, Cardamine flexuosa, Lepidium virginicum, Capsella bursapastoris, Olmarabidopsis pumila, Arabis hirsuta, Brassica napus, Brassica oleracea, Brassica rapa, Brassica juncacea, Brassica nigra, Raphanus sativus, Eruca vesicaria sativa, Citrus sinensis, Jatropha curcas, Glycine max, Gossypium ssp., or Populus trichocarpa*.

As used herein, "non-native", or "non-naturally occurring", or "artificial", or "synthetic" can refer to a nucleic acid or polypeptide sequence, or any other biomolecule like biotin or fluorescein that is not found in a native nucleic acid or protein. Non-native can refer to affinity tags. Non-native can refer to fusions. Non-native can refer to a naturally occurring nucleic acid or polypeptide sequence that comprises mutations, insertions and/or deletions. A non-native sequence may exhibit and/or encode for an activity (e.g., enzymatic activity, methyltransferase activity, acetyltransferase activity, kinase activity, ubiquitinating activity, etc.) that can also be exhibited by the nucleic acid and/or polypeptide sequence to which the non-native sequence is fused. A non-native nucleic acid or polypeptide sequence may be linked to a naturally-occurring nucleic acid or polypeptide sequence (or a variant thereof) by genetic engineering to generate a chimeric nucleic acid and/or polypeptide sequence encoding a chimeric nucleic acid and/or polypeptide. A non-native sequence can refer to a 3' hybridizing extension sequence, or a nuclear localization signal (NLS) attached to a molecule. A "synthetic transcription factor" as used herein thus refers to a molecule comprising at least two domains, a recognition domain and an activation domain not naturally occurring in nature.

An "organism" as used herein refers to an individual eukaryotic or prokaryotic life form, including inter alia an animal, plant, a fungus, or a single-celled life form. In the context of the present invention, an organism is preferably a plant or part of a plant.

The term "particle bombardment" as used herein, also named "biolistic transfection" or "biolistic bombardment" or "microparticle-mediated gene transfer", refers to a physical delivery method for transferring a coated microparticle or nanoparticle comprising a nucleic acid or a genetic construct of interest into a target cell or tissue. The micro- or nanoparticle functions as projectile and is fired on the target structure of interest under high pressure using a suitable device, often called "gene-gun". The transformation via particle bombardment uses a microprojectile of metal covered with the gene of interest, which is then shot onto the target cells using an equipment known as "gene-gun" (Sandford et al. 1987) at high velocity fast enough to penetrate the cell wall of a target tissue, but not harsh enough to cause cell death. For protoplasts, which have their cell wall entirely removed, the conditions are different logically. The precipitated nucleic acid or the genetic construct on the at least one microprojectile is released into the cell after bombardment, and integrated into the genome or expressed transiently according to the definition given above. The acceleration of microprojectiles is accomplished by a high voltage electrical discharge or compressed gas (helium). Concerning the metal particles used it is mandatory that they are non-toxic, non-reactive, and that they have a smaller diameter than the target cell. The most commonly used are gold or tungsten. There is plenty of information publicly available from the manufacturers and providers of gene-guns and associated system concerning their general use.

The terms "plant" or "plant cell" as used herein refer to a plant organism, a plant organ, differentiated and undifferentiated plant tissues, plant cells, seeds, and derivatives and progeny thereof. Plant cells include without limitation, for example, cells from seeds, from mature and immature cells or organs, including embryos, meristematic tissues, seedlings, callus tissues in different differentiation states, leaves, flowers, roots, shoots, male or female gametophytes, sporophytes, pollen, pollen tubes and microspores, protoplasts, macroalgae and microalgae. The different eukaryotic cells, for example, plant cells, can have any degree of ploidy, i.e. they may either be haploid, diploid, tetraploid, hexaploid or polyploid. Preferably a plant cell, plant or part of a plant as used herein, originates from or belongs to a plant species selected from the group consisting of *Hordeum vulgare, Hordeum bulbusom, Sorghum bicolor, Saccharum officinarium, Zea mays, Setaria italica, Oryza minuta, Oriza sativa, Oryza australiensis, Oryza alta, Triticum aestivum, Secale cereale, Malus domestica, Brachypodium distachyon, Hordeum marinum, Aegilops tauschii, Daucus*

*glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oeleracia, Brassica rapa, Raphanus sativus, Brassica juncea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicerjudaicum, Cajanus cajanifolius, Cajanus scarabaeoides, Phaseolus vulgaris, Glycine max, Astragalus sinicus, Lotus japonicas, Torenia fournieri, Allium cepa, Allium fistulosum, Allium sativum,* and *Allium tuberosum*.

A "promoter" refers to a DNA sequence capable of controlling expression of a coding sequence, i.e., a gene or part thereof, or of a functional RNA, i.e. a RNA which is active without being translated, for example, a miRNA, a siRNA, an inverted repeat RNA or a hairpin forming RNA. A promoter is usually located at the 5' part of a gene. Promoter structures occur in all kingdoms of life, i.e., in bacteria, archaea, and eucaryots, where they have different architectures. The promoter sequence usually consists of proximal and distal elements in relation to the regulated sequence, the latter being often referred to as enhancers. Promoters can have a broad spectrum of activity, but they can also have tissue or developmental stage specific activity. For example, they can be active in cells of roots, seeds and meristematic cells, etc. A promoter can be active in a constitutive way, or it can be inducible. The induction can be stimulated by a variety of environmental conditions and stimuli. There exist strong promoters which can enable a high transcription of the regulated sequence, and weak promoters. Often promoters are highly regulated. A promoter of the present disclosure may include an endogenous promoter natively present in a cell, or an artificial or transgenic promoter, either from another species, or an artificial or chimeric promoter, i.e. a promoter that does not naturally occur in nature in this composition and is composed of different promoter elements. The process of transcription begins with the RNA polymerase (RNAP) binding to DNA in the promoter region, which is in the immediate vicinity of the transcription start site (TSS). A typical promoter sequence is thought to comprise some sequence motifs positioned at specific sites relative to the TSS. For example, a prokaryotic promoter is observed to have two hexameric motifs centered at or near −10 (Pribnow box) and −35 positions relative to the TSS. Furthermore, there can be an AT rich UP ("upstream") element upstream of the −35 region. Procaryotic promoters are recognized by sigma factors as transcription factors. The structure of eukaryotic promoters is generally more complex and they have several different sequence motifs, such as TATA box, INR box, BRE, CCAAT-box and GC-box (Bucher P., J. Mol. Biol. 1990 Apr. 20; 212(4):563-78). Eukaryotic cells posses three RNAPs, RNA polymerase I, II, and III, respectively. RNAP I generates ribosomal RNA (rRNA), RNAP II generates messenger RNA (mRNA) and small nuclear RNA (snRNA), and RNAP III generates transfer RNA (tRNA), snRNA and 5S-RNA.

The term "regulatory sequence" as used herein refers to a nucleic acid or amino acid sequence, which can direct the transcription and/or translation and/or modification of a nucleic acid sequence of interest. Regulatory sequences can comprise sequences acting in cis or acting in trans. Exemplary regulatory sequences comprise promoters, enhancers, terminators, operators, transcription factors, transcription factor binding sites, introns and the like.

The term "terminator", as used herein, refers to DNA sequences located downstream, i.e. in 3' direction, of a coding sequence and can include a polyadenylation signal and other sequences, i.e. further sequences encoding regulatory signals that are capable of affecting mRNA processing and/or gene expression. The polyadenylation signal is usually characterized in that it adds poly-A-nucleotides at the 3' end of an mRNA precursor.

The terms "transient" or "transient introduction" as used herein refer to the transient introduction of at least one nucleic acid and/or amino acid sequence according to the present disclosure, preferably incorporated into a delivery vector and/or into a recombinant construct, with or without the help of a delivery vector, into a target structure, for example, a plant cell or cellular system, wherein the at least one nucleic acid or nucleotide sequence is introduced under suitable reaction conditions so that no integration of the at least one nucleic acid sequence into the endogenous nucleic acid material of a target structure, the genome as a whole, occurs, so that the at least one nucleic acid sequence will not be integrated into the endogenous DNA of the target cell. As a consequence, in the case of transient introduction, the introduced genetic construct will not be inherited to a progeny of the target structure, for example a plant cell. The at least one nucleic acid and/or amino acid sequence or the products resulting from transcription, translation, processing, post-translational modifications or complex building thereof are only present temporarily, i.e., in a transient way, in constitutive or inducible form, and thus can only be active in the target cell for exerting their effect for a limited time. Therefore, the at least one sequence introduced via transient introduction will not be heritable to the progeny of a cell. The effect mediated by at least one sequence or effector introduced in a transient way can, however, potentially be inherited to the progeny of the target cell. A "stable" introduction therefore implies the integration of a nucleic acid or nucleotide sequence into the genome of a target cell or cellular system of interest, wherein the genome comprises the nuclear genome as well as the genome comprised by further organelles.

The term "variant(s)" as used herein in the context of amino acid or nucleic acid sequences is intended to mean substantially similar sequences. For nucleic acid sequences, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For nucleic acid sequences, conservative variants include those sequences that, because of the degeneracy of the genetic code, encode the same amino acid sequence as a reference sequence of the present disclosure. A variant of a given nucleic acid sequence will thus also include synthetically derived nucleic acid sequences, such as those generated, for example, by using site-directed mutagenesis but which still encode the same protein as the reference sequence. Generally, variants of a particular polynucleotide of the disclosure will have at least about 60%, 65%, 70%, 75%, 80%, 85%, 90%, 91%, 92%, 93%, 94%, 95%, 96%, 97%, 98%, 99% or more sequence identity to that particular nucleic acid sequence as determined by sequence alignment programs and parameters described further below under this section.

A "variant" amino acid sequence, polypeptide or protein (said terms being used interchangeably herein) means an amino acid sequence derived from the native amino acid sequence by deletion or addition of one or more amino acids at one or more internal sites in the native protein and/or substitution of one or more amino acids at one or more sites in the native protein. Variant amino acid sequences according to the present disclosure are biologically active, that is they continue to possess the desired biological activity of the native protein. Active variants of a native amino acid sequence of the disclosure will have at least about 65%, 70%, 75%, 80%, 85%, 90%, 91%, 92%, 93%, 94%, 95%, 96%, 97%, 98%, 99% or more sequence identity to the amino acid sequence for the native amino acid sequence as determined by sequence alignment programs and parameters described further below under this section.

Whenever the present disclosure relates to the percentage of identity of nucleic acid or amino acid sequences to each other these values define those values as obtained by using the EMBOSS Water Pairwise Sequence Alignments (nucleotide) programme (www.ebi.ac.uk/Tools/psa/emboss_water/nucleotide.html) nucleic acids or the EMBOSS Water Pairwise Sequence Alignments (protein) programme (vvww.ebi.ac.uk/Tools/psa/emboss_water/) for amino acid sequences. Alignments or sequence comparisons as used herein refer to an alignment over the whole length of two sequences compared to each other. Those tools provided by the European Molecular Biology Laboratory (EMBL) European Bioinformatics Institute (EBI) for local sequence alignments use a modified Smith-Waterman algorithm (see www.ebi.ac.uk/Tools/psa/ and Smith, T. F. & Waterman, M. S. "Identification of common molecular subsequences" Journal of Molecular Biology, 1981 147 (1):195-197). When conducting an alignment, the default parameters defined by the EMBL-EBI are used. Those parameters are (i) for amino acid sequences: Matrix=BLOSUM62, gap open penalty=10 and gap extend penalty=0.5 or (ii) for nucleic acid sequences: Matrix=DNAfull, gap open penalty=10 and gap extend penalty=0.5. The skilled person is well aware of the fact that, for example, a sequence encoding a protein can be "codon-optimized" if the respective sequence is to be used in another organism in comparison to the original organism a molecule originates from.

DETAILED DESCRIPTION

The person skilled in the art will understand that the herein described aspects and embodiments should not be construed to be confined to the specific context in which they are disclosed, but rather that the aspects and embodiments described throughout the present specification can be combined with each other independently from their specific context.

The present invention is based on the finding that the selective modulation of the gene expression of endogenous genes by using specifically defined synthetic transcription factors (STFs) provides a suitable tool for specific temporal and spatial regulation of a gene of interest. In turn, this provides the basis for the optimization of transformation and genome editing approaches and thus provides higher frequencies in transformation/editing which in turn allows improved methods in agricultural biotechnology.

For example, instead of using the nucleotide sequences encoding the morphogenic genes, for example, BBM and WUS, as isolated or heterologous expression cassettes, it is possible to use specifically designed synthetic transcriptional modulators, such as TAL effectors or disarmed CRISPR/nuclease systems and others, to induce expression of the endogenous morphogenic genes to reprogram the cell and to induce cell division and regeneration at a specific time point in a transient way without the need to introduce a transgenic morphogenic effector, or the sequence encoding the same, into a cell or plant of interest. These principle findings were expanded to establish synthetic transcription factors (STFs) comprising at least one activation or silencing domain to specifically up- or downregulate the expression of a target gene in an inducible way. In turn, the direct effect of said specifically designed artificial STFs was then used in a variety of methods of molecular biology to synergistically profit from the modulation effect for optimizing transformation, gene editing, or targeted silencing, wherein these methods can be employed for plant breeding and for potential therapeutic applications.

In one aspect of the present invention, approaches were established to generate plants by using the synthetic transcription factors specific for BBM and WUS to induce cell division and regeneration of plant cells, which findings were then extrapolated to further methods and uses based on a variety of synthetic transcription factors. In turn, these specific transcription factors allow the provision of methods of improving the efficiency of plant transformation and/or regeneration of transgenic plants by using synthetic transcription factors specific for endogenous morphogenic genes which can reprogram the cell and induce cell division in a large variety of plant species, including those species or varieties known to be hard to transform and regenerate to dramatically increase the transformation efficiency of a variety of species and further of a variety of different cell types including those cell types being recalcitrant to transformation in standard settings. The present invention thus relates to both the molecular tools specific for a morphogenic gene of interest which is targeted for modulation, preferably activation, i.e., the present invention relates to the specific synthetic transcription factors and the sequences encoding the same, as well as to methods of using these specific synthetic or artificial transcription factors in a targeted way to optimize transformation and transfection based methods of plant biotechnology, in particular genome editing based methods, or methods for optimizing the transformation rates of transformation recalcitrant plant cells.

In one aspect, there is disclosed a synthetic transcription factor (STF), or a nucleotide sequence encoding the same, which may comprise at least one recognition domain and at least one gene expression modulation domain, in particular at least one activation domain, wherein the synthetic transcription factor may be configured to modulate the expression of a morphogenic gene in a cellular system.

A "modulation" of the expression of any endogenous gene, preferably a morphogenic gene, as disclosed herein includes both gene activation and gene repression as defined above. Such a modulation can be assayed by determining any parameter that is indirectly or directly affected by the expression of the target gene. Such parameters include, e.g., changes in RNA or protein levels; changes in protein activity; changes in product levels; changes in downstream gene expression; changes in transcription or activity of reporter genes such as, for example, luciferase, CAT, beta-galactosidase, or GFP (see, e.g., Mistili & Spector, (1997) Nature Biotechnology 15: 961-964). For morphogenic genes, a modulation of gene expression can also be monitored by visual means, including microscopy, observation of plant development and the like to monitor changes in any functional effect of gene expression. According to the various aspects of the present invention, a synthetic transcription factor as disclosed herein will preferably act on the transcriptional level and will thus modulate the transcription of at least one gene of interest, preferably a morphogenic gene of interest. In certain embodiments, the at least one synthetic transcription factor may be specifically designed to upregulate the transcription of a gene of interest, preferably a morphogenic gene of interest.

A "cellular system" as used herein refers to at least one element comprising all or part of the genome of a cell of interest to be modified. The cellular system may thus be any in vivo or in vitro system, including also a cell-free system. The cellular system thus comprises and provides the target genome or genomic sequence to be modified in a suitable way, i.e., in a form accessible to a genetic modification or manipulation. The cellular system may thus be selected from, for example, a eukaryotic cell, including a plant cell, or the cellular system may comprise a genetic construct as defined above comprising all or parts of the genome of a eukaryotic cell to be modified in a highly targeted way. The cellular system may be provided as isolated cell or vector, or the cellular system may be comprised by a network of cells in a tissue, organ, material or whole organism, either in vivo or as isolated system in vitro. In this context, the "genetic material" of a cellular system can thus be understood as all, or part of the genome of an organism the genetic material of which organism as a whole or in part is present in the cellular system to be modified.

In one aspect, the present invention provides a cellular system which may be obtained by a method according to any one of the above aspects and embodiments.

In one embodiment according to the various aspects of the present invention, the synthetic transcription factor may be designed to modulate the transcription of a morphogenic gene, wherein the morphogenic gene may be selected from the group consisting of BBM, WUS (Zuo et al., 2002, Plant J., 30(3):349-359), including WUS2 (Nardmann and Werr, 2006, Mol. Biol. Evol., 23:22492-22502), a WOX gene, a WUS or BBM homologue, Lec1, Lec2, WIND1, ESR1, PLT3, PLT5, or PLT7, IPT, IPT2, Knotted1, and RKD4.

According to the various aspects and embodiments of the present invention, the morphogenic gene may be selected from sequences having coding sequences of NM_001112491.1 (SEQ ID NO: 199), NM_127349.4 (SEQ ID NO: 200), NC_025817.2, KT285832.1 (SEQ ID NO: 201), KT285833.1 (SEQ ID NO: 202), KT285834.1 (SEQ ID NO: 203), KT285835.1 (SEQ ID NO: 204), KT285836.1 (SEQ ID NO: 205), KT285837.1 (SEQ ID NO: 206), XM_008676474.2 (SEQ ID NO: 207), CM007649.1, NM_103997.4 (SEQ ID NO: 208), XM_010675298.2 (SEQ ID NO: 209), XM_010675704.2 (SEQ ID NO: 210), AB458519.1 (SEQ ID NO: 211), AB458518.1 (SEQ ID NO: 212), AK451358.1 (SEQ ID NO: 213), AK335319.1 (SEQ ID NO: 214), KU593504.1 (SEQ ID NO: 215) or KU593503.1 (SEQ ID NO: 216).

In a further embodiment, there is provided a synthetic transcription factor, wherein the morphogenic gene comprises a nucleotide sequence selected from the group consisting of (i) a nucleotide sequence set forth in any one of SEQ ID NOs: 199 to 237, (ii) a nucleotide sequence having the coding sequences of the nucleotide sequence set forth in any one of SEQ ID NOs: 199 to 237, (iii) a nucleotide sequence complementary to the nucleotide sequence of (i) or (ii), (iv) a nucleotide sequence having at least 50%, 60%, 70%, 75%, 80%, 85%, 90%, 91%, 92%, 93%, 94%, 95%, 96%, 97%, 98%, or 99% identity, preferably over the whole length, to the nucleotide sequence of (i), (ii) or (iii), (v) a nucleotide sequence hybridzing the nucleotide sequence of (iii) under stringent conditions, (vi) a nucleotide sequence encoding a protein comprising the amino acid sequence set forth in any one of SEQ ID NOs: 238 to 258, (vii) a nucleotide sequence encoding a protein comprising the amino acid sequence at least 50%, 60%, 70%, 75%, 80%, 85%, 90%, 91%, 92%, 93%, 94%, 95%, 96%, 97%, 98%, or 99% identical to a sequence set forth in any one of SEQ ID NOs: 238 to 258, or (viii) a nucleotide sequence encoding a homologue, analogue or orthologue of protein comprising the amino acid sequence set forth in any one of SEQ ID NOs: 238 to 258.

In particular, the Wuschel (WUS) polypeptide has been identified as key player in the initiation and maintenance of the apical meristem, which contains a pool of pluripotent stem cells (Endrizzi et al., 1996, Plant Journal 10:967-979). *Arabidopsis* plants mutant for the WUS gene contain stem cells that are misspecified and that appear to undergo differentiation. WUS encodes a homeodomain protein, which functions as a transcriptional regulator (Mayer et al., 1998, Cell 95:805-815, US 2004/166563 A1). The stem cell population of *Arabidopsis* shoot meristems is believed to be maintained by a regulatory loop between the *CLAVATA* (CLV) genes which promote organ initiation and the WUS gene which is required for stem cell identity, with the CLV genes repressing WUS at the transcript level. WUS expression can be sufficient to induce meristem cell identity and the expression of the stem cell marker CLV3 (Brand et al. (2000) Science 289:617-619; Schoof et al. (2000) Cell 100:635-644). Constitutive expression of WUS in *Arabidopsis* has been shown to lead to adventitious shoot proliferation from leaves (in planta) (US 2004/166563 A1).

Further WUS/WOX homeobox polypeptides and genes encoding the same are known to the skilled person and can be targeted by the synthetic transcription factors and/or using the methods as disclosed herein. A WUS homeobox polypeptide may be selected from WUS 1, WUS2, WUS 3, WOX2A, WOX4, WOX5, or WOX9 polypeptide (van der Graaff et al., 2009, Genome Biology 10:248), or homolouges thereof. The WUS homeobox polypeptide can be a monocot WUSAVOX homeobox polypeptide. In various aspects, WUS homeobox polypeptide can be a barley, maize, millet, oats, rice, rye, *Setaria* sp., sorghum, sugarcane, switchgrass, triticale, turfgrass, or wheat WUSAVOX homeobox polypeptide. Alternatively, the WUS homeobox polypeptide can be a dicot WUS homeobox polypeptide (see WO 2017/074547 A1).

In addition, the AP2/ERF family of proteins is a plant-specific class of putative transcription factors that have been shown to regulate a wide-variety of developmental processes and are characterized by the presence of a AP2/ERF DNA binding domain. The AP2/ERF proteins have been subdivided into two distinct subfamilies based on whether they contain one (ERF subfamily) or two (AP2 subfamily) DNA binding domains. One member of the AP2 family that has been implicated in a variety of critical plant cellular functions is the Baby Boom (BBM) protein. The BBM protein from *Arabidopsis* is preferentially expressed in seed and has been shown to play a central role in regulating embryo-specific pathways. Overexpression of BBM has been shown to induce spontaneous formation of somatic embryos and cotyledon-like structures on seedlings. See, Boutiler et al. (2002) The Plant Cell 14:1737-1749. Thus, members of the AP2 (APETALA2) protein family promote cell proliferation and morphogenesis during embryogenesis. Such activity finds potential use in promoting apomixis in plants.

Another morphogenic target according to the present invention is Ovule Development Protein 2 (ODP2). It is also a member of the AP2 family of proteins. ODP2 polypeptides of the invention contain two predicted APETALA2 (AP2) domains and are members of the AP2 protein family (PFAM Accession PF00847). The AP2 domains of the maize ODP2 polypeptide are located from about amino acids S273 to N343 and from about S375 to R437 of SEQ ID NO:2). The AP2 family of putative transcription factors have been shown to regulate a wide range of developmental processes, and the family members are characterized by the presence of an AP2 DNA binding domain. This conserved core is predicted to form an amphipathic alpha helix that binds DNA. The AP2 domain was first identified in APETALA2, an *Arabidopsis* protein that regulates meristem identity, floral organ specification, seed coat development, and floral homeotic gene expression. The AP2 domain has now been found in a variety of proteins.

Therefore, morphogenic effectors of the AP2 family play critical roles in a variety of important biological events including development, plant regeneration, cell division, etc, these morphogenic effectors are valuable for the field of agronomic development to identify and characterize novel AP2 family members and develop novel methods to modulate embryogenesis, transformation efficiencies, and yield related traits, including oil content, starch content and the like in a plant, and are relevant targets of the synthetic transcription factors and the associated methods of the present invention.

Many attempts have been made to utilize the modulation of WUS, BBM and other morphogenic genes to improve transformation efficiency, to stimulate plant cell growth, including stem cells, to stimulate organogenesis, to stimulate somatic embryogenesis, to induce apomixis, and to provide a positive selection for cells and the like. The ability to stimulate organogenesis and/or somatic embryogenesis may be used to generate an apomictic plant. Apomixis has economic potential because it can cause any genotype, regardless of how heterozygous, to breed true. It is a reproductive process that bypasses female meiosis and syngamy to produce embryos genetically identical to the maternal parent. With apomictic reproduction, progeny of adaptive or hybrid genotypes would maintain their genetic fidelity throughout repeated life cycles. In addition to fixing hybrid vigor, apomixis can make possible commercial hybrid production in crops where efficient male sterility or fertility restoration systems for producing hybrids are not available. Apomixis can make hybrid development more efficient. It also simplifies hybrid production and increases genetic diversity in plant species with good male sterility.

Still, all current approaches of modulating the endogenous morphogenic gene pool of plant cells presently rely on the provision of genes encoding the morphogenic gene of interest to overexpress the respective morphogenic gene. Therefore, current methods rely on the stable or transient introduction and/or overexpression of a morphogenic gene of interest. In contrast, the present invention identified a solution to specifically design a synthetic transcription factor to modulate the transcription level of a morphogenic gene of interest, preferably in a transient and/or regulatable way, without the need to introduce an exogenous transgenic sequence of a morphogenic gene product, or the sequence encoding the same. This paves the way to provide methods for increasing the transformation efficiency in plants, e.g., for complex genome editing methods, even in transformation recalcitrant plants, and to provide methods for providing haploid or double haploid organisms or cellular systems.

A variety of different molecules can be used as the at least one recognition domain according to the present invention. According to the various aspects and embodiments disclosed herein, a recognition domain represent a protein domain, optionally as a fusion molecule, which possesses site-specific DNA recognition and thus binding and/or interaction activity. A recognition domain can be a domain from a naturally occurring protein, or the recognition domain may be a fragment of such a protein. Preferably, the at least one recognition domain has been specifically engineered to optimize the target specificity thereof for binding to a region of a morphogenic gene of interest, or to a region surrounding a morphogenic gene of interest.

More than one recognition domains may be used according to the present invention to increase the target specificity and/or binding characteristics to optimize modulation of the at least one morphogenic gene of interest.

In one embodiment, the synthetic transcription factor may comprise at least one recognition domain, or a fragment, of a molecule selected from the group consisting of at least one TAL effector, at least one disarmed CRISPR/nuclease system, at least one Zinc-finger domain, and at least one disarmed homing endonuclease, or any combination thereof.

In a further embodiment, the synthetic transcription factor may comprise at least one disarmed CRISPR/nuclease system selected from a CRISPR/dCas9 system, a CRISPR/dCpf1 system, a CRISPR/dCasX system or a CRISPR/dCasY system, or any combination thereof, wherein the at least one disarmed CRISPR/nuclease system, if present, comprises at least one guide RNA.

Naturally occurring DNA-binding transcription factors generally contain a minimum of two domains: a DNA-binding domain (DBD) and a transcriptional activation domain (TAD) (Latchman, 2008; Ptashne and Gann, 2002).

TAL effectors of plant pathogenic bacteria in the genus *Xanthomonas* play important roles in disease, or trigger defense, by binding host DNA and activating effector-specific host genes (see, e.g., Gu et al. (2005) Nature 435:1122; Römer et al. (2007) Science 318:645). Specificity depends on an effector-variable number of imperfect, typically 34 amino acid repeats (Schornack et al. (2006) J. Plant Physiol. 163:256). Polymorphisms are primarily at repeat positions 12 and 13, which are referred to herein as the repeat variable-diresidue (RVD). RVDs of TAL effectors correspond to the nucleotides in their target sites in a direct, linear fashion, one RVD to one nucleotide, with some degeneracy and no apparent context dependence. This finding represents a valuable mechanism for protein-DNA recognition that enables target site prediction for new target specific TAL effector. Therefore, TAL effectors are not only useful in research and biotechnology as targeted chimeric nucleases that can facilitate homologous recombination for GE approaches. TAL effectors per se do not comprise a nuclease domain. The so-called transcription activator-like effector endonucleases (TALENs) represent artificial or synthetic molecules combining the TAL effector function with a nuclease function for allowing the insertion of a site-specific DNA cleavage. For example, the TAL effector may enter the host cell nucleus via a C-terminal nuclear localization domain and may specifically activate the corresponding host gene through binding to an effector binding element in the promoter region of the host gene. The central domain of highly conserved, 33-35-amino acid repeats, each containing hypervariable dinucleotides or RVDs at positions 12 and 13, are responsible for the recognition of specific host gene promoter sequences. Each TAL effector wraps around the DNA in a right-handed superhelix positioning the second residue of each RVD into the major groove, where it contacts an individual nucleotide in the forward strand. These interactions define the specificity of each TAL effector. A C-terminal acidic activation domain then activates or enhances the expression of the corresponding endogenous gene, presumably by directly engaging the host RNA polymerase complex.

The modular mechanism by which TAL effectors recognize specific DNA sequences allows for the identification and design of artificial repeat arrays in the recognition domain of a TAL effector thereby designing TAL effectors which are capable to specifically induce expression of an endogenous gene of interest.

Computational analysis of genomic target sites of natural TALEs showed a preferential occurrence in apparent core promoter regions of −300 to +200 bp around the transcriptional start site (TSS) (Grau et al., PLoS Comput Biol. 2013; 9). Previous studies based on the TALEs AvrBs3, AvrXa7, and AvrXa27 showed that they shift the natural TSS of target genes around 40-60 bp downstream of the position at which the TALE is binding the DNA. Moving the AvrBs3-box in the Bs3 promoter to a position further upstream resulted in a concomitant upstream shift of the TSS. These observations led to the impression that TALEs control the onset and the place of transcription functionally analogous to the TATA-binding protein (Kay et al., Science. 2007; 318: 648-651).

Therefore, TAL effector binding domains represent suitable recognition domains according to the various aspects and embodiments of the present invention, as the binding and recognition specificities can be fine-tuned for a target site of interest. Therefore, expression, preferably transcription, of a morphogenic gene of interest can be modulated in a highly targeted manner, as at least one custom TAL effector can be designed as the at least one recognition domain of a synthetic transcription factor.

Functioning as heterologous transcription factors in their natural environment, TAL effectors (Yang et al., 2006) are delivered via the bacterial type III secretion system into host cells (Szurek et al., 2002), where C-terminal nuclear localization signals direct them to the nucleus (Gurlebeck et al., 2005; Szurek et al., 2001, 2002; Van den Ackerveken et al., 1996; Yang and Gabriel, 1995). The central domain of highly conserved, 33-35-amino-acid repeats, each containing hypervariable residues at positions 12 and 13 (the RVD), directs the recognition of specific host gene promoter sequences called effector binding elements (EBEs) (Boch et al., 2009; Moscou and Bogdanove, 2009). Each TAL effector wraps the DNA in a right-handed superhelix, positioning the second residue of each RVD into the major groove, where it contacts an individual nucleotide in the forward strand (Deng et al., 2012; Mak et al., 2012). Collectively, these interactions define, in a predictable way, the number and identity of adjacent nucleotides that constitute the EBE. A C-terminal acidic activation domain (AD) then activates or enhances transcription, presumably by directly engaging the host RNA polymerase complex (cf. Hummel et al., Molecular Plant Pathology, 2017, 18(1), 55-66).

In contrast to the teaching of the prior art, the present invention is partly based on the finding that synthetic TAL effector-based transcription factors, disarmed ZFP-based transcription factors, or disarmed CRISPR-based transcription factors specific for endogenous nucleotide sequences located at a specific upstream or downstream position relative to the start codon of a gene of interest, preferably a morphogenic gene, for example, BBM and WUS, can induce transcription and expression of said genes in a plant cell thereby boosting the regeneration frequency of such plant. Notably, this efficiency can be enhanced in case non-classical regulation regions outside of a TATA-box or the promoter region are targeted, whereas naturally occurring transcription factors as well as commercially available transcription factors usually exert their function by binding to a region within the promoter region of a gene of interest. There is evidence that the transcriptional activation is higher in proximity to the TATA box compared to directly targeting the TATA region. The transcription factors of the present invention based on the various different TAL effector, CRISPR, zinc-finger or homing endonuclease based recognition domain thus comprise a different architecture allowing a better and more precise modulation and regulation of a morphogenic gene of interest.

Therefore, it can be an advantage of the synthetic transcription factors and the methods of the present invention that the synthetic transcription factors can also act on TATA-less genes, or outside a TATA region, if correctly designed to comprise optimum recognition and activation regions. In certain embodiments, at least one recognition domain may also target a TATA region of a gene of interest.

For example, a TAL effector DNA binding domain can be specific for a target DNA, wherein the DNA binding domain comprises a plurality of DNA binding repeats, each repeat comprising a RVD that determines recognition of a base pair in the target DNA, wherein each DNA binding repeat is responsible for recognizing one base pair in the target DNA, and wherein the TALEN comprises one or more of the following RVDs: HD for recognizing C; NG for recognizing T; NI for recognizing A; NN for recognizing G or A; NS for recognizing A or C or G or T; N* for recognizing C or T; HG for recognizing T; H* for recognizing T; IG for recognizing T; NK for recognizing G; HA for recognizing C; ND for recognizing C; HI for recognizing C; HN for recognizing G; NA for recognizing G; SN for recognizing G or A; and YG for recognizing T. The TALEN can comprise one or more of the following RVDs: HA for recognizing C; ND for recognizing C; HI for recognizing C; HN for recognizing G; NA for recognizing G; SN for recognizing G or A; YG for recognizing T; and NK for recognizing G, and one or more of: HD for recognizing C; NG for recognizing T; NI for recognizing A; NN for recognizing G or A; NS for recognizing A or C or G or T; N* for recognizing C or T; HG for recognizing T; H* for recognizing T; and IG for recognizing T.

Zinc finger proteins (ZFPs) are proteins that can bind to DNA in a sequence specific manner. Zinc fingers were first identified in the transcription factor TFIIIA from the oocytes of the African clawed toad, *Xenopus laevis*. An exemplary motif characterizing one class of these proteins (Cys2His2 class) is Xaa-Cys-Xaa-Cys-Xaa-His-Xaa-His (SEQ ID NO: 275), where Xaa is any amino acid. Individual fingers from these proteins have a simple f3f3a structure that folds around a central zinc ion, and tandem sets of fingers can contact neighboring subsites of 3-4 base pairs along the major groove of the DNA (Pabo et al. (2001) *"Design and selection of novel Cys2His2 zinc finger proteins"*. Ann. Rev. Biochem. 70: 313-40). A single zinc finger domain is about 30 amino acids in length, and several structural studies have demonstrated that it contains a beta turn (containing the two invariant cysteine residues) and an alpha helix (containing the two invariant histidine residues), which are held in a particular conformation through coordination of a zinc atom by the two cystines and the two histidines. Several other class of zinc finger proteins are known, e.g., the treble-clef class comprising a motif consisting of a β-hairpin at the N-terminus and an α-helix at the C-terminus that each contribute two ligands for zinc binding, although a loop and a second β-hairpin of varying length and conformation can be present between the N-terminal β-hairpin and the C-terminal α-helix, or zinc ribbon like ZFPs having a fold being characterized by two beta-hairpins forming two structurally similar zinc-binding sub-sites.

For genome editing (GE) purposes techniques of molecular biology can be used to alter the DNA-binding specificity of zinc fingers and tandem repeats of such engineered zinc fingers can be used to target desired genomic DNA sequences (Jamieson et al., "Drug discovery with engineered zinc-finger proteins". Nature Reviews. Drug Discovery. 2 (5): 361-8). Fusing a second protein domain such as a transcriptional activator or repressor to an array of engineered zinc fingers that bind near the promoter of a given gene can be used to alter the transcription of that gene. Fusions between engineered zinc finger arrays and protein domains that cleave or otherwise modify DNA can also be used to target those activities to desired genomic loci. The most common applications for engineered zinc finger arrays include zinc finger transcription factors and zinc finger nucleases. Typical engineered zinc finger arrays have between 3 and 6 individual zinc finger motifs and bind target sites ranging from 9 basepairs (bp) to 18 bp in length.

Meganucleases are endodeoxyribonucleases characterized by a large recognition site (double-stranded DNA sequences of 12 to 40 base pairs). As a result, this site generally occurs only once in any given genome. Meganucleases can be used to achieve very high levels of gene targeting efficiencies in mammalian cells and plants (Rouet et al., Mol. Cell. Biol., 1994, 14, 8096-106; Choulika et al., Mol. Cell. Biol., 1995, 15, 1968-73). Among meganucleases, the LAGLIDADG family (SEQ ID NO: 276) of homing endonucleases has become a valuable tool for the study of genomes and genome engineering over the past years.

Disarmed, i.e., nuclease-deficient, homing endonucleases (HEs) represent a suitable class of recognition domains according to the present invention. HEs are a widespread family of natural meganucleases including hundreds of proteins (Chevalier and Stoddard, Nucleic Acids Res., 2001, 29, 3757-74). These proteins are encoded by mobile genetic elements which propagate by a process called "homing": the endonuclease cleaves a cognate allele from which the mobile element is absent, thereby stimulating a homologous recombination event that duplicates the mobile DNA into the recipient locus (Kostriken et al., Cell; 1983, 35, 167-74; Jacquier and Dujon, Cell, 1985, 41, 383-94). Given their natural function and their exceptional cleavage properties in terms of efficacy and specificity, HEs provide ideal scaffolds to derive novel endonucleases for genome engineering. One family of HEs is called the LAGLIDADG family (SEQ ID NO: 276). LAGLIDADG (SEQ ID NO: 276) refers to the only sequence actually conserved throughout the family and is found in one or (more often) two copies in the protein. Proteins with a single motif, such as I-CreI, form homodimers and cleave palindromic or pseudo-palindromic DNA sequences, whereas the larger, double motif proteins, such as 1-SceI are monomers and cleave non-palindromic targets. Seven different LAGLIDADG proteins (SEQ ID NO: 276) have been crystallized, and they exhibit a very striking conservation of the core structure, that contrasts with the lack of similarity at the primary sequence level (Jurica et al., Mol. Cell., 1998, 2, 469-76; Chevalier et al., Nat. Struct. Biol., 2001, 8, 312-6; Chevalier et al. J. Mol. Biol., 2003, 329, 253-69). Analysis of 1-Cre structure bound to its natural target shows that in each monomer, eight residues (Y33, Q38, N30, K28, Q26, Q44, R68 and R70) establish direct interactions with seven bases at positions ±3, 4, 5, 6, 7, 9 and 10 (Jurica et al., 1998). In addition, some residues establish water-mediated contact with several bases; for example, S40 and N30 with the base pair at position 8 and −8 (Chevalier et al., 2003). The catalytic core is central, with a contribution of both symmetric monomers/domains. HEs having a modified cleavage site are known to the skilled person and can be used to define a disarmed HE as the at least one recognition domain according to the present invention.

According to the various aspects and embodiments according to the present invention, zinc finger proteins and domains derived therefrom can be used as the at least one recognition domain, which at least one recognition domain can be designed to fulfill the recognition properties of a synthetic transcription factor according to the present invention.

Besides TAL effectors, disarmed ZFPs and meganucleases, non-functional CRISPR/nuclease systems can be used to specifically target morphogenic genes and to boost regeneration of plant cells. In these systems, a CRISPR nuclease such as Cas9, Cfp1, CasX and/or CasY is used in which the nuclease activity has been turned off to avoid cleavage of the target genomic sequences. The target specificity of the non-functional CRISPR/nuclease system is determined by crRNAs and/or sgRNAs specific for the upstream nucleotide promoter region of an endogenous morphogenic gene of interest. An activation domain which is fused to the CRISPR/nuclease system then recruits the transcription machinery to the gene locus thereby inducing the expression of the endogenous morphogenic gene of interest. Notably, the use of at least one guide RNA can dramatically increase the target specificity, as this CRISPR nucleic acid sequence additionally contributes in the recognition of genomic target DNA of interest. Moreover, the dual recognition properties of a disarmed CRISPR nuclease and the guide RNA allows a higher degree of flexibility in designing synthetic transcription factor recognition domains according to the present invention which in turn provides a better recognition and thus modulation activity of a morphogenic gene of interest.

A CRISPR system in its natural environment describes a molecular complex comprising at least one small and individual non-coding RNA in combination with a Cas nuclease or another CRISPR nuclease like a Cpf1 nuclease (Zetsche et al., 2015, supra) which can produce a specific DNA double-stranded break. Presently, CRISPR systems are categorized into 2 classes comprising five types of CRISPR systems, the type II system, for instance, using Cas9 as effector and the type V system using Cpf1 as effector molecule (Makarova et al., Nature Rev. Microbiol., 2015). In artificial CRISPR systems, a synthetic non-coding RNA and a CRISPR nuclease and/or optionally a modified CRISPR nuclease, modified to act as nickase or lacking any nuclease function, can be used in combination with at least one synthetic or artificial guide RNA or gRNA combining the function of a crRNA and/or a tracrRNA (Makarova et al., 2015, supra). The immune response mediated by CRISPR/Cas in natural systems requires CRISPR-RNA (crRNA), wherein the maturation of this guiding RNA, which controls the specific activation of the CRISPR nuclease, varies significantly between the various CRISPR systems which have been characterized so far. Firstly, the invading DNA, also known as a spacer, is integrated between two adjacent repeat regions at the proximal end of the CRISPR locus. Type II CRISPR systems, for example, can code for a Cas9 nuclease as key enzyme for the interference step, which system contains both a crRNA and also a trans-activating RNA (tracrRNA) as the guide motif. These hybridize and form double-stranded (ds) RNA regions which are recognized by RNAseIII and can be cleaved in order to form mature crRNAs. These then in turn associate with the Cas molecule in order to direct the nuclease specifically to the target nucleic acid region. Recombinant gRNA molecules can comprise both the variable DNA recognition region and also the Cas interaction region and thus can be specifically designed, independently of the specific target nucleic acid and the desired Cas nuclease. As a further safety mechanism, PAMs (protospacer adjacent motifs) must be present in the target nucleic acid region; these are DNA sequences which follow on directly from the Cas9/RNA complex-recognized DNA. The PAM sequence for the Cas9 from *Streptococcus pyogenes* has been described to be "NGG" or "NAG" (Standard IUPAC nucleotide code) (Jinek et al, "A programmable dual-RNA-guided DNA endonuclease in adaptive bacterial immunity", Science 2012, 337: 816-821). The PAM sequence for Cas9 from *Staphylococcus aureus* is "NNGRRT" or "NNGRR(N)". Further variant CRISPR/Cas9 systems are known. Thus, a *Neisseria meningitidis* Cas9 cleaves at the PAM sequence NNNNGATT. A *Streptococcus thermophilus* Cas9 cleaves at the PAM sequence NNAGAAW. Recently, a further PAM motif NNNNRYAC has been described for a CRISPR system of *Campylobacter* (WO 2016/021973 A1). For Cpf1 nucleases it has been described that the Cpf1-crRNA complex, without a tracrRNA, efficiently recognize and cleave target DNA proceeded by a short T-rich PAM in contrast to the commonly G-rich PAMs recognized by Cas9 systems (Zetsche et al., supra). Furthermore, by using modified CRISPR polypeptides, specific single-stranded breaks can be obtained. The combined use of Cas nickases with various recombinant gRNAs can also induce highly specific DNA double-stranded breaks by means of double DNA nicking. By using two gRNAs, moreover, the specificity of the DNA binding and thus the DNA cleavage can be optimized. Further CRISPR effectors like CasX and CasY effectors originally described for bacteria, are meanwhile available and represent further effectors, which can be used for genome engineering purposes (Burstein et al., "New CRISPR-Cas systems from uncultivated microbes", Nature, 2017, 542, 237-241).

Presently, for example, Type II systems relying on Cas9, or a variant or any chimeric form thereof, as endonuclease have been modified for genome engineering. Synthetic CRISPR systems consisting of two components, a "guide RNA" (gRNA) also called "single guide RNA" (sgRNA) or "CRISPR nucleic acid sequence" herein and a non-specific CRISPR-associated endonuclease can be used to generate knock-out cells or animals by co-expressing a gRNA specific to the gene to be targeted and capable of association with the endonuclease Cas9. Notably, the gRNA is an artificial molecule comprising one domain interacting with the Cas or any other CRISPR effector protein or a variant or catalytically active fragment thereof and another domain interacting with the target nucleic acid of interest and thus representing a synthetic fusion of crRNA and tracrRNA (as "single guide RNA" (sgRNA) or simply "gRNA"). The genomic target can be any ~20 nucleotide DNA sequence, provided that the target is present immediately upstream of a PAM sequence. The PAM sequence is of outstanding importance for target binding and the exact sequence is dependent upon the species of Cas9 and, for example, reads 5' NGG 3' or 5' NAG 3' (Standard IUPAC nucleotide code) (Jinek et al., Science 2012, supra) for a *Streptococcus pyogenes* derived Cas9. The PAM sequence for Cas9 from *Staphylococcus aureus* is NNGRRT or NNGRR(N). Many further variant CRISPR/Cas9 systems are known, including inter alia, *Neisseria meningitidis* Cas9 cleaving the PAM sequence NNNNGATT. A *Streptococcus thermophilus* Cas9 cleaving the PAM sequence NNAGAAW. Using modified Cas nucleases, targeted single-strand breaks can be introduced into a target sequence of interest. The combined use of such a Cas nickase with different recombinant gRNAs highly site-specific DNA double-strand breaks can be introduced using a double nicking system. Using one or more gRNAs can further increase the overall specificity and reduce off-target effects.

A third variant of a Cas or Cpf1 nuclease of particular interest for the purpose of the present invention is a nuclease-deficient Cas9 (dCas9) or dCpf1 (Qui et al, 2013, Cell, 154, 442-451). Mutations H840A in the HNH domain and D10A in the RuvC domain of Cas9 inactivate cleavage activity, but do not prevent DNA binding (Gasiunas et al., 2012, Proc. Natl. Acad. Sci. U.S.A., 111, E2579-2586). Therefore, these variants, if properly configured can be repurposed to sequence-specifically target a region of the genome without cleavage.

In one embodiment according to the various aspects of the present invention, the recognition domain may comprise at least one gRNA of a CRISPR complex. In certain embodiments, more than one gRNA may be present. The expression of multiple guide RNAs in a single cell or cellular system, e.g., the expression of two, three, four, five, or more gRNAs, may enable a synergistic modulation of endogenous gene targets, thereby enabling combinatorial control of endogenous gene expression over a wide dynamic range due to the fact that the at least one gRNA as recognition moiety if a STF according to the present invention can provide additional target specificity to the STF and reduce off-target effects, particularly when the STFs are designed to target a gene in a huge eukaryotic genome. Each gRNA may target an independent regulation/recognition region.

In one embodiment according to the various aspects of the present invention, the synthetic transcription factor may be configured to modulate expression, preferably transcription, of the morphogenic gene by binding to a regulation region located at a certain distance in relation to the start codon.

The "regulation region" as used herein refer to the binding site of at least one recognition domain to a target sequence in the genome at or near a morphogenic gene of interest. There may be two discrete regulation regions, or there may be overlapping regulation regions, depending on the nature of the at least one activation domain and the at least one recognition domain as further disclosed herein, which different domains of the synthetic transcription factor of the present invention can be assembled in a modular manner.

In certain embodiments, the at least one recognition domain may target at least one sequence (recognition site) relative to the start codon of a gene of interest, which sequence may be at least 1.000 bp upstream (−) or downstream (+), −700 bp to +700 bp, −550 bp to +500 bp, or −550 bp to +425 bp relative to of the start codon of a gene of interest. Promoter-near recognizing recognition domains might be preferable in certain embodiments, whereas it represents an advantage of the specific STFs of the present invention that the targeting range of the STFs is highly expanded over conventional or naturally occurring TFs. As the recognition and/or the activation domains can be specifically designed and constructed to specifically identify and target hot-spots of modulation.

In certain embodiments, the at least one recognition site may be −169 bp to −4 bp, −101 bp to −48 bp, −104 to −42 bp, or −175 to +450 bp (upstream (−) or downstream (+), respectively) relative to the start codon of a gene of interest to provide an optimum sterical binding environment allowing the best modulation, preferably transcriptional activation, activity. In particular for CRISPR-based synthetic transcription factors according to the present invention acting together with a guide RNA as recognition moiety, the binding site can also reside in within the coding region of a gene of interest (downstream of the start codon of a gene of interest).

In further embodiments of the synthetic transcription factors of the present invention, the recognition domain can bind to the 5' and/or 3' untranslated region (UTR) of a gene of interest. In embodiments, where different recognition domains are employed, the at least two recognition domains can bind to different target regions of a morphogenic gene of interest, including 5' and/or 3'UTRs, but they can also bind outside the gene region, but still in a certain distance of at most 1 to 1.500 bps thereto. One preferred region, where a recognition domain can bind, resides about −4 bp to about −300, preferably about −40 bp to about −170 bp upstream of the start codon of a morphogenic gene of interest. Notably, there is more recognition site flexibility for certain STFs disclosed herein, in particular for CRISPR-based STFs due to the additional functions of at least one gRNA in said STFs.

According to the various aspects and embodiments presented herein, the length of a recognition domain and thus the corresponding recognition site in a genome of interest may thus vary depending on the STF and the nature of the recognition domain applied. Based on the molecular characteristics of the at least one recognition domain, this will also determine the length of the corresponding at least one recognition site. For example, where individual zinc finger may be from about 8 bp to about 20 bp, wherein arrays of between three to six zinc finger motifs may be preferred, individual TALE recognition sites may be from about 11 to about 30 bp, or more. Recognition sites of gRNAs of a CRISPR-based STF comprise the targeting or "spacer" sequence of a gRNA hybridizing to a genomic region of interest, whereas the gRNA comprises further domains, including a domain interacting with a disarmed CRISPR effector according to the present disclosure. The recognition site of a STF based on a disarmed CRISPR effector will comprise a PAM motif, as the PAM sequence is necessary for target binding of any CRISPR effector and the exact sequence is dependent upon the species of the CRISPR effector, i.e., a disarmed CRISPR effector as disclosed herein.

In one embodiment of the various aspects of the present invention, the synthetic transcription factor may comprise at least one activation domain, wherein the at least one activation domain may be selected from the group consisting of an acidic transcriptional activation domain, preferably, wherein the at least one activation domain may be from an TAL effector gene of *Xanthomonas oryzae*, VP16 or tetrameric VP64 from Herpes simplex, VPR, SAM, Scaffold, Suntag, P300, VP160, or any combination thereof. To enhance modulation of at least one morphogenic gene of interest, two, three, four, five, or more than five activation domains may be present. In a preferred embodiment of the present invention, the activation domain is VP64.

VP16 is a transcription factor originally found in herpes simplex virus (HSV) type 1 that is involved in the activation of the viral immediate-early genes (Flint and Shenk, 1997; Wysocka and Herr, 2003). The VP16 wild-type sequence has 490 amino acids with a core domain in its central region required for indirect DNA binding and a carboxy-terminal TAD located within its last 81 amino acids (Greaves and O'Hare, 1989; Triezenberg et al., 1988). VP16 is originally contained within the virion (virus particle) of the HSV and released into animal cells upon infection. VP16 first binds to the host nuclear protein HCF through its core domain and subsequently binds to another host nuclear protein Oct-1 to form a three-component protein complex. This complex then binds to its target DNA sequence TAATGARAT (R is a purine) in the promoters of immediate-early genes. This is achieved through interactions between Oct-1 and the target DNA sequence or a consensus octamer motif that overlaps the 5' portion of this sequence. HCF then stabilizes the interaction between VP16 and Oct1. Once recruited to immediate-early genes, VP16 activates genes through interactions between the TAD and other transcription factors (Hirai et al., Int. J. Dev. Biol., 2010, 54(11-12):1589-1596). Meanwhile, the original VP16 domain has been extensively exploited for a variety of studies using artificial or synthetic transcription factors. Usually, a core domain comprising the minimal activation domain of VP16 in single form, or as, for example, triple (VP48) or as 10× tandem copies of VP16 (VP160) is used for these purposes.

The natural activation domain of the TAL effector genes of *Xanthomonas oryzae* is the most obvious activation domain for use with in TAL transcription factors, and also represents one activation domain, which can be used, alone or in combination, according to the various aspects of the present invention, but have been used in other settings as well. They belong to a family of acidic (transcriptional) activation domains.

The SAM (synergistic activation mediator) activation domain usually consists of three components: a nucleolytically inactive/inactivated CRISPR nuclease, usually in combination with a VP64 fusion, a guide RNA incorporating two MS2 RNA aptamers at the tetraloop and stem-loop, and the MS2-P65-HSF1 activation helper protein (Konermann et al., 2015, "Genome-scale transcriptional activation by an engineered CRISPR-Cas9 complex". Nature 517:583-588). Therefore, the guide RNA may contain two copies of an RNA hairpin from the MS2 bacteriophage, which interacts with the RNA-binding protein (RBP) MCP (MS2 coat protein).

The SAM system employs multiple transcriptional activators to create a synergistic effect, which makes the SAM system a highly versatile activation domain used alone, or in combination with further activation domains for the synthetic transcription factors according to the present invention. In a preferred embodiment, wherein the synthetic transcription factor uses a CRISPR-based recognition domain, the guide RNA can be further engineered to optimize the interplay between the activation and the recognition domain.

A further activation domain to be used alone or in combination according to the present invention is the tripartite effector VPR (VP64, p65, and Rta) fused to a recognition domain of interest linked in tandem (Russa and Qi, Mol. Cell. Biol. 2015 November; 35(22): 3800-3809).

Yet a further activation domain to be used alone or in combination according to the present invention is "scaffold" recruiting multiple copies of, e.g., VP64, to a special guide RNA, optionally together with further activators (Chavez et al., Nat. Methods, 2016, 13(7), 563-567).

Another activation domain to be used alone or in combination according to the present invention is "Suntag" comprising a repeating peptide array, which can recruit multiple copies of an antibody-fusion protein to create a potent synthetic transcription factor by recruiting multiple copies of a transcriptional activation domain to a nuclease-deficient recognition domain of a synthetic transcription factor of the present invention (Tanenbaum et al., Cell, 2014, 159(3):635-46).

In another embodiment, the SAM activation domain system may be employed to, in particular a SAM-modified guide RNA, together with a suntag activation domain to simultaneously recruit both a single-chain variable fragment (scFv) with a desired specificity, coupled to, for example VP64, to one end of a recognition domain, and p65-hsf1 to the guide RNA for CRISPR-based synthetic transcription factors. The scFvs, not representing activators per se, with their extremely high specificity and versatility of target recognition, which can be engineered, are thus highly suitable to recruit multiple copies of an activator of interest to a position of interest, i.e., the scFv can be used as amplifier according to the various aspects and embodiments of the present invention together with an activation domain as disclose herein.

Yet another activation domain to be used alone or in combination according to the present invention is p300 or EP300 or E1A (used interchangeably herein), or CBP (also known as CREB-binding protein or CREBBP). Both p300 and CBP interact with numerous transcription factors and act to increase the expression of their target genes (Kasper et al., 2006, Mol. Cell. Biol., 26(3), 789-809). P300 and CBP have similar structures. Both contain five protein interaction domains: the nuclear receptor interaction domain (RID), the KIX domain (CREB and MYB interaction domain), the cysteine/histidine regions (TAZ1/CH1 and TAZ2/CH3) and the interferon response binding domain (IBiD). The last four domains, KIX, TAZ1, TAZ2 and IBiD of p300, each bind tightly to a sequence spanning both transactivation domains 9aaTADs of transcription factor p53. In addition, p300 and CBP each contain a protein or histone acetyltransferase (PAT/HAT) domain and a bromodomain that binds acetylated lysines and a PHD finger motif with unknown function. The conserved domains are connected by long stretches of unstructured linkers. P300 and CBP may increase gene expression in three ways: by relaxing the chromatin structure at the gene promoter through their intrinsic histone acetyltransferase (HAT) activity; by recruiting the basal transcriptional machinery including RNA polymerase II to the promoter; and/or by acting as adaptor molecules.

According to the various embodiments of the present invention, the at least one recognition domain and the at least one activation domain of the synthetic transcription factor of the present invention may be individually optimized to allow a perfect binding and modulation activity. Therefore, a specific number of activation domains may be suitable for a given recognition domain, properly positioned in the synthetic transcription factor construct, to allow optimum modulation activity, preferably transcriptional activation. Therefore, the at least one activation domain according to the various aspects of the present invention may comprise certain modifications to optimize the at least one activation domain to interact with the at least one recognition domain in an optimum way so that both domains have access to a target site of interest to be modulated.

In one embodiment, the at least one activation domain may be located N-terminal and/or C-terminal relative to the at least one recognition domain within a synthetic transcription factor of the present invention. This configuration can be the best configuration for fusion molecules between at least one recognition domain and at least one activation domain. According to various embodiments, the at least one recognition domain and the at least one activation domain may be separated by a suitable linker sequence to allow optimum flexibility and to avoid sterical hindrance of the domains to fulfill their functions.

In one embodiment, the synthetic transcription factor may comprise at least one further element, including at least one nuclear localization signal (NLS), an organelle localization signal, including, for example, a mitochondrion localization signal or a chloroplast localization signal to target the STF to a compartment within a cell or cellular system, where the STF can exert its function. Furthermore, the synthetic transcription factor may comprise at least one tag, e.g. to visualize the synthetic transcription factor, to track the subcellular localization of the transcription factor and/or to provide a active moiety within the synthetic transcription factor, e.g. a scFv binding site, to attach further molecules to the synthetic transcription factor, a translocation domain, e.g. a translocation domain as present in TALE molecules, and the like as further disclosed herein, and as known to the skilled person. The at least one further domain may be positioned N-terminal and/or C-terminal relative to the at least one recognition domain, including a positioning between the at least one recognition and the at least one activation domain, e.g. at least one NLS may be positioned between one recognition domain and another recognition domain and/or an activation domain. If provided as a transcribable/translatable vector, the STF may comprise at least one promoter for optimum transcription within a target cell or cellular system of interest. The skilled person is able to define suitable promoters, preferably strong promoters, either with inducible or constitutive expression, depending on a cellular system of interest. An example for a very strong constitutive promoter in the plant system, e.g., Zea mays, is BdUbi10. A weaker promoter would be the BdEF1 for example. Inducible plant promoters are the tetracycline-, the dexamethasone-, and salicylic acid inducible promoters. Other promoters suitable according to the present invention are a CaMV (Cauliflower mosaic virus) 35S or a double 35S promoter. Other constitutive eukaryotic promoters are CMV (Cytomegalovirus), EF1a, TEF1, SV40, PGK1 (human or mouse), Ubc (ubiquitin 1), human beta-actin, GDS, GAL1 or 2 (for a yeast system), CAG (comprising a CMV enhancer, chicken beta actin promoter, and rabbit beta-globin splice acceptor), H1, or U6. A variety of inducible promoters is known to the skilled person.

Therefore, a variety of different architectures can be present in the STFs according to the present invention. As the STFs of the present application have a modular character, several STFs with a different domain architecture can be designed for a given target and can be evaluated in a comparative way in vitro to deduce the architecture providing the best modulation effect.

In one embodiment of the present invention, the STF comprises a N-terminal TAL recognition domain and a C-terminal VP64 activation domain, wherein the STF further comprises a SV40 nuclear localization signal (NLS) between the N-terminal recognition domain and the C-terminal activation domain.

In yet another embodiment of the present invention, the STF comprises a N-terminal CRISPR/dCas9 or CRISPR/ dCpf1 recognition domain and a C-terminal VP64 activation domain associated with a SV40 nuclear localization signal (NLS) at its C-terminus, wherein the STF further comprises two SV40 NLSs between the N-terminal recognition domain and the C-terminal activation domain.

In certain embodiments, the STFs, or the sequences encoding the same, according to the present invention can be provided as multiplex systems to target more than one gene of interest. For example, TALE and disarmed CRISPR-based STFs can be designed enabling the targeting of 2 to 7, or more, genetic loci of interests, or enabling the targeting of one gene of interest using two or more different STFs specifically designed to modulate said one gene of interest, by providing multiplex vectors, or by providing in vitro assembled multiplex STFs to be transformed or transfected in a cell or cellular system of interest.

In one embodiment, the synthetic transcription factor of the present invention, or the sequence encoding the same, may comprise at least one non-naturally occurring nucleotide, amino acid or synthetic sequence, or a combination thereof, covalently or non-covalently attached to at least one amino acid sequence of the synthetic transcription factor. This embodiment is particularly suitable in case that the synthetic transcription factor is delivered as pre-assembled complex into a cellular system of interest, and in particular for disarmed CRISPR-based synthetic transcription factors, wherein the recognition domain additionally comprises a gRNA component. As the ribonucleic acid is rather unstable, the gRNA recognition portion may be stabilized by a non-naturally occurring moiety, for example, a phosphorothioate backbone, or any other stabilizing nucleotide. Furthermore, the synthetic transcription factor, preferably in embodiments, wherein a pre-assembled protein complex is delivered into a cell or cellular system of interest, may comprise chemical modifications to stabilize, derivatize or functionalize the complex and/or to add at least one DNA repair template to the complex for embodiments aiming at a method for modifying the genetic material of a cellular system in a targeted way.

A challenge for any CRISPR-based approach is the fact that the RNA portion (gRNA) and the respective CRISPR polypeptide have to be transported to the nucleus or any other compartment comprising genomic DNA, i.e. the DNA target sequence, in a functional (not degraded) way. As RNA is less stable than a polypeptide or double-stranded DNA and has a higher turnover, especially as it can be easily degraded by nucleases, in some embodiments, a CRISPR RNA sequence and/or the DNA repair template nucleic acid sequence, if present in certain embodiments of the present invention, comprises at least one non-naturally occurring nucleotide. Preferred backbone modifications according to the present invention increasing the stability of the CRISPR RNA and/or increasing the stability of a DNA repair template nucleic acid sequence, if present, are selected from the group consisting of a phosphorothioate modification, a methyl phosphonate modification, a locked nucleic acid modification, an O-(2-methoxyethyl) modification, a di-phosphorothioate modification, and a peptide nucleic acid modification. Notably, all said backbone modifications still allow the formation of complementary base pairing between two nucleic acid strands, yet are more resistant to cleavage by endogenous nucleases. Depending on the disarmed CRISPR effector utilized in combination with a RNA/DNA nucleic acid sequence according to the present invention, it might be necessary not to modify those nucleotide positions of a CRISPR nucleic acid sequence, which are involved in sequence-independent interaction with the CRISPR polypeptide. Said information can be derived from the available structural information as available for CRISPR nuclease/CRISPR nucleic acid sequence complexes and for disarmed CRISPR effectors, e.g. dCas9.

In certain embodiments of the present invention, it is envisaged that at least one CRISPR nucleic acid sequence (gRNA) and/or at least one optionally present DNA repair template nucleic acid sequence may comprise a nucleotide and/or base modification, preferably at selected, not all, nucleotide sequence positions. These modifications are selected from the group consisting of addition of acridine, amine, biotin, cascade blue, cholesterol, Cy3, Cy5, Cy5.5, Daboyl, digoxigenin, dinitrophenyl, Edans, 6-FAM, fluorescein, 3'-glyceryl, HEX, IRD-700, IRD-800, JOE, phosphate psoralen, rhodamine, ROX, thiol (SH), spacers, TAMRA, TET, AMCA-S", SE, BODIPY®, Marina Blue®, Pacific Blue®, Oregon Green®, Rhodamine Green®, Rhodamine Red®, Rhodol Green® and Texas Red®. Preferably, said additions are incorporated at the 3' or the 5' end of the CRISPR nucleic acid sequence and/or the DNA repair template nucleic acid sequence. This modification has the advantageous effects, that the cellular localization of the CRISPR nucleic acid sequence and/or the optionally present DNA repair template nucleic acid sequence within a cell can be visualized to study the distribution, concentration and/or availability of the respective sequence. Furthermore, the interaction of the synthetic transcription factor of interest and the binding behavior can be studied. Methods of studying such interactions or for visualization of a nucleotide sequence modified or tagged as detailed above are available to the skilled person in the respective field.

In one embodiment, any nucleotide of the at least one CRISPR nucleic acid sequence or any other component of the sequence encoding at least one synthetic transcription factor of the present invention can comprise one of the above modifications as a label or linker. As used herein, "nucleotide" can thus generally refer to a base-sugar-phosphate combination. A nucleotide can comprise a synthetic nucleotide. A nucleotide can comprise a synthetic nucleotide analog. Nucleotides can be monomeric units of a nucleic acid sequence (e.g., deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example and not limitation, [αS]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide may be unlabeled or detectably labeled by well-known techniques. Labeling can also be carried out with quantum dots. Detectable labels can include, for example, radioactive isotopes, fluorescent labels, chemiluminescent labels, bioluminescent labels and enzyme labels. Fluorescent labels of nucleotides may include but are not limited to fluorescein, 5-carboxyfluorescein (FAM), 2'7'-5 dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminon-aphthalene-1-sulfonic acid (EDANS).

Labels or linkers can also comprise moieties suitable for click chemistry to link the at least one CRISPR guide nucleic acid sequence or a portion thereof and/or a DNA repair template nucleic acid sequence and/or at least one recognition domain of a synthetic transcription factor and/or at least one activation domain of a synthetic transcription factor to each other.

Of the reactions comprising the click chemistry field suitable to modify any nucleic acid or amino acid according to the present invention to build a molecular complex, in vitro or in vivo, one example is the Huisgen 1,3-dipolar cycloaddition of alkynes to azides to form 1,4-disubstituted-1,2,3-triazoles. The copper (I)-catalyzed reaction is mild and very efficient, requiring no protecting groups, and requiring no purification in many cases. The azide and alkyne functional groups are generally inert to biological molecules and aqueous environments. The triazole has similarities to the ubiquitous amide moiety found in nature, but unlike amides, is not susceptible to cleavage. Additionally, they are nearly impossible to oxidize or reduce.

As it is known to the skilled person, certain click chemistry reactions suitable for in vivo reactions rely on reactive groups, such as azides, terminal alkynes or strained alkynes (e.g., dibenzocyclooctyl (DBCO)), which reactive groups can be introduced into any form of RNA or DNA via accordingly modified nucleotides that are incorporated instead of their natural counterparts. Labels can be introduced enzymatically or chemically. The resulting CLICK-functionalized DNA can subsequently be processed via Cu(I)-catalyzed alkyne-azide (CuAAC) or Cu(I)-free strained alkyne-azide (SPAAC) click chemistry reactions, wherein copper-free reactions are preferable for applications within a cell or living system. These reactions can be used according to the present invention to introduce a biotin group for subsequent purification tasks (via azides, alkynes of biotin or DBCO-containing biotinylation reagents), to introduce a fluorescent group for subsequent microscopic imaging (via fluorescent azides, fluorescent alkynes or DBCO-containing fluorescent dyes), or to crosslink to biomolecules, e.g., the at least one domain of, or the at least one synthetic transcription factor of the present invention, and optionally a DNA repair template, if present, to covalently link and/or provide functionalized biomolecules.

In one embodiment, an optionally purified and functionally associated 5' or 3' end click-chemistry-labeled CRISPR nucleic acid sequence according to the present invention may be delivered by any transformation or transfection method to a cell or cell system stably or transiently expressing a corresponding disarmed CRISPR polypeptide. Thereby, as the CRISPR nucleic acid sequence interacts with and thereby directs the CRISPR polypeptide to act as a recognition domain according to the present invention. This allows the activation domain to precisely modulate the expression of at least one morphogenic gene of interest.

A variety of further chemical reactions and the corresponding modifications are available to the skilled person to link to nucleic acids according to the present disclosure to each other, or to any amino acid recognition and/or activation domain in a covalent way. This modifications include a variety of crosslinkers, such as thiol modifications, like a thioctic acid N-hydroxysuccinimide (NHS) ester, chemical groups that react with primary amines (—NH2). These primary amines are positively charged at physiologic pH; therefore, they occur predominantly on the outside surfaces of native protein tertiary structures where they are readily accessible to conjugation reagents introduced into the aqueous medium. Furthermore, among the available functional groups in typical biological or protein samples, primary amines are especially nucleophilic; this makes them easy to target for conjugation with several reactive groups. There are numerous synthetic chemical groups that will form chemical bonds with primary amines. These include isothiocyanates, isocyanates, acyl azides, NHS esters, sulfo-NHS esters containing a sulfonate (—SO3) group, for example, bis(sulfosuccinimidyl)suberate (BS3), sulfonyl chlorides, aldehydes, glyoxals, epoxides, oxiranes, carbonates, aryl halides, imidoesters, carbodiimides, such as, for example 1-Ethyl-3-(3-dimethylaminopropyl)carbodiimide (EDC) or dicyclohexylcarbodiimide (DCC), anhydrides, and fluorophenyl esters.

In certain embodiments, any nucleic acid sequences according to the various aspects of the present invention can be codon optimized to adapt the sequence for optimum performance in a target organism or cell of interest. For example, a sequence may be codon optimized to allow a high transcription rate in a plant cell of interest of a plant genus of interest, or the sequences may be codon optimized for use in a mammalian, e.g., a murine or human cell.

According to the various embodiments of the present invention, the synthetic transcription factor and/or the at least one recognition domain may comprises a sequence set forth in any one of SEQ ID NOs: 1 to 94, or a sequence having at least 85%, 86%, 87%, 88%, 89%, 90%, 91%, 92%, 93%, 94%, 95%, 96%, 97%, 98%, or 99% identity over the whole length of any one of SEQ ID NOs: 1 to 94, or wherein the synthetic transcription factor and/or at least one recognition domain, binds to a regulation region set forth in SEQ ID NOs: 95 to 190, or a sequence having at least 85%, 86%, 87%, 88%, 89%, 90%, 91%, 92%, 93%, 94%, 95%, 96%, 97%, 98%, or 99% identity over the whole length of any one of SEQ ID NOs: 95 to 190.

Synthetic transcription activators according to the present invention, preferably specific for WUS and/or BBM, can be easily co-delivered with gene editing machineries and/or T-DNAs to improve transformation efficiencies in a plant cell and to induce regeneration of the transgenic plant. The present invention therefore further relates to methods for inducing regeneration of transformed plant cells by promoting the expression of growth-stimulating genes (morphogenic genes) such as, for example, BBM and WUS.

According to the various embodiments and aspects disclosed herein, the cellular system may be selected from the group consisting of at least one eukaryotic cell or eukaryotic organism, preferably wherein the at least one eukaryotic cell may be at least one plant cell, and/or wherein the at least one eukaryotic organism may be a plant or a part of a plant.

In certain embodiments disclosed herein, the cellular system to be modulated, transformed and/or transfected may be selected from the group consisting of at least one eukaryotic cell or eukaryotic organism, preferably wherein the at least one eukaryotic cell may be at least one plant cell, and/or wherein the at least one eukaryotic organism is a plant or a part of a plant.

In certain embodiments according to the various embodiments and aspects disclosed herein, the at least one part of the plant may be selected from the group consisting of leaves, stems, roots, emerged radicles, flowers, flower parts, petals, fruits, pollen, pollen tubes, anther filaments, ovules, embryo sacs, egg cells, ovaries, zygotes, embryos, zygotic embryos, somatic embryos, apical meristems, vascular bundles, pericycles, seeds, roots, and cuttings.

In embodiments, wherein the cellular system is, or originates from, a plant cell, the at least one plant or the at least one part of a plant may originate from a plant species selected from the group consisting of *Hordeum vulgare, Hordeum bulbusom, Sorghum bicolor, Saccharum officinarium, Zea mays, Setaria italica, Oryza minuta, Oriza sativa, Oryza australiensis, Oryza alta, Triticum aestivum, Secale cereale, Malus domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Cruchihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oleracia, Brassica rapa, Raphanus sativus, Brassica juncea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Astragalus sinicus, Lotus japonicas, Torenia fournieri, Allium cepa, Mum fistulosum, Allium sativum,* and *Allium tuberosum.*

In a further aspect of the present invention provides a method for increasing the transformation efficiency in a cellular system, wherein the method may comprise the steps of: (a) providing a cellular system; (b) introducing into the cellular system at least one synthetic transcription factor, or a nucleotide sequence encoding the same; and (c) introducing into the cellular system at least one nucleotide sequence of interest; (d) optionally: culturing the cellular system under conditions to obtain a transformed progeny of the cellular system; wherein the at least one synthetic transcription factor, or the nucleotide sequence encoding the same, comprises at least one recognition domain and at least one activation domain, wherein the synthetic transcription factor is configured to modulate the expression, preferably the transcription, of at least one morphogenic gene in the cellular system; and wherein the at least one synthetic transcription factor, or the nucleotide sequence encoding the same, is introduced in parallel to, or sequentially with the introduction of the at least one nucleotide sequence of interest.

The present invention therefore discloses methods of improving the efficiency of plant transformation or transfection and/or regeneration of plants by using synthetic transcription factors specific for endogenous morphogenic genes which can reprogram the cell and induce cell division in a large variety of plant species to provide reliable methods of transforming cellular systems, including those cellular systems known to be hard to modify and/or transform by currently available methods. In particular, certain elite lines comprising a highly valuable elite event (i.e., events very rarely achieved and, if at all, derived from an extraordinary and thus surprising event) and germplasm of said elite lines may be highly recalcitrant to in vitro culture and transformation attempts. Such genotypes usually do not produce an appropriate embryogenic or organogenic culture response on culture media developed to elicit such responses from typically suitable explants such as immature embryos. Furthermore, when exogenous DNA or other biomolecules are introduced into these immature embryos, no successful modification event may be recovered after cumbersome rounds of selection, or only so few events may be recovered as to make transformation of such a genotype impractical.

In one embodiment, the method may comprise that (a) the at least one synthetic transcription factor, or the sequence encoding the same and (b) the at least one nucleotide sequence of interest is/are introduced into the cellular system by means independently selected from biological and/or physical means, including transfection, transformation, including transformation by *Agrobacterium* spp., preferably, *Agrobacterium tumefaciens,* a viral vector, biolistic bombardment, transfection using chemical agents, including polyethylene glycol transfection, electro-poration, cell fusion or any combination thereof.

Therefore, an "introduction" or the process of "introducing" can comprise any biological, chemical and/or physical means of introducing or delivering a biomolecule into a cellular system of interest. Notably, any combination of introduction or delivery techniques may be applied. Furthermore, different components to be introduced into a cellular system of interest may be introduced by the same technique, simultaneously or subsequently, for example, by co-bombardment, or they may be introduced simultaneously or subsequently by different introduction techniques.

The increase in transformation efficiency according to the various aspects and embodiments of the present invention can comprise any statistically significant increase when compared to a control plant or cellular system. For example, an increase in transformation efficiency can comprises about 0.2%, 0.5%, 5%, 10%, 15%, 20%, 25%, 30%, 35%, 40%, 45%, 50%, 55%, 60%, 65%, 70%, 75%, 80%, 85%, 90%, 95%, 120%, 125% or greater increase when compared to a control plant or a control plant part, or a control cellular system. Alternatively, the increase in transformation efficiency can include about a 0.2 fold, 0.5 fold, 1 fold, 2 fold, 4 fold, 8 fold, 16 fold, or 32 fold or greater increase in transformation efficiency in the plant, plant part or cellular system when compared to a control plant or plant part or cellular system.

In one embodiment, the methods of the present invention may comprise that the at least one nucleotide sequence of interest is provided as part of at least one vector, or as at least one linear molecule.

In one embodiment of the methods disclosed herein, the at least one nucleotide sequence of interest may be selected from the group consisting of a transgene, a modified endogenous gene, a synthetic sequence, an intronic sequence, a coding sequence or a regulatory sequence.

In one embodiment of the methods disclosed herein, the at least one nucleotide sequence of interest may be a transgene, wherein the transgene may comprise a nucleotide sequence encoding a gene of a genome of an organism of interest, or at least a part of said gene.

In one embodiment, a regulatory sequence according to the present invention may be a promoter sequence, wherein the editing or mutation or modulation of the promoter comprises replacing the promoter, or promoter fragment with a different promoter (also referred to as replacement promoter) or promoter fragment (also referred to as replacement promoter fragment), wherein the promoter replacement results in any one of the following or any one combination of the following: an increased promoter activity, an increased promoter tissue specificity, a decreased promoter activity, a decreased promoter tissue specificity, a new promoter activity, an inducible promoter activity, an extended window of gene expression, a modification of the timing or developmental progress of gene expression in the same cell layer or other cell layer, for example, extending the timing of gene expression in the tapetum of anthers, a mutation of DNA binding elements and/or a deletion or addition of DNA binding elements. The promoter (or promoter fragment) to be modified can be a promoter (or promoter fragment) that is endogenous, artificial, pre-existing, or transgenic to the cell that is being edited. The replacement promoter or fragment thereof can be a promoter or fragment thereof that is endogenous, artificial, pre-existing, or transgenic to the cell that is being edited. Any other regulatory sequence according to the present disclosure may be modified as detailed for a promoter or promoter fragment above.

Particularly in case of plant genomes to be modified, it may be desirable that the modification as mediated by the methods of the present invention does not result in a genetically modified organism by integrating foreign DNA into the parent genome in an imprecise way, as environmental, regulatory and political issues have to be concerned. Therefore, the embodiments according to the present invention providing methods for introducing a genetic material of interest in a cellular system in a transient way are particularly suitable for providing a cellular system comprising a modification at a predetermined location without inserting foreign DNA and thus without providing a cell or organism regarded as genetically modified organism, as all tools necessary to perform the methods of the present invention can be provided to the cellular system in a transient way in active form.

In one embodiment of the methods described herein, transcriptional activation is combined with modification of a plant genome in a fully transiently manner, thereby obtaining a plant organism comprising a modification at a predetermined genetic location without inserting foreign DNA into the plant genome and thus providing a plant organism which is not regarded as a genetically modified organism. The methods described herein therefore provide means to modify a plant genome which do not require labor-intensive deregulation procedures. In yet another embodiment of the methods described herein, the STFs and/or the site-specific nuclease are provided DNA-free, e.g. as protein or RNP, thereby providing a regulatory benefit. In one embodiment of the various methods disclosed herein, the methods may be performed in a fully transient way. In other embodiments, the methods may be performed by a combination of stable and transient approaches. In yet a further embodiment, the methods may also be performed by stably introducing suitable delivery tools to a cell or cellular system of interest.

In another embodiment of the various aspects of the present invention, the at least one nucleotide sequence of interest to be introduced into a cellular system may be a transgene of an organism of interest, wherein the transgene or part of the transgene may be selected from the group consisting of a gene encoding resistance or tolerance to abiotic stress, including drought stress, osmotic stress, heat stress, cold stress, oxidative stress, heavy metal stress, nitrogen deficiency, phosphate deficiency, salt stress or waterlogging, herbicide resistance, including resistance to glyphosate, glufosinate/phosphinotricin, hygromycin, resistance or tolerance to 2,4-D, protoporphyrinogen oxidase (PPO) inhibitors, ALS inhibitors, and Dicamba, a gene encoding resistance or tolerance to biotic stress, including a viral resistance gene, a fungal resistance gene, a bacterial resistance gene, an insect resistance gene, or a gene encoding a yield related trait, including lodging resistance, flowering time, shattering resistance, seed color, endosperm composition, or nutritional content.

In another embodiment of the various aspects of the present invention, the at least one nucleotide sequence of interest may be at least part of a modified endogenous gene of an organism of interest, wherein the modified endogenous gene may comprise at least one deletion, insertion and/or substitution of at least one nucleotide in comparison to the nucleotide sequence of the unmodified endogenous gene.

In yet a further embodiment of the various aspects of the present invention, the at least one nucleotide sequence of interest may be at least part of a modified endogenous gene of an organism of interest, wherein the modified endogenous gene may comprise at least one of a truncation, duplication, substitution and/or deletion of at least one nucleotide position encoding a domain of the modified endogenous gene.

In one embodiment, the at least one nucleotide sequence of interest may be at least part of a regulatory sequence, wherein the regulatory sequence may comprise at least one of a core promoter sequence, a proximal promoter sequence, a cis regulatory sequence, a trans regulatory sequence, a locus control sequence, an insulator sequence, a silencer sequence, an enhancer sequence, a terminator sequence, and/or any combination thereof.

Any synthetic transcription factor as disclosed herein below can be used for the different methods according to the present invention as mediator to specifically modulate the transcription of a morphogenic gene of interest. This modulation, preferably a transcriptional upregulation, allows a better transformation efficiency of a cellular system, preferably a plant or plant part of interest.

According to the various embodiments of the methods disclosed herein, the preferred morphogenic gene to be modulated may be selected from the group consisting of BBM, WUS, including WUS2, a WOX gene, a WUS or BBM homologue, Lec1 Lec2, WIND1, ESR1, PLT3, PLT5, PLT7, IPT, IPT2, Knotted1, and RKD4.

Preferably, the morphogenic gene comprises a nucleotide sequence selected from the group consisting of (i) a nucleotide sequence set forth in any one of SEQ ID NOs: 199 to 237, (ii) a nucleotide sequence having the coding sequences of the nucleotide sequence set forth in any one of SEQ ID NOs: 199 to 237, (iii) a nucleotide sequence complementary to the nucleotide sequence of (i) or (ii), (iv) a nucleotide sequence having at least 50%, 60%, 70%, 75%, 80%, 85%, 90%, 91%, 92%, 93%, 94%, 95%, 96%, 97%, 98%, or 99% identity, preferably over the whole length, to the nucleotide sequence of (i), (ii) or (iii), (v) a nucleotide sequence hybridzing the nucleotide sequence of (iii) under stringent conditions, (vi) a nucleotide sequence encoding a protein comprising the amino acid sequence set forth in any one of SEQ ID NOs: 238 to 258, (vii) a nucleotide sequence encoding a protein comprising the amino acid sequence at least 50%, 60%, 70%, 75%, 80%, 85%, 90%, 91%, 92%, 93%, 94%, 95%, 96%, 97%, 98%, or 99% identical to a sequence set forth in any one of SEQ ID NOs: 238 to 258, or (viii) a nucleotide sequence encoding a homologue, analogue or orthologue of protein comprising the amino acid sequence set forth in any one of SEQ ID NOs: 238 to 258.

In certain embodiments, the synthetic transcription factor used in the methods of the present invention may be configured to modulate expression, preferably transcription, of the morphogenic gene by binding to a regulation region located at a certain distance in relation to the start codon.

In certain embodiments, the synthetic transcription factor and/or the at least one recognition domain used in the methods of the present invention may comprise a sequence set forth in any one of SEQ ID Nos: 1 to 94, or a sequence having at least 85%, 86%, 87%, 88%, 89%, 90%, 91%, 92%, 93%, 94%, 95%, 96%, 97%, 98%, or 99% identity over the whole length of any one of SEQ ID NOs: 1 to 94, or wherein the synthetic transcription factor and/or at least one recognition domain, binds to a regulation region set forth in SEQ ID NOs: 95 to 190 or a sequence having at least 85%, 86%, 87%, 88%, 89%, 90%, 91%, 92%, 93%, 94%, 95%, 96%, 97%, 98%, or 99% identity over the whole length of any one of SEQ ID NOs: 95 to 190.

In certain embodiments of the methods of the present invention, the cellular system may be selected from the group consisting of at least one eukaryotic cell or eukaryotic organism, preferably wherein the at least one eukaryotic cell may be at least one plant cell, and/or wherein the at least one eukaryotic organism is a plant or a part of a plant.

In other embodiments of the methods of the present invention, the at least one part of the plant may be selected from the group consisting of leaves, stems, roots, emerged radicles, flowers, flower parts, petals, fruits, pollen, pollen tubes, anther filaments, ovules, embryo sacs, egg cells, ovaries, zygotes, embryos, zygotic embryos, somatic embryos, apical meristems, vascular bundles, pericycles, seeds, roots, and cuttings.

In further embodiments of the methods of the present invention, the at least one plant cell, the at least one plant or the at least one part of a plant may originate from a plant species selected from the group consisting of *Hordeum vulgare, Hordeum bulbusom, Sorghum bicolor, Saccharum officinarium, Zea mays, Setaria italica, Oryza minuta, Oriza sativa, Oryza australiensis, Oryza alta, Triticum aestivum, Secale cereale, Malus domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oeleracia, Brassica rapa, Raphanus sativus, Brassica juncea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicerjudaicum, Cajanus cajanifolius, Cajanus scarabaeoides, Phaseolus vulgaris, Glycine max, Astragalus sinicus, Lotus japonicas, Torenia fournieri, Allium cepa, Allium fistulosum, Allium sativum*, and *Allium tuberosum*.

In a further aspect of the present invention, independently or together with the further aspects and embodiments disclosed herein, provides a method of modifying the genetic material of a cellular system at a predetermined location, wherein the method may comprise the following steps: (a) providing a cellular system; (b) introducing at least one synthetic transcription factor, or a sequence encoding the same, into the cellular system, (c) further introducing into the cellular system (i) at least one site-specific nuclease, or a sequence encoding the same, wherein the site-specific nuclease induces a double-strand break at the predetermined location; (ii) optionally: at least one nucleotide sequence of interest, preferably flanked by one or more homology sequence(s) complementary to one or more nucleotide sequence(s) adjacent to the predetermined location in the genetic material of the cellular system; and; (e) optionally: determining the presence of the modification at the predetermined location in the genetic material of the cellular system; and (f) obtaining a cellular system comprising a modification at the predetermined location of the genetic material of the cellular system; wherein the at least one synthetic transcription factor, or the nucleotide sequence encoding the same, comprises at least one recognition domain and at least one activation domain, wherein the at least one synthetic transcription factor is configured to modulate the expression, preferably the transcription, of at least one morphogenic gene in the cellular system; and wherein the at least one synthetic transcription factor, or the nucleotide sequence encoding the same, may be introduced in parallel to, or sequentially with the introduction of the at least one site-specific nuclease, or the sequence encoding the same and the optional at least one nucleotide sequence of interest.

This aspect and the associated embodiments thus synergistically combine the advantages of the targeted modulation of the transcription rate of at least one morphogenic gene of interest in a cellular system with a highly site-directed genome editing (GE) method of introducing certain effectors into the cell. By providing an environment within a cellular system comprising at least one synthetic transcription factor according to the present invention, it is thus possible to specifically modulate the transcription of at least one morphogenic gene in the cellular system before or simultaneously with the introduction of at least one site-specific nuclease (SSN), i.e., an enzyme comprising DNA double-strand, or DNA single-strand cleavage capability, or a sequence encoding the same, and optionally further tools like repair templates (RTs) to provide an environment, wherein the cellular system is highly transformation competent and further possesses a high regeneration capability. These factors guarantee a successful editing and regeneration of the such edited genetic material within a cellular system of interest and further allows regenerating a plant or plant material from the modified cellular system, as the cellular system is much more tolerant and viable during the GE event based on the co- or pre-treatment with at least one synthetic transcription factor, or a sequence encoding the same.

In one embodiment, the method further comprises the step of culturing the cellular system under conditions to obtain a genetically modified progeny of the modified cellular system.

The term "adjacent" or "adjacent to" as used herein in the context of the predetermined location and the one or more homology region(s) may comprise an upstream and a downstream adjacent region, or both. Therefore, the adjacent region is determined based on the genetic material of a cellular system to be modified, said material comprising the predetermined location.

There may be an upstream and/or downstream adjacent region near the predetermined location. For site-specific nucleases (SSNs) inducing blunt double-strand breaks (DSBs), the "predetermined location" will represent the site the DSB is induced within the genetic material in a cellular system of interest. For SSNs leaving overhangs after DSB induction, the predetermined location means the region between the cut in the 5' end on one strand and the 3' end on the other strand. The adjacent regions in the case of sticky end SSNs thus may be calculated using the two different DNA strands as reference. The term "adjacent to a predetermined location" thus may imply the upstream and/or downstream nucleotide positions in a genetic material to be modified, wherein the adjacent region is defined based on the genetic material of a cellular system before inducing a DSB or modification. Based on the different mechanisms of SSNs inducing DSBs, the "predetermined location" meaning the location a modification is made in a genetic material of interest may thus imply one specific position on the same strand for blunt DSBs, or the region on different strands between two cut sites for sticky cutting DSBs, or for nickases used as SSNs between the cut at the 5' position in one strand and at the 3' position in the other strand.

If present, the upstream adjacent region defines the region directly upstream of the 5' end of the cutting site of a site-specific nuclease of interest with reference to a predetermined location before initiating a double-strand break, e.g., during targeted genome engineering. Correspondingly, a downstream adjacent region defines the region directly downstream of the 3' end of the cutting site of a SSN of interest with reference to a predetermined location before initiating a double-strand break, e.g., during targeted genome engineering. The 5' end and the 3' end can be the same, depending on the site-specific nuclease of interest.

In certain embodiments, it may also be favorable to design at least one homology region in a distance away from the DSB to be induced, i.e., not directly flanking the predetermined location/the DSB site. In this scenario, the genomic sequence between the predetermined location and the homology sequence (the homology arm) would be "deleted" after homologous recombination had occurred, which may be preferred for certain strategies as this allows the targeted deletion of sequences near the DSB. Different kinds of RT configuration and design are thus contemplated according to the present invention for those embodiments relying on a RT. RTs may be used to introduce site-specific mutations, or RTs may be used for the site-specific integration of nucleic acid sequences of interest, or RTs may be used to assist a targeted deletion.

A "homology sequence(s)" introduced and the corresponding "adjacent region(s)" can each have varying and different length from about 15 bp to about 15.000 bp, i.e., an upstream homology region can have a different length in comparison to a downstream homology region. Only one homology region may be present. There is no real upper limit for the length of the homology region(s), which length is rather dictated by practical and technical issues. According to certain embodiments, depending on the nature of the RT and the targeted modification to be introduced, asymmetric homology regions may be preferred, i.e., homology regions, wherein the upstream and downstream flanking regions have varying length. In certain embodiments, only one upstream and downstream flanking region may be present.

In one embodiment according to the methods of the present invention, the at least one site-specific nuclease may comprise a zinc-finger nuclease, a transcription activator-like effector nuclease, a CRISPR/Cas system, including a CRISPR/Cas9 system, a CRISPR/Cfp1 system, a CRISPR/CasX system, a CRISPR/CasY system, an engineered homing endonuclease, and a meganuclease, and/or any combination, variant, or catalytically active fragment thereof.

Once expressed, the Cas9 protein and the gRNA form a ribonucleoprotein complex through interactions between the gRNA "scaffold" domain and surface-exposed positively-charged grooves on Cas9. Cas9 undergoes a conformational change upon gRNA binding that shifts the molecule from an inactive, non-DNA binding conformation, into an active DNA-binding conformation. Importantly, the "spacer" sequence of the gRNA remains free to interact with target DNA. The Cas9-gRNA complex will bind any genomic sequence with a PAM, but the extent to which the gRNA spacer matches the target DNA determines whether Cas9 will cut. Once the Cas9-gRNA complex binds a putative DNA target, a "seed" sequence at the 3' end of the gRNA targeting sequence begins to anneal to the target DNA. If the seed and target DNA sequences match, the gRNA will continue to anneal to the target DNA in a 3' to 5' direction (relative to the polarity of the gRNA).

CRISPR/Cas, e.g. CRISPR/Cas9, and likewise CRISPR/Cpf1 or CRISPR/CasX or CRISPR/CasY and other CRISPR systems are highly specific when gRNAs are designed correctly, but especially specificity is still a major concern, particularly for clinical uses or targeted plant GE based on the CRISPR technology. The specificity of the CRISPR system is determined in large part by how specific the gRNA targeting sequence is for the genomic target compared to the rest of the genome. Therefore, the methods according to the present invention when combined with the use of at least one CRISPR nuclease as site-specific nuclease and further combined with the use of a suitable CRISPR nucleic acid can provide a significantly more predictable outcome of GE. Whereas the CRISPR complex can mediate a highly precise cut of a genome or genetic material of a cell or cellular system at a specific site, the methods presented herein provide an additional control mechanism guaranteeing a programmable and predictable repair mechanism.

According to the various embodiments of the present invention, the above disclosure with respect to covalent and non-covalent association or attachment also applies for CRISPR nucleic acid sequences, which may comprise more than one portion, for example, a crRNA and a tracrRNA portion, which may be associated with each other as detailed above. In one embodiment, a RT nucleic acid sequence of the present invention may be placed within a CRISPR nucleic acid sequence of interest to form a hybrid nucleic acid sequence according to the present invention, which hybrid may be formed by covalent and non-covalent association.

In yet a further embodiment according to the various aspects of the present invention, the one or more nucleic acid sequence(s) flanking the at least one nucleic acid sequence of interest at the predetermined location may have at least 85%-100% complementarity to the one or more nucleic acid sequence(s) adjacent to the predetermined location, upstream and/or downstream from the predetermined location, over the entire length of the respective adjacent region(s).

Notably, a lower degree of homology or complementarity of the at least one flanking region may be used, e.g. at least 70%, at least 75%, at least 80%, at least 81%, at least 82%, at least 83%, or at least 84% homology/complementarity to at least one adjacent region in the genetic material of interest. For high precision GE relying on HDR template, i.e., a RT as disclosed herein, more than 95% homology/complementarity are favorable to achieve a highly targeted repair event. As shown in Rubnitz et al., Mol. Cell Biol., 1984, 4(11), 2253-2258, also very low sequence homology might suffice to obtain a homologous recombination. As it is known to the skilled person, the degree of complementarity will depend on the genetic material to be modified, the nature of the planned edit, the complexity and size of a genome, the number of potential off-target sites, the genetic background and the environment within a cell or cellular system to be modified.

In yet a further embodiment according to the various aspects of the present invention, the genetic material of the cellular system may be selected from the group consisting of a protoplast, a viral genome transferred in a recombinant host cell, a eukaryotic cell, tissue, or organ, preferably a plant cell, plant tissue or plant organ, and a eukaryotic organism, preferably a plant organism.

In one embodiment of the methods of the present invention, (i) the at least one synthetic transcription factor, or the sequence encoding the same; and (ii) the at least one site-specific nuclease, or the sequence including the same; and optionally (iii) the at least one nucleotide sequence of interest may be introduced into the cellular system by means independently selected from biological and/or physical means, including transfection, transformation, including transformation by *Agrobacterium* spp. transformation, preferably by *Agrobacterium tumefaciens*, a viral vector, biolistic bombardment, transfection using chemical agents, including polyethylene glycol transfection, or any combination thereof.

In one embodiment of the methods for modifying the genetic material of a cellular system at a predetermined location of the present invention, the at least one recognition domain may be or may be a fragment of a molecule selected from the group consisting of at least one TAL effector, at least one disarmed CRISPR/nuclease system, at least one Zinc-finger domain, and at least one disarmed homing endonuclease, or any combination thereof.

In one embodiment of the methods for modifying the genetic material of a cellular system at a predetermined location of the present invention, the at least one disarmed CRISPR/nuclease system may be selected from a CRISPR/dCas9 system, a CRISPR/dCpf1 system, a CRISPR/dCasX system or a CRISPR/dCasY system, or any combination thereof, wherein the at least one disarmed CRISPR/nuclease system may comprise at least one guide RNA, preferably a guide RNA optimized for the specific disarmed CRISPR/nuclease system and the specific target site within or near a morphogenic system to increase the recognition and/or binding properties of the synthetic transcription factor of the present invention.

In a further embodiment of the methods for modifying the genetic material of a cellular system at a predetermined location of the present invention, the at least one activation domain of the at least one synthetic transcription factor may be selected from the group consisting of an acidic transcriptional activation domain, preferably, wherein the at least one activation domain may be from a TAL effector gene of *Xanthomonas oryzae*, VP16 or tetrameric VP64 from Herpes simplex, VPR, SAM, Scaffold, Suntag, P300, VP160, or any combination thereof. In a preferred embodiment of the methods for modifying the genetic material of a cellular system at a predetermined location of the present invention, the at least one activation domain is VP64.

In another embodiment of the methods for modifying the genetic material of a cellular system at a predetermined location of the present invention, the at least one activation domain of the at least one synthetic transcription factor may be located N-terminal and/or C-terminal relative to the at least one recognition domain of the at least one synthetic transcription factor.

In yet a further embodiment of the methods for modifying the genetic material of a cellular system at a predetermined location of the present invention, the at least one morphogenic gene may be selected from the group consisting of BBM, WUS, including WUS2, a WOX gene, a WUS or BBM homologue, Lec1, Lec2, WIND1, ESR1, PLT3, PLT5, PLT7, IPT, IPT2, Knotted1, and RKD4.

In a further embodiment, there is provided the methods for modifying the genetic material of a cellular system at a predetermined location of the present invention, wherein the at least one morphogenic gene comprises a nucleotide sequence selected from the group consisting of (i) a nucleotide sequence set forth in any one of SEQ ID NOs: 199 to 237, (ii) a nucleotide sequence having the coding sequences of the nucleotide sequence set forth in any one of SEQ ID NOs: 199 to 237, (iii) a nucleotide sequence complementary to the nucleotide sequence of (i) or (ii), (iv) a nucleotide sequence having at least 50%, 60%, 70%, 75%, 80%, 85%, 90%, 91%, 92%, 93%, 94%, 95%, 96%, 97%, 98%, or 99% identity, preferably over the whole length, to the nucleotide sequence of (i), (ii) or (iii), (v) a nucleotide sequence hybridzing the nucleotide sequence of (iii) under stringent conditions, (vi) a nucleotide sequence encoding a protein comprising the amino acid sequence set forth in any one of SEQ ID NOs: 238 to 258, (vii) a nucleotide sequence encoding a protein comprising the amino acid sequence at least 50%, 60%, 70%, 75%, 80%, 85%, 90%, 91%, 92%, 93%, 94%, 95%, 96%, 97%, 98%, or 99% identical to a sequence set forth in any one of SEQ ID NOs: 238 to 258, or (viii) a nucleotide sequence encoding a homologue, analogue or orthologue of protein comprising the amino acid sequence set forth in any one of SEQ ID NOs: 238 to 258.

In still another embodiment of the methods for modifying the genetic material of a cellular system at a predetermined location of the present invention, the synthetic transcription factor may be configured to modulate expression, preferably transcription, of the morphogenic gene by binding to a regulation region located at a certain distance in relation to the start codon.

In one embodiment of the methods for modifying the genetic material of a cellular system at a predetermined location of the present invention, the synthetic transcription factor and/or the at least one recognition domain comprises a sequence set forth in any one of SEQ ID NOs: 1 to 94, or a sequence having at least 85%, 86%, 87%, 88%, 89%, 90%, 91%, 92%, 93%, 94%, 95%, 96%, 97%, 98%, or 99% identity over the whole length of any one of SEQ ID NOs: 1 to 94, or wherein the synthetic transcription factor and/or at least one recognition domain, binds to a regulation region set forth in SEQ ID NOs: 95 to 190, or a sequence having at least 85%, 86%, 87%, 88%, 89%, 90%, 91%, 92%, 93%, 94%, 95%, 96%, 97%, 98%, or 99% identity over the whole length of any one of SEQ ID NOs: 95 to 190.

In another embodiment of the methods for modifying the genetic material of a cellular system at a predetermined location of the present invention, the cellular system may be selected from the group consisting of at least one eukaryotic cell or eukaryotic organism, preferably wherein the at least one eukaryotic cell may be at least one plant cell, and/or wherein the at least one eukaryotic organism is a plant or a part of a plant.

In yet another embodiment of the methods for modifying the genetic material of a cellular system at a predetermined location of the present invention, the one or more nucleotide sequence(s) flanking the at least one nucleotide sequence of interest at the predetermined location may be at least 85%-100% complementary to the one or more nucleotide sequence(s) adjacent to the predetermined location, upstream and/or downstream from the predetermined location, over the entire length of the respective adjacent region(s).

In one embodiment of the methods for modifying the genetic material of a cellular system at a predetermined location of the present invention, the at least one nucleotide sequence of interest may be selected from the group consisting of: a transgene, a modified endogenous gene, a synthetic sequence, an intronic sequence, a coding sequence or a regulatory sequence. If the at least one nucleotide sequence of interest is a transgene, the transgene may comprise a nucleotide sequence encoding a gene of a genome of an organism of interest, or at least a part of said gene.

In another embodiment of the methods for modifying the genetic material of a cellular system at a predetermined location of the present invention, the at least one nucleotide sequence of interest may be a transgene of an organism of interest, wherein the transgene or part of the transgene may selected from the group consisting of a gene encoding resistance or tolerance to abiotic stress, including drought stress, osmotic stress, heat stress, cold stress, oxidative stress, heavy metal stress, nitrogen deficiency, phosphate deficiency, salt stress or waterlogging, herbicide resistance, including resistance to glyphosate, glufosinate/phosphinotricin, hygromycin, resistance or tolerance to 2,4-D, protoporphyrinogen oxidase (PPO) inhibitors, ALS inhibitors, and Dicamba, a gene encoding resistance or tolerance to biotic stress, including a viral resistance gene, a fungal resistance gene, a bacterial resistance gene, an insect resistance gene, or a gene encoding a yield related trait, including lodging resistance, flowering time, shattering resistance, seed color, endosperm composition, or nutritional content.

In yet another embodiment of the methods for modifying the genetic material of a cellular system at a predetermined location of the present invention, the at least one nucleotide sequence of interest may be at least part of a modified endogenous gene of an organism of interest, wherein the modified endogenous gene may comprise at least one deletion, insertion and/or substitution of at least one nucleotide in comparison to the nucleotide sequence of the unmodified endogenous gene, and/or the at least one nucleotide sequence of interest may be at least part of a modified endogenous gene of an organism of interest, wherein the modified endogenous gene may comprise at least one of a truncation, duplication, substitution and/or deletion of at least one nucleotide position encoding a domain of the modified endogenous gene.

In still another embodiment of the methods for modifying the genetic material of a cellular system at a predetermined location of the present invention, the at least one nucleotide sequence of interest may be at least part of a regulatory sequence, wherein the regulatory sequence may comprise at least one of a core promoter sequence, a proximal promoter sequence, a cis regulatory sequence, a trans regulatory sequence, a locus control sequence, an insulator sequence, a silencer sequence, an enhancer sequence, a terminator sequence, and/or any combination thereof.

Further provided is an embodiment of the methods according to the various aspects disclosed herein, wherein the at least one site-specific nuclease or a catalytically active fragment thereof, may be introduced into the cellular system as a nucleic acid sequence encoding the site-specific nuclease or the catalytically active fragment thereof, wherein the nucleic acid sequence is part of at least one vector, or wherein the at least one site-specific nuclease or the catalytically active fragment thereof, is introduced into the cellular system as at least one amino acid sequence. In one embodiment, the at least one site-specific nuclease may be introduces as translatable RNA. In yet a further embodiment, the at least one site-specific nuclease may be introduced as part of a complex together with at least one further biomolecule, for example, a gRNA, the gRNA optionally being associated with a RT comprising or being associated with the at least one nucleic acid sequence of interest to be introduced into the cellular system.

In another aspect of the present invention, there is provided a method of selecting an optimum synthetic transcription factor (STF) for modulating, preferably activating, the expression of at least one gene of interest, preferably a morphogenic gene, wherein the method comprises (i) defining a gene of interest; (ii) defining and providing at least one recognition domain, wherein the recognition domain is designed to recognize a recognition site at or near the gene of interest; (iii) defining and providing at least one activation domain; (iv) optionally: providing at least one further element, the element being selected from at least one promoter, at least one NLS, at least one transactivation domain, and/or at least one tag; (iv) providing at least two STFs targeting the same gene of interest; (v) measuring the modulation rate of each individual STF tested; (vi) selecting the STF with the best molduation rate for a given gene of interest. Furthermore, the method described herein, may also be used to select at least two optimum STFs for modulating to finetune transcription of at least two morphogenic gene of interest and to increase transformation and regeneration.

According to the various embodiments provided herein and due to the modular nature of the STFs, more than one STF can be designed for molduating a given gene of interest. Due to sterical issues and potential off-target effects in complex eukaryotic genomes it might thus be favorable to provide different STFs comprising a different number of domains and a different domain architecture, e.g., by domain shuffling, or by testing a TALE-based versus a CRISPR-based STF, to ultimately select the best STF for a target gene of choice.

In another aspect of the present invention, there is provided a method of producing a haploid or double haploid organism or cellular system, wherein the method may comprise the following steps: (a) providing a haploid cellular system; (b) introducing into the haploid cellular system at least one synthetic transcription factor, or a nucleotide sequence encoding the same; (c) culturing the haploid cellular system under conditions to obtain at least one haploid or double haploid organism; and (d) optionally: selecting the at least one haploid or double haploid organism obtained in step (c), wherein the at least one synthetic transcription factor, or the nucleotide sequence encoding the same, may comprise at least one recognition domain and at least one activation domain, wherein the at least one synthetic transcription factor may be configured to modulate the expression, preferably the transcription, of at least one morphogenic gene in the haploid cellular system.

As haploids are homozygous at all loci and can represent a new variety (self-pollinated crops) or parental inbred line for the production of hybrid varieties (cross-pollinated crops) which makes them attractive cell types in plant breeding programs. Still, haploids are usually smaller and exhibit lower plant vigor compared to wild-type donor plants and are sterile due to the inability of their chromosomes to pair during meiosis. Therefore, the synthetic transcription factors and methods provided herein can be used in the development of haploid cells, cellular systems and plants, as the introduction of at least one synthetic transcription factor, or a nucleotide sequence encoding the same of the present invention into a haploid cellular system can dramatically increase the reproductive capabilities of the haploid cellular system to develop into a haploid embryo, which in turn can be used as basis for haploid and double haploid plants.

A "double haploid" cell, cellular system or organism is obtained through spontaneous chromosome doubling during the step of culturing a haploid cell or cellular system, or through induced chromosome doubling after selecting the obtained haploid organism. The terms "double haploid" and "doubled haploid" are used interchangeably herein.

In one embodiment, the method of producing a haploid or double haploid organism may use a haploid embryo as a haploid cellular system, or the at least one haploid or double haploid organism may be obtained through an intermediate step of generating at least one haploid embryo from the haploid cellular system.

Many plant cells have the ability to regenerate a complete organism from only single cells or tissues. This process is usually referred to as totipotency. A wide variety of cells have the potential to develop into embryos, including haploid gametophytic cells, such as the cells of pollen and embryo sacs (see Forster, B. P., et al. (2007) Trends Plant Sci. 12: 368-375 and Segui-Simarro, J. M. (2010) Bot. Rev. 76: 377-404), as well as somatic cells derived from all three tissue layers of the plant (Gaj, M. D. (2004) Plant Growth Regul. 43: 27-47 or Rose, R., et al. (2010) "Developmental biology of somatic embryogenesis" in: Plant Developmental Biology-Biotechnological Perspectives, Pua E-C and Davey M R, Eds. (Berlin Heidelberg: Springer), pp. 3-26). Embryo development also occurs in the absence of egg cell fertilisation during apomixis, a type of asexual seed development. Totipotency in apomictic plants is restricted to the gametophytic and sporophytic cells that normally contribute to the development of the seed and its precursors, including the unfertilised egg cell and surrounding sporophytic tissues (see Bicknell, R. A., and Koltunow, A. M. (2004) Plant Cell 16: S228-S245).

Notably, the phenomenon of totipotency of plant cells reaches its highest expression in tissue culture, i.e., in vitro. Therefore, relevant steps for haploid generation start from immature cell cultures in vitro which have to be treated under suitable conditions to induce embryogenesis. These steps usually are time-consuming and often rather inefficient, as only a small minority of cultured haploid cellular systems will mature to a morphological and cellular state, optionally comprising any further GE event, in a desired way. Assisted by the synthetic transcription factors and the methods disclosed herein, the generation of haploid and/or doubled haploid systems can thus be significantly enhanced, as the methods provide a cellular system having a much higher regenerative capability guaranteeing a higher frequency of positive events.

In one embodiment of the methods of producing a haploid or double haploid cellular system or organism, the methods may comprise an additional step of inducing microspore-derived embryogenesis. Microspore-derived embryogenesis is a unique process in which haploid, immature pollen (microspores) are induced by one or more stress treatments to form embryos in culture. These microspore-derived embryos can then be germinated and converted to homozygous doubled haploid plants by chromosome doubling agents and/or through spontaneous doubling. Double haploid production, as detailed above, is a major tool in plant breeding and trait discovery programs as it allows homozygous lines to be produced in a single generation. This quick route to homozygosity not only drastically reduces the breeding period, but also unmasks traits controlled by recessive alleles. Doubled haploids are widely used in crop improvement as parents for F1 hybrid seed production, to facilitate backcross conversion, for mutation breeding, and to generate immortal populations for molecular mapping studies.

The term "immature" as used herein in the context of a cellular system is intended to mean any immature cell or genetic material obtainable from a plant. "Immature" cells or cellular systems may include male or female immature cells, or immature vegetative cells. Immature female or male cells or cellular systems may be selected from immature embryos or immature callus tissue, male gametophyte, e.g., microspore, or vegetative, generative or sperm cells of the pollen grain, or female gametophytes, including a megaspore and its derivatives, including the egg cell, the polar nuclei, the central cell, the synergids, the antipodals. The female gametophyte material may be comprised in an ovule and the ovule may represent a cellular system according to the present invention. Where a microspsore is used as haploid cellular system of the present invention, a callus may be formed which may then undergo organogenesis to form an embryo.

Methods for obtaining haploid and double haploid cellular systems and organisms using chemical approaches are known to the skilled person (see, for example, WO 2015/044199 A1). According to certain embodiments of the methods for producing a haploid cellular system, the methods may thus comprise an additional step of treating or culturing a haploid cellular system prior to introducing into the haploid cellular system at least one synthetic transcription factor, or a nucleotide sequence encoding the same of the present invention, wherein the additional step of treating or culturing may comprise adding a histone deacetylase inhibitor or at least one chemical to the developing cellular system. A histone deacetylase inhibitor (HDACi) is preferably a compound which is capable of interacting with a histone deacetylase and inhibiting its enzymatic activity, thereby reducing the ability of a histone deacetylase to remove an acetyl group from a histone and may include, for example, hydroxamic acids (other than salicyl hydroxamic acid), cyclic tetrapeptides, aliphatic acids, benzamides, polyphenols or electrophilic ketones, trichostatin A (TSA), butyric acid, a butyrate salt, potassium butyrate, sodium butyrate, ammonium butyrate, lithium butyrate, phenylbutyrate, sodium phenylbutyrate or sodium n-butyrate, wherein the term butyric acid in the context of this specification does not include isobutyric acid or $\alpha,\beta$-dichlorobutyric acid, or suberoylanilide hydroxamic acid all compounds being commercially available.

In another embodiment, physical stress may be applied to the haploid cellular system or organism. The physical stress may be any of temperature, darkness, light or ionizing radiation, for example. The light may be full spectrum sunlight, or one or more frequencies selected from the visible, infrared or UV spectrum. One or more physical stresses or combinations of stress may be used. The stresses may be continuous or interrupted (periodic); regular or random over time. When stresses are combined over time they may be simultaneous (coterminous or partly overlapping) or separate.

In a further embodiment, an additional step of adding chemical stress may be applied in the methods of the present invention. Haploid embryo development or microspore embryogenesis, pollen embryogenesis or androgenesis, can thus be additionally induced by exposing anthers or isolated gametophytes to abiotic or chemical stress during in vitro culture (Touraev, A., et al (1997) Trends Plant Sci. 2: 297-302).

In a further embodiment the method of producing a haploid cellular system or organism may comprise an additional step of generating at least one doubled haploid cellular system or organism from the haploid cellular system.

In yet a further embodiment the method of producing a haploid or double haploid cellular system or organism may comprises an additional step of generating seedling from the at least one haploid cellular system or organism, or from the at least one doubled haploid cellular system or organism. The ability of haploid embryos to convert spontaneously or after treatment with chromosome doubling agents to double-haploid plants is widely exploited and known to the skilled person (Touraev, A., et al. (1997) Trends Plant Sci. 2: 297-302; Forster et al. (2007) supra). In certain embodiments, haploid embryogenesis and chromosome doubling may take place substantially simultaneously. In other embodiments, there may be a time delay between haploid embryogenesis and chromosome doubling. The time delay may relate to the developmental stage reached by the growing haploid embryo, seedling or plantlet. Should growth of haploid seedlings, plants or plantlets not involve a spontaneous chromosome doubling event, then a chemical chromosome doubling agent may be used in accordance with procedures which the average skilled person will be familiar with. Chromosome doubling and chromosome doubling agents suitable according to the various aspects and embodiments of the present invention are provided in Segui-Simarro J. M., & Nuez F. (2008) Cytogenet. Genome Res. 120: 358-369). Suitable chromosome doubling agents include, for example, colchicine, anti-microtubule agents or anti-microtubule herbicides such as pronamide, nitrous oxide, or any mitotic inhibitor. Where colchicine is used, the concentration in the medium may be generally 0.01%-0.2% or approximately 0.05% or APM (5-225 µM). The range of colchicine concentration may be from about 400-600 mg/L or about 500 mg/L. Where pronamide is used the medium concentration may be about 0.5-20 µM. Other agents such as DMSO, adjuvants or surfactants may be used with the mitotic inhibitors to improve doubling efficiency. Common or trade names of suitable chromosome doubling agents include: colchicine, acetyltrimethylcolchicinic acid derivatives, carbetamide, chloropropham, propham, pronamide/propyzamide tebutam, chlorthal dimethyl (DCPA), Dicamba/dianat/disugran (dicamba-methyl) (BANVEL, CLARITY), benfluralin/benefin/(BALAN), butralin, chloralin, dinitramine, ethalfluralin (Sonalan), fluchloralin, isopropalin, methalpropalin, nitralin, oryzalin (SURFLAN), pendimethalin, (PROWL), prodiamine, profluralin, trifluralin (TREFLAN, TRIFIC, TRILLIN), AMP (Amiprofos methyl); amiprophos-methyl Butamifos, Dithiopyr and Thiazopyr. The result of applying said agents is a homozygous double haploid cell or cellular system, organism.

In one embodiment of the above methods, the at least one synthetic transcription factor, or a sequence encoding the same may be introduced into the haploid cellular system by means independently selected from biological and/or physical means, including transfection, transformation, including transformation by *Agrobacterium* spp. transformation, preferably by *Agrobacterium tumefaciens*, a viral vector, biolistic bombardment, transfection using chemical agents, including polyethylene glycol transfection, or any combination thereof.

In preferred embodiment, the method of providing a haploid or double haploid cellular system or organism may utilize at least one synthetic transcription factor comprising at least one recognition and at least one activation domain as further disclosed herein above, wherein said embodiments and aspects relating to a synthetic transcription factor of the present invention may be employed to provide optimized methods for obtaining a haploid or a doubled haploid cellular system or organism.

Preferred morphogenic genes to be modified according to the methods disclosed herein may be selected from the group consisting of BBM, WUS, a WOX gene, a WUS or BBM homologue, Lec1, Lec2, WIND1, ESR1, PLT3, PLT5, PLT7, IPT, IPT2, Knotted1, and RKD4. More preferred morphogenic genes to be modified according to the methods disclosed herein may be a gene comprising a nucleotide sequence selected from the group consisting of (i) a nucleotide sequence set forth in any one of SEQ ID NOs: 199 to 237, (ii) a nucleotide sequence having the coding sequences of the nucleotide sequence set forth in any one of SEQ ID NOs: 199 to 237, (iii) a nucleotide sequence complementary to the nucleotide sequence of (i) or (ii), (iv) a nucleotide sequence having at least 50%, 60%, 70%, 75%, 80%, 85%, 90%, 91%, 92%, 93%, 94%, 95%, 96%, 97%, 98%, or 99% identity, preferably over the whole length, to the nucleotide sequence of (i), (ii) or (iii), (v) a nucleotide sequence hybridzing the nucleotide sequence of (iii) under stringent conditions, (vi) a nucleotide sequence encoding a protein comprising the amino acid sequence set forth in any one of SEQ ID NOs: 238 to 258, (vii) a nucleotide sequence encoding a protein comprising the amino acid sequence at least 50%, 60%, 70%, 75%, 80%, 85%, 90%, 91%, 92%, 93%, 94%, 95%, 96%, 97%, 98%, or 99% identical to a sequence set forth in any one of SEQ ID NOs: 238 to 258, or (viii) a nucleotide sequence encoding a homologue, analogue or orthologue of protein comprising the amino acid sequence set forth in any one of SEQ ID NOs: 238 to 258.

In one embodiment, the at least one haploid cellular system may be selected from the group consisting of at least one eukaryotic cell or eukaryotic organism, preferably wherein the at least one eukaryotic cell may be at least one plant cell, and/or wherein the at least one eukaryotic organism may be a plant or a part of a plant.

In a further embodiment, the at least one part of the plant may be selected from the group consisting of leaves, stems, roots, emerged radicles, flowers, flower parts, petals, fruits, pollen, pollen tubes, anther filaments, ovules, embryo sacs, egg cells, ovaries, zygotes, embryos, zygotic embryos, somatic embryos, apical meristems, pericycles, and seeds.

In a further embodiment, the plant cell, the at least one plant or part of a plant originates from a plant species which may be selected from the group consisting of *Hordeum vulgare, Hordeum bulbusom, Sorghum bicolor, Saccharum officinarium, Zea mays, Setaria italica, Oryza minuta, Oriza sativa, Oryza australiensis, Oryza alta, Triticum aestivum, Secale cereale, Malus domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oeleracia, Brassica rapa, Raphanus sativus, Brassica juncea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Astragalus sinicus, Lotus japonicas, Torenia fournieri, Allium cepa, Allium fistulosum, Allium sativum*, and *Allium tuberosum*.

In one aspect of the present invention, at least one cellular system, at least one haploid cellular system and/or at least one haploid or double (d) haploid cellular system or organism may be provided obtainable by the methods disclosed herein using at least one synthetic transcription factor specifically modulating the transcription of at least one morphogenic gene of interest. The cellular system such obtained may then be used for further genome editing methods as used herein, or for regenerating a plant from the modified cellular system.

In one aspect of the present invention, there is provided a method or use based on a synthetic transcription factor, or a sequence encoding the same, according to the various methods as disclosed herein.

Due to the modular character of the synthetic transcription factors disclosed herein, there may also be provided at least one synthetic transcription factor comprising at least one recognition domain as disclosed herein and further comprising a silencing domain. The silencing domain thus substitutes the activation domain to provide a highly specific synthetic transcription factor for modulating, in this setting decreasing, the transcription of a gene of interest.

Transcriptional repression in eukaryotes is achieved through "silencers", of which there are different types, namely "silencer elements" and "negative regulatory elements" (NREs). Silencer elements are classical, position-independent elements that direct an active repression mechanism, and NREs are position-dependent elements that direct a passive repression mechanism. In addition, "repressors" are DNA-binding transcription factors that interact directly with silencers. The silencer itself and its context within a given promoter, rather than the interacting repressor, usually determines the mechanism of repression. Silencers form an intrinsic part of many eukaryotic promoters and are thus highly important for gene regulation in eukaryotes, including plant and animal cells. Silencer elements can be located in the 5' or 3' direction relative to a transcription initiation site.

Therefore, the synthetic transcription factors of the present invention, or a nucleotide sequence encoding the same, can also comprise at least one recognition domain and at least one silencing domain, wherein the synthetic transcription factor is configured to modulate the expression of a morphogenic gene in a cell or cellular system of interest, preferably in a plant cell.

In one aspect there is provided a method for producing a transgenic cellular system or organism comprising performing any of the method as detailed herein, wherein the method further comprises the regeneration of a cellular system or organism comprising at least one nucleotide sequence of interest as a transgene. A "transgene" in this context refers to any nucleic acid sequence artificially introduced into a cell, cellular system or organism.

According to certain embodiments, the method for producing a transgenic cellular system or organism may preferably use the synthetic transcription factors as disclosed herein to obtain a higher transformation frequency and/or regeneration rate of the such transformed material.

In yet another aspect there is provided a method for producing a genetically modified cellular system or organism, wherein the method may comprise performing a method of modifying the genetic material of a cellular system at a predetermined location detailed herein above, wherein the method further comprises the regeneration of a cellular system or organism comprising a modification at a predetermined location in the genetic material of the cellular system or organism. Again, said methods rely on the use of a synthetic transcription factor according to the various aspects and embodiments of the present invention. This aspect can be advantageously used for the transient introduction of at least one construct or genetic material into a cell or cellular system of interest to modify the transcription of a gene of interest, preferably a morphogenic gene, in a targeted way to boost the regenerability of the targeted cell or cellular system potentially harboring the insertion and/or deletion and/or edit. This, in turn, dramatically decreases the number of cells to be screened for a positive genetic modification or edit.

In one embodiment according to the various aspects of the present invention, the at least one nucleic acid sequence of interest may be provided as part of at least one vector, or as at least one linear molecule. In another aspect, the at least one nucleic acid sequence of interest may be provided as a complex, preferably a complex physically associating the at least one nucleic acid sequence and another RT, and/or with a gRNA, and/or with a site-specific nuclease. The at least one nucleic acid sequence of interest may further comprise a sequence allowing the rapid traceability, including the visual traceability, of the sequence of interest, e.g., a tag, including a fluorescent tag. The at least one nucleic acid sequence of interest may be double-stranded, single-stranded, or a mixture thereof. Furthermore, the at least one nucleic acid sequence of interest may comprise a mixture of DNA and RNA nucleotide, including also synthetic, i.e., non-naturally occurring nucleotides.

Delivery and analytical methods:

Any suitable delivery method to introduce at least one biomolecule into a cell or cellular system can be applied, depending on the cell or cellular system of interest. The term "introduction" as used herein thus implies a functional transport of a biomolecule or genetic construct (DNA, RNA, single- or double-stranded, protein, comprising natural and/or synthetic components, or a mixture thereof) into at least one cell or cellular system, which allows the transcription and/or translation and/or the catalytic activity and/or binding activity, including the binding of a nucleic acid molecule to another nucleic acid molecule, including DNA or RNA, or the binding of a protein to a target structure within the at least one cell or cellular system, and/or the catalytic activity of an enzyme such introduced, optionally after transcription and/or translation. Where pertinent, a functional integration of a genetic construct may take place in a certain cellular compartment of the at least one cell, including the nucleus, the cytosol, the mitochondrium, the chloroplast, the vacuole, the membrane, the cell wall and the like. Consequently, the term "functional integration" implies that a molecular complex of interest is introduced into the at least one cell or cellular system by any means of transformation, transfection or transduction by biological means, including *Agrobacterium* transformation, or physical means, including particle bombardment, as well as the subsequent step, wherein the molecular complex can exert its effect within or onto the at least one cell or cellular in which it was introduced regardless of whether the construct or complex is introduced in a stable or in a transient way.

According to the various embodiments, at least one STF according to the present invention may thus be provided in the form of at least one vector, e.g., a plasmid vector, as at least one linear molecule, or as at least one complex pre-assembled ex vivo.

Depending on the nature of the genetic construct or biomolecule to be introduced, said effect naturally can vary and including, alone or in combination, inter alia, the transcription of a DNA encoded by the genetic construct to a ribonucleic acid, the translation of an RNA to an amino acid sequence, the activity of an RNA molecule within a cell, comprising the activity of a guide RNA, a crRNA, a tracrRNA, or an miRNA or an siRNA for use in RNA interference, and/or a binding activity, including the binding of a nucleic acid molecule to another nucleic acid molecule, including DNA or RNA, or the binding of a protein to a target structure within the at least one cell, or including the integration of a sequence delivered via a vector or a genetic construct, either transiently or in a stable way. Said effect can also comprise the catalytic activity of an amino acid sequence representing an enzyme or a catalytically active portion thereof within the at least one cell and the like. Said effect achieved after functional integration of the molecular complex according to the present disclosure can depend on the presence of regulatory sequences or localization sequences which are comprised by the genetic construct of interest as it is known to the person skilled in the art.

A variety of suitable transient and stable delivery techniques suitable according to the methods of the present invention for introducing genetic material, biomolecules, including any kind of single-stranded and double-stranded DNA and/or RNA, or amino acids, synthetic or chemical substances, into a eukaryotic cell, preferably a plant cell, or into a cellular system comprising genetic material of interest, are known to the skilled person, and comprise inter alia choosing direct delivery techniques ranging from polyethylene glycol (PEG) treatment of protoplasts (Potrykus et al. 1985), procedures like electroporation (D'Halluin et al., 1992), microinjection (Neuhaus et al., 1987), silicon carbide fiber whisker technology (Kaeppler et al., 1992), viral vector mediated approaches (Gelvin, Nature Biotechnology 23, "Viral-mediated plant transformation gets a boost", 684-685 (2005)) and particle bombardment (see e.g. Sood et al., 2011, Biologia Plantarum, 55, 1-15). Transient transfection of mammalian cells with PEI is disclosed in Longo et al., Methods Enzymol., 2013, 529:227-240. Protocols for transformation of mammalian cells are disclosed in Methods in Molecular Biology, Nucleic Acids or Proteins, ed. John M. Walker, Springer Protocols.

For plant cells to be modified, despite transformation methods based on biological approaches, like *Agrobacterium* transformation or viral vector mediated plant transformation, and methods based on physical delivery methods, like particle bombardment or microinjection, have evolved as prominent techniques for introducing genetic material into a plant cell or tissue of interest. Helenius et al. ("Gene delivery into intact plants using the Helios™ Gene Gun", Plant Molecular Biology Reporter, 2000, 18 (3):287-288) discloses a particle bombardment as physical method for introducing material into a plant cell.

Currently, there thus exists a variety of plant transformation methods to introduce genetic material in the form of a genetic construct into a plant cell or cellular system of interest, comprising biological and physical means known to the skilled person on the field of plant biotechnology which are applicable to the various introduction techniques of biomolecules or complexes thereof according to the present invention. Notably, said delivery methods for transformation and transfection can be applied to introduce the tools of the present invention simultaneously. A common biological means is transformation with *Agrobacterium* spp. which has been used for decades for a variety of different plant materials. Viral vector mediated plant transformation represents a further strategy for introducing genetic material into a cell of interest. Physical means finding application in plant biology are particle bombardment, also named biolistic transfection or microparticle-mediated gene transfer, which refers to a physical delivery method for transferring a coated microparticle or nanoparticle comprising a nucleic acid or a genetic construct of interest into a target cell or tissue. Physical introduction means are suitable to introduce nucleic acids, i.e., RNA and/or DNA, and proteins. Likewise, specific transformation or transfection methods exist for specifically introducing a nucleic acid or an amino acid construct of interest into a plant cell, including electroporation, microinjection, nanoparticles, and cell-penetrating peptides (CPPs). Furthermore, chemical-based transfection methods exist to introduce genetic constructs and/or nucleic acids and/or proteins, comprising inter alia transfection with calcium phosphate, transfection using liposomes, e.g., cationic liposomes, or transfection with cationic polymers, including DEAD-dextran or polyethylenimine, or combinations thereof. Said delivery methods and delivery vehicles or cargos thus inherently differ from delivery tools as used for other eukaryotic cells, including animal and mammalian cells and every delivery method may have to be specifically fine-tuned and optimized for a construct of interest for introducing and/or modifying the genetic material of at least one cellular system, plant cell, tissue, organ, or whole plant; and/or can be introduced into a specific compartment of a target cell of interest in a fully functional and active way.

The above delivery techniques, alone or in combination, can be used for in vivo (in planta) or in vitro approaches. According to the various embodiments of the present invention, different delivery techniques may be combined with each other, simultaneously or subsequently, for example, using a chemical transfection for the at least synthetic transcription factor, or the sequence encoding the same, one site-specific nuclease, or a mRNA or DNA encoding the same, and optionally further molecules, for example, a gRNA, whereas this is combined with the transient provision of the (partial) inactivation(s) using an *Agrobacterium* based technique.

A synthetic transcription factor of the present invention may thus be introduced together with, before, or subsequently to the transformation and/or transfection of relevant tools for inducing a targeted genomic edit and/or further chemicals to induce haploid or doubled haploid development.

Likewise, methods for analyzing a successful transformation or transfection event according to the present invention are known to the person skilled in the art and comprise, but are not limited to polymerase chain reaction (PCR), including inter alia real time quantitative PCR, multiplex PCR, RT-PCR, nested PCR, analytical PCR and the like, microscopy, including bright and dark field microscopy, dispersion staining, phase contrast, fluorescence, confocal, differential interference contrast, deconvolution, electron microscopy, UV microscopy, IR microscopy, scanning probe microscopy, the analysis of plant or plant cell metabolites, RNA analysis, proteome analysis, functional assays for determining a functional integration, e.g. of a marker gene or a transgene of interest, or of a knock-out, Southern-Blot analysis, sequencing, including next generation sequencing, including deep sequencing or multiplex sequencing and the like, and combinations thereof.

In yet another embodiment of the above aspect according to the present invention, the introduction of a construct of interest is conducted using physical and/or biological means selected from the group consisting of a device suitable for particle bombardment, including a gene gun, including a hand-held gene gun (e.g. Helios® Gene Gun System, BIO-RAD) or a stationary gene gun, transformation, including transformation using *Agrobacterium* spp. or using a viral vector, microinjection, electroporation, whisker technology, including silicon carbide whisker technology, and transfection, or a combination thereof.

The practice of the disclosed methods employs, unless otherwise indicated, conventional techniques in molecular biology, biochemistry, genetics, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989; Ausubel et al., CURRENT PROTOCOLS IN MOLECULAR BIOLOGY, John Wiley & Sons, New York, 1987 and periodic updates; and the series METHODS IN ENZYMOLOGY, Academic Press, San Diego.

The present invention is further described with reference to the following non-limiting examples.

EXAMPLES

Example 1: TAL Transcription Factors for Transient Expression of Endogenous Morphogenic Genes in Zea mays (Zm)

In one example, commercially designed and constructed TAL transcription factors are used to transiently increase the expression of BBM and WUS. The TAL transcription factors are designed to bind to about 24 bp of the regulation region of BBM set forth in SEQ ID NO: 95, 109 to 147 and 217 to 219 and/or about 18 bp of the regulation region of WUS set forth in SEQ ID NO: 96, 148 to 190 (see FIGS. 3A and B). The TAL transcription factor recognition domains for BBM comprise a sequence set forth in SEQ ID NOs: 13 to 51 and/or the TAL transcription factor recognition domain for WUS comprise a sequence set forth in SEQ ID NO: 52 to 94.

The TAL Effector sequences can be designed and cloned, and an activation domain of Herpes simplex (VP16 or tetrameric VP64) can be added to the constructs in a fusion protein-like manner.

Transient induction of expression is first tested in maize protoplasts by PEG-mediated transformation and quantitative reverse transcriptase PCR or western blot against the ZmBBM and ZmWUS mRNA or protein respectively. To do this, 20 µg plasmid DNA encoding TALE transcription factors were delivered to approximately 600,000 protoplasts via a PEG-based transformation system commonly known in the art (see FIG. 4). The experiments were performed in triplicates and repeated four times (biological replicates). 24 hours after transformation, RNA was extracted and converted into cDNA using a commercially available kit. Expression of endogenous ZmWUS and ZmBBM was then determined using a SYBR Green qRT-PCR approach. The results clearly indicate that the synthetic transcription factors TALE1 (SEQ ID NO: 151) and TALE5 (SEQ ID NO: 218) are able to induce endogenous gene expression of WUS (60-fold induction) and BBM (490-fold induction), respectively (see FIGS. 4A and 4B).

Next, the phenotypic function of transient ZmWUS expression induced by TALE transcription factors was tested in regenerable tissue (see FIG. 5). Therefore, single cells of callus tissue from corn A188 were transformed by particle bombardment with the fluorescent marker tdT, TALE1 and PLT7 (PLT7 expression construct see also FIG. 6; PLT7 sequences: cDNA: SEQ ID NO: 273; amino acid sequence: SEQ ID NO: 274). Induction of cell proliferation was confirmed by fluorescent microscopy upon detection of the red fluorescent signal of tdTomato (see FIG. 5, white circle and arrow). The results clearly indicate that TALE transcription factors are able to induce regeneration and embryogenesis via transient expression of WUS and/or BBM.

Furthermore, quantitative reverse transcriptase PCR, or a western blot using a specific antibody against the ZmBBM and ZmWUS mRNA or protein, respectively, indicate the link between expression and embryogenic phenotype. The transient behavior of the expression can be detected by reverse transcriptase PCR or western blot against the ZmBBM and ZmWUS mRNA or protein respectively over time.

Example 2: Fusion Protein Between a Non-Functional CRISPR-Nuclease and an Activation Domain for Transient Expression of Endogenous Morphogenic Genes in Zea mays Similar to Example 1, a construct for transient delivery is designed, in this case expressing a dCas9 (PAM variants available) or dCpf1 (PAM variants available) as a fusion protein with an activation domain such as VP16 or VP64. Potential target sites/regulation regions include: Cas9 target sequences for ZmBBM set forth in SEQ ID Nos: 97 to 99; Cpf1 target sequences for ZmBBM set forth in SEQ ID Nos: 100 to 102; Cas9 target sequences for ZmWUS2 set forth in SEQ ID NOs: 103 to 105; Cpf1 target sequences for ZmWUS2 set forth in SEQ ID Nos: 106 to 108.

Based on the above described regulation regions for CRISPR/dCas9 and CRISPR/dCpf1, CRISPR based transcription factor systems can be designed and commercially obtained having a recognition domain comprising a sequence set forth in SEQ ID NOs: 1 to 12.

Transient induction of expression is first tested in maize protoplasts by PEG-mediated transformation and quantitative reverse transcriptase PCR, or western blot against the ZmBBM and ZmWUS mRNA or protein, respectively. The phenotypic function of transient ZmBBM and ZmWUS expression is then tested in regenerable tissue such as callus or immature embryos by either particle delivery or Agrobacterium mediated transformation. The successful induction of embryogenesis is recognizable by a skilled person. Furthermore, quantitative reverse transcriptase PCR, or western blot against the ZmBBM and ZmWUS mRNA or protein, respectively, indicate the link between expression and embryogenic phenotype.

The transient behavior of the expression can be detected by reverse transcriptase PCR or western blot against the ZmBBM and ZmWUS mRNA or protein respectively over time.

Example 3: Replacement of the Activating Domain for Optimized Expression of Morphogenic Genes This example is designed to test the behavior of different, previously described, activation domains in a systematic manner. This will allow assessing their effect on the level of expression of ZmWUS and ZmBBM. As detailed above, different STFs for a specific target gene of interest may comprise different activation and recognition domains and further elements. Therefore, it can be very suitable to design different STFs for one and the same target to ultimately define the best STF for modulating a gene of interest.

The natural activation domain of the TAL effector genes of Xanthomonas oryzae is the most obvious activation domain for use with in TAL transcription factors, and also represents one activation domain, which can be used, alone or in combination, according to the various aspects of the present invention, but have been used in other settings as well. They belong to a family of acidic (transcriptional) activation domains.

Other available activation domains have been previously tested in mammalian and insect cell systems (Chavez, Alejandro et al. "Comparative Analysis of Cas9 Activators Across Multiple Species" Nature methods 13.7 (2016): 563-567. PMC. Web. 22 Sep. 2017), but little is known about the optimum activation domains in a synthetic transcription factor to be used in a plant system, for the specific use of modulating transcription of a morphogenic gene of interest.

In this example, VP16 or VP64 in Examples 1 and 2 is replaced by either VPR, SAM, Scaffold, Suntag, P300, VP160, or a combination of at least two of these factors or VP16 and VP64 on either the N- or C-terminal or both terminal ends of the amino acid chain.

Assessment of the efficacy of activator domains in conjunction with either a TAL or dCas9 is done by quantitative reverse transcriptase PCR or western blot against the activated genes ZmBBM and ZmWUS, but it is ultimately assessed by the phenotypic response in callus or immature embryo.

Example 4: Replacement of the Recognition Domain for Increased Targeting Variability and Flexibility In this example, the TAL, dCas9, or dCpf1 from Examples 1, 2, and 3 are replaced with a sequence specific Zinc-Finger domain or homing endonuclease. As a fusion protein with the optimal activation domain identified in Example 3, it is possible to combine multiple transcriptional activators causing different intensities of expression for different genes. Solely relying on a dCas9 system, for example, might not allow specifically targeting of activation domains (at least for certain genes of interest) since the dCas9 or dCpf1 does not provide sufficient specificity in sgRNA binding. Specifically, dCas9 and dCpf1 systems are limited in target site specificity because they require a specific PAM motif in the regulation region of a target gene, which might not be present in at least certain genes of interest (Gao, L., et al. (2017). "Engineered Cpf1 variants with altered PAM specificities." Nat Biotech; and Kleinstiver, B. P., et al. (2015). "Engineered CRISPR-Cas9 nucleases with altered PAM specificities." Nature 523(7561): 481-485)). On the contrary, TAL transcription factors commonly require an initial T for target site recognition. Hence, in order to improve the binding to regulation regions of a specific target gene of interest which are difficult to access with e.g. a TAL STF, one could replace the TAL recognition domain with a dCpf1-based system in order to be able to narrow down the optimal distance to the ATG or to identify a wider target range to achieve enhanced transcriptional activation. Furthermore, the information obtained by the herein described experiments can be used to design and combine different STF systems for different endogenous regulation regions in order to improve transcriptional activation of at least one target gene of interest.

Another option to improve target site specificity and transcriptional activation is the combined use of at least two recognition domains specific for the same regulation region of the same target gene of interest (Bolukbasi, M. F., et al. (2015). "DNA-binding-domain fusions enhance the targeting range and precision of Cas9." Nat Meth 12(12): 1150-1156).

Assessment of the additional recognition domains in conjunction with the activators from Example 3 would again be done first by quantitative reverse transcriptase PCR or western blot against the activated genes ZmBBM and ZmWUS. Ultimately, it is assessed by the phenotypic response in callus or immature embryo.

Example 5: Morphogenic and Embryogenic Gene Targets Aside from ZmBBM and ZmWUS

Multiple genes have been described where transient overexpression in callus or immature embryos, but also leaf or other tissue, caused induction of embryogenesis. These genes or homologues thereof are individually or in a combined fashion used with the transcriptional activators in Examples 1 through 4. The list includes, but is not limited to WOX genes, other WUS and BBM homologues, Lec1 and Lec2, WIND1, ESR1, PLT3, PLT5, PLT7, IPT and IPT2, Knotted1, and RKD4 (see for example FIG. 5). Preferably, the synthetic transcription factor designed to regulate one of the morphogenic genes disclosed herein comprises a fusion of at least two activation domains to provide for optimum recognition properties which cannot be achieved with one activation domain (e.g., dCas9 or dCpf1) alone. Furthermore, at least two activation domains properly positioned to avoid steric hindrance and to allow for a high activation rate are present.

Example 6: Application of Transcriptional Activators for Morphogenic and Embryogenic Genes in Sugar Beet and Wheat The processes described in Examples 1 through 5 can be transferred to all relevant crops that have a transformation protocol involving an in vitro regeneration or tissue culture step. All procedures and optimization steps as well as target genes and homologues thereof including the assessment protocols described in Examples 1 through 5 can be transferred to other crop systems. The genomic sequences of the morphogenic and embryogenic genes have to be known so that it is possible to design targets for dCas9, dCpf1 (PAM variants available for both), TAL Effectors, Zinc Fingers, and homing endonucleases can be designed and tested. Preferably, the synthetic transcription factor comprises a fusion of at least two activation domains to provide for optimum recognition properties which cannot be achieved with one activation domain (e.g., dCas9 or dCpf1) alone. Furthermore, at least two activation domains properly positioned to avoid steric hindrance and to allow for a high activation rate are present.

Example 7: Quantitative Analysis of Increased ZmBBM and ZmWUS Transcription

The induction of BBM and WUS transcription can be measured by simple PCR system or a quantitative reverse transcriptase PCR. The advantage of the latter is the higher degree of normalization for absolute quantification of transcription. A simple PCR system would be preferably used for relative comparison of transcription against wildtype or between transformation events.

For measuring the transcriptional activation of BBM, a simple PCR assay is used. The primers are BBM-1 set forth in SEQ ID NO: 191 and BBM-2 set forth in SEQ ID NO: 192. Hot-Fire Polymerase is used in a 34 cycle PCR.

For measuring the transcriptional activation of WUS, a qRT-PCR (Taq-Man Assay) is used. The EF1 gene is used a reference. In a 40 cycle qPCR, ZmEF1 is amplified using the primers ZmEF1xxxr01 set forth in SEQ ID NO: 193 and ZmEF1xxxf01 as set forth in SEQ ID NO: 194 and detected by ZmEF1xxxMGB.1 set forth in SEQ ID NO: 195. ZmWUS is amplified using the primers WUSxxxFw1 set forth in SEQ ID NO: 196 and WUSxxxRv1 set forth in SEQ ID NO: 197 and detected by WUSxxxMGB set forth in SEQ ID NO: 198.

Statistical analysis can be performed by established and previously published methods.

Example 8: Delivery of Synthetic Transcription Factors and Verification of Increased Morphogenesis in Corn and Sugar Beet Callus and Immature Embryos Synthetic transcription factors as described in Examples 1 through 6 can be delivered either as DNA, RNA, or protein. Transformation of corn or sugar beet callus and immature embryos using DNA has been described and can be accomplished by either *Agrobacterium tumefaciens* or particle delivery. Transformation of DNA can be transient, meaning that the expression cassette is not integrated into the genome and therefore not inherited, or stable, meaning that the intention of transformation is to insert a transgene cassette. Synthetic or in vitro transcribed RNA can be delivered using bombardment. Protein delivery has been accomplished by either modified strains of *Agrobacterium tumefaciens* or particle delivery.

A gene or gene fragment or any other synthetic construct, e.g., including a suitable tag, transformed transiently or stably, can be introduced with or without a marker gene. Marker genes can aid in selection or screening of transformed cells or tissues. This can range from a fluorescent marker such as tdTomato to detect transformed cells to herbicide resistance genes that allow for positive selection.

A knowledgeable and skilled person can identify the effects of increased morphogenesis in corn or sugar beet tissues by eye or various forms of microscopy, i.e., by visual inspection. Typically, it is distinguishable by the increased cell division and the induction of embryogenesis in affected tissues. Embryogenesis results in the affected cells to be reprogrammed to an early embryonic developmental stage, even if they were somatic cells prior.

Depending on the effects detected, it will be potentially necessary to modify the transcription strength and expression profile to obtain the desired effect. This optimization might involve identifying the optimal transcriptional activator (Example 3), the target site (Examples 1 and 2), the promoters driving the expression, the method of delivery (Examples 8 and 10), the timing of delivery (possibility of using an inducible system), and other factors.

Example 9: Combination of Synthetic Transcription Factors with Gene Editing for Improved Rates of Regenerated Plants Harboring Edits The optimized transcriptional activators described in Examples 1 through 8 can be co-delivered with gene editing reagents or to T-DNA vectors. Typical transformation methods such as particle bombardment and *Agrobacterium* can be disadvantageous to the cells transformed or exposed. In light of the recent advances for transient activation of morphogenic genes, it is possible to co-deliver the T-DNA cassette with a plasmid containing the above described transcription factors. This gives the transformed or exposed cells an advantage instead of a disadvantage.

In this example, any plasmid encoded transient transcriptional activator from Examples 1 through 8 can be delivered by particle bombardment with an expression cassette containing a Cpf1 gene and a specifically designed crRNA (e.g. for a relevant trait gene). This cassette does not contain a resistance gene for selection. All plants regenerated from this callus are screened for the INDELs at the target site. Compared to the non-selected tissues that did not receive the transcriptional activator, we would expect the INDEL efficiency to be significantly lower.

Taking the successful edited plants to the next generation and reconfirming the modification by Cpf1 or other site-directed nucleases, we would expect to have higher counts of edited T1 plants than in the control.

Example 10: Protein-Based Co-Delivery of Synthetic Transcriptional Activators with Site-Directed Nuclease RNPs for Improved Transient Gene Editing In this example, the components of Example 9 are delivered into plant tissue such as callus or immature embryo as purified protein. The transcription factors described in Examples 1 through 8 are expressed in and purified from a pro- or eukaryotic cell system. Cpf1 is equally produced and incubated with synthetic or in vitro transcribed crRNA to form ribonucleoprotein (RNP). Protein delivery has been demonstrated by particle bombardment or fusion to cell penetrating peptides. It would be expected to get lower counts of edited T1 plants compared to Example 9. However, the complete absence of heritable material makes this approach highly desirable.

Example 11: Combination of Synthetic Transcription Factors with Base Editing for Improved Rates of Regenerated Plants Harboring Edits The optimized transcriptional activators described in Examples 1 through 8 are co-delivered with base editing reagents on co-bombarded DNA cassettes or on one or more T-DNA vectors harboring their expression cassettes. Typical transformation methods such as particle bombardment and *Agrobacterium* can be disadvantageous to the cells transformed or exposed. In light of the recent advances for transient activation of morphogenic genes, it is possible to co-deliver the T-DNA cassette with a plasmid containing the above described transcription factors. This gives the transformed or exposed cells an advantage instead of a disadvantage.

In this example, any plasmid-encoded transcriptional activator from Examples 1 through 8 can be delivered by particle bombardment with an expression cassette containing a base editor gene and a specifically designed guide RNA (e.g. for a relevant trait gene) to direct the base editor to the appropriate target. This cassette may or may not contain a resistance gene for selection. The base editor gene can encode a cytidine deaminase, an adenine deaminese, or another deaminase or other catalytic activity suitable for making base conversions. The base editor can further be based on any CRISPR domain suitable for delivering the base editing function to the target site. This can include, but is not limited to, Cas9, Cpf1, CasX, CasY, or other suitable domains. All plants regenerated from this callus are screened for base substitutions at the target site. Compared to cells that did not receive the transcriptional activator(s), we would expect the regeneration efficiency to be much higher.

Example 12: Protein-Based Co-Delivery of Synthetic Transcriptional Activators with Base Editor RNPs for Improved Transient Gene Editing In this example, the components of Example 11 are delivered into plant tissue such as callus or immature embryo as purified protein and RNA. The transcription factors described in Examples 1 through 8 are expressed in and purified from a pro- or eukaryotic cell system. The base editor is equally produced and incubated with synthetic or in vitro transcribed crRNA to form ribonucleoprotein (RNP). Protein delivery has been demonstrated by particle bombardment or fusion to cell penetrating peptides. It would be expected to get lower counts of edited T1 plants compared to Example 11. However, the complete absence of heritable material makes this approach highly desirable.

Example 13: Formation of Embryogenic Callus in Corn Promoted by Transient Delivery of Synthetic Transcriptional Activators To demonstrate the effect of the synthetic transcriptional activators, a biolistic maize transformation was conducted. Two independent biolistic transformations were conducted following a standard maize transformation protocol. The emersion of embryogenic callus was assessed four weeks after bombardment. As shown in FIG. 7A, about 5.5% of immature embryos showed embryogenic callus when mock-treated. Known morphogenic genes were delivered as a positive control (average 12.4%). Delivery of synthetic transcriptional activators for BBM and WUS2 under three different constitutive and tissue specific promoters showed an increase in embryogenic callus formation, but not to the level of the positive control. In said experiment the activity of all of the tested promoters was sufficient to increase the formation of embryogenic callus (FIGS. 7A and B).

Example 14: Induction of ZmWUS2 Promoter by Synthetic Transcriptional Activator in Leaf and Embryo Tissue In a biolistic delivery experiment, we showed that the synthetic transcriptional activator TALE1 induces expression of a fluorescent protein (tdTomato) under control of a WUS2 promoter (see FIG. 8). As shown in FIG. 9, the left panels show that the WUS2 promoter does not or only at very low intensity lead to expression of tdTomato in immature embryos of maize genotype A188 (upper panel) and in leaf tissue of A188 genotype (lower panel). When co-delivered with the synthetic transcriptional activator TALE1, tdTomato is expressed strongly in immature embryos (right upper panel) and notably in leaves (right lower panel).

The invention claimed is:

1. A synthetic transcription factor, or a nucleotide sequence encoding the same, comprising at least one recognition domain and at least one activation domain, wherein the synthetic transcription factor is configured to modulate the expression of an endogenous morphogenic gene in a cellular system, wherein the modulation is a targeted activation, and wherein:
   wherein the morphogenic gene comprises a nucleotide sequence selected from the group consisting of:
   (i) a nucleotide sequence set forth in any one of SEQ ID NOs: 199, 207, 217, 218, or 219;
   (ii) a nucleotide sequence having the coding sequences of the nucleotide sequence set forth in SEQ ID NOs: 199, 207, 217, 218, or 219;
   (iii) the nucleotide sequence complementary to the nucleotide sequence of (i) or (ii);
   (iv) a nucleotide sequence having at least 95% identity to the nucleotide sequence of (i), (ii) or (iii); and
   (v) a nucleotide sequence encoding a protein comprising the amino acid sequence set forth in any one of SEQ ID NOs: 238 to 240;
   and
   wherein the synthetic transcription factor comprises a nucleotide sequence selected from the group consisting of SEQ ID NO: 151 and SEQ ID NO: 218, and combinations thereof, and/or the at least one recognition domain comprises a sequence set forth in any one of SEQ ID NOs: 13 to 51 or SEQ ID NOs: 52 to 94, and
   wherein the synthetic transcription factor and/or the at least one recognition domain binds to a regulation region having the sequence set forth in SEQ ID NOs: 95, 109 to 147 or SEQ ID NOs: 96, 148 to 190.

2. The synthetic transcription factor of claim 1, wherein the at least one recognition domain is, or is a fragment, of at least one TAL effector.

3. The synthetic transcription factor of claim 1, wherein the at least one activation domain is selected from the group consisting of an acidic transcriptional activation domain from an TAL effector gene of *Xanthomonas oryzae*, VP16 or tetrameric VP64 from Herpes simplex, VPR, SAM, Scaffold, Suntag, P300, VP160, and any combination thereof.

4. The synthetic transcription factor of claim 1, wherein the at least one activation domain is located N-terminal and/or C-terminal relative to the at least one recognition domain.

5. The synthetic transcription factor of claim 1, wherein the synthetic transcription factor is configured to modulate expression of the morphogenic gene by binding to a regulation region located at a certain distance in relation to the start codon.

6. The synthetic transcription factor of claim 1, wherein the cellular system is selected from the group consisting of at least one eukaryotic cell or eukaryotic organism, at least one plant cell, and at least one plant or part of a plant.

7. The synthetic transcription factor of claim 6, wherein the at least one part of the plant is selected from the group consisting of leaves, stems, roots, emerged radicles, flowers, flower parts, petals, fruits, pollen, pollen tubes, anther filaments, ovules, embryo sacs, egg cells, ovaries, zygotes, embryos, zygotic embryos, somatic embryos, apical meristems, vascular bundles, pericycles, seeds, roots, and cuttings.

8. The synthetic transcription factor of claim 7, wherein the at least one plant cell, the at least one plant or the at least one part of a plant originates from a plant species selected from the group consisting of *Hordeum vulgare*, *Hordeum bulbusom*, *Sorghum bicolor*, *Saccharum officinarium*, *Zea mays*, *Setaria italica*, *Oryza minuta*, *Oriza sativa*, *Oryza australiensis*, *Oryza alta*, *Triticum aestivum*, *Secale cereale*, *Malta domestica*, *Brachypodium distachyon*, *Hordeum* marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oeleracia, Brassica rapa, Raphanus sativus, Brassica juncea, Brassica nigra, Eruca vesicaria subsp. sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Astragalus sinicus, Lotus japonicas, Torenia fournieri, Allium cepa, Allium fistulosum, Allium sativum, and Allium tuberosum.

9. A method for increasing the transformation efficiency in a cellular system, wherein the method comprises the steps of:
(a) providing a cellular system;
(b) introducing into the cellular system at least one synthetic transcription factor, or a nucleotide sequence encoding the same; and
(c) introducing into the cellular system at least one nucleotide sequence of interest;
(d) optionally culturing the cellular system under conditions to obtain a transformed progeny of the cellular system;
wherein the at least one synthetic transcription factor, or the nucleotide sequence encoding the same, comprises at least one recognition domain and at least one activation domain, wherein the synthetic transcription factor is configured to modulate the expression of at least one endogenous morphogenic gene in the cellular system;
wherein the at least one synthetic transcription factor, or the nucleotide sequence encoding the same, is introduced in parallel to, or sequentially with the introduction of the at least one nucleotide sequence of interest, wherein the modulation is a targeted activation, and wherein:
wherein the morphogenic gene comprises a nucleotide sequence selected from the group consisting of:
(i) a nucleotide sequence set forth in any one of SEQ ID NOs: 199, 207, 217, 218, or 219;
(ii) a nucleotide sequence having the coding sequences of the nucleotide sequence set forth in any one of SEQ ID NOs: 199, 207, 217, 218, or 219;
(iii) a nucleotide sequence complementary to the nucleotide sequence of (i) or (ii);
(iv) a nucleotide sequence having at least 95% identity to the nucleotide sequence of (i), (ii) or (iii); and
(v) a nucleotide sequence encoding a protein comprising the amino acid sequence set forth in any one of SEQ ID NOs: 238 to 240;
wherein the synthetic transcription factor comprises a nucleotide sequence selected from the group consisting of SEQ ID NO: 151 and SEQ ID NO: 218, and combinations thereof, and/or the at least one recognition domain comprises a sequence set forth in any one of SEQ ID NOs: 13 to 51 or SEQ ID NOs: 52 to 94, and wherein the synthetic transcription factor and/or the at least one recognition domain binds to a regulation region having the sequence set forth in SEQ ID NOs: 95, 109 to 147 or SEQ ID NOs: 96, 148 to 190.

10. The method of claim 9, wherein
(a) the at least one synthetic transcription factor, or the sequence encoding the same, or at least one component of the at least one synthetic transcription factor, or the sequence encoding the same; and
(b) the at least one nucleotide sequence of interest
is/are introduced into the cellular system by means independently selected from biological and/or physical means, including transfection, transformation, including transformation by *Agrobacterium* spp., a viral vector, biolistic bombardment, transfection using chemical agents, including polyethylene glycol transfection, or any combination thereof.

11. The method of claim 9, wherein the at least one recognition domain is or is part of at least one TAL effector.

12. The method of claim 9, wherein the at least one activation domain of the at least one synthetic transcription factor is selected from the group consisting of an acidic transcriptional activation domain from a TAL effector gene of *Xanthomonas oryzae*, VP16 or tetrameric VP64 from Herpes simplex, VPR, SAM, Scaffold, Suntag, P300, VP160, and any combination thereof.

13. The method of claim 9, wherein the at least one activation domain of the at least one synthetic transcription factor is located N-terminal and/or C-terminal relative to the at least one recognition domain of the at least one synthetic transcription factor.

14. The method of claim 9, wherein the synthetic transcription factor is configured to modulate expression of the morphogenic gene by binding to a regulation region located at a certain distance in relation to the start codon.

15. The method of claim 9, wherein the cellular system is selected from the group consisting of at least one eukaryotic cell or eukaryotic organism, at least one plant cell, and at least one plant or part of a plant.

16. The method of claim 15, wherein the at least one part of the plant is selected from the group consisting of leaves, stems, roots, emerged radicles, flowers, flower parts, petals, fruits, pollen, pollen tubes, anther filaments, ovules, embryo sacs, egg cells, ovaries, zygotes, embryos, zygotic embryos, somatic embryos, apical meristems, vascular bundles, pericycles, seeds, roots, and cuttings.

17. The method of claim 16, wherein the at least one plant cell, the at least one plant or the at least one part of a plant originates from a plant species selected from the group consisting of Hordeum vulgare, Hordeum bulbusom, Sorghum bicolor, Saccharum officinarium, Zea mays, Setaria italica, Oryza minuta, Oriza sativa, Oryza australiensis, Oryza alta, Triticum aestivum, Secale cereale, Malta domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oeleracia, Brassica rapa, Raphanus sativus, Brassica juncea, Brassica nigra, Eruca vesicaria subsp. sativa, Citrus sinensis, Jatropha curcas, Populus trichocarpa, Medicago truncatula, Cicer yamashitae, Cicer bijugum, Cicer arietinum, Cicer reticulatum, Cicer judaicum, *Cajanus cajanifohus, Cajanus scarabaeoides, Phaseolus vulgaris, Glycine max, Astragalus sinicus, Lotus japonicas, Torenia fournieri, Allium cepa, Allium fistulosum, Allium sativum*, and *Allium tuberosum*.

* * * * *

SEQUENCE LISTING

```
<160> NUMBER OF SEQ ID NOS: 278

<210> SEQ ID NO 1
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: synthetic construct

<400> SEQUENCE: 1
caccgcucug aucacaagca guuuuagagc uagaaauagc aaguuaaaau aaggcuaguc      60
cguuaucaac uugaaaaagu ggcaccgagu cggugcuuuu                          100

<210> SEQ ID NO 2
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: synthetic construct

<400> SEQUENCE: 2
cccauguguu guucuauccc guuuuagagc uagaaauagc aaguuaaaau aaggcuaguc      60
cguuaucaac uugaaaaagu ggcaccgagu cggugcuuuu                          100

<210> SEQ ID NO 3
<211> LENGTH: 100
<212> TYPE: RNA
<213> ORGANISM: Artificial Sequence
<220> FEATURE:
```

```
<223> OTHER INFORMATION: Description of Artificial Sequence: Synthetic
      polynucleotide
<220> FEATURE:
<223> OTHER INFORMATION: synthetic construct

<400> SEQUENCE: 3
acacaugggu cagugugaag guuuuagagc uagaaauagc aaguuaaaau aaggcuaguc    60
cguuaucaac uugaaaaagu ggcaccgagu cggugcuuuu                        100

<210> SEQ ID NO 4
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: synthetic construct

<400> SEQUENCE: 4
gucuauggca agagaggcga guuuuagagc uagaaauagc aaguuaaaau aaggcuaguc    60
cguuaucaac uugaaaaagu ggcaccgagu cggugcuuuu                        100

<210> SEQ ID NO 5
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: synthetic construct

<400> SEQUENCE: 5
uuuauaagga gggagugcau guuuuagagc uagaaauagc aaguuaaaau aaggcuaguc    60
cguuaucaac uugaaaaagu ggcaccgagu cggugcuuuu                        100

<210> SEQ ID NO 6
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: synthetic construct

<400> SEQUENCE: 6
uagcaugcag agagcgagag guuuuagagc uagaaauagc aaguuaaaau aaggcuaguc    60
cguuaucaac uugaaaaagu ggcaccgagu cggugcuuuu                        100

<210> SEQ ID NO 7
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct

<400> SEQUENCE: 7
uaauuucuac uaaguguaga uaccgcucug aucacaagca aggca                   45

<210> SEQ ID NO 8
```

```
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct

<400> SEQUENCE: 8
uaauuucuac uaaguguaga uuggaaagcu auaccuccuu acccc              45

<210> SEQ ID NO 9
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct

<400> SEQUENCE: 9
uaauuucuac uaaguguaga uugcccucuu cacacugacc caugu              45

<210> SEQ ID NO 10
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct

<400> SEQUENCE: 10
uaauuucuac uaaguguaga ugcaagagag gcgaaggagg guucc              45

<210> SEQ ID NO 11
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct

<400> SEQUENCE: 11
uaauuucuac uaaguguaga uuaaggaggg agugcauugg accua              45

<210> SEQ ID NO 12
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct

<400> SEQUENCE: 12
uaauuucuac uaaguguaga ugcucucgcu cucugcaugc uagcu              45

<210> SEQ ID NO 13
<211> LENGTH: 36
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<223> OTHER INFORMATION: recognition domain

<400> SEQUENCE: 13

His Asp His Asp Asn Gly Asn His His Asp Asp His Asp Asn Gly
1               5                   10                  15

His Asp Asn Gly Asn Gly His Asp Asn Ile His Asp Asn Ile His Asp
            20                  25                  30

Asn Gly Asn His
        35

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 14

His Asp Asn Gly Asn Gly Asn Gly Asn Ile Asn Gly His Asp His Asp
1               5                   10                  15

Asn Gly Asn Gly Asn Ile Asn Ile Asn Ile Asn Gly Asn Ile Asn Ile
            20                  25                  30

Asn His Asn Ile
        35

<210> SEQ ID NO 15
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 15

Asn His His Asp His Asp His Asp Asn Gly His Asp Asn Gly Asn Gly
1               5                   10                  15

His Asp Asn Ile His Asp Asn Ile His Asp Asn Gly Asn His Asn Ile
            20                  25                  30

His Asp His Asp
        35

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 16

Asn Ile Asn Gly His Asp His Asp Asn Gly Asn Gly Asn Ile Asn Ile
1               5                   10                  15

Asn Ile Asn Gly Asn Ile Asn Ile Asn His Asn Ile Asn Ile Asn His
            20                  25                  30
```

His Asp Asn Ile
        35

<210> SEQ ID NO 17
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 17

His Asp His Asp Asn Gly Asn Gly Asn Ile Asn Ile Asn Ile Asn Gly
1               5                   10                  15

Asn Ile Asn Ile Asn His Asn Ile Asn Ile Asn His His Asp Asn Ile
            20                  25                  30

Asn Gly Asn Ile
        35

<210> SEQ ID NO 18
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 18

His Asp Asn Gly Asn Gly His Asp Asn Ile His Asp Asn Ile His Asp
1               5                   10                  15

Asn Gly Asn His Asn Ile His Asp His Asp His Asp Asn Ile Asn Gly
            20                  25                  30

Asn His Asn Gly
        35

<210> SEQ ID NO 19
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 19

Asn His Asn Gly Asn Gly His Asp Asn Gly Asn Ile Asn Gly His Asp
1               5                   10                  15

Asn Ile Asn Ile His Asp Asn His His Asp His Asp His Asp His Asp
            20                  25                  30

Asn Gly His Asp
        35

<210> SEQ ID NO 20
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 20

His Asp Asn Gly Asn Ile Asn Gly His Asp Asn Ile Asn Ile His Asp
1               5                   10                  15

Asn His His Asp His Asp His Asp His Asp Asn Gly His Asp His Asp
            20                  25                  30

His Asp Asn Gly
        35

<210> SEQ ID NO 21
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 21

Asn Ile Asn Gly His Asp Asn Ile Asn Ile His Asp Asn His His Asp
1               5                   10                  15

His Asp His Asp His Asp Asn Gly His Asp His Asp His Asp Asn Gly
            20                  25                  30

Asn Gly Asn Ile
        35

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 22

Asn His Asn Gly Asn Gly Asn His Asn Gly Asn Gly His Asp Asn Gly
1               5                   10                  15

Asn Ile Asn Gly His Asp His Asp His Asp Asn Gly Asn His Asn His
            20                  25                  30

Asn Ile Asn Ile
        35

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 23

Asn His Asn Gly Asn Gly His Asp Asn Gly Asn Ile Asn Gly His Asp
1               5                   10                  15

His Asp His Asp Asn Gly Asn His Asn His Asn Ile Asn Ile Asn Ile
            20                  25                  30

Asn His His Asp
        35

```
<210> SEQ ID NO 24
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 24

His Asp Asn Gly Asn Ile Asn Gly His Asp His Asp His Asp Asn Gly
1               5                   10                  15

Asn His Asn His Asn Ile Asn Ile Asn Ile Asn His Asn His Asp Asn Gly
            20                  25                  30

Asn Ile Asn Gly
        35

<210> SEQ ID NO 25
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 25

Asn Ile Asn Gly His Asp His Asp His Asp Asn Gly Asn His Asn His
1               5                   10                  15

Asn Ile Asn Ile Asn Ile Asn His His Asp Asn Gly Asn Ile Asn Gly
            20                  25                  30

Asn Ile His Asp
        35

<210> SEQ ID NO 26
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 26

His Asp Asn Gly His Asp Asn Ile Asn His Asp His Asp Asn Ile
1               5                   10                  15

Asn His Asn Gly Asn Gly His Asp Asn Gly Asn Gly Asn Ile Asn Ile
            20                  25                  30

His Asp Asn Gly
        35

<210> SEQ ID NO 27
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain
```

```
<400> SEQUENCE: 27

Asn His Asn His Asn Ile Asn Ile Asn Ile Asn His His Asp Asn Gly
1               5                   10                  15

Asn Ile Asn Gly Asn Ile His Asp His Asp Asn Gly His Asp His Asp
            20                  25                  30

Asn Gly Asn Gly
        35

<210> SEQ ID NO 28
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 28

Asn Ile Asn Gly Asn Ile His Asp His Asp Asn Gly His Asp His Asp
1               5                   10                  15

Asn Gly Asn Gly Asn Ile His Asp His Asp His Asp His Asp Asn Gly
            20                  25                  30

Asn Ile Asn Gly
        35

<210> SEQ ID NO 29
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 29

Asn Ile His Asp His Asp Asn Gly His Asp His Asp Asn Gly Asn Gly
1               5                   10                  15

Asn Ile His Asp His Asp His Asp His Asp Asn Gly Asn Ile Asn Gly
            20                  25                  30

His Asp Asn Ile
        35

<210> SEQ ID NO 30
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 30

His Asp His Asp Asn Gly Asn Gly Asn Ile His Asp His Asp His Asp
1               5                   10                  15

His Asp Asn Gly Asn Ile Asn Gly His Asp Asn Ile Asn His His Asp
            20                  25                  30

Asn Gly Asn Gly
        35
```

```
<210> SEQ ID NO 31
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 31

His Asp Asn Gly His Asp Asn Gly Asn Gly Asn Ile Asn Gly Asn Ile
1               5                   10                  15

Asn Ile Asn Ile Asn Gly Asn Ile His Asp Asn Ile Asn His Asn Ile
            20                  25                  30

His Asp His Asp
        35

<210> SEQ ID NO 32
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 32

His Asp Asn Gly Asn Gly Asn Ile Asn Gly Asn Ile Asn Ile Asn Ile
1               5                   10                  15

Asn Gly Asn Ile His Asp Asn Ile Asn His Asn Ile His Asp His Asp
            20                  25                  30

Asn Gly Asn Gly
        35

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 33

Asn Ile His Asp His Asp His Asp His Asp Gly Asn Ile Asn Gly
1               5                   10                  15

His Asp Asn Ile Asn His His Asp Asn Gly Asn Gly His Asp Asn Gly
            20                  25                  30

His Asp His Asp
        35

<210> SEQ ID NO 34
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain
```

```
<400> SEQUENCE: 34

Asn Ile Asn Gly Asn Ile Asn Ile Asn Ile Asn Gly Asn Ile His Asp
1               5                   10                  15

Asn Ile Asn His Asn Ile His Asp His Asp Asn Gly Asn Gly Asn His
            20                  25                  30

Asn Gly Asn Ile
        35

<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 35

Asn Ile Asn Gly His Asp Asn Ile Asn His His Asp Asn Gly Asn Gly
1               5                   10                  15

His Asp Asn Gly His Asp His Asp Asn Gly His Asp Asn Ile His Asp
            20                  25                  30

Asn Ile Asn Gly
        35

<210> SEQ ID NO 36
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 36

Asn Ile His Asp Asn Ile Asn His Asn Ile His Asp His Asp Asn Gly
1               5                   10                  15

Asn Gly Asn His Asn Gly Asn Ile His Asp Asn Ile Asn Ile His Asp
            20                  25                  30

Asn Ile His Asp
        35

<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 37

His Asp Asn Gly His Asp His Asp Asn Gly His Asp Asn Ile His Asp
1               5                   10                  15

Asn Ile Asn Gly His Asp Asn Gly His Asp His Asp Asn Gly His Asp
            20                  25                  30

Asn Gly His Asp
        35
```

```
<210> SEQ ID NO 38
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 38

His Asp His Asp Asn Gly His Asp Asn Ile His Asp Asn Ile Asn Gly
1               5                   10                  15

His Asp Asn Gly His Asp His Asp Asn Gly His Asp Asn Gly His Asp
            20                  25                  30

Asn His Asn Gly
        35

<210> SEQ ID NO 39
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 39

Asn His Asn Gly Asn Ile His Asp Asn Ile Asn Ile His Asp Asn Ile
1               5                   10                  15

His Asp Asn Gly Asn Gly Asn Gly His Asp Asn Ile His Asp His Asp
            20                  25                  30

Asn Gly His Asp
        35

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 40

Asn Ile His Asp Asn Ile Asn Ile His Asp Asn Ile His Asp Asn Gly
1               5                   10                  15

Asn Gly Asn Gly His Asp Asn Ile His Asp His Asp Asn Gly His Asp
            20                  25                  30

His Asp Asn Gly
        35

<210> SEQ ID NO 41
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain
```

<400> SEQUENCE: 41

His Asp Asn Gly His Asp His Asp Asn Gly His Asp Asn Gly His Asp
1               5                   10                  15

Asn His Asn Gly His Asp Asn His His Asp His Asp Asn Ile His Asp
                20                  25                  30

His Asp His Asp
        35

<210> SEQ ID NO 42
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 42

His Asp His Asp Asn Gly His Asp Asn Gly His Asp Asn His Asn Gly
1               5                   10                  15

His Asp Asn His His Asp His Asp Asn Ile His Asp His Asp His Asp
                20                  25                  30

Asn Ile Asn Gly
        35

<210> SEQ ID NO 43
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 43

His Asp Asn Gly His Asp Asn His Asn Gly His Asp Asn His His Asp
1               5                   10                  15

His Asp Asn Ile His Asp His Asp His Asp Asn Ile Asn Gly Asn His
                20                  25                  30

His Asp Asn Gly
        35

<210> SEQ ID NO 44
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 44

His Asp Asn His Asn Gly His Asp Asn His His Asp His Asp Asn Ile
1               5                   10                  15

His Asp His Asp His Asp Asn Ile Asn Gly Asn His Asp Asn Gly
                20                  25                  30

Asn Ile Asn Gly
        35

```
<210> SEQ ID NO 45
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 45

His Asp Asn His His Asp His Asp Asn Ile His Asp His Asp His Asp
1               5                   10                  15

Asn Ile Asn Gly Asn His His Asp Asn Gly Asn Ile Asn Gly His Asp
            20                  25                  30

Asn Ile His Asp
        35

<210> SEQ ID NO 46
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 46

His Asp His Asp His Asp Asn Gly Asn His Asn His Asn Ile Asn Ile
1               5                   10                  15

Asn Ile Asn His His Asp Asn Gly Asn Ile Asn Gly Asn Ile His Asp
            20                  25                  30

His Asp Asn Gly
        35

<210> SEQ ID NO 47
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 47

Asn His His Asp Asn Gly Asn Ile Asn Gly His Asp Asn Ile His Asp
1               5                   10                  15

His Asp Asn His His Asp Asn Gly His Asp Asn Gly Asn His Asn Ile
            20                  25                  30

Asn Gly His Asp
        35

<210> SEQ ID NO 48
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain
```

```
<400> SEQUENCE: 48

Asn Ile Asn Gly His Asp Asn Ile His Asp His Asp Asn His His Asp
1               5                   10                  15

Asn Gly His Asp Asn Gly Asn His Asn Ile Asn Gly His Asp Asn Ile
            20                  25                  30

His Asp Asn Ile
        35

<210> SEQ ID NO 49
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 49

His Asp Asn Gly Asn His Asn Ile Asn Gly His Asp Asn Ile His Asp
1               5                   10                  15

Asn Ile Asn Ile Asn His His Asp Asn Ile Asn Ile Asn His Asn His
            20                  25                  30

His Asp Asn Ile
        35

<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 50

His Asp Asn Gly Asn His Asn His His Asp His Asp His Asp His Asp
1               5                   10                  15

Asn Gly Asn Gly His Asp His Asp Asn Gly Asn His His Asp His Asp
            20                  25                  30

His Asp Asn Gly
        35

<210> SEQ ID NO 51
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 51

Asn His Asn His His Asp His Asp His Asp His Asp Asn Gly Asn Gly
1               5                   10                  15

His Asp His Asp Asn Gly Asn His Asp His Asp His Asp Asn Gly
            20                  25                  30

His Asp Asn Gly
        35
```

```
<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 52

His Asp Asn Gly Asn Gly His Asp Asn Gly His Asp His Asp His Asp
1               5                   10                  15

Asn His His Asp Asn Gly His Asp Asn Gly His Asp Asn His His Asp
            20                  25                  30

Asn Gly His Asp
        35

<210> SEQ ID NO 53
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 53

His Asp Asn Gly His Asp His Asp His Asp Asn His His Asp Asn Gly
1               5                   10                  15

His Asp Asn Gly His Asp Asn His His Asp Asn Gly His Asp Asn Gly
            20                  25                  30

His Asp Asn Gly
        35

<210> SEQ ID NO 54
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 54

Asn His His Asp Asn Ile Asn Gly Asn His His Asp Asn Gly Asn Ile
1               5                   10                  15

Asn His His Asp Asn Gly Asn Ile His Asp His Asp Asn Gly Asn Gly
            20                  25                  30

His Asp Asn Gly
        35

<210> SEQ ID NO 55
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain
```

<400> SEQUENCE: 55

His Asp His Asp His Asp Asn His His Asp Asn Gly His Asp Asn Gly
1               5                   10                  15

His Asp Asn His His Asp Asn Gly His Asp Asn Gly His Asp Asn Gly
            20                  25                  30

Asn His His Asp
        35

<210> SEQ ID NO 56
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 56

His Asp Asn Gly His Asp Asn His His Asp Asn Gly His Asp Asn Gly
1               5                   10                  15

His Asp Asn Gly Asn His His Asp Asn Ile Asn Gly Asn His His Asp
            20                  25                  30

Asn Gly Asn Ile
        35

<210> SEQ ID NO 57
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 57

His Asp Asn His His Asp Asn Gly His Asp Asn Gly His Asp Asn Gly
1               5                   10                  15

Asn His His Asp Asn Ile Asn Gly Asn His His Asp Asn Gly Asn Ile
            20                  25                  30

Asn His His Asp
        35

<210> SEQ ID NO 58
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 58

His Asp Asn Gly His Asp Asn Gly Asn His His Asp Asn Ile Asn Gly
1               5                   10                  15

Asn His His Asp Asn Gly Asn Ile Asn His His Asp Asn Gly Asn Ile
            20                  25                  30

His Asp His Asp
        35

```
<210> SEQ ID NO 59
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 59

His Asp Asn Gly Asn His His Asp Asn Ile Asn Gly Asn His His Asp
1               5                   10                  15

Asn Gly Asn Ile Asn His His Asp Asn Gly Asn Ile His Asp His Asp
            20                  25                  30

Asn Gly Asn Gly
        35

<210> SEQ ID NO 60
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 60

Asn Ile Asn Gly Asn His Asn Gly His Asp Asn Ile Asn Ile His Asp
1               5                   10                  15

Asn Gly Asn Gly His Asp Asn Ile His Asp Asn Gly Asn Gly Asn His
            20                  25                  30

Asn Gly His Asp
        35

<210> SEQ ID NO 61
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 61

Asn His Asn Gly His Asp Asn Ile Asn Ile His Asp Asn Gly Asn Gly
1               5                   10                  15

His Asp Asn Ile His Asp Asn Gly Asn Gly Asn His Asn Gly His Asp
            20                  25                  30

Asn Gly His Asp
        35

<210> SEQ ID NO 62
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain
```

<400> SEQUENCE: 62

Asn His His Asp Asn Gly Asn Ile Asn His His Asp Asn Gly Asn Ile
1               5                   10                  15

His Asp His Asp Asn Gly Asn Gly His Asp Asn Gly Asn Ile Asn His
                20                  25                  30

His Asp Asn Gly
        35

<210> SEQ ID NO 63
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 63

Asn Ile Asn His His Asp Asn Gly Asn Ile His Asp His Asp Asn Gly
1               5                   10                  15

Asn Gly His Asp Asn Gly Asn Ile Asn His His Asp Asn Gly Asn Ile
                20                  25                  30

Asn Gly His Asp
        35

<210> SEQ ID NO 64
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 64

Asn Ile His Asp His Asp Asn Gly Asn Gly His Asp Asn Gly Asn Ile
1               5                   10                  15

Asn His His Asp Asn Gly Asn Ile Asn Gly His Asp Asn Gly Asn Ile
                20                  25                  30

Asn His His Asp
        35

<210> SEQ ID NO 65
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 65

Asn His Asn Gly His Asp Asn Gly His Asp Asn Gly His Asp Asn Gly
1               5                   10                  15

His Asp His Asp Asn Ile Asn Ile Asn Ile Asn Ile Asn His Asn Ile
                20                  25                  30

Asn Gly Asn Ile
        35

```
<210> SEQ ID NO 66
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 66

His Asp Asn Gly Asn Ile Asn His His Asp Asn Gly Asn Ile Asn Gly
1               5                   10                  15

His Asp Asn Gly Asn Ile Asn His His Asp His Asp Asn Gly His Asp
            20                  25                  30

Asn Gly Asn Ile
        35

<210> SEQ ID NO 67
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 67

His Asp Asn Gly His Asp Asn Gly His Asp Asn Gly His Asp His Asp
1               5                   10                  15

Asn Ile Asn Ile Asn Ile Asn Ile Asn His Asn Ile Asn Gly Asn Ile
            20                  25                  30

Asn Gly His Asp
        35

<210> SEQ ID NO 68
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 68

Asn Ile Asn His His Asp Asn Gly Asn Ile Gly His Asp Asn Gly
1               5                   10                  15

Asn Ile Asn His His Asp His Asp Asn Gly His Asp Asn Gly Asn Ile
            20                  25                  30

Asn His Asn His
        35

<210> SEQ ID NO 69
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain
```

<400> SEQUENCE: 69

His Asp Asn Gly His Asp Asn Gly His Asp His Asp Asn Ile Asn Ile
1               5                   10                  15

Asn Ile Asn Ile Asn His Asn Ile Asn Gly Asn Ile Asn Gly His Asp
                20                  25                  30

Asn His Asn Gly
        35

<210> SEQ ID NO 70
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 70

His Asp Asn Gly His Asp His Asp Asn Ile Asn Ile Asn Ile Asn Ile
1               5                   10                  15

Asn His Asn Ile Asn Gly Asn Ile Asn Gly His Asp Asn His Asn Gly
                20                  25                  30

Asn Ile Asn Gly
        35

<210> SEQ ID NO 71
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 71

Asn Ile Asn Gly His Asp Asn Gly Asn Ile Asn His His Asp His Asp
1               5                   10                  15

Asn Gly His Asp Asn Gly Asn Ile Asn His Asn His Asn Gly His Asp
                20                  25                  30

His Asp Asn Ile
        35

<210> SEQ ID NO 72
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 72

His Asp His Asp Asn Ile Asn Ile Asn Ile Asn Ile Asn His Asn Ile
1               5                   10                  15

Asn Gly Asn Ile Asn Gly His Asp Asn His Asn Gly Asn Ile Asn Gly
                20                  25                  30

His Asp Asn Ile
        35

```
<210> SEQ ID NO 73
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 73

His Asp Asn Gly Asn Ile Asn His His Asp His Asp Asn Gly His Asp
1               5                   10                  15

Asn Gly Asn Ile Asn His Asn His Asn Gly His Asp His Asp Asn Ile
            20                  25                  30

Asn Ile Asn Gly
        35

<210> SEQ ID NO 74
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 74

Asn Ile Asn His His Asp His Asp Asn Gly His Asp Asn Gly Asn Ile
1               5                   10                  15

Asn His Asn His Asn Gly His Asp His Asp Asn Ile Asn Ile Asn Gly
            20                  25                  30

Asn His His Asp
        35

<210> SEQ ID NO 75
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 75

His Asp Asn Gly Asn Ile Asn His Asn His Asn Gly His Asp His Asp
1               5                   10                  15

Asn Ile Asn Ile Asn Gly Asn His His Asp Asn Ile His Asp Asn Gly
            20                  25                  30

His Asp His Asp
        35

<210> SEQ ID NO 76
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain
```

```
<400> SEQUENCE: 76

Asn Ile Asn Gly His Asp Asn His Asn Gly Asn Ile Asn Gly His Asp
1               5                   10                  15

Asn Ile His Asp His Asp His Asp Asn Ile Asn Gly Asn His Asn His
                20                  25                  30

Asn His His Asp
        35

<210> SEQ ID NO 77
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 77

Asn Ile Asn His Asn His Asn Gly His Asp His Asp Asn Ile Asn Ile
1               5                   10                  15

Asn Gly Asn His His Asp Asn Ile His Asp Asn Gly His Asp His Asp
                20                  25                  30

His Asp Asn Gly
        35

<210> SEQ ID NO 78
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 78

His Asp Asn His Asn Gly Asn Ile Asn Gly His Asp Asn Ile His Asp
1               5                   10                  15

His Asp His Asp Asn Ile Asn Gly Asn His Asn His Asn His His Asp
                20                  25                  30

Asn Ile Asn Ile
        35

<210> SEQ ID NO 79
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 79

His Asp His Asp Asn Ile Asn Ile Asn Gly Asn His His Asp Asn Ile
1               5                   10                  15

His Asp Asn Gly His Asp His Asp His Asp Asn Gly His Asp His Asp
                20                  25                  30

Asn Gly Asn Gly
        35
```

```
<210> SEQ ID NO 80
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 80

His Asp Asn Gly Asn Gly Asn His His Asp His Asp Asn Ile Asn Gly
1               5                   10                  15

Asn Ile Asn His Asn Ile His Asp His Asp Asn His Asn His Asn Ile
            20                  25                  30

His Asp Asn Ile
        35

<210> SEQ ID NO 81
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 81

Asn His His Asp Asn Ile His Asp Asn Gly His Asp His Asp His Asp
1               5                   10                  15

Asn Gly His Asp His Asp Asn Gly Asn Gly Asn Ile Asn Gly Asn Ile
            20                  25                  30

Asn Ile Asn Ile
        35

<210> SEQ ID NO 82
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 82

His Asp His Asp His Asp Asn Gly His Asp His Asp Asn Gly Asn Gly
1               5                   10                  15

Asn Ile Asn Gly Asn Ile Asn Ile Asn Ile His Asp Asn Ile Asn Ile
            20                  25                  30

Asn His Asn His
        35

<210> SEQ ID NO 83
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain
```

```
<400> SEQUENCE: 83

His Asp His Asp Asn Gly Asn Gly Asn Ile Asn Gly Asn Ile Asn Ile
1               5                   10                  15

Asn Ile His Asp Asn Ile Asn Ile Asn His Asn His Asn Ile Asn Ile
            20                  25                  30

His Asp His Asp
        35

<210> SEQ ID NO 84
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 84

Asn His Asn His His Asp His Asp Asn Ile Asn Gly Asn His Asn Ile
1               5                   10                  15

His Asp His Asp His Asp His Asp His Asp His Asp Asn Gly His Asp
            20                  25                  30

His Asp His Asp
        35

<210> SEQ ID NO 85
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 85

Asn Ile Asn Gly Asn Ile Asn Ile Asn Ile His Asp Asn Ile Asn Ile
1               5                   10                  15

Asn His Asn His Asn Ile Asn Ile His Asp His Asp His Asp Asn Gly
            20                  25                  30

His Asp His Asp
        35

<210> SEQ ID NO 86
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 86

His Asp His Asp His Asp Asn Ile Asn His His Asp His Asp His Asp
1               5                   10                  15

His Asp Asn Ile Asn Ile His Asp His Asp Asn Gly Asn Ile Asn Gly
            20                  25                  30

Asn Ile Asn Gly
        35
```

```
<210> SEQ ID NO 87
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 87

His Asp His Asp Asn Gly Asn Gly His Asp Asn His His Asp His Asp
1               5                   10                  15

Asn Gly His Asp Asn Gly His Asp Asn Gly Asn Gly Asn His His Asp
            20                  25                  30

His Asp Asn Ile
        35

<210> SEQ ID NO 88
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 88

His Asp Asn His His Asp His Asp Asn Gly His Asp Asn Gly His Asp
1               5                   10                  15

Asn Gly Asn Gly Asn His His Asp His Asp Asn Ile Asn Gly Asn Ile
            20                  25                  30

Asn His Asn Ile
        35

<210> SEQ ID NO 89
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 89

His Asp Asn Gly His Asp Asn Gly Asn Gly Asn His His Asp His Asp
1               5                   10                  15

Asn Ile Asn Gly Asn Ile Asn His Asn Ile His Asp His Asp Asn His
            20                  25                  30

Asn His Asn Ile
        35

<210> SEQ ID NO 90
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain
```

```
<400> SEQUENCE: 90

Asn Ile Asn Gly Asn Ile Asn Gly His Asp Asn Ile His Asp His Asp
1               5                   10                  15

Asn Gly Asn Ile Asn His His Asp Asn His His Asp Asn Ile Asn His
                20                  25                  30

His Asp Asn Gly
        35

<210> SEQ ID NO 91
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 91

Asn Ile Asn Gly His Asp Asn Ile His Asp His Asp Asn Gly Asn Ile
1               5                   10                  15

Asn His His Asp Asn His His Asp Asn Ile Asn His His Asp Asn Gly
                20                  25                  30

Asn Ile His Asp
        35

<210> SEQ ID NO 92
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 92

Asn Ile Asn His His Asp Asn His His Asp Asn Ile Asn His His Asp
1               5                   10                  15

Asn Gly Asn Ile His Asp Asn His His Asp Asn Gly His Asp Asn Gly
                20                  25                  30

His Asp Asn Gly
        35

<210> SEQ ID NO 93
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 93

Asn Ile His Asp Asn His His Asp Asn Gly His Asp Asn Gly His Asp
1               5                   10                  15

Asn Gly Asn Gly His Asp Asn Gly His Asp His Asp His Asp Asn His
                20                  25                  30

His Asp Asn Gly
        35
```

```
<210> SEQ ID NO 94
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: recognition domain

<400> SEQUENCE: 94

His Asp Asn Gly His Asp Asn Gly Asn Gly His Asp Asn Gly His Asp
1               5                   10                  15

His Asp His Asp Asn His His Asp Asn Gly His Asp Asn Gly His Asp
            20                  25                  30

Asn His His Asp
        35

<210> SEQ ID NO 95
<211> LENGTH: 303
<212> TYPE: DNA
<213> ORGANISM: Zea mays

<400> SEQUENCE: 95
cctctttatc cttaaataag aagcataaaa cgggatttct cagccagttc ttaacttctc    60
ttataaatac agaccttgta caacactttc acctcctctc aggtggccag gatattttt   120 ctggcccctt cctgccctct tcacactgac ccatgtgttg ttctatccct ggaaagctat   180
acctccttac ccctatcagc ttctcctcac atctcctctc gtcgccaccc atgctatcac   240
cgctctgatc acaagcaagg caaaccctca ctgttctatc aacgcccctc ccttagctag   300
atg                                                                303

<210> SEQ ID NO 96
<211> LENGTH: 303
<212> TYPE: DNA
<213> ORGANISM: Zea mays

<400> SEQUENCE: 96
gcaagagcca gccccggcc gtatgtcaac ttcacttgtc tctctccaaa agatatcgta    60
tcacccatgg gcaatggcca tgacccccct cccagcccca acctatatca cctagcgcag   120
ctacgctctc ttctcccgct ctcgctctct gcatgctagc taccttctag ctatctagcc   180
tctaggtcca atgcactccc tccttataaa caaggaaccc tccttcgcct ctcttgccat   240
agaccggaca ccggagagct aggtcacagg agcgctcagg aaggccgctg agatagaggc   300
atg                                                                303

<210> SEQ ID NO 97
<211> LENGTH: 23
<212> TYPE: DNA
<213> ORGANISM: Zea mays

<400> SEQUENCE: 97
caccgctctg atcacaagca agg                                           23

<210> SEQ ID NO 98
<211> LENGTH: 23
<212> TYPE: DNA
<213> ORGANISM: Zea mays
```

-continued

```
<400> SEQUENCE: 98
cccatgtgtt gttctatccc tgg                                          23

<210> SEQ ID NO 99
<211> LENGTH: 23
<212> TYPE: DNA
<213> ORGANISM: Zea mays

<400> SEQUENCE: 99
acacatgggt cagtgtgaag agg                                          23

<210> SEQ ID NO 100
<211> LENGTH: 27
<212> TYPE: DNA
<213> ORGANISM: Zea mays

<400> SEQUENCE: 100
atcaccgctc tgatcacaag caaggca                                      27

<210> SEQ ID NO 101
<211> LENGTH: 28
<212> TYPE: DNA
<213> ORGANISM: Zea mays

<400> SEQUENCE: 101
tccctggaaa gctataccct cttacccc                                     28

<210> SEQ ID NO 102
<211> LENGTH: 28
<212> TYPE: DNA
<213> ORGANISM: Zea mays

<400> SEQUENCE: 102
ttcctgccct cttcacactg acccatgt                                     28

<210> SEQ ID NO 103
<211> LENGTH: 23
<212> TYPE: DNA
<213> ORGANISM: Zea mays

<400> SEQUENCE: 103
gtctatggca agagaggcga agg                                          23

<210> SEQ ID NO 104
<211> LENGTH: 23
<212> TYPE: DNA
<213> ORGANISM: Zea mays

<400> SEQUENCE: 104
tttataagga gggagtgcat tgg                                          23

<210> SEQ ID NO 105
<211> LENGTH: 23
<212> TYPE: DNA
<213> ORGANISM: Zea mays

<400> SEQUENCE: 105
tagcatgcag agagcgagag cgg                                          23

<210> SEQ ID NO 106
<211> LENGTH: 28
<212> TYPE: DNA
```

<213> ORGANISM: Zea mays

<400> SEQUENCE: 106
tatggcaaga gaggcgaagg agggttcc                               28

<210> SEQ ID NO 107
<211> LENGTH: 28
<212> TYPE: DNA
<213> ORGANISM: Zea mays

<400> SEQUENCE: 107
tttataagga gggagtgcat tggaccta                               28

<210> SEQ ID NO 108
<211> LENGTH: 28
<212> TYPE: DNA
<213> ORGANISM: Zea mays

<400> SEQUENCE: 108
tcccgctctc gctctctgca tgctagct                               28

<210> SEQ ID NO 109
<211> LENGTH: 19
<212> TYPE: DNA
<213> ORGANISM: Zea mays

<400> SEQUENCE: 109
tcctgccctc ttcacactg                                         19

<210> SEQ ID NO 110
<211> LENGTH: 19
<212> TYPE: DNA
<213> ORGANISM: Zea mays

<400> SEQUENCE: 110
tctttatcct taaataaga                                         19

<210> SEQ ID NO 111
<211> LENGTH: 19
<212> TYPE: DNA
<213> ORGANISM: Zea mays

<400> SEQUENCE: 111
tgccctcttc acactgacc                                         19

<210> SEQ ID NO 112
<211> LENGTH: 19
<212> TYPE: DNA
<213> ORGANISM: Zea mays

<400> SEQUENCE: 112
tatccttaaa taagaagca                                         19

<210> SEQ ID NO 113
<211> LENGTH: 19
<212> TYPE: DNA
<213> ORGANISM: Zea mays

<400> SEQUENCE: 113
tccttaaata agaagcata                                         19

<210> SEQ ID NO 114
<211> LENGTH: 19

```
<212> TYPE: DNA
<213> ORGANISM: Zea mays

<400> SEQUENCE: 114
tcttcacact gacccatgt                                              19

<210> SEQ ID NO 115
<211> LENGTH: 19
<212> TYPE: DNA
<213> ORGANISM: Zea mays

<400> SEQUENCE: 115
tgttctatca acgcccctc                                              19

<210> SEQ ID NO 116
<211> LENGTH: 19
<212> TYPE: DNA
<213> ORGANISM: Zea mays

<400> SEQUENCE: 116
tctatcaacg cccctccct                                              19

<210> SEQ ID NO 117
<211> LENGTH: 19
<212> TYPE: DNA
<213> ORGANISM: Zea mays

<400> SEQUENCE: 117
tatcaacgcc cctccctta                                              19

<210> SEQ ID NO 118
<211> LENGTH: 19
<212> TYPE: DNA
<213> ORGANISM: Zea mays

<400> SEQUENCE: 118
tgttgttcta tccctggaa                                              19

<210> SEQ ID NO 119
<211> LENGTH: 19
<212> TYPE: DNA
<213> ORGANISM: Zea mays

<400> SEQUENCE: 119
tgttctatcc ctggaaagc                                              19

<210> SEQ ID NO 120
<211> LENGTH: 19
<212> TYPE: PRT
<213> ORGANISM: Zea mays

<400> SEQUENCE: 120

Thr Cys Thr Ala Thr Cys Cys Cys Thr Gly Gly Ala Ala Ala Gly Cys
1               5                   10                  15

Thr Ala Thr

<210> SEQ ID NO 121
<211> LENGTH: 19
<212> TYPE: DNA
<213> ORGANISM: Zea mays

<400> SEQUENCE: 121
tatccctgga aagctatac                                              19
```

<210> SEQ ID NO 122
<211> LENGTH: 19
<212> TYPE: DNA
<213> ORGANISM: Zea mays

<400> SEQUENCE: 122
tctcagccag ttcttaact                                                19

<210> SEQ ID NO 123
<211> LENGTH: 19
<212> TYPE: DNA
<213> ORGANISM: Zea mays

<400> SEQUENCE: 123
tggaaagcta tacctcctt                                                19

<210> SEQ ID NO 124
<211> LENGTH: 19
<212> TYPE: DNA
<213> ORGANISM: Zea mays

<400> SEQUENCE: 124
tatacctcct taccectat                                                19

<210> SEQ ID NO 125
<211> LENGTH: 19
<212> TYPE: PRT
<213> ORGANISM: Zea mays

<400> SEQUENCE: 125

Thr Ala Cys Cys Thr Cys Cys Thr Thr Ala Cys Cys Cys Cys Thr Ala
1               5                   10                  15

Thr Cys Ala

<210> SEQ ID NO 126
<211> LENGTH: 19
<212> TYPE: DNA
<213> ORGANISM: Zea mays

<400> SEQUENCE: 126
tccttacccc tatcagctt                                                19

<210> SEQ ID NO 127
<211> LENGTH: 19
<212> TYPE: DNA
<213> ORGANISM: Zea mays

<400> SEQUENCE: 127
tctcttataa atacagacc                                                19

<210> SEQ ID NO 128
<211> LENGTH: 19
<212> TYPE: DNA
<213> ORGANISM: Zea mays

<400> SEQUENCE: 128
tcttataaat acagacctt                                                19

<210> SEQ ID NO 129
<211> LENGTH: 19
<212> TYPE: DNA
<213> ORGANISM: Zea mays

```
<400> SEQUENCE: 129
tacccctatc agcttctcc                                               19

<210> SEQ ID NO 130
<211> LENGTH: 19
<212> TYPE: DNA
<213> ORGANISM: Zea mays

<400> SEQUENCE: 130
tataaataca gaccttgta                                               19

<210> SEQ ID NO 131
<211> LENGTH: 19
<212> TYPE: DNA
<213> ORGANISM: Zea mays

<400> SEQUENCE: 131
tatcagcttc tcctcacat                                               19

<210> SEQ ID NO 132
<211> LENGTH: 19
<212> TYPE: DNA
<213> ORGANISM: Zea mays

<400> SEQUENCE: 132
tacagacctt gtacaacac                                               19

<210> SEQ ID NO 133
<211> LENGTH: 19
<212> TYPE: DNA
<213> ORGANISM: Zea mays

<400> SEQUENCE: 133
tctcctcaca tctcctctc                                               19

<210> SEQ ID NO 134
<211> LENGTH: 19
<212> TYPE: DNA
<213> ORGANISM: Zea mays

<400> SEQUENCE: 134
tcctcacatc tcctctcgt                                               19

<210> SEQ ID NO 135
<211> LENGTH: 19
<212> TYPE: DNA
<213> ORGANISM: Zea mays

<400> SEQUENCE: 135
tgtacaacac tttcacctc                                               19

<210> SEQ ID NO 136
<211> LENGTH: 19
<212> TYPE: DNA
<213> ORGANISM: Zea mays

<400> SEQUENCE: 136
tacaacactt tcacctcct                                               19

<210> SEQ ID NO 137
<211> LENGTH: 19
<212> TYPE: DNA
```

<213> ORGANISM: Zea mays

<400> SEQUENCE: 137
tctcctctcg tcgccaccc					19

<210> SEQ ID NO 138
<211> LENGTH: 19
<212> TYPE: DNA
<213> ORGANISM: Zea mays

<400> SEQUENCE: 138
tcctctcgtc gccacccat					19

<210> SEQ ID NO 139
<211> LENGTH: 19
<212> TYPE: DNA
<213> ORGANISM: Zea mays

<400> SEQUENCE: 139
tctcgtcgcc acccatgct					19

<210> SEQ ID NO 140
<211> LENGTH: 19
<212> TYPE: DNA
<213> ORGANISM: Zea mays

<400> SEQUENCE: 140
tcgtcgccac ccatgctat					19

<210> SEQ ID NO 141
<211> LENGTH: 19
<212> TYPE: DNA
<213> ORGANISM: Zea mays

<400> SEQUENCE: 141
tcgccaccca tgctatcac					19

<210> SEQ ID NO 142
<211> LENGTH: 19
<212> TYPE: DNA
<213> ORGANISM: Zea mays

<400> SEQUENCE: 142
tccctggaaa gctatacct					19

<210> SEQ ID NO 143
<211> LENGTH: 19
<212> TYPE: DNA
<213> ORGANISM: Zea mays

<400> SEQUENCE: 143
tgctatcacc gctctgatc					19

<210> SEQ ID NO 144
<211> LENGTH: 19
<212> TYPE: DNA
<213> ORGANISM: Zea mays

<400> SEQUENCE: 144
tatcaccgct ctgatcaca					19

<210> SEQ ID NO 145
<211> LENGTH: 19

```
<212> TYPE: DNA
<213> ORGANISM: Zea mays

<400> SEQUENCE: 145
tctgatcaca agcaaggca                                              19

<210> SEQ ID NO 146
<211> LENGTH: 19
<212> TYPE: DNA
<213> ORGANISM: Zea mays

<400> SEQUENCE: 146
tctggcccct tcctgccct                                              19

<210> SEQ ID NO 147
<211> LENGTH: 19
<212> TYPE: DNA
<213> ORGANISM: Zea mays

<400> SEQUENCE: 147
tggccccttc ctgccctct                                              19

<210> SEQ ID NO 148
<211> LENGTH: 19
<212> TYPE: DNA
<213> ORGANISM: Zea mays

<400> SEQUENCE: 148
tcttctcccg ctctcgctc                                              19

<210> SEQ ID NO 149
<211> LENGTH: 19
<212> TYPE: DNA
<213> ORGANISM: Zea mays

<400> SEQUENCE: 149
tctcccgctc tcgctctct                                              19

<210> SEQ ID NO 150
<211> LENGTH: 19
<212> TYPE: DNA
<213> ORGANISM: Zea mays

<400> SEQUENCE: 150
tgcatgctag ctaccttct                                              19

<210> SEQ ID NO 151
<211> LENGTH: 19
<212> TYPE: DNA
<213> ORGANISM: Zea mays

<400> SEQUENCE: 151
tcccgctctc gctctctgc                                              19

<210> SEQ ID NO 152
<211> LENGTH: 19
<212> TYPE: DNA
<213> ORGANISM: Zea mays

<400> SEQUENCE: 152
tctcgctctc tgcatgcta                                              19

<210> SEQ ID NO 153
```

```
<211> LENGTH: 19
<212> TYPE: DNA
<213> ORGANISM: Zea mays

<400> SEQUENCE: 153
tcgctctctg catgctagc                                                19

<210> SEQ ID NO 154
<211> LENGTH: 19
<212> TYPE: DNA
<213> ORGANISM: Zea mays

<400> SEQUENCE: 154
tctctgcatg ctagctacc                                                19

<210> SEQ ID NO 155
<211> LENGTH: 19
<212> TYPE: DNA
<213> ORGANISM: Zea mays

<400> SEQUENCE: 155
tctgcatgct agctacctt                                                19

<210> SEQ ID NO 156
<211> LENGTH: 19
<212> TYPE: DNA
<213> ORGANISM: Zea mays

<400> SEQUENCE: 156
tatgtcaact tcacttgtc                                                19

<210> SEQ ID NO 157
<211> LENGTH: 19
<212> TYPE: DNA
<213> ORGANISM: Zea mays

<400> SEQUENCE: 157
tgtcaacttc acttgtctc                                                19

<210> SEQ ID NO 158
<211> LENGTH: 19
<212> TYPE: DNA
<213> ORGANISM: Zea mays

<400> SEQUENCE: 158
tgctagctac cttctagct                                                19

<210> SEQ ID NO 159
<211> LENGTH: 19
<212> TYPE: DNA
<213> ORGANISM: Zea mays

<400> SEQUENCE: 159
tagctacctt ctagctatc                                                19

<210> SEQ ID NO 160
<211> LENGTH: 19
<212> TYPE: DNA
<213> ORGANISM: Zea mays

<400> SEQUENCE: 160
taccttctag ctatctagc                                                19
```

```
<210> SEQ ID NO 161
<211> LENGTH: 19
<212> TYPE: DNA
<213> ORGANISM: Zea mays

<400> SEQUENCE: 161
tgtctctctc caaaagata                                               19

<210> SEQ ID NO 162
<211> LENGTH: 19
<212> TYPE: DNA
<213> ORGANISM: Zea mays

<400> SEQUENCE: 162
tctagctatc tagcctcta                                               19

<210> SEQ ID NO 163
<211> LENGTH: 19
<212> TYPE: DNA
<213> ORGANISM: Zea mays

<400> SEQUENCE: 163
tctctctcca aaagatatc                                               19

<210> SEQ ID NO 164
<211> LENGTH: 19
<212> TYPE: DNA
<213> ORGANISM: Zea mays

<400> SEQUENCE: 164
tagctatcta gcctctagg                                               19

<210> SEQ ID NO 165
<211> LENGTH: 19
<212> TYPE: DNA
<213> ORGANISM: Zea mays

<400> SEQUENCE: 165
tctctccaaa agatatcgt                                               19

<210> SEQ ID NO 166
<211> LENGTH: 19
<212> TYPE: DNA
<213> ORGANISM: Zea mays

<400> SEQUENCE: 166
tctccaaaag atatcgtat                                               19

<210> SEQ ID NO 167
<211> LENGTH: 19
<212> TYPE: DNA
<213> ORGANISM: Zea mays

<400> SEQUENCE: 167
tatctagcct ctaggtcca                                               19

<210> SEQ ID NO 168
<211> LENGTH: 19
<212> TYPE: DNA
<213> ORGANISM: Zea mays

<400> SEQUENCE: 168
tccaaaagat atcgtatca                                               19
```

```
<210> SEQ ID NO 169
<211> LENGTH: 19
<212> TYPE: DNA
<213> ORGANISM: Zea mays

<400> SEQUENCE: 169
tctagcctct aggtccaat                                                19

<210> SEQ ID NO 170
<211> LENGTH: 19
<212> TYPE: DNA
<213> ORGANISM: Zea mays

<400> SEQUENCE: 170
tagcctctag gtccaatgc                                                19

<210> SEQ ID NO 171
<211> LENGTH: 19
<212> TYPE: DNA
<213> ORGANISM: Zea mays

<400> SEQUENCE: 171
tctaggtcca atgcactcc                                                19

<210> SEQ ID NO 172
<211> LENGTH: 19
<212> TYPE: DNA
<213> ORGANISM: Zea mays

<400> SEQUENCE: 172
tatcgtatca cccatgggc                                                19

<210> SEQ ID NO 173
<211> LENGTH: 19
<212> TYPE: DNA
<213> ORGANISM: Zea mays

<400> SEQUENCE: 173
taggtccaat gcactccct                                                19

<210> SEQ ID NO 174
<211> LENGTH: 19
<212> TYPE: DNA
<213> ORGANISM: Zea mays

<400> SEQUENCE: 174
tcgtatcacc catgggcaa                                                19

<210> SEQ ID NO 175
<211> LENGTH: 19
<212> TYPE: DNA
<213> ORGANISM: Zea mays

<400> SEQUENCE: 175
tccaatgcac tccctcctt                                                19

<210> SEQ ID NO 176
<211> LENGTH: 19
<212> TYPE: DNA
<213> ORGANISM: Zea mays

<400> SEQUENCE: 176
tcttgccata gaccggaca                                                19
```

```
<210> SEQ ID NO 177
<211> LENGTH: 19
<212> TYPE: DNA
<213> ORGANISM: Zea mays

<400> SEQUENCE: 177
tgcactccct ccttataaa                                                  19

<210> SEQ ID NO 178
<211> LENGTH: 19
<212> TYPE: DNA
<213> ORGANISM: Zea mays

<400> SEQUENCE: 178
tccctcctta taaacaagg                                                  19

<210> SEQ ID NO 179
<211> LENGTH: 19
<212> TYPE: DNA
<213> ORGANISM: Zea mays

<400> SEQUENCE: 179
tccttataaa caaggaacc                                                  19

<210> SEQ ID NO 180
<211> LENGTH: 19
<212> TYPE: DNA
<213> ORGANISM: Zea mays

<400> SEQUENCE: 180
tggccatgac cccctccc                                                   19

<210> SEQ ID NO 181
<211> LENGTH: 19
<212> TYPE: DNA
<213> ORGANISM: Zea mays

<400> SEQUENCE: 181
tataaacaag gaaccctcc                                                  19

<210> SEQ ID NO 182
<211> LENGTH: 19
<212> TYPE: DNA
<213> ORGANISM: Zea mays

<400> SEQUENCE: 182
tcccagcccc aacctatat                                                  19

<210> SEQ ID NO 183
<211> LENGTH: 19
<212> TYPE: DNA
<213> ORGANISM: Zea mays

<400> SEQUENCE: 183
tccttcgcct ctcttgcca                                                  19

<210> SEQ ID NO 184
<211> LENGTH: 19
<212> TYPE: DNA
<213> ORGANISM: Zea mays
```

```
<400> SEQUENCE: 184
tcgcctctct tgccataga                                                19

<210> SEQ ID NO 185
<211> LENGTH: 19
<212> TYPE: DNA
<213> ORGANISM: Zea mays

<400> SEQUENCE: 185
tctcttgcca tagaccgga                                                19

<210> SEQ ID NO 186
<211> LENGTH: 19
<212> TYPE: DNA
<213> ORGANISM: Zea mays

<400> SEQUENCE: 186
tatatcacct agcgcagct                                                19

<210> SEQ ID NO 187
<211> LENGTH: 19
<212> TYPE: DNA
<213> ORGANISM: Zea mays

<400> SEQUENCE: 187
tatcacctag cgcagctac                                                19

<210> SEQ ID NO 188
<211> LENGTH: 19
<212> TYPE: DNA
<213> ORGANISM: Zea mays

<400> SEQUENCE: 188
tagcgcagct acgctctct                                                19

<210> SEQ ID NO 189
<211> LENGTH: 19
<212> TYPE: DNA
<213> ORGANISM: Zea mays

<400> SEQUENCE: 189
tacgctctct tctcccgct                                                19

<210> SEQ ID NO 190
<211> LENGTH: 19
<212> TYPE: DNA
<213> ORGANISM: Zea mays

<400> SEQUENCE: 190
tgggcaatgg ccatgaccc                                                19

<210> SEQ ID NO 191
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
ggtacagctg gtgatggta                                                19
```

```
<210> SEQ ID NO 192
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
gactcttctt cctccctt                                                    18

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
cgtctccccc ttcaggatgt                                                  20

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gtccaacagg gacagttcca a                                                21

<210> SEQ ID NO 195
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
accaccaatc ttg                                                         13

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
caggatgctg aaggagctct acta                                             24

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
tggaaccagt agaagacgtt cttg                                             24

<210> SEQ ID NO 198
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
atccggtcgc ccagc                                                      15

<210> SEQ ID NO 199
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Zea mays WUS2 protein (wus2)

<400> SEQUENCE: 199
atggcggcca atgcgggcgg cggtggagcg ggaggaggca gcggcagcgg cagcgtggct      60
gcgccggcgg tgtgccgccc cagcggctcg cggtggacgc cgacgccgga gcagatcagg     120
atgctgaagg agctctacta cggctgcggc atccggtcgc ccagctcgga gcagatccag     180
cgcatcaccg ccatgctgcg gcagcacggc aagatcgagg caagaacgt cttctactgg      240 ttccagaacc acaaggcccg cgagcgccag aagcgccgcc tcaccagcct cgacgtcaac     300
gtgcccgccg ccggcgcggc cgacgccacc accagccaac tcggcgtcct ctcgctgtcg     360
tcgccgcctt caggcgcggc gcctccctcg cccaccctcg gcttctacgc cgccggcaat     420
ggcggcggat cggctgggct gctggacacg agttccgact ggggcagcag cggcgctgcc     480
atggccaccg agacatgctt cctgcaggac tacatgggcg tgacgacac gggcagctcg      540 tcgcagtggc catgcttctc gtcgtcggac acgataatgg cggcggcggc ggccgcggcg     600
cgggtggcga cgacgcgggc gcccgagaca ctccctctct tcccgacctg cggcgacgac     660
gacgacgacg acagccagcc cccgccgcgg ccgcggcacg cagtcccagt cccggcaggc     720
gagaccatcc gcggcggcgg cggcagcagc agcagctact gccgttctg gggtgccggt      780 gccgcgtcca caactgccgg cgccacttct tccgttgcga tccagcagca acaccagctg     840
caggagcagt acagctttta cagcaacagc acccagctgg ccggcaccgg cagccaagac     900
gtatcggctt cagcggccgc cctggagctg agcctcagct catggtgctc cccttaccct     960
gctgcaggga gcatgtga                                                   978

<210> SEQ ID NO 200
<211> LENGTH: 879
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Arabidopsis thaliana Homeodomain-like
      superfamily protein (WUS)

<400> SEQUENCE: 200
atggagccgc acagcatca gcatcatcat catcaagccg accaagaaag cggcaacaac       60
aacaacaaca agtccggctc tggtggttac acgtgtcgcc agaccagcac gaggtggaca     120
ccgacgacga agcaaatcaa aatcctcaaa gaactttact acaacaatgc aatccggtca     180
ccaacagccg atcagatcca gaagatcact gcaaggctga cagttcgg aaagattgag       240
```

```
ggcaagaacg tcttttactg gttccagaac cataaggctc gtgagcgtca gaagaagaga    300
ttcaacggaa caaacatgac cacaccatct tcatcaccca actcggttat gatggcggct    360
aacgatcatt atcatcctct acttcaccat catcacggtg ttcccatgca gagacctgct    420
aattccgtca acgttaaact taaccaagac catcatctct atcatcataa caagccatat    480
cccagcttca ataacgggaa tttaaatcat gcaagctcag gtactgaatg tggtgttgtt    540
aatgcttcta tggctacat  gagtagccat gtctatggat ctatgaaca  agactgttct    600 atgaattaca acaacgtagg tggaggatgg gcaaacatgg atcatcatta ctcatctgca    660
ccttacaact tcttcgatag agcaaagcct ctgtttggtc tagaaggtca tcaagaagaa    720
gaagaatgtg gtggcgatgc ttatctggaa catcgacgta cgcttcctct cttccctatg    780
cacggtgaag atcacatcaa cggtggtagt ggtgccatct ggaagtatgg ccaatcggaa    840
gttcgccctt gcgcttctct tgagctacgt ctgaactag                            879
```

<210> SEQ ID NO 201
<211> LENGTH: 795
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of Triticum aestivum cultivar Avalon WUSCHEL-Like-B1 (WUSCHELL-B1) gene

<400> SEQUENCE: 201

```
atggcggcga cggcgactgc gacggcggcg gcgacgagcg tggtgacggg gacgacgcgg     60
tggtgcccga cgccggagca gctgatgatc ctggaggaga tgtaccgcgg cgggctgcgc    120 accccccaacg cgtcgcagat ccagcagatc acggcgcacc tggcccacta cggccgcatc    180
gagggcaaga acgtcttcta ctggttccag aaccacaagg cccgggaccg ccagaagctc    240
cgccgcaggc tctgcatgag ccaccacctc ctctcctgcg cccactacta cgccgccgcc    300
aacgccggcc agtaccacca ccagcagcag ctcctcggcg ccggcgcggt tccccctccg    360
ctgctgcagc accagcagca gcagcagtac tactccgcct cctgcgccgg cggcagctac    420
gaccagcacc tgctcccgac gaccgtccca gcttccgctt atgctgctgc tgctgctggg    480
tacgcctacc ccttcgccgc cgtgccggcg agccggtgcg ccgacccctc gccgcccaac    540
acgccgctgt ccttccatca ccagggtgga ggcgtagtag gatcgccgga gtactcactg    600
gggaggctgg gcaacttcgg cgtggtggac gacacgtgcc ggccgtcgcg gtgcgagcag    660
cagccacagc agctggccgt ggcgacggaa gatcaggcgg cgccggtgac ggcgacgggg    720
ctgttctgcc ggccgctgaa gacgctggac ctcttccccg gcgcgatcaa ggaggagcag    780
cgcgatgtcg cctag                                                     795
```

<210> SEQ ID NO 202
<211> LENGTH: 795
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of Triticum aestivum cultivar Cadenza WUSCHEL-Like-B1 (WUSCHELL-B1) gene

<400> SEQUENCE: 202

```
atggcggcga cggcgactgc gacggcggcg gcgacgagcg tggtgacggg gacgacgcgg    60
tggtgcccga cgccggagca gctgatgatc ctggaggaga tgtaccgcgg cgggctgcgc   120
accccccaacg cgtcgcagat ccagcagatc acggcgcacc tggcccacta cggccgcatc   180
gagggcaaga acgtcttcta ctggttccag aaccacaagg cccgggaccg ccagaagctc   240
cgccgcaggc tctgcatgag ccaccacctc ctctcctgcg cccactacta cgccgccgcc   300
aacgccggcc agtaccacca ccagcagcag ctcctcggcg ccggcgcggt tcccctccg   360
ctgctgcagc accagcagca gcagcagtac tactccgcct cctgcgccgg cggcagctac   420
gaccagcacc tgctcccgac gaccgtccca gcttccgctt atgctgctgc tgctgctggg   480
tacgcctacc ccttcgccgc cgtgccggcg agccggtgcg ccgaccccctc gccgcccaac   540
acgccgctgt ccttccatca ccagggtgga ggcgtagtag gatcgccgga gtactcactg   600
gggaggctgg gcaacttcgg cgtggtggac gacacgtgcc ggccgtcgcg gtgcgagcag   660
cagccacagc agctggccgt ggcgacggaa gatcaggcgg cgccggtgac ggcgacgggg   720
ctgttctgcc ggccgctgaa gacgctggac ctcttccccg gcgcgatcaa ggaggagcag   780
cgcgatgtcg cctag                                                   795
```

<210> SEQ ID NO 203
<211> LENGTH: 795
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: cDNA of Triticum aestivum cultivar Badger
WUSCHEL-Like-B1 (WUSCHELL-B1) gene

<400> SEQUENCE: 203

```
atggcggcga cggcgactgc gacggcggcg gcgacgagcg tggtgacggg gacgacgcgg    60
tggtgcccga cgccggagca gctgatgatc ctggaggaga tgtaccgcgg cgggctgcgc   120
accccccaacg cgtcgcagat ccagcagatc acggcgcacc tggcccacta cggccgcatc   180
gagggcaaga acgtcttcta ctggttccag aaccacaagg cccgggaccg ccagaagctc   240
cgccgcaggc tctgcatgag ccaccacctc ctctcctgcg cccactacta cgccgccgcc   300
aacgccggcc agtaccacca ccagcagcag ctcctcggcg ccggcgcggt tcccctccg   360
ctgctgcagc accagcagca gcagcagtac tactccgcct cctgcgccgg cggcagctac   420
gaccagcacc tgctcccgac gaccgtccca gcttccgctt atgctgctgc tgctgctggg   480
tacgcctacc ccttcgccgc cgtgccggcg agccggtgcg ccgaccccctc gccgcccaac   540
acgccgctgt ccttccatca ccagggtgga ggcgtagtag gatcgccgga gtactcactg   600
gggaggctgg gcaacttcgg cgtggtggac gacacgtgcc ggccgtcgcg gtgcgagcag   660
cagccacagc agctggccgt ggcgacggaa gatcaggcgg cgccggtgac ggcgacgggg   720
ctgttctgcc ggccgctgaa gacgctggac ctcttccccg gcgcgatcaa ggaggagcag   780
cgcgatgtcg cctag                                                   795
```

<210> SEQ ID NO 204
<211> LENGTH: 795
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: cDNA of Triticum aestivum cultivar Charger
      WUSCHEL-Like-B1 (WUSCHELL-B1) gene

<400> SEQUENCE: 204

```
atggcggcga cggcgactgc gacggcggcg gcgacgagcg tggtgacggg gacgacgcgg    60
tggtgcccga cgccggagca gctgatgatc ctggaggaga tgtaccgcgg cgggctgcgc   120 accccaacg cgtcgcagat ccagcagatc acggcgcacc tggcccacta cggccgcatc   180
gagggcaaga acgtcttcta ctggttccag aaccacaagg cccgggaccg ccagaagctc   240
cgccgcaggc tctgcatgag ccaccacctc ctctcctgcg cccactacta cgccgccgcc   300
aacgccggcc agtaccacca ccagcagcag ctcctcggcg ccggcgcggt tccccctccg   360
ctgctgcagc accagcagca gcagcagtac tactccgcct cctgcgccgg cggcagctac   420
gaccagcacc tgctcccgac gaccgtccca gcttccgctt atgctgctgc tgctgctggg   480
tacgcctacc ccttcgccgc cgtgccggcg agccggtgcg ccgaccctc gccgcccaac   540 acgccgctgt ccttccatca ccagggtgga ggcgtagtag gatcgccgga gtactcactg   600
gggaggctgg gcaacttcgg cgtggtggac gacacgtgcc ggccgtcgcg gtacgagcag   660
cagccacagc agctggccgt ggcgacggaa gatcaggcgg cgccggtgac ggcgacgggg   720
ctgttctgcc ggccgctgaa gacgctggac ctcttccccg gcgcgatcaa ggaggagcag   780
cgcgatgtcg cctag                                                    795
```

<210> SEQ ID NO 205
<211> LENGTH: 795
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Triticum aestivum cultivar Claire
      WUSCHEL-Like-B1 (WUSCHELL-B1) gene

<400> SEQUENCE: 205

```
atggcggcga cggcgactgc gacggcggcg gcgacgagcg tggtgacggg gacgacgcgg    60
tggtgcccga cgccggagca gctgatgatc ctggaggaga tgtaccgcgg cgggctgcgc   120 accccaacg cgtcgcagat ccagcagatc acggcgcacc tggcccacta cggccgcatc   180
gagggcaaga acgtcttcta ctggttccag aaccacaagg cccgggaccg ccagaagctc   240
cgccgcaggc tctgcatgag ccaccacctc ctctcctgcg cccactacta cgccgccgcc   300
aacgccggcc agtaccacca ccagcagcag ctcctcggcg ccggcgcggt tccccctccg   360
ctgctgcagc accagcagca gcagcagtac tactccgcct cctgcgccgg cggcagctac   420
gaccagcacc tgctcccgac gaccgtccca gcttccgctt atgctgctgc tgctgctggg   480
tacgcctacc ccttcgccgc cgtgccggcg agccggtgcg ccgaccctc gccgcccaac   540 acgccgctgt ccttccatca ccagggtgga ggcgtagtag gatcgccgga gtactcactg   600
gggaggctgg gcaacttcgg cgtggtggac gacacgtgcc ggccgtcgcg gtacgagcag   660
cagccacagc agctggccgt ggcgacggaa gatcaggcgg cgccggtgac ggcgacgggg   720
ctgttctgcc ggccgctgaa gacgctggac ctcttccccg gcgcgatcaa ggaggagcag   780
cgcgatgtcg cctag                                                    795
```

<210> SEQ ID NO 206
<211> LENGTH: 795
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Triticum aestivum cultivar Spark
      WUSCHEL-Like-B1 (WUSCHELL-B1) gene

<400> SEQUENCE: 206

```
atggcggcga cggcgactgc gacggcggcg gcgacgagcg tggtgacggg gacgacgcgg      60
tggtgcccga cgccggagca gctgatgatc ctggaggaga tgtaccgcgg cgggctgcgc     120
accccccaacg cgtcgcagat ccagcagatc acggcgcacc tggcccacta cggccgcatc    180
gagggcaaga acgtcttcta ctggttccag aaccacaagg cccgggaccg ccagaagctc     240
cgccgcaggc tctgcatgag ccaccacctc ctctcctgcg cccactacta cgccgccgcc     300
aacgccggcc agtaccacca ccagcagcag ctcctcggcg ccggcgcggt tccccctccg     360
ctgctgcagc accagcagca gcagcagtac tactccgcct cctgcgccgg cggcagctac     420
gaccagcacc tgctcccgac gaccgtccca gcttccgctt atgctgctgc tgctgctggg     480
tacgcctacc ccttcgccgc cgtgccggcg agccggtgcg ccgacccctc gccgcccaac     540
acgccgctgt ccttccatca ccagggtgga ggcgtagtag gatcgccgga gtactcactg     600
gggaggctgg gcaacttcgg cgtggtggac gacacgtgcc ggccgtcgcg gtacgagcag     660
cagccacagc agctggccgt ggcgacggaa gatcaggcgg cgccggtgac ggcgacgggg     720
ctgttctgcc ggccgctgaa gacgctggac ctcttccccg gcgcgatcaa ggaggagcag     780
cgcgatgtcg cctag                                                      795
```

<210> SEQ ID NO 207
<211> LENGTH: 2130
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Zea mays AP2-like ethylene-responsive
      transcription factor BBM2 (LOC103650883)

<400> SEQUENCE: 207

```
atggccactg tgaacaactg gctcgctttc tccctctccc cgcaggagct gccgccctcc      60
cagacgacgg actccacgct catctcggcc gccaccgccg accatgtctc cggcgatgtc     120
tgcttcaaca tcccccaaga ttggagcatg aggggatcag agctttcggc gctcgtcgcg     180
gagccgaagc tggaggactt cctcggcggc atctccttct ccgagcagca tcacaagtcc     240
aactgcaact tgatacccag cactagcagc acagtttgct acgcgagctc agctgctagc     300
accggctacc atcaccagct gtaccagccc accagctccg cgctccactt cgcggactcc     360
gtcatggtgg cctcctcggc cggtgtccac gacggcggtt ccatgctcag cgcggccgcc     420
gctaacggtg tcgctggcgc tgccagtgcc aacggcggcg gcatcgggct gtccatgatc     480
aagaactggc tgcggagcca accggcgccc atgcagccga gggcggcggc ggctgagggc     540
gcgcagggc tctctttgtc catgaacatg gcggggacga cccaaggcgc tgctggcatg     600
ccacttctcg ctggagagcg cgcacggcg cccgagagtg tatcgacgtc agcacagggt     660
ggtgccgtcg tcgtcacggc gccgaaggag gatagcggtg gcagcggtgt tgccggtgct     720
```

```
ctagtagccg tgagcacgga cacgggtggc agcggcggcg cgtcggctga caacacggca    780
aggaagacgg tggacacgtt cgggcagcgc acgtcgattt accgtggcgt gacaaggcat    840
agatggactg ggagatatga ggcacatctt tgggataaca gttgcagaag ggaaggacaa    900
actcgtaagg gtcgtcaagt ctatttaggt ggctatgata agaggagaa agctgctagg     960 gcttatgatc ttgctgctct gaagtactgg ggtgccacaa caacaacaaa ttttccagtg   1020
agtaactacg aaaaggagct cgaggacatg aagcacatga caaggcagga gtttgtagcg   1080
tctctgagaa ggaagagcag tggtttctcc agaggtgcat ccatttacag gggagtgact   1140
aggcatcacc aacatggaag atggcaagca cggattggac gagttgcagg gaacaaggat   1200
ctttacttgg gcaccttcag cacccaggag gaggcagcgg aggcgtacga catcgcggcg   1260
atcaagttcc gcggcctcaa cgccgtcacc aacttcgaca tgagccgcta cgacgtgaag   1320
agcatcctgg acagcagcgc cctccccatc ggcagcgccg ccaagcgtct caaggaggcc   1380
gaggccgcag cgtccgcgca gcaccaccac gccggcgtgg tgagctacga cgtcggccgc   1440
atcgcctcgc agctcggcga cggcggagcc ctagcggcgc gtacggcgc gcactaccac    1500 ggcgccgcct ggccgaccat cgcgttccag ccgggcgccg ccaccacagg cctgtaccac   1560
ccgtacgcgc agcagccaat gcgcggcggc gggtggtgca agcaggagca ggaccacgcg   1620
gtgatcgcgg ccgcgcacag cctgcaggac ctccaccact tgaacctggg cgcggccggc   1680
gcgcacgact ttttctcggc agggcagcag gccgccgccg cagctgcgat gcacggcctg   1740
gctagcatcg acagtgcgtc gctcgagcac agcaccggct ccaactccgt cgtctacaac   1800
ggcggggtcg gcgatagcaa cggcgccagc gccgttggca gcggcggtgg ctacatgatg   1860
ccgatgagcg ctgccggagc aaccactaca tcggcaatgg tgagccacga gcagatgcat   1920
gcacgggcct acgacgaagc caagcaggct gctcagatgg ggtacgagag ctacctggtg   1980
aacgcggaga acaatggtgg cggaaggatg tctgcatggg ggaccgtcgt ctctgcagcc   2040
gcggcggcag cagcaagcag caacgacaac attgccgccg acgtcggcca tggcggcgcg   2100
cagctcttca gtgtctggaa cgacacttaa                                    2130
```

<210> SEQ ID NO 208
<211> LENGTH: 1707
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of Arabidopsis thaliana Integrase-type DNA-binding superfamily protein (PLT2)

<400> SEQUENCE: 208

```
atgaattcta caactggct cgcgttccct ctatcaccaa ctcactcttc tttgccgcct     60
cacattcact cttcacaaaa ttctcatttc aatctaggtt tggtcaacga caatatcgac   120
aacccttttc aaaccaagg atggaatatg atcaatccac atggtggagg cggcgaaggt   180
ggagaggttc caaaagtggc tgatttctta ggagtgagca atcgggggga tcatcacacc   240
gatcacaacc tcgtacctta taacgacatt catcaaacca acgcctccga ctactacttt   300
caaaccaata gcttgttacc tacagtcgtc acttgtgcct ctaatgctcc taataattat   360
gagcttcaag agagtgcaca caatttgcaa tctctcactc tctctatggg aagtactgga   420 gctgccgctca cagaagtcgc cactgtgaaa gcctcgccgg ctgagactag tgccgataat   480
agtagcagca ctaccaacac aagtggagga gccatcgttg aggctacacc gagacggact   540
```

-continued

```
ttggaaactt ttggacaacg aacctctatc tatcgtggag ttacaagaca tagatggacc      600
ggtagatatg aagctcatct ttgggataat agctgtagaa gagaaggaca atcaaggaaa      660
ggaagacaag tctacttagg tgggtatgac aaagaagaga agcagccag agcatatgat      720 ctagctgcac ttaaatattg gggtccctct actactacca actttccgat aactaactac      780
gagaaggaag tagaggagat gaaaaacatg acgagacaag agtttgtggc ttctataaga      840
aggaaaagta gcggattctc gcgtggtgca tccatgtatc gtggagtaac aaggcatcat      900
caacatggaa gatggcaagc aaggatcggc cgagttgctg aaacaaaga tctctacttg      960 ggaacattca gcacggagga agaagcagca gaagcttatg acatagctgc gataaagttt      1020
cgaggtctaa acgcggttac aaactttgag ataaatcggt atgatgtgaa agccatcctg      1080
gagagcaaca cacttcctat aggaggtggt gcggctaaac ggctcaaaga agctcaagct      1140
ctagaatcat caagaaaacg agaggaaatg atagccctcg gatcaaatt ccatcaatat      1200 ggtgcagcga gcggctcgag ctctgttgct tccagctcta ggcttcagct tcaaccttac      1260
cctctaagca ttcaacaacc ttttgagcat cttcatcatc atcagccttt acttactcta      1320
cagaacaaca acgatatctc tcagtatcat gattcccttta gttacattca gacgcagctt      1380
catcttcacc aacaacaaac caacaattac ttgcagtctt ctagtcacac ttcacagctc      1440
tacaatgctt atcttcagag taaccctggt ctgcttcatg gattttgtctc tgataataac      1500 aacacttcag ggtttcttgg aaacaatggg attggtattg ggtcaagctc taccgttgga      1560
tcatcggctg aggaagagtt tccagccgtg aaagtcgatt acgatatgcc tccttccggt      1620
ggagctacag ggtatggagg atggaatagt ggagagtctg ctcaaggatc gaatccagga      1680
ggtgtttcca cgatgtggaa tgaataa                                         1707
```

<210> SEQ ID NO 209
<211> LENGTH: 1818
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of Beta vulgaris subsp. vulgaris AP2-like ethylene-responsive transcription factor PLT2 (LOC104889956)

<400> SEQUENCE: 209

```
atgggctcaa tgaattcaaa caattggttg tcttttcctc tttctcctac acatccttca      60
cttcaatcac atcttcaaac caatgattca caacctcatc aacaattctc cttgggtctt     120
gtatctgacc acattgacaa cccctttggt caagcgcaag aatggaactt gctcaatcca     180
caagggccaa atgaagtacc caaaatagca gatttcttag gagtagggaa ttcagaaact     240
catcattcac cagaccttac agcgttcagt gacatgagcc aaggtggtga atcagattat     300
cttttctccg gcaacggcgg cggcttaatg gcggtgcaaa acaccgtagc agcagctact     360
aatagtagcc aatatgatca ataccaagag aactctaata attgcttgca atctttgact     420
ctatcaatgg gaagtagtgg acaacagcct caacaacagc aacaaccacc ttcaagcact     480
aataattgtg agactagtgg tgacaataat agcaccgcta gtgtcgccgc ctctactgcc     540
gccactgtca ccaccgcgat tactcctgtg gttgaagcca cccctaggag aaccttggat     600
acttttggcc aaaggacttc tatttataga ggtgttacaa ggcataggtg gacaggaaga     660
tatgaagctc atctttggga taatagttgt agaagggaag gacagtcaag gaagggtcgt     720
```

| | |
|---|---|
| caagtgtatc ttggagggta tgataaggaa gagaaggccg ctaggtctta tgatttagct | 780 |
| gcaatcaagt attggggaac ttcaactact acaaattttc caataagcaa ctatgagaaa | 840 |
| gaaatagaag acatgaaaca catgactaga caagaatttg tagcagctat tagaaggaag | 900 |
| agtagtggat tctctagagg tgcatcaatt tatcgtggtg taacaagaca ccatcaacat | 960 |
| gggagatggc aagcaagaat tggaagggtg gcaggaaaca aggatctcta cttaggaaca | 1020 |
| tttagcacag aggaagaggc tgcagaagct tatgatatcg cggctatcaa gtttagaggc | 1080 |
| cttaatgctg tgacaaattt tgacatgagc cggtatgatg ttaaagccat cctagagagc | 1140 |
| aacactcttc ccataggagg aggggcggcg aagcgcctta aggaagctca agctatagaa | 1200 |
| tcctctagga agagggaaga aatgcttgcc ctaagcaata gtagctaccc atatggagct | 1260 |
| agtagctcga gctcgactcg atatggagcc catcaacaag caacaactca tgcataccct | 1320 |
| ttgttaccat accaccatca agaccatcaa ccacaacctt tgctaaccct acaaaataac | 1380 |
| catggtcaag aaagcaatat ttccctatca cattactctc aagaggctca attccttcag | 1440 |
| ttgtaccaac aatcaagtta ctcaaaccct agtagcatgt acaacaatta cctccaaact | 1500 |
| aaccctagtt tgcttcatgg gttcatgaac atgggctcaa actcttgtgg tgttattgat | 1560 |
| actaacaata ctaatggaag ttcaagtggg agttatagtg gtggagggta ccttggtggt | 1620 |
| ggggctggga tcaatgccat gggtgccgcc tcgacaacga gcaatgcggt ggtttccggt | 1680 |
| gaaccggagc cacttgcatt ggtgaaggtg gactatgata tgccttctgc tggtggtggt | 1740 |
| ggaggaagtt atgaggggtg gtcaactgag acggttcaag gacctaataa tggggttttt | 1800 |
| acaatgtgga atgactaa | 1818 |

<210> SEQ ID NO 210
<211> LENGTH: 2157
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Beta vulgaris subsp. vulgaris AP2-like
      ethylene-responsive transcription factor BBM (LOC104890283)

<400> SEQUENCE: 210

| | |
|---|---|
| atgggttcaa tgaattggtt aggtttctct ttatctcctc aagaacttcc ttcacaaact | 60 |
| cctgatcatg gtagtaatca agatcaccat catcatcact ttacaagcaa caacaatgga | 120 |
| gagtgtttcg atctcgggcc cggctcaacg cctcattctt ctctcaatca catcccttct | 180 |
| tcctttggaa tccttgaggc cttccataga tcaactaatg atcaatccca agattggaac | 240 |
| aatatgaagg gaaactcaga gcttagtatg ctaatgggaa accaagaagt tgaagaggag | 300 |
| ccaaaactag aaaactttct agggagtagt cactctttta gagagaatca tcatcaaaat | 360 |
| aatggagatc tctacatgtt taatactaca catgataaca acaataatag tactatgtca | 420 |
| aaccctaagg atattactag tcctgctagt aataataata ataataataa taacggactc | 480 |
| aatgtttcaa tgatcaagac atggttgaga tcaaaccacc ctcctcaatc aaatatagtg | 540 |
| gatggtggtg gtgcagtgg tggcggcggg gcgaatgcac aaacattatc cctttcaatg | 600 |
| ggaactggtg tgtcccaatc cgccttgccg ctactagcgg caggaggagg aggtggtggt | 660 |
| ggtggaggag agatagagag tagtttgtct gagaatagta gtagtaataa taaacaacaa | 720 |
| ttaagtgata caacggccgg gatatgtaat aacacagctg tactattac tgctatcgtt | 780 |
| gatgttcaaa gtagtgcact agaaagcgtt cctaggaaat ctattgatac atttggacaa | 840 |

```
cgtacatcca tttaccgtgg tgtaacaaga cataggtgga ctgggagata tgaagctcat    900
ctatgggata atagctgtag gagagaaggg cagactcgta agggcagaca agtttatttg    960
gggggttatg acaaagaaga aaaagcggct agagcttatg atttggctgc acttaaatat   1020
tggggtacca ctaccaccac caactttcct attactgatt atgaaaagga agttgaggat   1080
atgaagcata tgacacgcca agaatatgtg gcatctctac gaaggaaaag tagtggattt   1140
tctcgtggtg catcaattta tcgaggagta acaaggcatc atcagcatgg tcgttggcaa   1200
gcaaggatag gtagggttgc aggcaacaaa gacctctacc tgggaacttt cagtacacaa   1260
gaagaagcag cagaagcata tgatatagca gcaataaagt ttaggggatt aaatgcagta   1320
acaaactttg agataaacag gtatgatgtg aaagccatac ttgatagcac cacacttcct   1380
ataggaggag cagcaaagag gttaaaagat gtggaggatt taaccacaat tactccagat   1440
aaacagatta ttagggcaat tacttcgagt aatgataata atcatgaaaa ttctcagctt   1500
actaattttg gtaatgggac tcccaatttc cattcctggc ctggaatcgc attcccacaa   1560
gctcaaccac ttgcaatgca ttacccttat gcaacttctc aacaacaaca acaacaacaa   1620
caaaggtttt ggtgtaagca agaagttcaa gatactacta atgattacca agatcatctt   1680
aatcagcagc ttcaaatgaa taatgggaca cataatttct ttcagatgca taatttgatg   1740
gggttggaga attcttctac tagtttggag catagttctg ggtcgaattc cgtcgtttat   1800
gggaatggga atgggaatgg gaatggaaat gatcatggtg ttgggaatgg gtatggatta   1860
ccctttggga tgtcaacagt aattgctcat gatgggaatg ggaatggaag tgggaatggg   1920
aatgaacaaa gtgggtatga gaattattac tatctttcac accaaggaaa taataataat   1980
catggtaatg ctgctggtgt aagaggagct gttgggactt atgatcaagg gtcagcttgt   2040
aacaattggg tcccaacggc gattccgaca ctcgttccga ggccgaataa tatggcggct   2100
gttggtggtc atggtggagg aggaatccct actttcactg tgtggaatga cacctaa     2157
```

<210> SEQ ID NO 211
<211> LENGTH: 1884
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of Triticum aestivum WANT1-2 mRNA for AP2 transcription factor

<400> SEQUENCE: 211

```
atgagagcga tggccagcgg cggcggcaac tggttaggct tctccctctc cccgcacatg     60
gccatggagg tgccctcctc ctctgaaccc gaccacgctc agcctgctag cgctagtgct    120
atgtctgctt ctcccaccaa cgccgcgacc tgcaacctcc tattctccca acccgcgcaa    180
atggccgctc cacctcctgg atactactac gtcggcggcg cctatgggga tggcaccagc    240
accgctggcg tctactactc ccaccacccc gtcatgccca tcacgtccga tggatctctg    300
tgcatcatgg aagggatgat gccgtcgtcc tcgccgaagc tcgaggactt cttgggtggc    360
ggcaatggca gcggacatga gcggtcacc tactacagcc accagcagca ggaccaacaa    420
gaccaggagg caagcagaat ctaccagcac catcaacagc agcagcagca gctagcgccc    480
tacaacttcc agcacttgac ggaagcagag gcgatctacc aagaggccac ggcgccgatg    540
gacgaggcaa tggccgctgc caagaaccag ctggtgacga gctacggctc atgctacagc    600
```

```
aacgcggga tgcagccgct gagcctgtcc atgagcccca ggtcccagtc cagcagctgc    660
gtcagcgcag ctcctcagca gcatcagatg gctgcggctg ctgctgctgc ctccttggct    720
gcttcccagg gaggcagtaa tggtggtggg gagcaggagc agtgcgtggg gaagaagagg    780
ggcactggga agggaggcca gaagcagccc gttcatcgca agtccatcga cacgtttggg    840
cagaggacct cccagtatag gggcgtcacc aggcacaggt ggactgggag atatgaagcc    900
cacctctggg acaacagctg caagaaggat gggcagacaa ggaaagggag gcaagtttat    960
ctaggtggtt atgacaatga agacaaggct gccagggctt atgatctggc tgctctgaaa   1020 tattggggc cgtcgacgaa caccaatttc ccgctagaaa attatcgaga ggaggtcgag    1080
gagatgaaaa gcatgacaag gcaggaattc gttgcacact tgagaaggag aagcagcggg   1140 tttctcgtg gtgcttcgat atatcgagga gtaacgaggc atcatcagca tggaagatgg   1200
caagctagga ttggcagggt tgctggcaac aaagacttgt atctcggcac tttcaccact   1260
caggaagaag cagccgaggc ctacgacgta gccgcgatca agttccgtgg cctgaacgcc   1320
gtgaccaact tcgacataac cagatacgac gtggacaaga tcatggagag cagctctctg   1380
ctgcccggtg acgaagcgcg caaggtcaag gcggtcgagg cagccaacca cgtgcctgcc   1440
atgcacaacg gcggcgggga gatcagccat gccgaagaag gaagctccgg cgtctggagg   1500
atggtactcc atggaacacc gcagcaagct gcacagtgca ccccgaggt ggcagacctt    1560 cagaagggct tcatgggcgg cggcgaccct cgctcgtccc tgcatggcat cgccgggttc   1620
gacgtcgagt cggcggcgca tgacatcgac gtctcaggca agatcaacta ctccaacccg   1680
tcctccctgg tgaccagcct cagcaactcg agagagggga gcccagagag gttcagcctg   1740
ccctcgctgt acgccaagca tcccaacgcc gtcagcgtcg ccagcatgag cccgtggatg   1800
gcgatgccag cgccggccgc cgcccacgtg ttaaggggc cgaattcctc catgcctgtg   1860
ttcgctgcct ggacggacgc atag                                           1884

<210> SEQ ID NO 212
<211> LENGTH: 1896
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Triticum aestivum WANT1 mRNA for AP2
      transcription factor

<400> SEQUENCE: 212
atgagagcga tggccagcgg cggcggcaac tggttaggtt tctccctctc cccgcacatg     60
gccatggagg tgccctcctc tgaacccgac cacgctcagg ctcaacctgc tagcgctagc    120
gctatgtccg cttctcccac aaacgccgcg acctgcaacc tcctattctc ccaacccgcg    180
caaatggccg ctccacctcc tggctactac tacgtcggcg gcgcctatgg ggatggcacc    240
agcaccgccg gcgtctacta ctcccaccac tccgtcatgc ccatcacgtc cgatggatcc    300
ctgtgcatca tggaagggat gatgccatcg tcctcgccga agctcgagga cttcttgggt    360
ggcggcaatg gaagtgggca cgacgcggtc acctactaca gccaccacca gcagcagcag    420
gaccaacagg accaggaggc aagcagaatc taccagcacc atcagcagca gctagcgccc    480
tacaacttcc agcacttgac ggaaacggag gcgatctacc aagagaccac ggcgccgatg    540
gatgaggcaa tggccgctgc caagaacctg ctcgtgacga gctatggctc atgctacagc    600
aacgcgggga tgcagccgct gagcctgtcc atgagcccca ggtcccagtc cagcagctgc    660
```

```
gtcaccgcag ctcctcagca gcatcagatg gctgcggctg ctgctgctg tgctgcctct      720 atggctgctt cccagggagg cagtaatggt ggtggggagc agtgcgtggg gaagaagagg      780
ggcactggga agggaggcca gaagcagccc gttcaccgca agtccatcga cacgtttggg      840
cagaggacct cccagtatag gggcgtcacc aggcacaggt ggactgggag atatgaagcc      900
cacctgtggg acaacagttg caagaaggat gggcagacaa ggaaagggag gcaagtttat      960
ctaggtggtt atgataatga agacaaggct gccagggctt atgatctggc tgctctgaaa     1020 tactggggc cgtcgacgaa caccaatttc ccgctagaaa attatcgaga ggaggtcgag       1080
gagatgaaaa gcatgacaag gcaggaattc gttgcacact gagaaggag aagcagcggg      1140 ttttctcgtg gtgcttcgat atatcgagga gtaacgaggc atcatcagca tggaagatgg     1200
caagctagga ttggcagggt tgctggcaac aaagacttgt atctcggcac tttcaccact     1260
caagaagaag cagccgaggc ctatgacgta gccgcgatca agttccgtgg cctgaacgcc     1320
gtgaccaact tcgacataac cagatacgac gtggacaaga tcatggagag cagctctctg     1380
ctgcccgggg acgaagcgcg caaggtcagg ccgatcgagg cggccaacca cgtgccttcc     1440
atgcacaacg gcggcgggga gctcagccat gccgaagaag gaagctcagg cgtctggagg     1500
atggtgctcc atggaacacc gcagcaagct gcacagtgca ccccgaggt ggccgacctt     1560 cagaagggct tcatggacgg cgaccctcgc tcgtccctgc atggcaatgg cattgccggg     1620
ttcgacgtcg agtctgccgc gcatgacatc gacgtttcag gcaagattaa ctactccaac     1680
tcgtcttccc tggtgaccag cctcagcaac tcgagagagg ggagccccga gaggttcagc     1740
ctgccctcgc tgtacgccaa gcatcccaac gccgtcagcc tcgccaccat gagcccgtgg     1800
atggcgatgc cggcgccgac cgccacccac gcgttgaggg ggccgaattc ctccatccct     1860
cccatgcctg tgtttgctgc ctggacagac gcatag                               1896
```

<210> SEQ ID NO 213
<211> LENGTH: 2382
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Triticum aestivum clone: tplb0046e23,
      cultivar Chinese Spring

<400> SEQUENCE: 213

```
gggttggccc ctccctctca ttccttttgc tcagctcacg ggtccctctc gcccgtcttc       60
ctcgtagttc acttctcttt taccaccact gcctccatct ccatgtcgtc gctcggacaa      120
gggtagtggt gccgcagtag cagtagagct cagctcagag tgaaagcgaa gcaagaagcg      180
ttttcgtctg tgtttgtttg ttgatgagag cgatggccag cggcggcaac tggttaggct      240
tctccctctc cccgcacatg gccatggagg tgccctcctc ctctgagccc gaccacgctc      300
agcctgctag cgctagcgct atgtccgctt ctcccaccaa cgccgccacc tgcaacctcc      360
tcttctcccc tccctcgcaa atggccgctc cacctcctgg ctactactac gtcggcgggg      420
cctacgggga tggcaccagc accgccgcg tttactactc ccaccacccc gtcatgccca      480
tcacgtccga tggatccctg tgcatcatgg aagggatgat gccgtcgtcc tcgccgaagc      540
tcgaggactt cttgggtggc ggcaatggca gtgcgcacga cgcggtcacc tactacagcc      600
accaccagca gcagcagcag gaccaacagg accaggaggt aagcagaatc taccagcacc      660
```

```
atcagcagca gctagcgccc tacaacttcc agcacttgac ggaggcagag gcgatctacc      720
aagaggccac ggcgccgacg gatgaggcaa tggccgctgc caagaacctg ctcgtgacga      780
gctatggctc atgctacagc aacgcgggga tgcagccgct gagcctgtcc atgagcccca      840
ggtcccagtc cagcagctgc gtcagcgcag ctcctcagca gcatcagatg gctgcggttg      900
ctgctgcggc tgctgcctct atggttgctt cccagggagg cagtaatggt ggtggggagc      960
agtgcgtggg gaagaagagg ggcactggga agggaggcca gaagcagccc gttcatcgca     1020
agtccatcga cacgtttggg cagaggacct cccagtatag gggcgtcacc aggcacaggt     1080
ggactgggag atatgaagcc cacctgtggg acaacagttg caagaaggat gggcagacaa     1140
ggaaagggag gcaagtttat ctaggtggtt atgacaatga agacaaggct gccagggctt     1200
atgatctggc tgctctgaaa tattgggggc catcgacgaa caccaatttc ccgctagaaa     1260
attatcgaga ggaggtcgag gagatgaaaa gcatgacaag acaggaattc gttgcacact     1320
tgagaaggag aagcagcggg ttttctcgtg gtgcttcgat atatcgagga gtaacgaggc     1380
atcatcagca tggaagatgg caagctagga ttggcagggt tgctggcaac aaagacttgt     1440
atctcggcac tttcaccact caggaagaag cagctgaggc ctacgacgta gcggcgatca     1500
agttccgtgg cctgaacgcc gtgaccaact tcgacataac cagatacgac gtggacaaga     1560
tcatggagag cagctctctg ctgcccgggg acgaagcgcg caaggtcagg ccgatcgagg     1620
cagccagcca cgtgtctccc atgcacaacg gcggcgggga gctcagccat gccgaagaag     1680
gaagctccgg cgtctggagg atggtgctcc atggaacacc gcagcaagct gcgccgtgca     1740
cccccgaggt ggccgacctt cagaagggct tcatggacgg cgaccctcgc tcgtccctgc     1800
atggcaatgg cattgccggg ttcgacgtgg agtctgcggc gcatgacatc gacgtctcag     1860
gcaagatcaa ctactccaac tcgtcttccc tggtgaccag cctcagcaac tcgagagagg     1920
ggagccccga gaggttcagc ctaccctcgc tgtacgccaa gcatcccaac gccgtcagcc     1980
tcgccagcat gagcccgtgg atggcgatgc cggcgccgac cgccgcccac acgttgaggg     2040
gaccgaattc ctccatccct tctatgcctg tgtttgctgc ctggacggac gcatagccgt     2100
gttgcagctg ctcaaatctt gctgtcactg gccatgttgt agtaaactgg agctggatta     2160
gtagcgtcgt tgctcatgtc gcttaagttt aatctgggaa ggctggttaa ttggttatca     2220
cgaaggcggt gtagtggtag tggtagtggt acgtaggaga agcatgcatt agtctctagc     2280
tcaccgaact tgtagcagta cgtagtgttc ttacttactt tcttttgagc ctataacaat     2340
gcatggaagg aggctgtccc aagaaaaaaa aaaaaaaaac ga                        2382
```

<210> SEQ ID NO 214
<211> LENGTH: 2528
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Triticum aestivum clone: WT012_J17,
      cultivar: Chinese Spring

<400> SEQUENCE: 214

```
gacacacgcg cgcacagacc aaagtccccc ttcaaacccg ctgagcttgc aatggagagc       60
agcggcatca ttgcgacatg tgctccccaa tgattgatcc tctcattccc atctaagcta      120
gatcttcttg aatcttgaga ccaccacagc ctcatcccca gtcgtgctcg tgcgcccttg      180
ctcccatccg ctccgcccga tgaccaacgg cggccacagc atgagcggcg ccagcatcgc      240
```

-continued

```
gagcggtgct ggcggctggc tgggtttctc gctgtcgcct cacgtcgcca tggaggcggc    300
ggccggctcc ggcatcgtcg acgtggccgg ccaccaccac gcgcagcacg gcggggtcta    360
ctatcaccct gacgcggtcg cctcctcccc catgtccttc tacttcggtg ggagcgacaa    420
tgtcggcgcc gcgagcggcg ggtactactc cgggatctcc gcactgcctc tcaggtccga    480
cggctccctc tgcctcgccg acgcgctccg gaggagcgag cagaaacacc acggggcgga    540
ggtgtcggcg ccgccgaagc tcgaggactt cctgggcgcg agtcccgcca tggcgctgag    600
cctggacaac tcgggctact actacggcgg ccaaggccat ggccatggcg acgcaggagg    660
cggccagcac cagctgccgt acgccatgat gcctggctcc ggtggccacc acatgtacta    720
cgacgcccac gcggcgttgc tggacgagca ggctgcagcc acgtcggccg cgatggaagc    780
ggccggctgg atggcgcgtg ccggagacgt ctacgacgtg gacgccggca acggcgagga    840
cgccatcgtg gcgaccggcc acgacaaccc cggtgggtac gtacaccgc tgacgctgtc    900
catgagctcc gggtcccagt ccagctgcgt caccatgcag caggcggctg cacacgccca    960
cgcctacgtc ggtgccggcg gcgagtgcgt cggccaggcg accgcggcca gcaagaagcg   1020
cggcgcgggc gccgggcaga acaagcagcc ggtcgtgcac cgcaagtgca tcgacacctt   1080
cggccagcgc acgtccaagt accggggcgt caccaggcat aggtggacgg ggaggtatga   1140
ggcgcacctc tgggacaaca gctgccggaa ggaaggccag accaggaaag ccggcaagt   1200
ttatcttggt gggtatgaca tggaggagaa ggcggcgagg gcgtatgacc tcgcggcgct   1260
caagtactgg ggcgcgtcca cgcacatcaa cttcccggtg gaggactacc aggaggagct   1320
ggaggtgatg aagaacatga ccaggcagga gtatgtggct cacctcagaa ggaagagcag   1380
cgggttctcg cgcggcgcct cggtgtaccg gggagtcacc aggcaccacc agcaggggcg   1440
gtggcaggcg cgcatcggcc gcgtctccgg caacaaggac ctctacctcg gcacattcag   1500
cgcggaggcg gacgcggcgg aggcgtacga cgtggcggcg atcaagttcc gcggcctcaa   1560
cgcggtcacc aacttcgaca tcaaccgcta cgacgtggac aagatcatgg agagcagcac   1620
gctcctgccc ggcgaccagg tgcggcgcag gaaggacggc cccgacgaga gcgccgccgt   1680
ggtggcaagc gcggcggccg ccctcgtgca ggccggcagc gccgcggact actggaggca   1740
gcctgcggcg gtgaccacgg aagagcacag ccgccaccac ctggaccttc tgtcgagcga   1800
gtccttctcc ctgctgcgcg gcgtggtgtc cctggacggc gacgcggctg gtgctcaggg   1860
gcagggcaac cgcatgtcgg gcgcgtcgtc cctggccacg agcctgagca actcccggga   1920
gcagagcccg gaccagggag gcggcctggc catgctgttc gcccgccccg aggcgccgaa   1980
gctggcgagc tcgctgccca tgggcacctg ggtctcatcg ccggcgccgg ccaggcccgg   2040
tgtgtccgtg gcgcacatgc cagtgttcgc cgcgtgggcc gacgcctgac ttgctcgact   2100
acagcgtcgt cctttggcc ctgcatccac gaggagatag caaggttgtt taactaggac   2160
tggttaccta gcattagtag ctgcgttagc aaggaactgt aaggtggttt tattagccat   2220
agctggtagc ttagcggcgc atgcatgcat ctgcctgggc tctcgtggtt ccttccccag   2280
ctgcgtctgg gacgaagggt ttttgtagta tcgagccatg gcacggcagc agcagcgtcg   2340
cctccggccc ggcggagagc cgccgccgct gatcggagct ggatgggtag ctgtagctcc   2400
tgtctctaga cctcctaact ttcatcaaac caaaatgttg gaccttcgtg ttcgtgtggc   2460
ctcgcggcgc gtctgaacat ctgattttt tatttttttt gagggtaagc aaaaaaaaaa   2520
aaaaacga                                                           2528
```

<210> SEQ ID NO 215
<211> LENGTH: 1803
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: cDNA of Triticum aestivum PARG-2D

<400> SEQUENCE: 215

```
atgaccaaca acaacggcaa tggcaatggc ggcagcaacg cggcggcgag tggctggctg       60
ggcttctcgc tctcgccgca catggacgaa cacaaccacg tgcagcagca gcaacagcac      120
cagggcctat tctacccag ctccgtcgcc gccgcctaca gcctcggcgg cgacgtcgcc       180
accgacgggt actattcgca gctagcctcc atgcctctca agtcagacgg ctccctctgc      240
atcatggaag ctctacgccg aaccgatcaa caagatcacc acggtccgaa gctggaggac      300
tttctgggcg cggggcaacc ggcgatggcg ctgagcctgg acaacacctc caacttctat      360
tactacggcg gcggtggcgg agccggtggg caacacggac agagccacgg cggcagcttc      420
ctgcagcaag catacgacgt gtacagcggg cccgcaacgg catcggtgct ggcggccaat      480
gaggacgccg cggcagccac ggccatggcg aactgggtgc aggtcgcgcg cggtgccacc      540
gcgtacgcca cagccgagaa cgtcttgtcc gcggcggcgg accggcagca gcatcttcac      600
caccaccctc tggcactctc catgagctcc gccgggtcgc tctccagctg cgttaccgcg      660
ggggccgagt acggcggcgt cggggcgacg gtggacggcg gcgaaagcg cggcggcgcg       720
acggcgggc agaagcagcc ggtgcaccac cgcaagtcca tcgacacgtt cgggcagcgc       780
acgtcgcagt accgtggcgt caccaggcat aggtggacgg gcggtatga ggcgacctg        840
tgggacaaca gctgcaagaa ggaaggccag accaggaaag ggaggcaagt ttacctcgga      900
ggatatgaca tggaggagaa ggcggcgaga gcctacgacc aggcggcgct caagtactgg      960
ggcccttcca cccatatcaa cttcccgctc gaggactacc agcaggagct ggaggagatg     1020
aagaacatga cgaggcagga gtacgtggca caccttagaa ggaagagcag cggcttctcg     1080
cgtggcgcgt ccatgtaccg tggcgtgacc cggcaccacc agcacgggcg gtggcaggcg     1140
cgcatcggcc gcgtctccgg caacaaggac ctctacctcg gcactttcgg cacccaggag     1200
gaggccgcga ggcgtacga catcgccgcc atcaagttcc ggggcctcaa cgccgtcacc      1260
aacttcgaca tcacccgcta cgacgtcgac aagatcatgg ccagcaacac gctcctcccg     1320
ggcgagcacg ccaggcgcaa caaggacgac aacgccgcgc cctgcccct ccccgccccc      1380
gacgactgcg ccgcctctgc cctggtgccc gtgtccactc cggggacgga caccggcggc     1440
agcggccagc accgctacca cgacgtcatg tcctcgggcg aggccttctc ggcgctacac     1500
gacctggtca ccgtggacgg ccacaccgcg cagggcggga acggcgcgca cgtgcacatg     1560
tcgatgtcgg gcgcatcgtc gctggtgacg agcctgagca actcccgaga ggagagccca     1620
gaccgggggcg gcgggctgtc catgctcttc gccaagccgc cgcagcagcc ggccacgaca     1680
acggcggcgt ccccgaagct gatgagcact ctgaagccgc tgggctcctg ggcgtcgtcg     1740
gcgaggccgc ccgccgtttc catcgctcac atgcccatgt cgccgcgtg gagcgacgca     1800
tga                                                                   1803
```

<210> SEQ ID NO 216
<211> LENGTH: 1806
<212> TYPE: DNA

<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: cDNA of Triticum aestivum PARG-2A

<400> SEQUENCE: 216

```
atgaccaaca acaacggcaa tgggaatggc ggcagcaacg cggcggcgag tggctggctg      60
ggcttctcgc tctcgccgca catggacgaa cacaaccacg tgcagcagca gcagcaacaa     120
caccagggcc tattctaccc cagctccgtc gccgccgcct acagcctcgg cagcgacgtc     180
gccaccggcg gtactattc gcagctagcc tccatgcctc tcaagtcaga cggctccctc      240
tgcatcatgg aagctctacg ccgaaccgat caacaagatc accacggtcc gaagctggag     300
gactttctgg gcgcggggca accgcgatg gcgctgagcc tggacaacac ctccaacttc      360
tattactaca gcggcggtgg cggagcaggt gggcaacacg gacagagcca cggcggcggc     420
ttcctgcagc aagcatacga cgtgtacggc gggcccgcaa cggcatcggt gctggcggcc     480
gatgaggacg ccgcggcagc cacggccatg gcgaactggg tgcaggtcgc gcgcggtgcc     540
accgcgtacg ccacagccga gaacgtcttg tccgcggcgg cggaccggca gcagcatctt     600
caccaccacc ctctggcact ctccatgagc tccgccgggt cgctctccag ctgcgttacc     660
gcggggggccg agtacggcgg cgtcgtggcg acggtggacg gcgggcgaaa acgcggtggc     720
gcgacggcgg ggcagaagca gccggtgcac caccgcaagt ccatcgacac gttcgggcag     780
cgcacgtcgc agcaccgtgg cgtcaccagg cataggtgga cggggcggta tgaggcgcac     840
ctgtgggaca cagctgcaa gaaggaaggc cagaccagga aagggaggca agtttacctc      900
ggagggtatg acatggagga gaaggcgcg agagcctacg accaggcggc gctcaagtac      960
tgggggccctt ccacccatat caacttcccg ctcgaggact accagcagga gctggaggag    1020
atgaagaaca tgacgaggca ggagtacgtg gcacaccta gaaggaagag cagcggcttc     1080
tcgcgtggcg cgtccatgta ccgtggcgtg acccggcacc accagcacgg gcggtggcag    1140
gcgcgcatcg gccgcgtctc cggcaacaag gacctctatc tcggcacttt cggcacccag    1200
gaggaggccg cggaggcgta cgacatcgcc gccatcaagt tccggggact caacgccgtc    1260
accaacttcg acatcacccg ctacgacgtc gacaagatca tggccagcaa cacgctcctc    1320
ccgggcgagc tcgccaggcg caacaaggac gccaacgccg cgcccctgcc cctccccgcc    1380
cccgacgact gcgccgcctc tgccctggtg cccgtgtcta ctccggggac ggacaccggc    1440
ggcagcggcc agcaccgaaa ccaggacgtc atgtcctcgg gcgaggcctt ctcggcgctg    1500
cacgacctgg tcaccgtgga cggccacacc gcgcagggcg gcaacggcgc gcgcgtgcac    1560
atgtcgatgt cggcgcatc gtcgctggtg acgagcctga gcaactcccg cgaggagagc    1620
ccagaccggg gcggtggcct gtctatgctc ttcgccaagc gccgcagca gccggccacg    1680
acaacggcgg cgtccccgaa gctgatgagc actctggcgc gctgggttc ctgggcgtcg    1740
tcggcgaggc cggccgccgt ttccatcgct cacatgccca tgttcgccgc gtggagcgac    1800
gcatga                                                              1806
```

<210> SEQ ID NO 217
<211> LENGTH: 2040
<212> TYPE: DNA
<213> ORGANISM: Artificial Sequence
<220> FEATURE:
<223> OTHER INFORMATION: Description of Artificial Sequence: Synthetic
    polynucleotide <220> FEATURE:
<223> OTHER INFORMATION: cDNA of Zea mays BBM

<400> SEQUENCE: 217

```
atggcttcag cgaacaactg gctgggcttc tcgctctcgg gccaggataa cccgcagcct      60
aaccaggata gctcgcctgc cgccggtatc gacatctccg gcgccagcga cttctatggc     120
ctgcccacgc agcagggctc cgacgggcat ctcggcgtgc cgggcctgcg ggacgatcac     180
gcttcttatg gtatcatgga ggcctacaac agggttcctc aagaaaccca agattggaac     240
atgaggggct ggactacaa cggcggtggc tcggagctct cgatgcttgt ggggtccagc      300
ggcggcggcg gggcaacgg caagagggcc gtggaagaca gcgagcccaa gctcgaagat      360
ttcctcggcg gcaactcgtt cgtctccgat caagatcagt ccggcggtta cctgttctct     420
ggagtcccga tagccagcag cgccaatagc aacagcggga gcaacaccat ggagctctcc     480
atgatcaaga cctggctacg gaacaaccag gtggcccagc ccagccgcc agctccacat      540
cagccgcagc ctgaggaaat gagcaccgac gccagcggca gcagctttgg atgctcggat     600
tcgatgggaa ggaacagcat ggtggcggct ggtgggagct cgcagagcct ggcgctctcg     660
atgagcacgg gctcgcacct gcccatggtt gtgcccagcg cgccgccag cggagcggcc      720
tcggagagca tcgtcgga gaacaagcga gcgagcggtg ccatggattc gcccggcagc       780
gcggtagaag ccgtaccgag gaagtccatc gacacgttcg ggcaaaggac ctctatatat     840
cgaggtgtaa caaggcatag atggacaggg cggtatgagg ctcatctatg ggataatagt     900
tgtagaaggg aagggcagag tcgcaagggt aggcaagttt accttggtgg ctatgacaag     960
gaggacaagg cagcaagggc ttatgatttg gcagctctca gtattgggg cactacgaca     1020
acaacaaatt tccctataag caactacgaa aaggagctag aagaaatgaa acatatgact    1080
agacaggagt acattgcata cctaagaaga aatagcagtg gattttctcg tggggcgtca    1140
aagtatcgtg gagtaactag acatcatcag catgggagat ggcaagcaag gataggggaga   1200
gttgcaggaa acaaggatct ctacttgggc acattcagca ccgaggagga ggcggcggag    1260
gcctacgaca tcgccgcgat caagttccgc ggtctcaacg ccgtcaccaa cttcgacatg    1320
agccgctacg acgtgaagag catcctcgag agcagcacac tgcctgtcgg cggtgcggcc    1380
aggcgcctca aggacgccgt ggaccacgtg gaggccggcg ccaccatctg gcgcgccgac    1440
atggacggcg ccgtgatctc ccagctggcc gaagccggga tgggcggcta cgcctcgtac    1500
ggccaccacg gctggccgac catcgcgttc cagcagccgt cgccgctctc cgtccactac    1560
ccgtacggcc agccgtcccg cgggtggtgc aaacccgagc aggacgcggc cgccgccgcg    1620
gcgcacagcc tgcaggacct ccagcagctg cacctcggca gcgcggccca caacttcttc    1680
caggcgtcgt cgagctccac agtctacaac ggcggcgccg cgccagtgg tgggtaccag     1740
ggcctcggtg gtggcagctc tttcctcatg ccgtcgagca ctgtcgtggc ggcggccgac    1800
cagggggcaca gcagcacggc caaccagggg agcacgtgca gctacgggga cgaccaccag    1860
gaggggaagc tcatcggtta cgacgccgcc atggtggcga ccgcagctgg tggagacccg    1920
tacgctgcgg cgaggaacgg gtaccagttc tcgcagggct cgggatccac ggtgagcatc    1980
gcgagggcga acgggtacgc taacaactgg agctctcctt tcaacaacgg catggggtga    2040
```

<210> SEQ ID NO 218
<211> LENGTH: 963
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: cDNA of Zea mays WUS1

<400> SEQUENCE: 218

| | |
|---|---:|
| atggcggcca acgtgggcgc gggcaggagt gctggcggcg gcggagccgg cactggcact | 60 |
| ggcactgctg ctggcagcgg cggcgtgtcg acggccgtgt gccgccctag cggctcgcgg | 120 |
| tggacgccga cgccggagca gatcaggatc ctcaaggagc tctactacgg ctgcggcatc | 180 |
| cggtcgccca actcggagca gatccagcgc atcaccgcca tgctgcggca gcacggcaag | 240 |
| atcgagggca agaacgtctt ctactggttc agaaccaca aggcccgcga cgccagaag | 300 |
| cgccgcctca ccaacctcga cgtcaacgtg cccgtcgccg ccgacgacag cgcccaccgc | 360 |
| cttggcgtcc tctcgttgtc gccttcttca ggttgttcag gcgcggcgcc tccgtcgccc | 420 |
| accctcggct tctacgccgg cggcaatggc tccgctgtga tgctggacac gagttccgat | 480 |
| tggggcagcg ctgctgccat ggccactgag gcatgcttca tgcaggacta catgggcgtg | 540 |
| atgggcggcg cgtcaccgtg ggcatgctcc tcctcgtcgt cggaggaccc gatggcggcg | 600 |
| ctggcgctgg cgccgaaggt gacccggggcg cccgagacgc tccctctctt cccgaccggc | 660 |
| ggcggcggag acgataggca gccccgcgg ccgcggcagt ctgtcccagc aggcgaggcc | 720 |
| atccgcggcg gcagcagcag cagcagctac cttccgttct ggggtgccgc gcccacccca | 780 |
| actggcagtg ccacttccgt tgcgatccag cagcaacacc agctgatgca gatgcaagag | 840 |
| cagtacagct tttacagcaa cgcccagctg ctgcccggca ccggcagcca ggatgcagca | 900 |
| gcaacatccc tggagctgag cctcagctcc tggtgctccc cttaccctgc agggaccatg | 960 |
| tga | 963 |

<210> SEQ ID NO 219
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Zea mays WUS2

<400> SEQUENCE: 219

| | |
|---|---:|
| atggcggcca atgcgggcgg cggtggagcg ggaggaggca gcggcagcgg cagcgtggct | 60 |
| gcgccggcgg tgtgccgccc cagcggctcg cggtggacgc cgacgccgga gcagatcagg | 120 |
| atgctgaagg agctctacta cggctgcggc atccggtcgc ccagctcgga gcagatccag | 180 |
| cgcatcaccg ccatgctgcg gcagcacggc aagatcgagg gcaagaacgt cttctactgg | 240 |
| ttccagaacc acaaggcccg cgagcgccag aagcgccgcc tcaccagcct cgacgtcaac | 300 |
| gtgcccgccg ccggcgcggc cgacgccacc accagccaac tcggcgtcct ctcgctgtcg | 360 |
| tcgccgcctt caggcgcggc gcctccctcg cccacccgcg gcttctacgc cgccggcaat | 420 |
| ggcggcggat cggctgggct gctggacacg agttccgact ggggcagcag cggcgctgcc | 480 |
| atggccaccg agacatgctt cctgcaggac tacatgggcg tgacggacac gggcagctcg | 540 |
| tcgcagtggc catgcttctc gtcgtcggac acgataatgg cggcggcggc ggccgcggcg | 600 |
| cgggtggcga cgacgcgggc gcccgagaca ctccctctct tcccgacctg cggcgacgac | 660 |
| gacgacgacg cagccagcc cccgccgcgg ccgcggcacg cagtcccagt cccggcaggc | 720 |
| gagaccatcc gcggcggcgg cggcagcagc agcagctact tgccgttctg gggtgccggt | 780 |

| | |
|---|---|
| gccgcgtcca caactgccgg cgccacttct tccgttgcga tccagcagca acaccagctg | 840 |
| caggagcagt acagcttta cagcaacagc acccagctgg ccggcaccgg cagccaagac | 900 |
| gtatcggctt cagcggccgc cctggagctg agcctcagct catggtgctc cccttaccct | 960 |
| gctgcaggga gcatgtga | 978 |

<210> SEQ ID NO 220
<211> LENGTH: 975
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Zea mays WOX2

<400> SEQUENCE: 220

| | |
|---|---|
| atggagacgc cacagcagca atccgccgcc gccgccgccg ccgccgccca cgggcaggac | 60 |
| gacggcgggt cgccgccgat gtcgccgccc tccgccgcgg cggcggcgct ggcgaacgcg | 120 |
| cggtggaacc cgaccaagga gcaggtggcc gtgctggagg gctgtacga gcacggcctg | 180 |
| cgcaccccca gcgcggagca gatacagcag atcacgggca ggctgcggga gcacggcgcc | 240 |
| atcgagggca agaacgtctt ctactggttc cagaaccaca aggcccgcca gcgccagagg | 300 |
| cagaagcagg acagcttcgc ctacttcagc aggctcctcc gccggccccc gccgctgccc | 360 |
| gtgctctcca tgccccccgc gccaccgtac catcacgccc cgtcccggc gccgcccgcg | 420 |
| ataccgatgc cgatggcgcc gccgccgccc gctgcatgca cgacaacgg cggcgcgcgt | 480 |
| gtgatctaca ggaacccatt ctacgtggct cgccgcagg cgccccctgc aaatgccgcc | 540 |
| tactactacc cacagccaca gcagcagcag cagcagcagg tgacagtcat gtaccagtac | 600 |
| ccgagaatgg aggtagccgg ccaggacaag atgatgacca gggccgcggc gcaccagcag | 660 |
| cagcagcaca acgcgccgg gcaacaaccg ggacgcgccg gccaccccag ccgcgagacg | 720 |
| ctccagctgt tcccgctcca gcccaccttc gtgctgcggc acgacaaggg gcgcgccgcc | 780 |
| aacggcagta ataacgactc cctgacgtcg acgtcgacgg cgactgcgac agcgacagcg | 840 |
| acagcgacag cgtccgcttc catctccgag gactcggatg gcctggagag cggcagctcc | 900 |
| ggcaagggcg tcgaggaggc gcccgcgctg ccgttctatg acttcttcgg gctccagtcc | 960 |
| tccggaggcc gctga | 975 |

<210> SEQ ID NO 221
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Zea mays WOX5

<400> SEQUENCE: 221

| | |
|---|---|
| atggaggcgc tgagcgggcg ggtaggcgtc aagtgcgggc ggtggaaccc tacggcggag | 60 |
| caggtgaagg tcctgacgga gctcttccgc gcggggctgc ggacgcccag cacggagcag | 120 |
| atccagcgca tctccacccca cctcagcgcc ttcggcaagg tggagagcaa gaacgtcttc | 180 |
| tactggttcc agaaccacaa ggcccgcgag cgccaccacc acaagaagcg acgccgcggc | 240 |
| gcgtcgtcgt cctccccga cagcggcagc ggcaggggaa gcaacaacga ggaagacggc | 300 |

```
cgtggtgccg cctcgcagtc gcacgacgcc gacgccgacg ccgacctcgt gctgcaaccg      360
ccagagagca agcgggaggc cagaagctat ggccaccatc accggctcgt gacatgctac      420
gtcagggacg tggtggagca gcaggaggcg tcgccgtcgt gggagcggcc gacgagggag      480
gtggagacgc tagagctctt ccccctcaag tcgtacggcg acctcgaggc ggcggagaag      540
gtccggtcgt acgtcagagg aagcggcgcc accagcgagc agtgcaggga gttgtccttc      600
ttcgacgtcg tctccgccgg ccgggatccg ccgctcgagc tcaggctctg cagcttcggt      660
ccctag                                                                 666
```

<210> SEQ ID NO 222
<211> LENGTH: 1521
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of Zea Mays WOX8

<400> SEQUENCE: 222

```
atggcgtcct cgaacaggca ctggccgagc atgtacaggt ccagtctcgc ctgcaacttc      60
cagcagccgc agccgcagcc tgacatgaac aacggcggca agtcctcact catgtcctca     120
aggtgcgagg agaacggcgg aaggaacccg gagccgaggc cgcggtggaa cccgcggccg     180
gagcagatca ggatcctgga agggatcttc aactccggca tggtgaaccc gccgcgcgac     240
gagatccgcc gcatccgcct ccaactgcag gagtacgggc ccgtcggcga cgccaacgtc     300
ttctactggt tccagaaccg caagtcccgc accaagcaca gctgcgcgc gcggggcag      360 ctgcagccgt cgggctcggg ccgctccgcc ctgcaggcgc gcgcgtgcgc cccggcgccc     420
gtgacgcctc ccaggaacct gcagctcgcg gccgctgctc ccgtggcgcc gcccacgtcc     480
tcgtcctcgt cgtcctccga ccggtcctcg gggtcatcat cgagcaagtc ggtgaccgtg     540
accccgacga ccgccgtcgc gcttgcttct cccgcaggcg ccgcgccggc tgctgtcttc     600
cgccagcagg gcgtgatgcc gacgacggcc atggacctgc ttacgccgct gccgtcgtcg     660
tcggccgctc tggccgcgcg ccagctctac tatcagtacc acagccagat catggcgcct     720
gccgcgccgc cgatgcccga tacggtgatc gcctctccgg agcagttcct tccgcagtgg     780
cagcagggcg gacagcagca ttattacctg ccggccaccg agctcggtgg cgtcctcgac     840
ggccactccc accacacaca cgagccccg gcggccatac accggcccgt ctcgctctca     900
cccagcgtgc tctttggcct gtgcaacgaa gctctaaggc aagactactg cgccgacatc     960
agcgtcgtcc ccaccaaggg actcggccat ggccaccagt tctggaacag caccacctgc    1020
ggctctgata tgggcaatag caatagcaag atcgacgccg tgagcgccgt gatcagggac    1080
gacgagaagt ccaggctggg gttactccac tactacggct tggcgggcgc gacgacgacc    1140
gctgctgcgg ctgtcgctcc ggcccctctc gctgcagatg ccgccgccgg tacggccacg    1200
ctgcttccaa gctctgcggc gagcgaccag ttgcaagggc tgttggatgc tgctgggctg    1260
ctgatggggg agacgccgcc gacgccgacg gcgacggtgg tggccgtggc ccggacgcc     1320 gtgacgtgcg cggccaccgc caccgcgcag ttcagcgtgc cggcgtcgat gcgcctggac    1380
gtgaggctgg cgttcggcga ggccgccctt ctggcgcgcc acaccggcga ggcggtcccc    1440
gtcgacgagt ccggcgtcac ggtggagccg ctccagcagg acactctcta ctacgtgctc    1500
atgcaggcga ctaataactg a                                              1521
```

<210> SEQ ID NO 223
<211> LENGTH: 822
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of Zea mays WOX10

<400> SEQUENCE: 223

| | | | | | |
|---|---|---|---|---|---|
| atggagtggg | tggacaggac | caaggcctcc | gccgccgccg | ccgcagcggc | ggcggacgag | 60 |
| agggctgggg | gagcggaagg | gctcgcggga | tacgtcaagg | tcatgaccga | cgaacagatg | 120 |
| gaggtgctcc | gcaagcagat | ctccatctac | gccaccatct | gcgagcagct | tgtcgagatg | 180 |
| caccgcgccc | tcaccgagca | ccaggacacc | attgcaggaa | ttaggtttag | taatctgtac | 240 |
| tgtgatcctc | aaattatccc | tggaggccac | aagatcacag | caaggcaacg | atggcaacca | 300 |
| acaccaatgc | agctgcagat | cttggagaac | atctttgacc | aaggcaatgg | aacaccaagc | 360 |
| aagcagagga | taaaggagat | aacggcagag | ctctcgcacc | atggccaaat | ctcggagaca | 420 |
| aatgtgtaca | actggttcca | gaacagacgg | cacggtcaa | agcggaagca | ggccgcttct | 480 |
| ttaccgaaca | atgctgaatc | tgaagctgag | gtggacgagg | agtctctcac | cgataagaag | 540 |
| ccgaagtcag | atcggtcgct | ccaggacaac | aaggctatgg | cgctcacaa | cgctgacagg | 600 |
| atatctggga | tgcatcactt | ggacactgat | catgaccaaa | tcggtggcat | gatgtatgga | 660 |
| tgcaatgaca | acggcttgag | atcgtctggc | agttctggcc | agatgtcctt | ctacgggaac | 720 |
| atcatgccga | atccaagaat | cgatcatttc | ccggggaagg | tggagagctc | ccggagcttc | 780 |
| tcccatctcc | aacacgggga | aggctttgac | atgtttggat | ga | | 822 |

<210> SEQ ID NO 224
<211> LENGTH: 849
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of Zea mays WOX13

<400> SEQUENCE: 224

| | | | | | |
|---|---|---|---|---|---|
| atggactggg | ggaacaggac | caaggccgcc | gccgccgctg | cggcgccgga | cgagagggcc | 60 |
| gggggagggg | aagggctcgg | aggatacgtc | aaggtcatga | ccgacgaaca | gatggaggtg | 120 |
| ctccgcaagc | agatctccat | ctacgccacc | atctgcgagc | agcttgtcga | gatgcatcgc | 180 |
| gtcctcaccg | agcaccagga | caccattgca | ggattgaggt | ttagcaatct | gtactgtgac | 240 |
| cctctaatca | tccccggcgg | tcacaagatc | acggcaaggc | agcggtggca | accaacaccg | 300 |
| atgcagctgc | agatcctgga | gagcatcttc | gaccagggca | acgggacacc | gagcaagcag | 360 |
| aagataaagg | agataacagc | ggagctctcg | cagcacggcc | agatctcgga | gacgaacgtg | 420 |
| tacaactggt | tccagaacag | gcgggcacgg | tcgaagcgga | agcaggccgc | tgcttcctta | 480 |
| ccgaacaacg | ccgaatccga | agccgaggcg | gacgaggagc | tctctcgccga | caagaagccg | 540 |
| aagtcagaca | ggccgccgcc | gccgccgccg | ccgatccagg | ataataccaa | ggctacgggc | 600 |
| gctctcagcg | ccgacagggt | ctctggtggg | acgcgtcact | tggacacggg | tcatgaccag | 660 |
| accagtggcg | tgatgtatgg | gtgcaacgac | agtggcttgt | tgagatcgtc | cggcagttcg | 720 |
| ggccagatgt | ccttgtacga | gaacttcatg | tcgaatccaa | gaatcgatcg | tttccggcg | 780 |

```
aaggtggaga gctcccggag cttcccccat ctccaacaac acggggaagg ctttggcatg    840
tttggatga                                                            849

<210> SEQ ID NO 225
<211> LENGTH: 795
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Zea mays Lec1

<400> SEQUENCE: 225
atggactcca gcttcctccc tgccggcgcg gacaatggct cggcgggcgg cgccaacaat     60
ggcggcggcg ctgctcagca ggcgccgccg atccgcgagc aggaccggct gatgccgatc    120
gcgaacgtca tccgcatcat gcggcgcgtg ctgccggcgc acgccaagat ctcggacgac    180
gccaaggaga cgatccagga gtgcgtgtcg gagtacatca gcttcatcac ggggg aggcc    240 aacgagcggt gccagcggga gcagcgcaag accatcaccg ccgaggacgt gctgtgggcc    300
atgagccgcc tcggcttcga cgactacgtc gagccgctca gcgtctacct ccaccgctac    360
cgcgagttcg agggcgaggc gcggggcgtc ggcctcgccc ggcccctcc gcgcggcgac     420 caccaccacc accaccactc cgtgccgcca tcgatgctac acaagtcccg cgggcccggc    480
tccggagccg tcatgctacc gcaccaccac caccacgaca tgcacgcctc catgtacggg    540
ggcgccgtgc ccccgccgcc gcaccacggc ttcctcatgc acacccaca gggcggccac     600 tacctgcctt accccta cga gcccacgtcg tacgcggcg agcacgcctt ggccagcggg    660
tactatggag gggccgcgta cgcgccgggc aacaacggcg ggagcggcga tgcagcggc     720 gggagcgcgt cgcacgcacc gccgggcggc agcggcggcg gcttcgacca cccgcacacg    780
ttcgcgtaca agtag                                                    795

<210> SEQ ID NO 226
<211> LENGTH: 1179
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA od Zea mays Lec2

<400> SEQUENCE: 226
atgccagccc gcgcctccca cccggcgctt gccacctcgc gcgcgcgcgg ttggccgcgc     60
ctgcgcgccc tcggcatcgc ccccgacggg gggcgttggc gttgcctccc ccactttgca    120
cccatttcag agcccgcccg acacttgtca ccgcgcgccc ccgcctccgc gtctccgccc    180
gcccgccccc atccggctat aaaagcctcg ccctctccaa ccctagccgc cgctgccgct    240
gccgccgccg ccgctacctc ctcccttcct tccttctccg ctcgtcgtcg ttctaccggc    300
atggccggca ttaccaagcg ccgcacctcc ccggcctcca cctcctcttc gtccggcgac    360
gtcttgccgc agcgggtcac ccggaagcgt cggtccgccc gccgcgggcc ccggagcacc    420
gcccgtaggc cgtcggcgcc tccacctatg aatgaactgg acttgaatac agctgctctt    480
gatccggatc attatgctac aggattgaga gttcttcttc agaaggagct ccgaaatagc    540
gatgtaagcc agcttgggag aattgttctc ccaaagaagg aggcggagtc ttacctccct    600
```

```
attctgatgg caaaggatgg aaagagttta tgcatgcatg acttgctaaa ttcacaactg    660
tggaccttca agtatagata ttggttcaac aacaaaagca ggatgtatgt gcttgaaaat    720
accggagatt atgtaaaagc tcatgacctt cagcaaggag acttcatcgt gatctacaag    780
gacgacgaga acaaccgctt tgtcatagga gcaaagaagg caggagatga gcagaccgcc    840
actgtacctc aagtccatga acacatgcac atctctgccg cactgccagc tccacaagcg    900
ttccatgact atgcaggccc cgtcgcagca gaagctggta tgctcgcgat cgtgccacag    960
ggtgacgaga tattcgacgg catactgaac tccctgccgg agataccagt ggcgaacgtg   1020
aggtactccg acttcttcga cccgttcggt gactccatgg acatggcgaa tccgctgagc   1080
tcctccaata acccctcggt caacctggct acgcatttcc atgacgagag gatcgggagc   1140
tgctcgtttc cctacccaaa atccgggcct cagatgtga                          1179

<210> SEQ ID NO 227
<211> LENGTH: 1026
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Zea mays WIND1_1

<400> SEQUENCE: 227
atggccgcag ccatcgacat gtacaagtac tacaatacca gcgcacacca gatcccctcc     60
tcatccccct cggatcagga gctcgcgaaa gcactcgagc cttttataac gagtgcttcc    120
tcctcttcat cctcctcccc ctaccatggc tactcgtcct ctccatccat gtcccaagat    180
tcttacatgc ctacaccctc ttacaccagc tacgccacct cgcctcttcc cactcccgcc    240
gccgcctcct cctcgcagct tccgccgctc tactcgtcgc cttatgcggc gccgtgcatg    300
gccggccaga tgggcctgaa ccagctcggc ccggcccaga tccagcagat ccaggcccag    360
ttcatgttcc agcagcagca gcagcagcag aggggcctgc acgcggcgtt cctgggcccg    420
cgggcgcagc cgatgaagca gtcagggtcg ccgtcgccgc cgccgccgct ggcgccggcg    480
cagtcgaagc tgtaccgcgg cgtgcggcag cgccactggg gcaagtgggt ggcggagatc    540
cggctcccga gaaccgcac gcggctgtgg ctcggcacct tcgacaccgc ggaggacgcg    600
gcgctcgcct acgacaaggc ggccttccgc ctccgcggcg acacgcgcg cctcaacttc    660 ccggccctcc ggcgcggcgg cgcgcacctc gccggcccgc tgcacgcctc cgtggacgcc    720
aagctgaccg ccatctgcca gtccctgtcg gagtccaagt ccaagagcgg ctcgtccggc    780
gacgagtcgg ccgcgtcccc gccggactcc ccaagtgct cggcgtcgac gacggaggga    840
gagggggagg aggagtcggg ctccgccggc tcccctcctc ctcctcctcc tccccgacg    900 ctggcgccgc ccgtgccgga gatggcgaag ctggacttca cggaggcgcc gtgggacgag    960
acggaggcct ccaccctgcg caagtacccg tcctgggaga tcgactggga ttccatcctg   1020
tcatga                                                               1026

<210> SEQ ID NO 228
<211> LENGTH: 951
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Zea mays WIND1_2
```

<400> SEQUENCE: 228

```
atggccgcag ccatagacat gtacaagtac tgcaatacca gcgcacacct tatcgcctcc        60
tcgtccccct cggatcagga gctcgcgaaa gcactcgagc cttttataac gagtgcttcc       120
tcccccctacc atcgctactc gttggcccca gattcttaca tgcctacacc ctcctcctac      180
accacctcgc ctcttcccac ccccacctcc tcgcctttct cgcagcttcc gccactctac       240
tcgtcgcctt acgcggcttc gacggcgtcg ggcgtggctg ggccgatggg cctgaaccag       300
ctcggcccgg cccagatcca gcagatccag gcccagctca tgttccagca ccagcagcag       360
aggggcctgc acgcggcgtt cctgggcccg cgggcgcagc cgatgaagca gtccgggtcg       420
ccgccggcgc agtcgaagct gtaccgcggc gtgcgccagc gccactgggg caagtgggtg       480
gcggagatcc gcctccccaa gaaccgcacg cggctgtggc tcggcacctt cgacaccgcc       540
gagggcgcgg cgctggccta cgacgaggcg gccttccgcc tccgcggcga cacggcgcgc       600
ctcaacttcc cgtccctccg ccgcggcggc ggcgcgcgcc tcgccggccc gctccacgcc       660
tccgtggacg ccaagctcac cgccatctgc cagtccctgg cggggtccaa gaacagctcg       720
tccagcgacg agtcggccgc gtccctgccg gactccccca agtgctcagc gtcgacggag       780
ggggatgagg actcggcctc cgccggctcc cctccttccc cgacgcaggc gccgcccgtg       840
ccggagatgg cgaagctgga cttcaccgag gcgccgtggg acgaaacgga ggccttccac       900
ctgcgcaagt acccgtcctg ggagatcgac tgggattcca tcctctcatg a               951
```

<210> SEQ ID NO 229
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Zea mays ESR1_1

<400> SEQUENCE: 229

```
atggcgccga aacgtcaga gaaaaccatg gcaccggcgg cggccgctgc cacggggctc        60
gcgctcagcg tcggcggcgg cggcggggcc ggcgcccgc actacagagg cgtgaggaag       120
cggccgtggg gccggtacgc ggcggagatc cgcgacccgg cgaagaagag ccgggtgtgg       180
ctcggcacct acgacacggc cgaggacgcc gcgcgggcct acgacgccgc cgcgcgcgag       240
taccgcggcg ccaaggccaa gaccaacttc ccttacccct cgtgcgtgcc cctctccgca       300
gccggttgcc ggagcagcaa cagcagcacc gtcgagtcct tcagcagcga cgcgcaggcg       360
cccatgcagg ccatgccgct cccgccgtcg ctcgagctgg acctgttcca ccgcgcggcg       420
gccgcggcca cgggcacggg cgctgccgcc gtacgcttcc ctttcggcag catccccgtt       480
acgcacccgt actacttctt cgggcaggcc gcagccgcag ccgcggaagc agggtgccgt       540
gtgctcaagc tggcgccggc ggtcaccgtg gcgcagagcg actccgactg ttcgtcggta       600
gtggatctgt cgccgtcgcc accggccgct gtgtcggcga ggaagcccgc cgcgttcgat       660
ctcgacctga actgctcacc gccgacggag gcggaagcct ag                         702
```

<210> SEQ ID NO 230
<211> LENGTH: 885
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<223> OTHER INFORMATION: cDNA of Zea mays ESR1_2

<400> SEQUENCE: 230
atggaggacg tggccaacgc acacatctac gcccacgccc accggagcaa gcgtccccag      60
tcggccgcga tcaaagacgg ggacggggac gtcgacctgt ccatgaaagg cgcgcggtac     120
cgcggcgtgc ggcgccggcc gtggggccgg ttcgcggcag agatccgcga ccccatgtcc     180
aaggagcggc ggtggctcgg caccttcgac accgccgagc aggccgcctg cgcctacgac     240
atcgcggcgc gcgccatgcg cggcaacaag gcgcgcacca acttcccggg ccacgccacg     300
gcgggctact ggccgtgggg cgcgccgcag ccggcggcgg tggcgcaccc gatcaaccct     360
ttcctcctgc acaacctcat catgagctcc tccaaccacg gctgccgcct gctcaaccac     420
gcaggccacg gacacgtcca ctccgcagcc cccagacctc cggcgccggc ggcggacgcc     480
acgtccacga ccatcgcagc gcccttccct gtcgccgcac accccgccgt agcgatggac     540
gaggacgtgg acgactggga cggcgtcctg cggagcgagc ccgcggacgc cgggctgctg     600
caggacgcgc tgcacgactt ctacccttt cacgcgtccgc gcgccggcgg gggcaggcgc      660
ggcctgtccg cggccggaac cgacgccagg gcggcagctg cgttggtggc gccggtaaag     720
ccggatgctt tcgtcgttcc cagcccttt gccggcgtcg aggggacgg tgaataccccg      780 atgatgccgc agggcctgct cgaggacgtg atccactccc cggcgttcgt ggaggttgtg     840
gccgcgccgc cgtccgtccc cacgcgccgc ggccgccggg gctga                     885

<210> SEQ ID NO 231
<211> LENGTH: 2130
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Zea mays PLT3

<400> SEQUENCE: 231
atggccactg tgaacaactg gctcgctttc tccctctccc cgcaggagct gccgccctcc      60
cagacgacgg actccacgct catctcggcc gccaccgccg accatgtctc cggcgatgtc     120
tgcttcaaca tcccccaaga ttggagcatg aggggatcag agctttcggc gctcgtcgcg     180
gagccgaagc tggaggactt cctcggcggc atctccttct ccgagcagca tcacaagtcc     240
aactgcaact tgatacccag cactagcagc acagtttgct acgcgagctc agctgctagc     300
accggctacc atcaccagct gtaccagccc accagctccg cgctccactt cgcggactcc     360
gtcatggtgg cctcctcggc cggtgtccac gacggcggtt ccatgctcag cgcggccgcc     420
gctaacggtg tcgctggcgc tgccagtgcc aacggcggcg catcgggct gtccatgatc      480 aagaactggc tgcggagcca accggcgccc atgcagccga gggcggcggc ggctgagggc     540
gcgcaggggc tctctttgtc catgaacatg gcggggacga cccaaggcgc tgctggcatg     600
ccacttctcg ctggagagcg cgcacgggcg cccgagagtg tatcgacgtc agcacagggt     660
ggtgccgtcg tcgtcacggc gccgaaggag gatagcggtg gcagcggtgt tgccggtgct     720
ctagtagccg tgagcacgga cacgggtggc agcggcggcg cgtcggctga caacacggca     780
aggaagacgg tggacacgtt cgggcagcgc acgtcgattt accgtggcgt gacaaggcat     840
```

```
agatggactg ggagatatga ggcacatctt tgggataaca gttgcagaag ggaaggacaa    900
actcgtaagg gtcgtcaagt ctatttaggt ggctatgata agaggagaa  agctgctagg    960 gcttatgatc ttgctgctct gaagtactgg ggtgccacaa caacaacaaa ttttccagtg   1020
agtaactacg aaaaggagct cgaggacatg aagcacatga caaggcagga gtttgtagcg   1080
tctctgagaa ggaagagcag tggtttctcc agaggtgcat ccatttacag gggagtgact   1140
aggcatcacc aacatggaag atggcaagca cggattggac gagttgcagg gaacaaggat   1200
ctttacttgg gcaccttcag cacccaggag gaggcagcgg aggcgtacga catcgcggcg   1260
atcaagttcc gcggcctcaa cgccgtcacc aacttcgaca tgagccgcta cgacgtgaag   1320
agcatcctgg acagcagcgc cctccccatc ggcagcgccg ccaagcgtct caaggaggcc   1380
gaggccgcag cgtccgcgca gcaccaccac gccggcgtgg tgagctacga cgtcggccgc   1440
atcgcctcgc agctcggcga cggcggagcc ctagcggcgg cgtacggcgc gcactaccac   1500
ggcgccgcct ggccgaccat cgcgttccag ccgggcgccg ccaccacagg cctgtaccac   1560
ccgtacgcgc agcagccaat gcgcggcggc gggtggtgca agcaggagca ggaccacgcg   1620
gtgatcgcgg ccgcgcacag cctgcaggac ctccaccact tgaacctggg cgcggccggc   1680
gcgcacgact ttttctcggc agggcagcag gccgccgccg cagctgcgat gcacggcctg   1740
gctagcatcg acagtgcgtc gctcgagcac agcaccggct ccaactccgt cgtctacaac   1800
ggcggggtcg gcgatagcaa cggcgccagc gccgttggca gcggcggtgg ctacatgatg   1860
ccgatgagcg ctgccggagc aaccactaca tcggcaatgg tgagccacga gcagatgcat   1920
gcacgggcct acgacgaagc caagcaggct gctcagatgg ggtacgagag ctacctggtg   1980
aacgcggaga acaatggtgg cggaaggatg tctgcatggg ggaccgtcgt ctctgcagcc   2040
gcggcggcag cagcaagcag caacgacaac attgccgccg acgtcggcca tggcggcgcg   2100
cagctcttca gtgtctggaa cgacacttaa                                    2130
```

<210> SEQ ID NO 232
<211> LENGTH: 1479
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of Zea mays PLT5

<400> SEQUENCE: 232

```
atggacacct cgcaccacta tcatccatgg ctcaacttct ccctcgccca ccactgtgac     60
ctcgaggagg aggagagggg cgcggccgcc gagctggccg cgatagccgg cgccgcgccg    120
ccgccgaagc tggaggactt cctcggcgga ggcgtcgcca ccgtggtcc  ggaggcggtg    180 gcgcccgcgg agatgtacga ctcggacctc aagttcatag ccgccgccgg gttccttggc    240
ggctcggcgg cggcggcggc gacgtcgccg ctgtcctccc tcgaccaggc cggttccaag    300
ctggccttgc ctgcggcggc ggctgctccg gcgccggagc agaggaaggc cgtcgactcc    360
tttgggcagc gcacgtccat ctaccgcggc gtcacacggc accggtggac tggcaggtac    420
gaggcacatc tgtgggacaa cagctgccga cgcgaagggc agagccgcaa gggccgccaa    480
gtatatttgg gtggctatga taaggaggag aaggctgcca gggcgtatga tcttgcagct    540
ttgaagtact ggggttctag caccaccacc aactttccgg ttgctgagta tgagaaggag    600
gtcgaggaga tgaagaacat gacgcgacaa gagtttgttg cttcccttcg aaggaagagc    660
```

| | | | | |
|---|---|---|---|---|
| agtggattct | ctcggggtgc | ttccatctac | cgaggtgtaa | ccagacatca ccagcatgga | 720 |
| cggtggcagg | cgaggatcgg | aagggtggcc | ggtaacaagg | acctctacct tgggacgttc | 780 |
| agcaccgagg | aggaagctgc | agaggcctac | gacatagcgg | ccatcaagtt cagaggcctg | 840 |
| aacgccgtca | caaacttcga | gatcagccgg | tacaacgtgg | agaccataat gagcagcaac | 900 |
| cttccagtcg | cgagcatgtc | gtcgtcggcg | gcggcggcgg | cgggtggccg gagcagcaag | 960 |
| gcgctggagt | cccctccgtc | cggctcgctt | gacggcggcg | gcggcatgcc agtcgtcgaa | 1020 |
| gccagcacgg | caccgccgct | gttcattccg | gtgaagtacg | accagcagca gcaggagtac | 1080 |
| ctgtcgatgc | tcgcgttgca | gcagcaccac | cagcagcaac | aagcagggaa cctgttgcag | 1140 |
| gggccgctag | tagggttcgg | cggcctctac | tcctccgggg | tgaacctgga tttcgccaac | 1200 |
| tcccacggca | cggcggctcc | gtcgtcgatg | gcccaccact | gctacgccaa tggcaccgcc | 1260 |
| tccgcctcgc | atgagcacca | gcaccagatg | cagcagggcg | gcgagaacga gacgcagccg | 1320 |
| cagccgcagc | agagctccag | cagctgctcc | tccctgccat | cgccaccccc ggtcgctttc | 1380 |
| aatgggtcct | atgaaagctc | catcacggcg | gcaggcccct | tggatactc ctacccaaat | 1440 |
| gtggcagcct | tcagacgcc | gatctatgga | atggaatga | | 1479 |

<210> SEQ ID NO 233
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Zea mays PLT7

<400> SEQUENCE: 233

| | | | | |
|---|---|---|---|---|
| atggacatgg | acatgagctc | agcttatccc | caccattggc | tctccttctc cctctccaac | 60 |
| aactaccacc | atggcctact | cgaagccttc | tctaactcct | ccggtactcc tcttggagac | 120 |
| gagcagggcg | cagtggagga | gtccccgagg | acggtggagg | acttcctcgg cggcgtcggt | 180 |
| ggcgccggcg | ccccgccgca | gccggcggcg | gctgcagatc | aggatcacca gcttgtgtgc | 240 |
| ggcgagctgg | gcagcatcac | agccaggttc | ttgcgccact | accggcggc gccagctggg | 300 |
| acgacggtgg | agaaccccgg | cgcggtgacc | gtggcggcca | tgtcgtcgac ggacgtggcc | 360 |
| ggggcggagt | ccgaccaggc | gaggcggccc | gccgagacgt | cggccagcg cacatccatc | 420 |
| taccgtggcg | tcaccaggca | ccggtggacg | gggagatatg | aggcgcacct gtgggacaac | 480 |
| agctgccgcc | gggagggcca | aagccgcaaa | ggacggcaag | tctacctagg aggctatgac | 540 |
| aaggaggaga | aggcggctag | agcttacgac | ctcgccgcgc | tcaagtactg ggggcctaca | 600 |
| accacgacca | acttcccggt | gtccaactac | gagaaggagc | tggaggagat gaagtccatg | 660 |
| acgcggcagg | agttcatcgc | gtcgttgcgc | aggaagagca | gcggcttctc acgaggcgcc | 720 |
| tccatctaca | gaggagtcac | aaggcatcat | cagcacggcc | ggtggcaggc gaggatcggc | 780 |
| agggtggccg | gaaacaagga | cctgtacttg | ggcactttca | gtactcagga gaggcggcg | 840 |
| gaggcgtacg | acatcgctgc | gatcaagttc | cgcgggctca | cgccgtcac caactttgac | 900 |
| atgagccgct | acgacgtgga | gagcatcctc | agcagcgacc | tccccgtcgg gggcggagct | 960 |
| agcggtcgcg | ccccgccaa | gttcccgttg | gactcgctgc | agccggggag cgctgccgcc | 1020 |
| atgatgctcg | ccggggctgc | tgccgcttcg | caggccacca | tgccgccgtc cgagaaggac | 1080 |
| tactggtctc | tgctcgccct | gcactaccag | cagcagcagg | agcaggagcg gcagttcccg | 1140 |

| gcttctgctt acgaggctta cggctccggc ggcgtgaacg tggacttcac gatgggcacc | 1200 |
| agtagcggca acaacaacaa caacaccggc agcggcgtca tgtgggggcgc caccactggt | 1260 |
| gcagtagtag tgggacagca agacagcagc ggcaagcagg gcaacggcta tgccagcaac | 1320 |
| attccttatg ctgctgctgc tatggtttct ggatctgctg gctacgaggg ctccaccggc | 1380 |
| gacaatggaa cctgggttac tacgactacc agcagcaaca ccggcacggc tccccactac | 1440 |
| tacaactatc tcttcgggat ggagtag | 1467 |

<210> SEQ ID NO 234
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Zea mays IPT

<400> SEQUENCE: 234

| atggcccacc cctccgccgc cgccgccgcc gtatcctcca cggcgcccgc tgcaaaccct | 60 |
| agttctggcg cccgcgagga aggaggcgcc cgctctccgc cgtcgccgtc tccgtctcag | 120 |
| aggggcggg ccaaggtggt gatcgttatg ggcgccacgg gcgccggcaa gtcgcggctg | 180 |
| gccgtcgacc tcgcggccca cttcgccggc gtcgaagtgg tcagcgccga ctccatgcag | 240 |
| ctctaccgcg gcctcgacgt cctcaccaac aaggctcccc tccacgagca gaacggtgtt | 300 |
| cctcatcatc tacttagcgt gattgatccc tctgtcgagt tcacttgccg tgatttccgc | 360 |
| gaccgtgccg tgccgattat acaggaaata gtggaccgcg gtggcctccc tgtggttgtc | 420 |
| ggcggcacaa acttctacat ccaggctctc gttagcccat tcctcttgga tgatatggca | 480 |
| gaagaaatgc agggctgtac tctgagagat cacatagatg atggtcttac tgatgaagat | 540 |
| gaaggcaatg ggtttgaacg cttgaaggag atcgatcctg tggctgcgca gaggatccat | 600 |
| ccaaacgacc atagaaaaat caaacgctac ctcgagttgt atgcaaccac gggtgcccta | 660 |
| cccagcgatc tgttccaagg agaggccgct aagaaatggg gtcggcctag taactccaga | 720 |
| ctcgactgct gtttcctgtg ggtagatgct gatcttcaag tcctggacag ttatgtcaac | 780 |
| aaaagggtcg attgcatgat ggatggtggc ctgctggacg aagtatgcag catatatgat | 840 |
| gcggatgctg tctataccca ggggctgcgg caggctattg ggttcgtga gtttgacgag | 900 |
| ttttcagag catatttacc cagaaaagaa tctggtgagg ttcctgtgc aagcctgtta | 960 |
| ggtatgcatg acgatcagct taagagcttg ttggacgaag ctgtttccca gctgaaggca | 1020 |
| aacactcgta gactagttcg acgtcaaaga cggagattgc atcggctgag taaagatttt | 1080 |
| gggtggaact tgcatcgtgt tgacgcaacc gaagcattct tctgtgccac tgacgactca | 1140 |
| tggcaaaaga agttgtcaa accatgtgtg gatgtcgtaa gaaggttttt gtcggacaat | 1200 |
| tccactgttt tgccaagcac aagcgcaagt gacccctctt caagagagct gtggacgcaa | 1260 |
| tatgtgtgcg aggcctgcgg caaccgggtg ctgcgaggtg cgcacgagtg ggagcagcac | 1320 |
| aggcaagggc gaggccaccg gaagcgagtg cagcgcctga gcagaagag cctgaggcca | 1380 |
| tggccatcgc tgctgcccca agaccgcagc tga | 1413 |

<210> SEQ ID NO 235
<211> LENGTH: 1080
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: cDNA of Zea mays Knotted1

<400> SEQUENCE: 235

| | | | | | |
|---|---|---|---|---|---|
| atggaggaga | tcacccaaca | ctttggagtt | ggcgcaagca | gccacggcca | tggccacggc | 60 |
| cagcaccacc | atcatcacca | ccaccaccac | ccgtgggcat | cctccctcag | cgccgtcgta | 120 |
| gcgccgctgc | cgccgcaacc | gccaagcgca | ggcctgccgc | tgaccctgaa | cacggtggcg | 180 |
| gccactggga | acagcggcgg | tagcggcaac | ccggtgctgc | agcttgccaa | cggtggcggc | 240 |
| ctcctcgacg | catgcgtcaa | ggcgaaggag | ccctcgtcgt | cgtctcccta | cgcaggcgac | 300 |
| gtcgaggcca | tcaaggccaa | gatcatctcg | cacccacact | actactcgct | cctcactgcc | 360 |
| tacctcgagt | gcaacaaggt | gggggcacca | ccggaggtgt | cggcgaggct | gacgagata | 420 |
| gcgcaggagg | tggaggcgcg | gcagcgcacg | gcgctcggcg | gcctggccgc | tgcgacggag | 480 |
| ccggagctgg | accagttcat | ggaggcgtac | cacgagatgc | tggtgaagtt | caggaggag | 540 |
| ctgacgaggc | cgctgcagga | ggcgatggag | ttcatgcgaa | gggtggagtc | gcagctgaac | 600 |
| tcgctttcca | tctccggaag | gtcgctgcgc | aacatccttt | catctggctc | ttctgaggag | 660 |
| gatcaagaag | gtagcggagg | agagaccgag | ctccctgaag | ttgatgcaca | tggtgtggac | 720 |
| caagagctga | agcaccatct | cctgaagaaa | tacagtggct | atctaagctc | gctcaagcaa | 780 |
| gaactgtcaa | agaagaagaa | gaagggaag | ctccccaagg | aggctcgcca | gcagctcctt | 840 |
| agctggtggg | atcagcacta | caaatggcct | taccctcag | agactcagaa | ggtggcactg | 900 |
| gctgagtcta | ccgggcttga | cctgaagcag | atcaacaact | ggttcatcaa | ccagcggaag | 960 |
| cggcactgga | agccatccga | ggagatgcac | cacctgatga | tggacgggta | ccacaccacc | 1020 |
| aatgccttct | acatggacgg | ccacttcatc | aacgacggcg | ggctgtaccg | gctcggctag | 1080 |

<210> SEQ ID NO 236
<211> LENGTH: 936
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Zea mays RKD4_1

<400> SEQUENCE: 236

| | | | | | |
|---|---|---|---|---|---|
| atgacgggcc | tcgacgaggc | gctcatgctg | ccgttcaccg | acatcgatct | tgaggccttc | 60 |
| gacaacgccg | aagagcaaaa | gcctcctgtc | gaccaaatgg | ttatgatgcc | gccgacggtt | 120 |
| gaacaccccg | ccgccgccgg | gacgcgagcc | ccaatcatca | ttgatggtac | ggcgaccgtt | 180 |
| ggccaaaatg | taggtggtgg | tgtcgtccac | gctcatcaga | aggcggccat | gacgaccata | 240 |
| gaggactcca | gctgcttccg | acgaggagcc | agctgtgtcg | acgacgacat | ggccgtcgtc | 300 |
| attcaccatg | tcgagcgtcg | tcgtcaagca | ggctctaccg | ccgtgcgct | attgccgccg | 360 |
| ccgcagccgt | cactgccgcg | gccgcgtgca | agggcgagcg | gcggcgcggg | cgagcggtca | 420 |
| gctccggcgg | ccgccgggaa | gacgaggatg | gaccacatcg | gcttcgacga | gctgcgcaag | 480 |
| tacttctaca | tgcccatcac | cagggcggcc | agggagatga | acgtggggct | caccgtgctc | 540 |
| aagaagcgct | gccgcgagct | cggcgtggcg | cggtggcctc | accggaagat | gaagagcctc | 600 |
| aagtccctca | tggccaacgt | acaggaaatg | gggaacggca | tgtcgccggt | ggctgtgcag | 660 |
| catgagcttg | cggcgctgga | gacgtactgc | gcgctcatgg | aggagaaccc | atggatcgag | 720 |

```
ctcacggacc ggacgaagag gctgcggcag gcctgcttca aggagagcta caagcggagg    780
aaggcggccg caggcaacgc tatcgagacg gatcacattg tctacagctt tggacagcat    840
cgtcgttaca agcagcagct gctgcctccg ccaactgcgg gtagtaccag tgctgacgac    900
cgccatggcc agagcagccg tttcttttgc tactga                              936
```

<210> SEQ ID NO 237
<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of Zea mays RKD4_2

<400> SEQUENCE: 237

```
atggcgatgg tgccatgtgg cggtgacgac gcggaatggt gcaatatgat ggaggccatc     60
aaccacctga tgatgtcttc catgtcctcg ccgcacgtcg ccatgggcgc cagcagttgc    120
agggaagagg acgacgacag tttgtacttg cccatgtact actcatctgc gccaccgcca    180
gccgtcgtca gcgatcagta ctgccccgaa caactcccac cgctgcctgc tgccggtgca    240
atgacgggcc tcgacgaggc gctcatgctg ccgttcaccg acatcgatct tgaggccttc    300
gacaacgcca agagcaaaa gcctcctgtc gaccaaatgg ttatgatgcc gccgacggtt    360
gaacaccccg ccgccgccgg gacgcgagcc ccaatcatca ttgatggtac ggcgaccgtt    420
ggccaaaatg taggtggtgg tgtcgtccac gctcatcaga aggcggccat gacgaccata    480
gaggactcca gctgcttccg acgaggagcc agctgtgtcg acgacgacat ggccgtcgtc    540
attcaccatg tcgagcgtcg tcgtcaagca ggctctaccg ccgtggcgct attgccgccg    600
ccgcagccgt cactgccgcg gccgcgtgca agggcgagcg gcggcgcggg cgagcggtca    660
gctccggcgg ccgccgggaa gacgaggatg gaccacatcg gcttcgacga gctgcgcaag    720
tacttctaca tgcccatcac cagggcggcc agggagatga acgtggggct caccgtgctc    780
aagaagcgct gccgcgagct cggcgtggcg cggtggcctc accggaagat gaagagcctc    840 aagtcccctca tggccaacgt acaggaaatg gggaacggca tgtcgccggt ggctgtgcag    900
catgagcttg cggcgctgga gacgtactgc gcgctcatgg aggagaaccc atggatcgag    960
ctcacggacc ggacgaagag gctgcggcag gcctgcttca aggagagcta caagcggagg   1020
aaggcggccg caggcaacgc tatcgagacg gatcacattg tctacagctt tggacagcat   1080
cgtcgttaca agcagcagct gctgcctccg ccaactgcgg gtagtaccag tgctgacgac   1140
cgccatggcc agagcagccg tttcttttgc tactga                             1176
```

<210> SEQ ID NO 238
<211> LENGTH: 679
<212> TYPE: PRT
<213> ORGANISM: Zea mays

<400> SEQUENCE: 238

```
Met Ala Ser Ala Asn Asn Trp Leu Gly Phe Ser Leu Ser Gly Gln Asp
1               5                   10                  15

Asn Pro Gln Pro Asn Gln Asp Ser Ser Pro Ala Ala Gly Ile Asp Ile
            20                  25                  30

Ser Gly Ala Ser Asp Phe Tyr Gly Leu Pro Thr Gln Gln Gly Ser Asp
        35                  40                  45
```

```
Gly His Leu Gly Val Pro Gly Leu Arg Asp Asp His Ala Ser Tyr Gly
    50                  55                  60

Ile Met Glu Ala Tyr Asn Arg Val Pro Gln Glu Thr Gln Asp Trp Asn
65                  70                  75                  80

Met Arg Gly Leu Asp Tyr Asn Gly Gly Ser Glu Leu Ser Met Leu
                85                  90                  95

Val Gly Ser Ser Gly Gly Gly Gly Asn Gly Lys Arg Ala Val Glu
            100                 105                 110

Asp Ser Glu Pro Lys Leu Glu Asp Phe Leu Gly Gly Asn Ser Phe Val
            115                 120                 125

Ser Asp Gln Asp Gln Ser Gly Gly Tyr Leu Phe Ser Gly Val Pro Ile
    130                 135                 140

Ala Ser Ser Ala Asn Ser Asn Ser Gly Ser Asn Thr Met Glu Leu Ser
145                 150                 155                 160

Met Ile Lys Thr Trp Leu Arg Asn Asn Gln Val Ala Gln Pro Gln Pro
                165                 170                 175

Pro Ala Pro His Gln Pro Gln Pro Glu Glu Met Ser Thr Asp Ala Ser
            180                 185                 190

Gly Ser Ser Phe Gly Cys Ser Asp Ser Met Gly Arg Asn Ser Met Val
        195                 200                 205

Ala Ala Gly Gly Ser Ser Gln Ser Leu Ala Leu Ser Met Ser Thr Gly
    210                 215                 220

Ser His Leu Pro Met Val Val Pro Ser Gly Ala Ala Ser Gly Ala Ala
225                 230                 235                 240

Ser Glu Ser Thr Ser Ser Glu Asn Lys Arg Ala Ser Gly Ala Met Asp
                245                 250                 255

Ser Pro Gly Ser Ala Val Glu Ala Val Pro Arg Lys Ser Ile Asp Thr
            260                 265                 270

Phe Gly Gln Arg Thr Ser Ile Tyr Arg Gly Val Thr Arg His Arg Trp
        275                 280                 285

Thr Gly Arg Tyr Glu Ala His Leu Trp Asp Asn Ser Cys Arg Arg Glu
    290                 295                 300

Gly Gln Ser Arg Lys Gly Arg Gln Val Tyr Leu Gly Gly Tyr Asp Lys
305                 310                 315                 320

Glu Asp Lys Ala Ala Arg Ala Tyr Asp Leu Ala Ala Leu Lys Tyr Trp
                325                 330                 335

Gly Thr Thr Thr Thr Thr Asn Phe Pro Ile Ser Asn Tyr Glu Lys Glu
            340                 345                 350

Leu Glu Glu Met Lys His Met Thr Arg Gln Glu Tyr Ile Ala Tyr Leu
        355                 360                 365

Arg Arg Asn Ser Ser Gly Phe Ser Arg Gly Ala Ser Lys Tyr Arg Gly
    370                 375                 380

Val Thr Arg His His Gln His Gly Arg Trp Gln Ala Arg Ile Gly Arg
385                 390                 395                 400

Val Ala Gly Asn Lys Asp Leu Tyr Leu Gly Thr Phe Ser Thr Glu Glu
                405                 410                 415

Glu Ala Ala Glu Ala Tyr Asp Ile Ala Ala Ile Lys Phe Arg Gly Leu
            420                 425                 430

Asn Ala Val Thr Asn Phe Asp Met Ser Arg Tyr Asp Val Lys Ser Ile
        435                 440                 445

Leu Glu Ser Ser Thr Leu Pro Val Gly Gly Ala Ala Arg Arg Leu Lys
    450                 455                 460
```

```
Asp Ala Val Asp His Val Glu Ala Gly Ala Thr Ile Trp Arg Ala Asp
465                 470                 475                 480

Met Asp Gly Ala Val Ile Ser Gln Leu Ala Glu Ala Gly Met Gly Gly
                485                 490                 495

Tyr Ala Ser Tyr Gly His His Gly Trp Pro Thr Ile Ala Phe Gln Gln
            500                 505                 510

Pro Ser Pro Leu Ser Val His Tyr Pro Tyr Gly Gln Pro Ser Arg Gly
            515                 520                 525

Trp Cys Lys Pro Glu Gln Asp Ala Ala Ala Ala Ala His Ser Leu
            530                 535                 540

Gln Asp Leu Gln Gln Leu His Leu Gly Ser Ala Ala His Asn Phe Phe
545                 550                 555                 560

Gln Ala Ser Ser Ser Ser Thr Val Tyr Asn Gly Gly Ala Gly Ala Ser
                565                 570                 575

Gly Gly Tyr Gln Gly Leu Gly Gly Gly Ser Ser Phe Leu Met Pro Ser
            580                 585                 590

Ser Thr Val Val Ala Ala Ala Asp Gln Gly His Ser Ser Thr Ala Asn
            595                 600                 605

Gln Gly Ser Thr Cys Ser Tyr Gly Asp Asp His Gln Glu Gly Lys Leu
            610                 615                 620

Ile Gly Tyr Asp Ala Ala Met Val Ala Thr Ala Gly Gly Asp Pro
625                 630                 635                 640

Tyr Ala Ala Ala Arg Asn Gly Tyr Gln Phe Ser Gln Gly Ser Gly Ser
                645                 650                 655

Thr Val Ser Ile Ala Arg Ala Asn Gly Tyr Ala Asn Asn Trp Ser Ser
            660                 665                 670

Pro Phe Asn Asn Gly Met Gly
            675

<210> SEQ ID NO 239
<211> LENGTH: 320
<212> TYPE: PRT
<213> ORGANISM: Zea mays

<400> SEQUENCE: 239

Met Ala Ala Asn Val Gly Ala Gly Arg Ser Ala Gly Gly Gly Gly Ala
1               5                   10                  15

Gly Thr Gly Thr Gly Thr Ala Ala Gly Ser Gly Gly Val Ser Thr Ala
                20                  25                  30

Val Cys Arg Pro Ser Gly Ser Arg Trp Thr Pro Thr Pro Glu Gln Ile
            35                  40                  45

Arg Ile Leu Lys Glu Leu Tyr Tyr Gly Cys Gly Ile Arg Ser Pro Asn
        50                  55                  60

Ser Glu Gln Ile Gln Arg Ile Thr Ala Met Leu Arg Gln His Gly Lys
65                  70                  75                  80

Ile Glu Gly Lys Asn Val Phe Tyr Trp Phe Gln Asn His Lys Ala Arg
                85                  90                  95

Glu Arg Gln Lys Arg Arg Leu Thr Asn Leu Asp Val Asn Val Pro Val
            100                 105                 110

Ala Ala Asp Asp Ser Ala His Arg Leu Gly Val Leu Ser Leu Ser Pro
            115                 120                 125

Ser Ser Gly Cys Ser Gly Ala Ala Pro Pro Ser Pro Thr Leu Gly Phe
        130                 135                 140
```

-continued

```
Tyr Ala Gly Gly Asn Gly Ser Ala Val Met Leu Asp Thr Ser Ser Asp
145                 150                 155                 160

Trp Gly Ser Ala Ala Met Ala Thr Glu Ala Cys Phe Met Gln Asp
                165                 170                 175

Tyr Met Gly Val Met Gly Gly Ala Ser Pro Trp Ala Cys Ser Ser Ser
            180                 185                 190

Ser Ser Glu Asp Pro Met Ala Ala Leu Ala Leu Ala Pro Lys Val Thr
        195                 200                 205

Arg Ala Pro Glu Thr Leu Pro Leu Phe Pro Thr Gly Gly Gly Asp
210                 215                 220

Asp Arg Gln Pro Pro Arg Pro Arg Gln Ser Val Pro Ala Gly Glu Ala
225                 230                 235                 240

Ile Arg Gly Gly Ser Ser Ser Ser Tyr Leu Pro Phe Trp Gly Ala
                245                 250                 255

Ala Pro Thr Pro Thr Gly Ser Ala Thr Ser Val Ala Ile Gln Gln Gln
                260                 265                 270

His Gln Leu Met Gln Met Gln Glu Gln Tyr Ser Phe Tyr Ser Asn Ala
            275                 280                 285

Gln Leu Leu Pro Gly Thr Gly Ser Gln Asp Ala Ala Ala Thr Ser Leu
        290                 295                 300

Glu Leu Ser Leu Ser Ser Trp Cys Ser Pro Tyr Pro Ala Gly Thr Met
305                 310                 315                 320

<210> SEQ ID NO 240
<211> LENGTH: 325
<212> TYPE: PRT
<213> ORGANISM: Zea mays

<400> SEQUENCE: 240

Met Ala Ala Asn Ala Gly Gly Gly Ala Gly Gly Gly Ser Gly Ser
1               5                   10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
        35                  40                  45

Cys Gly Ile Arg Ser Pro Ser Ser Glu Gln Ile Gln Arg Ile Thr Ala
    50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95

Leu Asp Val Asn Val Pro Ala Ala Gly Ala Ala Asp Ala Thr Thr Ser
            100                 105                 110

Gln Leu Gly Val Leu Ser Leu Ser Ser Pro Ser Gly Ala Ala Pro
        115                 120                 125

Pro Ser Pro Thr Leu Gly Phe Tyr Ala Ala Gly Asn Gly Gly Ser
    130                 135                 140

Ala Gly Leu Leu Asp Thr Ser Asp Trp Gly Ser Ser Gly Ala Ala
145                 150                 155                 160

Met Ala Thr Glu Thr Cys Phe Leu Gln Asp Tyr Met Gly Val Thr Asp
                165                 170                 175

Thr Gly Ser Ser Ser Gln Trp Pro Cys Phe Ser Ser Ser Asp Thr Ile
            180                 185                 190
```

```
Met Ala Ala Ala Ala Ala Ala Arg Val Thr Thr Arg Ala Pro
    195                 200                 205

Glu Thr Leu Pro Leu Phe Pro Thr Cys Gly Asp Asp Asp Asp Asp
    210                 215                 220

Ser Gln Pro Pro Arg Pro Arg His Ala Val Pro Val Pro Ala Gly
225                 230                 235                 240

Glu Thr Ile Arg Gly Gly Gly Ser Ser Ser Tyr Leu Pro Phe
            245                 250                 255

Trp Gly Ala Gly Ala Ala Ser Thr Thr Ala Gly Ala Thr Ser Ser Val
        260                 265                 270

Ala Ile Gln Gln Gln His Gln Leu Gln Glu Gln Tyr Ser Phe Tyr Ser
    275                 280                 285

Asn Ser Thr Gln Leu Ala Gly Thr Gly Ser Gln Asp Val Ser Ala Ser
290                 295                 300

Ala Ala Ala Leu Glu Leu Ser Leu Ser Ser Trp Cys Ser Pro Tyr Pro
305                 310                 315                 320

Ala Ala Gly Ser Met
            325

<210> SEQ ID NO 241
<211> LENGTH: 324
<212> TYPE: PRT
<213> ORGANISM: Zea mays

<400> SEQUENCE: 241

Met Glu Thr Pro Gln Gln Gln Ser Ala Ala Ala Ala Ala Ala
1               5                   10                  15

His Gly Gln Asp Asp Gly Gly Ser Pro Pro Met Ser Pro Ala Ser Ala
                20                  25                  30

Ala Ala Ala Ala Leu Ala Asn Ala Arg Trp Asn Pro Thr Lys Glu Gln
            35                  40                  45

Val Ala Val Leu Glu Gly Leu Tyr Glu His Gly Leu Arg Thr Pro Ser
50                  55                  60

Ala Glu Gln Ile Gln Gln Ile Thr Gly Arg Leu Arg Glu His Gly Ala
65                  70                  75                  80

Ile Glu Gly Lys Asn Val Phe Tyr Trp Phe Gln Asn His Lys Ala Arg
                85                  90                  95

Gln Arg Gln Arg Gln Lys Gln Asp Ser Phe Ala Tyr Phe Ser Arg Leu
            100                 105                 110

Leu Arg Arg Pro Pro Pro Leu Pro Val Leu Ser Met Pro Pro Ala Pro
        115                 120                 125

Pro Tyr His His Ala Arg Val Pro Ala Pro Ala Ile Pro Met Pro
    130                 135                 140

Met Ala Pro Pro Pro Ala Ala Cys Asn Asp Asn Gly Gly Ala Arg
145                 150                 155                 160

Val Ile Tyr Arg Asn Pro Phe Tyr Val Ala Ala Pro Gln Ala Pro Pro
                165                 170                 175

Ala Asn Ala Ala Tyr Tyr Tyr Pro Gln Pro Gln Gln Gln Gln Gln
            180                 185                 190

Gln Val Thr Val Met Tyr Gln Tyr Pro Arg Met Glu Val Ala Gly Gln
        195                 200                 205

Asp Lys Met Met Thr Arg Ala Ala His Gln Gln Gln Gln His Asn
    210                 215                 220
```

```
Gly Ala Gly Gln Gln Pro Gly Arg Ala Gly His Pro Ser Arg Glu Thr
225                 230                 235                 240

Leu Gln Leu Phe Pro Leu Gln Pro Thr Phe Val Leu Arg His Asp Lys
                245                 250                 255

Gly Arg Ala Ala Asn Gly Ser Asn Asn Asp Ser Leu Thr Ser Thr Ser
            260                 265                 270

Thr Ala Thr Ala Thr Ala Thr Ala Thr Ala Ser Ala Ser Ile
        275                 280                 285

Ser Glu Asp Ser Asp Gly Leu Glu Ser Gly Ser Ser Gly Lys Gly Val
        290                 295                 300

Glu Glu Ala Pro Ala Leu Pro Phe Tyr Asp Phe Phe Gly Leu Gln Ser
305                 310                 315                 320

Ser Gly Gly Arg

<210> SEQ ID NO 242
<211> LENGTH: 221
<212> TYPE: PRT
<213> ORGANISM: Zea mays

<400> SEQUENCE: 242

Met Glu Ala Leu Ser Gly Arg Val Gly Val Lys Cys Gly Arg Trp Asn
1               5                   10                  15

Pro Thr Ala Glu Gln Val Lys Val Leu Thr Glu Leu Phe Arg Ala Gly
                20                  25                  30

Leu Arg Thr Pro Ser Thr Glu Gln Ile Gln Arg Ile Ser Thr His Leu
            35                  40                  45

Ser Ala Phe Gly Lys Val Glu Ser Lys Asn Val Phe Tyr Trp Phe Gln
        50                  55                  60

Asn His Lys Ala Arg Glu Arg His His Lys Lys Arg Arg Arg Gly
65                  70                  75                  80

Ala Ser Ser Ser Ser Pro Asp Ser Gly Ser Gly Arg Gly Ser Asn Asn
                85                  90                  95

Glu Glu Asp Gly Arg Gly Ala Ala Ser Gln Ser His Asp Ala Asp Ala
            100                 105                 110

Asp Ala Asp Leu Val Leu Gln Pro Pro Glu Ser Lys Arg Glu Ala Arg
        115                 120                 125

Ser Tyr Gly His His His Arg Leu Val Thr Cys Tyr Val Arg Asp Val
    130                 135                 140

Val Glu Gln Gln Glu Ala Ser Pro Ser Trp Glu Arg Pro Thr Arg Glu
145                 150                 155                 160

Val Glu Thr Leu Glu Leu Phe Pro Leu Lys Ser Tyr Gly Asp Leu Glu
                165                 170                 175

Ala Ala Glu Lys Val Arg Ser Tyr Val Arg Gly Ser Gly Ala Thr Ser
            180                 185                 190

Glu Gln Cys Arg Glu Leu Ser Phe Phe Asp Val Val Ser Ala Gly Arg
        195                 200                 205

Asp Pro Pro Leu Glu Leu Arg Leu Cys Ser Phe Gly Pro
    210                 215                 220

<210> SEQ ID NO 243
<211> LENGTH: 506
<212> TYPE: PRT
<213> ORGANISM: Zea mays
```

<400> SEQUENCE: 243

```
Met Ala Ser Ser Asn Arg His Trp Pro Ser Met Tyr Arg Ser Ser Leu
1               5                   10                  15

Ala Cys Asn Phe Gln Gln Pro Gln Pro Gln Pro Asp Met Asn Asn Gly
            20                  25                  30

Gly Lys Ser Ser Leu Met Ser Ser Arg Cys Glu Glu Asn Gly Gly Arg
        35                  40                  45

Asn Pro Glu Pro Arg Pro Trp Asn Pro Arg Pro Glu Gln Ile Arg
    50                  55                  60

Ile Leu Glu Gly Ile Phe Asn Ser Gly Met Val Asn Pro Pro Arg Asp
65                  70                  75                  80

Glu Ile Arg Arg Ile Arg Leu Gln Leu Gln Glu Tyr Gly Pro Val Gly
                85                  90                  95

Asp Ala Asn Val Phe Tyr Trp Phe Gln Asn Arg Lys Ser Arg Thr Lys
            100                 105                 110

His Lys Leu Arg Ala Ala Gly Gln Leu Gln Pro Ser Gly Ser Gly Arg
        115                 120                 125

Ser Ala Leu Gln Ala Arg Ala Cys Ala Pro Ala Pro Val Thr Pro Pro
    130                 135                 140

Arg Asn Leu Gln Leu Ala Ala Ala Pro Val Ala Pro Pro Thr Ser
145                 150                 155                 160

Ser Ser Ser Ser Ser Asp Arg Ser Ser Gly Ser Ser Ser Ser Lys
                165                 170                 175

Ser Val Thr Val Thr Pro Thr Thr Ala Val Ala Leu Ala Ser Pro Ala
            180                 185                 190

Gly Ala Ala Pro Ala Ala Val Phe Arg Gln Gln Gly Val Met Pro Thr
        195                 200                 205

Thr Ala Met Asp Leu Leu Thr Pro Leu Pro Ser Ser Ser Ala Ala Leu
    210                 215                 220

Ala Ala Arg Gln Leu Tyr Tyr Gln Tyr His Ser Gln Ile Met Ala Pro
225                 230                 235                 240

Ala Ala Pro Pro Met Pro Asp Thr Val Ile Ala Ser Pro Glu Gln Phe
                245                 250                 255

Leu Pro Gln Trp Gln Gln Gly Gly Gln Gln His Tyr Tyr Leu Pro Ala
            260                 265                 270

Thr Glu Leu Gly Gly Val Leu Asp Gly His Ser His Thr His Glu
        275                 280                 285

Pro Pro Ala Ala Ile His Arg Pro Val Ser Leu Ser Pro Ser Val Leu
    290                 295                 300

Phe Gly Leu Cys Asn Glu Ala Leu Arg Gln Asp Tyr Cys Ala Asp Ile
305                 310                 315                 320

Ser Val Val Pro Thr Lys Gly Leu Gly His Gly His Gln Phe Trp Asn
                325                 330                 335

Ser Thr Thr Cys Gly Ser Asp Met Gly Asn Ser Asn Ser Lys Ile Asp
            340                 345                 350

Ala Val Ser Ala Val Ile Arg Asp Glu Lys Ser Arg Leu Gly Leu
        355                 360                 365

Leu His Tyr Tyr Gly Leu Ala Gly Ala Thr Thr Thr Ala Ala Ala
    370                 375                 380

Val Ala Pro Ala Pro Leu Ala Ala Asp Ala Ala Ala Gly Thr Ala Thr
385                 390                 395                 400
```

```
Leu Leu Pro Ser Ser Ala Ala Ser Asp Gln Leu Gln Gly Leu Leu Asp
                405                 410                 415

Ala Ala Gly Leu Leu Met Gly Glu Thr Pro Pro Thr Pro Thr Ala Thr
            420                 425                 430

Val Val Ala Val Ala Arg Asp Ala Val Thr Cys Ala Ala Thr Ala Thr
            435                 440                 445

Ala Gln Phe Ser Val Pro Ala Ser Met Arg Leu Asp Val Arg Leu Ala
        450                 455                 460

Phe Gly Glu Ala Ala Leu Leu Ala Arg His Thr Gly Glu Ala Val Pro
465                 470                 475                 480

Val Asp Glu Ser Gly Val Thr Val Glu Pro Leu Gln Gln Asp Thr Leu
                485                 490                 495

Tyr Tyr Val Leu Met Gln Ala Thr Asn Asn
                500                 505

<210> SEQ ID NO 244
<211> LENGTH: 273
<212> TYPE: PRT
<213> ORGANISM: Zea mays

<400> SEQUENCE: 244

Met Glu Trp Val Asp Arg Thr Lys Ala Ser Ala Ala Ala Ala Ala Ala
1               5                   10                  15

Ala Ala Asp Glu Arg Ala Gly Gly Ala Glu Gly Leu Ala Gly Tyr Val
            20                  25                  30

Lys Val Met Thr Asp Glu Gln Met Glu Val Leu Arg Lys Gln Ile Ser
        35                  40                  45

Ile Tyr Ala Thr Ile Cys Glu Gln Leu Val Glu Met His Arg Ala Leu
50                  55                  60

Thr Glu His Gln Asp Thr Ile Ala Gly Ile Arg Phe Ser Asn Leu Tyr
65                  70                  75                  80

Cys Asp Pro Gln Ile Ile Pro Gly Gly His Lys Ile Thr Ala Arg Gln
                85                  90                  95

Arg Trp Gln Pro Thr Pro Met Gln Leu Gln Ile Leu Glu Asn Ile Phe
            100                 105                 110

Asp Gln Gly Asn Gly Thr Pro Ser Lys Gln Arg Ile Lys Glu Ile Thr
        115                 120                 125

Ala Glu Leu Ser His His Gly Gln Ile Ser Glu Thr Asn Val Tyr Asn
    130                 135                 140

Trp Phe Gln Asn Arg Arg Ala Arg Ser Lys Arg Lys Gln Ala Ala Ser
145                 150                 155                 160

Leu Pro Asn Asn Ala Glu Ser Glu Ala Glu Val Asp Glu Glu Ser Leu
                165                 170                 175

Thr Asp Lys Lys Pro Lys Ser Asp Arg Ser Leu Gln Asp Asn Lys Ala
            180                 185                 190

Met Gly Ala His Asn Ala Asp Arg Ile Ser Gly Met His His Leu Asp
        195                 200                 205

Thr Asp His Asp Gln Ile Gly Gly Met Met Tyr Gly Cys Asn Asp Asn
    210                 215                 220

Gly Leu Arg Ser Ser Gly Ser Ser Gly Gln Met Ser Phe Tyr Gly Asn
225                 230                 235                 240

Ile Met Pro Asn Pro Arg Ile Asp His Phe Pro Gly Lys Val Glu Ser
                245                 250                 255
```

```
Ser Arg Ser Phe Ser His Leu Gln His Gly Glu Gly Phe Asp Met Phe
            260                 265                 270

Gly

<210> SEQ ID NO 245
<211> LENGTH: 282
<212> TYPE: PRT
<213> ORGANISM: Zea mays

<400> SEQUENCE: 245

Met Asp Trp Gly Asn Arg Thr Lys Ala Ala Ala Ala Ala Ala Ala Pro
1               5                   10                  15

Asp Glu Arg Ala Gly Gly Gly Glu Gly Leu Gly Gly Tyr Val Lys Val
            20                  25                  30

Met Thr Asp Glu Gln Met Glu Val Leu Arg Lys Gln Ile Ser Ile Tyr
        35                  40                  45

Ala Thr Ile Cys Glu Gln Leu Val Glu Met His Arg Val Leu Thr Glu
    50                  55                  60

His Gln Asp Thr Ile Ala Gly Leu Arg Phe Ser Asn Leu Tyr Cys Asp
65                  70                  75                  80

Pro Leu Ile Ile Pro Gly Gly His Lys Ile Thr Ala Arg Gln Arg Trp
                85                  90                  95

Gln Pro Thr Pro Met Gln Leu Gln Ile Leu Glu Ser Ile Phe Asp Gln
            100                 105                 110

Gly Asn Gly Thr Pro Ser Lys Gln Lys Ile Lys Glu Ile Thr Ala Glu
        115                 120                 125

Leu Ser Gln His Gly Gln Ile Ser Glu Thr Asn Val Tyr Asn Trp Phe
    130                 135                 140

Gln Asn Arg Arg Ala Arg Ser Lys Arg Lys Gln Ala Ala Ala Ser Leu
145                 150                 155                 160

Pro Asn Asn Ala Glu Ser Glu Ala Glu Ala Asp Glu Glu Pro Leu Ala
                165                 170                 175

Asp Lys Lys Pro Lys Ser Asp Arg Pro Pro Pro Pro Pro Pro Pro Ile
            180                 185                 190

Gln Asp Asn Thr Lys Ala Thr Gly Ala Leu Ser Ala Asp Arg Val Ser
        195                 200                 205

Gly Gly Thr Arg His Leu Asp Thr Gly His Asp Gln Thr Ser Gly Val
    210                 215                 220

Met Tyr Gly Cys Asn Asp Ser Gly Leu Leu Arg Ser Ser Gly Ser Ser
225                 230                 235                 240

Gly Gln Met Ser Leu Tyr Glu Asn Phe Met Ser Asn Pro Arg Ile Asp
                245                 250                 255

Arg Phe Pro Ala Lys Val Glu Ser Ser Arg Ser Phe Pro His Leu Gln
            260                 265                 270

Gln His Gly Glu Gly Phe Gly Met Phe Gly
        275                 280

<210> SEQ ID NO 246
<211> LENGTH: 264
<212> TYPE: PRT
<213> ORGANISM: Zea mays

<400> SEQUENCE: 246

Met Asp Ser Ser Phe Leu Pro Ala Gly Ala Asp Asn Gly Ser Ala Gly
1               5                   10                  15
```

Gly Ala Asn Asn Gly Gly Gly Ala Ala Gln Gln Ala Pro Pro Ile Arg
                20                  25                  30

Glu Gln Asp Arg Leu Met Pro Ile Ala Asn Val Ile Arg Ile Met Arg
            35                  40                  45

Arg Val Leu Pro Ala His Ala Lys Ile Ser Asp Asp Ala Lys Glu Thr
50                  55                  60

Ile Gln Glu Cys Val Ser Glu Tyr Ile Ser Phe Ile Thr Gly Glu Ala
65                  70                  75                  80

Asn Glu Arg Cys Gln Arg Glu Gln Arg Lys Thr Ile Thr Ala Glu Asp
                85                  90                  95

Val Leu Trp Ala Met Ser Arg Leu Gly Phe Asp Asp Tyr Val Glu Pro
            100                 105                 110

Leu Ser Val Tyr Leu His Arg Tyr Arg Glu Phe Glu Gly Glu Ala Arg
        115                 120                 125

Gly Val Gly Leu Ala Pro Ala Pro Pro Arg Gly Asp His His His
    130                 135                 140

His His Ser Val Pro Pro Ser Met Leu Asn Lys Ser Arg Gly Pro Gly
145                 150                 155                 160

Ser Gly Ala Val Met Leu Pro His His His His Asp Met His Ala
                165                 170                 175

Ser Met Tyr Gly Gly Ala Val Pro Pro Pro His His Gly Phe Leu
            180                 185                 190

Met Pro His Pro Gln Gly Gly His Tyr Leu Pro Tyr Pro Tyr Glu Pro
        195                 200                 205

Thr Ser Tyr Gly Gly Glu His Ala Leu Ala Ser Gly Tyr Tyr Gly Gly
210                 215                 220

Ala Ala Tyr Ala Pro Gly Asn Asn Gly Gly Ser Gly Asp Gly Ser Gly
225                 230                 235                 240

Gly Ser Ala Ser His Ala Pro Pro Gly Gly Ser Gly Gly Phe Asp
                245                 250                 255

His Pro His Thr Phe Ala Tyr Lys
            260

<210> SEQ ID NO 247
<211> LENGTH: 392
<212> TYPE: PRT
<213> ORGANISM: Zea mays

<400> SEQUENCE: 247

Met Pro Ala Arg Ala Ser His Pro Ala Leu Ala Thr Ser Arg Ala Arg
1               5                   10                  15

Gly Trp Pro Arg Leu Arg Ala Leu Gly Ile Ala Pro Asp Gly Gly Arg
            20                  25                  30

Trp Arg Cys Leu Pro His Phe Ala Pro Ile Ser Glu Pro Ala Arg His
        35                  40                  45

Leu Ser Pro Arg Ala Pro Ala Ser Ala Ser Pro Ala Arg Pro His
    50                  55                  60

Pro Ala Ile Lys Ala Ser Pro Ser Pro Thr Leu Ala Ala Ala Ala
65                  70                  75                  80

Ala Ala Ala Ala Ala Thr Ser Ser Leu Pro Ser Phe Ser Ala Arg Arg
                85                  90                  95

Arg Ser Thr Gly Met Ala Gly Ile Thr Lys Arg Arg Thr Ser Pro Ala
            100                 105                 110

Ser Thr Ser Ser Ser Ser Gly Asp Val Leu Pro Gln Arg Val Thr Arg
        115                 120                 125

```
Lys Arg Arg Ser Ala Arg Arg Gly Pro Arg Ser Thr Ala Arg Arg Pro
        130                 135                 140

Ser Ala Pro Pro Met Asn Glu Leu Asp Leu Asn Thr Ala Ala Leu
145                 150                 155                 160

Asp Pro Asp His Tyr Ala Thr Gly Leu Arg Val Leu Leu Gln Lys Glu
                165                 170                 175

Leu Arg Asn Ser Asp Val Ser Gln Leu Gly Arg Ile Val Leu Pro Lys
                180                 185                 190

Lys Glu Ala Glu Ser Tyr Leu Pro Ile Leu Met Ala Lys Asp Gly Lys
                195                 200                 205

Ser Leu Cys Met His Asp Leu Leu Asn Ser Gln Leu Trp Thr Phe Lys
210                 215                 220

Tyr Arg Tyr Trp Phe Asn Asn Lys Ser Arg Met Tyr Val Leu Glu Asn
225                 230                 235                 240

Thr Gly Asp Tyr Val Lys Ala His Asp Leu Gln Gln Gly Asp Phe Ile
                245                 250                 255

Val Ile Tyr Lys Asp Asp Glu Asn Asn Arg Phe Val Ile Gly Ala Lys
                260                 265                 270

Lys Ala Gly Asp Glu Gln Thr Ala Thr Val Pro Gln Val His Glu His
                275                 280                 285

Met His Ile Ser Ala Ala Leu Pro Ala Pro Gln Ala Phe His Asp Tyr
290                 295                 300

Ala Gly Pro Val Ala Ala Glu Ala Gly Met Leu Ala Ile Val Pro Gln
305                 310                 315                 320

Gly Asp Glu Ile Phe Asp Gly Ile Leu Asn Ser Leu Pro Glu Ile Pro
                325                 330                 335

Val Ala Asn Val Arg Tyr Ser Asp Phe Phe Asp Pro Phe Gly Asp Ser
                340                 345                 350

Met Asp Met Ala Asn Pro Leu Ser Ser Asn Pro Ser Val Asn
                355                 360                 365

Leu Ala Thr His Phe His Asp Glu Arg Ile Gly Ser Cys Ser Phe Pro
370                 375                 380

Tyr Pro Lys Ser Gly Pro Gln Met
385                 390

<210> SEQ ID NO 248
<211> LENGTH: 341
<212> TYPE: PRT
<213> ORGANISM: Zea mays

<400> SEQUENCE: 248

Met Ala Ala Ala Ile Asp Met Tyr Lys Tyr Tyr Asn Thr Ser Ala His
1               5                   10                  15

Gln Ile Pro Ser Ser Pro Ser Asp Gln Glu Leu Ala Lys Ala Leu
                20                  25                  30

Glu Pro Phe Ile Thr Ser Ala Ser Ser Ser Ser Ser Ser Pro Tyr
                35                  40                  45

His Gly Tyr Ser Ser Pro Ser Met Ser Gln Asp Ser Tyr Met Pro
                50                  55                  60

Thr Pro Ser Tyr Thr Ser Tyr Ala Thr Ser Pro Leu Pro Thr Pro Ala
65                  70                  75                  80

Ala Ala Ser Ser Ser Gln Leu Pro Pro Leu Tyr Ser Ser Pro Tyr Ala
                85                  90                  95
```

```
Ala Pro Cys Met Ala Gly Gln Met Gly Leu Asn Gln Leu Gly Pro Ala
            100                 105                 110

Gln Ile Gln Gln Ile Gln Ala Gln Phe Met Phe Gln Gln Gln Gln Gln
        115                 120                 125

Gln Gln Arg Gly Leu His Ala Ala Phe Leu Gly Pro Arg Ala Gln Pro
130                 135                 140

Met Lys Gln Ser Gly Ser Pro Ser Pro Pro Pro Leu Ala Pro Ala
145                 150                 155                 160

Gln Ser Lys Leu Tyr Arg Gly Val Arg Gln Arg His Trp Gly Lys Trp
                165                 170                 175

Val Ala Glu Ile Arg Leu Pro Lys Asn Arg Thr Arg Leu Trp Leu Gly
            180                 185                 190

Thr Phe Asp Thr Ala Glu Asp Ala Ala Leu Ala Tyr Asp Lys Ala Ala
        195                 200                 205

Phe Arg Leu Arg Gly Asp Thr Ala Arg Leu Asn Phe Pro Ala Leu Arg
    210                 215                 220

Arg Gly Gly Ala His Leu Ala Gly Pro Leu His Ala Ser Val Asp Ala
225                 230                 235                 240

Lys Leu Thr Ala Ile Cys Gln Ser Leu Ser Glu Ser Lys Ser Lys Ser
                245                 250                 255

Gly Ser Ser Gly Asp Glu Ser Ala Ala Ser Pro Pro Asp Ser Pro Lys
            260                 265                 270

Cys Ser Ala Ser Thr Thr Glu Gly Glu Gly Glu Glu Ser Gly Ser
        275                 280                 285

Ala Gly Ser Pro Pro Pro Pro Pro Pro Pro Thr Leu Ala Pro Pro
290                 295                 300

Val Pro Glu Met Ala Lys Leu Asp Phe Thr Glu Ala Pro Trp Asp Glu
305                 310                 315                 320

Thr Glu Ala Phe His Leu Arg Lys Tyr Pro Ser Trp Glu Ile Asp Trp
                325                 330                 335

Asp Ser Ile Leu Ser
            340

<210> SEQ ID NO 249
<211> LENGTH: 316
<212> TYPE: PRT
<213> ORGANISM: Zea mays

<400> SEQUENCE: 249

Met Ala Ala Ala Ile Asp Met Tyr Lys Tyr Cys Asn Thr Ser Ala His
1               5                   10                  15

Leu Ile Ala Ser Ser Pro Ser Asp Gln Glu Leu Ala Lys Ala Leu
            20                  25                  30

Glu Pro Phe Ile Thr Ser Ala Ser Ser Pro Tyr His Arg Tyr Ser Leu
        35                  40                  45

Ala Pro Asp Ser Tyr Met Pro Thr Pro Ser Ser Tyr Thr Thr Ser Pro
    50                  55                  60

Leu Pro Thr Pro Thr Ser Ser Pro Phe Ser Gln Leu Pro Pro Leu Tyr
65                  70                  75                  80

Ser Ser Pro Tyr Ala Ala Ser Thr Ala Ser Gly Val Ala Gly Pro Met
                85                  90                  95

Gly Leu Asn Gln Leu Gly Pro Ala Gln Ile Gln Gln Ile Gln Ala Gln
            100                 105                 110
```

-continued

```
Leu Met Phe Gln His Gln Gln Arg Gly Leu His Ala Ala Phe Leu
        115                 120                 125

Gly Pro Arg Ala Gln Pro Met Lys Gln Ser Gly Ser Pro Pro Ala Gln
    130                 135                 140

Ser Lys Leu Tyr Arg Gly Val Arg Gln Arg His Trp Gly Lys Trp Val
145                 150                 155                 160

Ala Glu Ile Arg Leu Pro Lys Asn Arg Thr Arg Leu Trp Leu Gly Thr
                165                 170                 175

Phe Asp Thr Ala Glu Gly Ala Ala Leu Ala Tyr Asp Glu Ala Ala Phe
            180                 185                 190

Arg Leu Arg Gly Asp Thr Ala Arg Leu Asn Phe Pro Ser Leu Arg Arg
        195                 200                 205

Gly Gly Gly Ala Arg Leu Ala Gly Pro Leu His Ala Ser Val Asp Ala
    210                 215                 220

Lys Leu Thr Ala Ile Cys Gln Ser Leu Ala Gly Ser Lys Asn Ser Ser
225                 230                 235                 240

Ser Ser Asp Glu Ser Ala Ala Ser Leu Pro Asp Ser Pro Lys Cys Ser
                245                 250                 255

Ala Ser Thr Glu Gly Asp Glu Ser Ala Ser Ala Gly Ser Pro Pro
            260                 265                 270

Ser Pro Thr Gln Ala Pro Pro Val Pro Glu Met Ala Lys Leu Asp Phe
        275                 280                 285

Thr Glu Ala Pro Trp Asp Glu Thr Glu Ala Phe His Leu Arg Lys Tyr
    290                 295                 300

Pro Ser Trp Glu Ile Asp Trp Asp Ser Ile Leu Ser
305                 310                 315

<210> SEQ ID NO 250
<211> LENGTH: 233
<212> TYPE: PRT
<213> ORGANISM: Zea mays

<400> SEQUENCE: 250

Met Ala Pro Arg Thr Ser Glu Lys Thr Met Ala Pro Ala Ala Ala Ala
1               5                   10                  15

Ala Thr Gly Leu Ala Leu Ser Val Gly Gly Gly Gly Ala Gly Gly
            20                  25                  30

Pro His Tyr Arg Gly Val Arg Lys Arg Pro Trp Gly Arg Tyr Ala Ala
        35                  40                  45

Glu Ile Arg Asp Pro Ala Lys Lys Ser Arg Val Trp Leu Gly Thr Tyr
50                  55                  60

Asp Thr Ala Glu Asp Ala Ala Arg Ala Tyr Asp Ala Ala Ala Arg Glu
65                  70                  75                  80

Tyr Arg Gly Ala Lys Ala Lys Thr Asn Phe Pro Tyr Pro Ser Cys Val
                85                  90                  95

Pro Leu Ser Ala Ala Gly Cys Arg Ser Ser Asn Ser Ser Thr Val Glu
            100                 105                 110

Ser Phe Ser Ser Asp Ala Gln Ala Pro Met Gln Ala Met Pro Leu Pro
        115                 120                 125

Pro Ser Leu Glu Leu Asp Leu Phe His Arg Ala Ala Ala Ala Thr
    130                 135                 140

Gly Thr Gly Ala Ala Ala Val Arg Phe Pro Phe Gly Ser Ile Pro Val
145                 150                 155                 160
```

```
Thr His Pro Tyr Tyr Phe Phe Gly Gln Ala Ala Ala Ala Ala Glu
            165                 170                 175

Ala Gly Cys Arg Val Leu Lys Leu Ala Pro Ala Val Thr Val Ala Gln
        180                 185                 190

Ser Asp Ser Asp Cys Ser Ser Val Val Asp Leu Ser Pro Ser Pro Pro
            195                 200                 205

Ala Ala Val Ser Ala Arg Lys Pro Ala Ala Phe Asp Leu Asp Leu Asn
        210                 215                 220

Cys Ser Pro Pro Thr Glu Ala Glu Ala
225                 230

<210> SEQ ID NO 251
<211> LENGTH: 294
<212> TYPE: PRT
<213> ORGANISM: Zea mays

<400> SEQUENCE: 251

Met Glu Asp Val Ala Asn Ala His Ile Tyr Ala His Ala His Arg Ser
1               5                   10                  15

Lys Arg Pro Gln Ser Ala Ala Ile Lys Asp Gly Asp Gly Asp Val Asp
            20                  25                  30

Leu Ser Met Lys Gly Ala Arg Tyr Arg Gly Val Arg Arg Arg Pro Trp
        35                  40                  45

Gly Arg Phe Ala Ala Glu Ile Arg Asp Pro Met Ser Lys Glu Arg Arg
    50                  55                  60

Trp Leu Gly Thr Phe Asp Thr Ala Glu Gln Ala Ala Cys Ala Tyr Asp
65                  70                  75                  80

Ile Ala Ala Arg Ala Met Arg Gly Asn Lys Ala Arg Thr Asn Phe Pro
                85                  90                  95

Gly His Ala Thr Ala Gly Tyr Trp Pro Trp Gly Ala Pro Gln Pro Ala
            100                 105                 110

Ala Val Ala His Pro Ile Asn Pro Phe Leu Leu His Asn Leu Ile Met
        115                 120                 125

Ser Ser Ser Asn His Gly Cys Arg Leu Leu Asn His Ala Gly His Gly
    130                 135                 140

His Val His Ser Ala Ala Pro Arg Pro Ala Pro Ala Ala Asp Ala
145                 150                 155                 160

Thr Ser Thr Thr Ile Ala Ala Pro Phe Pro Val Ala Ala His Pro Ala
                165                 170                 175

Val Ala Met Asp Glu Asp Val Asp Asp Trp Asp Gly Val Leu Arg Ser
            180                 185                 190

Glu Pro Ala Asp Ala Gly Leu Leu Gln Asp Ala Leu His Asp Phe Tyr
        195                 200                 205

Pro Phe Thr Arg Pro Arg Ala Gly Gly Gly Arg Arg Gly Leu Ser Ala
    210                 215                 220

Ala Gly Thr Asp Ala Arg Ala Ala Ala Leu Val Ala Pro Val Lys
225                 230                 235                 240

Pro Asp Ala Phe Val Val Pro Ser Pro Phe Ala Gly Val Glu Gly Asp
                245                 250                 255

Gly Glu Tyr Pro Met Met Pro Gln Gly Leu Leu Glu Asp Val Ile His
            260                 265                 270
```

```
Ser Pro Ala Phe Val Glu Val Ala Ala Pro Pro Ser Val Pro Thr
        275                 280                 285

Arg Arg Gly Arg Arg Gly
    290

<210> SEQ ID NO 252
<211> LENGTH: 709
<212> TYPE: PRT
<213> ORGANISM: Zea mays

<400> SEQUENCE: 252

Met Ala Thr Val Asn Asn Trp Leu Ala Phe Ser Leu Ser Pro Gln Glu
1               5                   10                  15

Leu Pro Pro Ser Gln Thr Thr Asp Ser Thr Leu Ile Ser Ala Ala Thr
            20                  25                  30

Ala Asp His Val Ser Gly Asp Val Cys Phe Asn Ile Pro Gln Asp Trp
        35                  40                  45

Ser Met Arg Gly Ser Glu Leu Ser Ala Leu Val Ala Glu Pro Lys Leu
    50                  55                  60

Glu Asp Phe Leu Gly Gly Ile Ser Phe Ser Glu Gln His His Lys Ser
65                  70                  75                  80

Asn Cys Asn Leu Ile Pro Ser Thr Ser Ser Thr Val Cys Tyr Ala Ser
                85                  90                  95

Ser Ala Ala Ser Thr Gly Tyr His His Gln Leu Tyr Gln Pro Thr Ser
            100                 105                 110

Ser Ala Leu His Phe Ala Asp Ser Val Met Val Ala Ser Ser Ala Gly
        115                 120                 125

Val His Asp Gly Gly Ser Met Leu Ser Ala Ala Ala Asn Gly Val
    130                 135                 140

Ala Gly Ala Ala Ser Ala Asn Gly Gly Gly Ile Gly Leu Ser Met Ile
145                 150                 155                 160

Lys Asn Trp Leu Arg Ser Gln Pro Ala Pro Met Gln Pro Arg Ala Ala
                165                 170                 175

Ala Ala Glu Gly Ala Gln Gly Leu Ser Leu Ser Met Asn Met Ala Gly
            180                 185                 190

Thr Thr Gln Gly Ala Ala Gly Met Pro Leu Leu Ala Gly Glu Arg Ala
        195                 200                 205

Arg Ala Pro Glu Ser Val Ser Thr Ser Ala Gln Gly Gly Ala Val Val
    210                 215                 220

Val Thr Ala Pro Lys Glu Asp Ser Gly Gly Ser Gly Val Ala Gly Ala
225                 230                 235                 240

Leu Val Ala Val Ser Thr Asp Thr Gly Gly Ser Gly Gly Ala Ser Ala
                245                 250                 255

Asp Asn Thr Ala Arg Lys Thr Val Asp Thr Phe Gly Gln Arg Thr Ser
            260                 265                 270

Ile Tyr Arg Gly Val Thr Arg His Arg Trp Thr Gly Arg Tyr Glu Ala
        275                 280                 285

His Leu Trp Asp Asn Ser Cys Arg Arg Glu Gly Gln Thr Arg Lys Gly
    290                 295                 300

Arg Gln Val Tyr Leu Gly Gly Tyr Asp Lys Glu Glu Lys Ala Ala Arg
305                 310                 315                 320

Ala Tyr Asp Leu Ala Ala Leu Lys Tyr Trp Gly Ala Thr Thr Thr Thr
                325                 330                 335
```

```
Asn Phe Pro Val Ser Asn Tyr Glu Lys Glu Leu Glu Asp Met Lys His
            340                 345                 350

Met Thr Arg Gln Glu Phe Val Ala Ser Leu Arg Arg Lys Ser Ser Gly
            355                 360                 365

Phe Ser Arg Gly Ala Ser Ile Tyr Arg Gly Val Thr Arg His His Gln
        370                 375                 380

His Gly Arg Trp Gln Ala Arg Ile Gly Arg Val Ala Gly Asn Lys Asp
385                 390                 395                 400

Leu Tyr Leu Gly Thr Phe Ser Thr Gln Glu Glu Ala Glu Ala Tyr
                405                 410                 415

Asp Ile Ala Ala Ile Lys Phe Arg Gly Leu Asn Ala Val Thr Asn Phe
            420                 425                 430

Asp Met Ser Arg Tyr Asp Val Lys Ser Ile Leu Asp Ser Ser Ala Leu
            435                 440                 445

Pro Ile Gly Ser Ala Ala Lys Arg Leu Lys Glu Ala Glu Ala Ala
        450                 455                 460

Ser Ala Gln His His His Ala Gly Val Val Ser Tyr Asp Val Gly Arg
465                 470                 475                 480

Ile Ala Ser Gln Leu Gly Asp Gly Gly Ala Leu Ala Ala Ala Tyr Gly
                485                 490                 495

Ala His Tyr His Gly Ala Ala Trp Pro Thr Ile Ala Phe Gln Pro Gly
            500                 505                 510

Ala Ala Thr Thr Gly Leu Tyr His Pro Tyr Ala Gln Gln Pro Met Arg
            515                 520                 525

Gly Gly Gly Trp Cys Lys Gln Glu Gln Asp His Ala Val Ile Ala Ala
            530                 535                 540

Ala His Ser Leu Gln Asp Leu His His Leu Asn Leu Gly Ala Ala Gly
545                 550                 555                 560

Ala His Asp Phe Phe Ser Ala Gly Gln Gln Ala Ala Ala Ala Ala
                565                 570                 575

Met His Gly Leu Ala Ser Ile Asp Ser Ala Ser Leu Glu His Ser Thr
            580                 585                 590

Gly Ser Asn Ser Val Val Tyr Asn Gly Gly Val Gly Asp Ser Asn Gly
        595                 600                 605

Ala Ser Ala Val Gly Ser Gly Gly Tyr Met Met Pro Met Ser Ala
        610                 615                 620

Ala Gly Ala Thr Thr Thr Ser Ala Met Val Ser His Glu Gln Met His
625                 630                 635                 640

Ala Arg Ala Tyr Asp Glu Ala Lys Gln Ala Gln Met Gly Tyr Glu
                645                 650                 655

Ser Tyr Leu Val Asn Ala Glu Asn Asn Gly Gly Gly Arg Met Ser Ala
            660                 665                 670

Trp Gly Thr Val Val Ser Ala Ala Ala Ala Ala Ala Ser Ser Asn
        675                 680                 685

Asp Asn Ile Ala Ala Asp Val Gly His Gly Gly Ala Gln Leu Phe Ser
        690                 695                 700

Val Trp Asn Asp Thr
705

<210> SEQ ID NO 253
<211> LENGTH: 492
<212> TYPE: PRT
<213> ORGANISM: Zea mays
```

```
<400> SEQUENCE: 253

Met Asp Thr Ser His His Tyr His Pro Trp Leu Asn Phe Ser Leu Ala
1               5                   10                  15

His His Cys Asp Leu Glu Glu Glu Arg Gly Ala Ala Ala Glu Leu
            20                  25                  30

Ala Ala Ile Ala Gly Ala Ala Pro Pro Lys Leu Glu Asp Phe Leu
            35                  40                  45

Gly Gly Gly Val Ala Thr Gly Gly Pro Glu Ala Val Ala Pro Ala Glu
50                  55                  60

Met Tyr Asp Ser Asp Leu Lys Phe Ile Ala Ala Gly Phe Leu Gly
65                  70                  75                  80

Gly Ser Ala Ala Ala Ala Thr Ser Pro Leu Ser Ser Leu Asp Gln
                85                  90                  95

Ala Gly Ser Lys Leu Ala Leu Pro Ala Ala Ala Ala Pro Ala Pro
            100                 105                 110

Glu Gln Arg Lys Ala Val Asp Ser Phe Gly Gln Arg Thr Ser Ile Tyr
            115                 120                 125

Arg Gly Val Thr Arg His Arg Trp Thr Gly Arg Tyr Glu Ala His Leu
130                 135                 140

Trp Asp Asn Ser Cys Arg Arg Glu Gly Gln Ser Arg Lys Gly Arg Gln
145                 150                 155                 160

Val Tyr Leu Gly Gly Tyr Asp Lys Glu Glu Lys Ala Ala Arg Ala Tyr
                165                 170                 175

Asp Leu Ala Ala Leu Lys Tyr Trp Gly Ser Ser Thr Thr Thr Asn Phe
            180                 185                 190

Pro Val Ala Glu Tyr Glu Lys Glu Val Glu Glu Met Lys Asn Met Thr
            195                 200                 205

Arg Gln Glu Phe Val Ala Ser Leu Arg Arg Lys Ser Ser Gly Phe Ser
210                 215                 220

Arg Gly Ala Ser Ile Tyr Arg Gly Val Thr Arg His His Gln His Gly
225                 230                 235                 240

Arg Trp Gln Ala Arg Ile Gly Arg Val Ala Gly Asn Lys Asp Leu Tyr
                245                 250                 255

Leu Gly Thr Phe Ser Thr Glu Glu Glu Ala Ala Glu Ala Tyr Asp Ile
            260                 265                 270

Ala Ala Ile Lys Phe Arg Gly Leu Asn Ala Val Thr Asn Phe Glu Ile
            275                 280                 285

Ser Arg Tyr Asn Val Glu Thr Ile Met Ser Ser Asn Leu Pro Val Ala
            290                 295                 300

Ser Met Ser Ser Ser Ala Ala Ala Ala Gly Gly Arg Ser Ser Lys
305                 310                 315                 320

Ala Leu Glu Ser Pro Pro Ser Gly Ser Leu Asp Gly Gly Gly Met
                325                 330                 335

Pro Val Val Glu Ala Ser Thr Ala Pro Pro Leu Phe Ile Pro Val Lys
            340                 345                 350

Tyr Asp Gln Gln Gln Gln Glu Tyr Leu Ser Met Leu Ala Leu Gln Gln
            355                 360                 365

His His Gln Gln Gln Gln Ala Gly Asn Leu Leu Gln Gly Pro Leu Val
            370                 375                 380

Gly Phe Gly Gly Leu Tyr Ser Ser Gly Val Asn Leu Asp Phe Ala Asn
385                 390                 395                 400

Ser His Gly Thr Ala Ala Pro Ser Ser Met Ala His His Cys Tyr Ala
                405                 410                 415
```

```
Asn Gly Thr Ala Ser Ala Ser His Glu His Gln His Gln Met Gln Gln
            420                 425                 430

Gly Gly Glu Asn Glu Thr Gln Pro Gln Pro Gln Gln Ser Ser Ser Ser
            435                 440                 445

Cys Ser Ser Leu Pro Phe Ala Thr Pro Val Ala Phe Asn Gly Ser Tyr
450                 455                 460

Glu Ser Ser Ile Thr Ala Ala Gly Pro Phe Gly Tyr Ser Tyr Pro Asn
465                 470                 475                 480

Val Ala Ala Phe Gln Thr Pro Ile Tyr Gly Met Glu
                485                 490

<210> SEQ ID NO 254
<211> LENGTH: 488
<212> TYPE: PRT
<213> ORGANISM: Zea mays

<400> SEQUENCE: 254

Met Asp Met Asp Met Ser Ser Ala Tyr Pro His His Trp Leu Ser Phe
1               5                   10                  15

Ser Leu Ser Asn Asn Tyr His His Gly Leu Leu Glu Ala Phe Ser Asn
            20                  25                  30

Ser Ser Gly Thr Pro Leu Gly Asp Glu Gln Gly Ala Val Glu Glu Ser
        35                  40                  45

Pro Arg Thr Val Glu Asp Phe Leu Gly Val Gly Gly Ala Gly Ala
    50                  55                  60

Pro Pro Gln Pro Ala Ala Ala Asp Gln Asp His Gln Leu Val Cys
65                  70                  75                  80

Gly Glu Leu Gly Ser Ile Thr Ala Arg Phe Leu Arg His Tyr Pro Ala
                85                  90                  95

Ala Pro Ala Gly Thr Thr Val Glu Asn Pro Gly Ala Val Thr Val Ala
            100                 105                 110

Ala Met Ser Ser Thr Asp Val Ala Gly Ala Glu Ser Asp Gln Ala Arg
            115                 120                 125

Arg Pro Ala Glu Thr Phe Gly Gln Arg Thr Ser Ile Tyr Arg Gly Val
        130                 135                 140

Thr Arg His Arg Trp Thr Gly Arg Tyr Glu Ala His Leu Trp Asp Asn
145                 150                 155                 160

Ser Cys Arg Arg Glu Gly Gln Ser Arg Lys Gly Arg Gln Val Tyr Leu
                165                 170                 175

Gly Gly Tyr Asp Lys Glu Glu Lys Ala Ala Arg Ala Tyr Asp Leu Ala
            180                 185                 190

Ala Leu Lys Tyr Trp Gly Pro Thr Thr Thr Asn Phe Pro Val Ser
        195                 200                 205

Asn Tyr Glu Lys Glu Leu Glu Glu Met Lys Ser Met Thr Arg Gln Glu
    210                 215                 220

Phe Ile Ala Ser Leu Arg Arg Lys Ser Ser Gly Phe Ser Arg Gly Ala
225                 230                 235                 240

Ser Ile Tyr Arg Gly Val Thr Arg His His Gln His Gly Arg Trp Gln
                245                 250                 255

Ala Arg Ile Gly Arg Val Ala Gly Asn Lys Asp Leu Tyr Leu Gly Thr
            260                 265                 270

Phe Ser Thr Gln Glu Glu Ala Ala Glu Ala Tyr Asp Ile Ala Ala Ile
        275                 280                 285
```

```
Lys Phe Arg Gly Leu Asn Ala Val Thr Asn Phe Asp Met Ser Arg Tyr
            290                 295                 300

Asp Val Glu Ser Ile Leu Ser Ser Asp Leu Pro Val Gly Gly Gly Ala
305                 310                 315                 320

Ser Gly Arg Ala Pro Ala Lys Phe Pro Leu Asp Ser Leu Gln Pro Gly
                325                 330                 335

Ser Ala Ala Ala Met Met Leu Ala Gly Ala Ala Ala Ser Gln Ala
                340                 345                 350

Thr Met Pro Pro Ser Glu Lys Asp Tyr Trp Ser Leu Leu Ala Leu His
                355                 360                 365

Tyr Gln Gln Gln Gln Glu Gln Glu Arg Gln Phe Pro Ala Ser Ala Tyr
            370                 375                 380

Glu Ala Tyr Gly Ser Gly Gly Val Asn Val Asp Phe Thr Met Gly Thr
385                 390                 395                 400

Ser Ser Gly Asn Asn Asn Asn Asn Thr Gly Ser Gly Val Met Trp Gly
                405                 410                 415

Ala Thr Thr Gly Ala Val Val Gly Gln Gln Asp Ser Ser Gly Lys
                420                 425                 430

Gln Gly Asn Gly Tyr Ala Ser Asn Ile Pro Tyr Ala Ala Ala Met
            435                 440                 445

Val Ser Gly Ser Ala Gly Tyr Glu Gly Ser Thr Gly Asp Asn Gly Thr
450                 455                 460

Trp Val Thr Thr Thr Thr Ser Ser Asn Thr Gly Thr Ala Pro His Tyr
465                 470                 475                 480

Tyr Asn Tyr Leu Phe Gly Met Glu
                485

<210> SEQ ID NO 255
<211> LENGTH: 470
<212> TYPE: PRT
<213> ORGANISM: Zea mays

<400> SEQUENCE: 255

Met Ala His Pro Ser Ala Ala Ala Ala Val Ser Ser Thr Ala Pro
1               5                   10                  15

Ala Ala Asn Pro Ser Ser Gly Ala Arg Glu Glu Gly Gly Ala Arg Ser
                20                  25                  30

Pro Pro Ser Pro Ser Pro Ser Gln Arg Gly Arg Ala Lys Val Val Ile
                35                  40                  45

Val Met Gly Ala Thr Gly Ala Gly Lys Ser Arg Leu Ala Val Asp Leu
50                  55                  60

Ala Ala His Phe Ala Gly Val Glu Val Val Ser Ala Asp Ser Met Gln
65                  70                  75                  80

Leu Tyr Arg Gly Leu Asp Val Leu Thr Asn Lys Ala Pro Leu His Glu
                85                  90                  95

Gln Asn Gly Val Pro His His Leu Leu Ser Val Ile Asp Pro Ser Val
                100                 105                 110

Glu Phe Thr Cys Arg Asp Phe Arg Asp Arg Ala Val Pro Ile Ile Gln
                115                 120                 125

Glu Ile Val Asp Arg Gly Gly Leu Pro Val Val Val Gly Gly Thr Asn
130                 135                 140

Phe Tyr Ile Gln Ala Leu Val Ser Pro Phe Leu Leu Asp Asp Met Ala
145                 150                 155                 160
```

-continued

Glu Glu Met Gln Gly Cys Thr Leu Arg Asp His Ile Asp Asp Gly Leu
            165                 170                 175

Thr Asp Glu Asp Gly Asn Gly Phe Glu Arg Leu Lys Glu Ile Asp
        180                 185                 190

Pro Val Ala Ala Gln Arg Ile His Pro Asn Asp His Arg Lys Ile Lys
        195                 200                 205

Arg Tyr Leu Glu Leu Tyr Ala Thr Thr Gly Ala Leu Pro Ser Asp Leu
        210                 215                 220

Phe Gln Gly Glu Ala Ala Lys Lys Trp Gly Arg Pro Ser Asn Ser Arg
225                 230                 235                 240

Leu Asp Cys Cys Phe Leu Trp Val Asp Ala Leu Gln Val Leu Asp
            245                 250                 255

Ser Tyr Val Asn Lys Arg Val Asp Cys Met Met Asp Gly Gly Leu Leu
            260                 265                 270

Asp Glu Val Cys Ser Ile Tyr Asp Ala Asp Ala Val Tyr Thr Gln Gly
            275                 280                 285

Leu Arg Gln Ala Ile Gly Val Arg Glu Phe Asp Glu Phe Phe Arg Ala
            290                 295                 300

Tyr Leu Pro Arg Lys Glu Ser Gly Glu Gly Ser Cys Ala Ser Leu Leu
305                 310                 315                 320

Gly Met His Asp Asp Gln Leu Lys Ser Leu Leu Asp Glu Ala Val Ser
                325                 330                 335

Gln Leu Lys Ala Asn Thr Arg Arg Leu Val Arg Gln Arg Arg
                340                 345                 350

Leu His Arg Leu Ser Lys Asp Phe Gly Trp Asn Leu His Arg Val Asp
            355                 360                 365

Ala Thr Glu Ala Phe Phe Cys Ala Thr Asp Asp Ser Trp Gln Lys Lys
        370                 375                 380

Val Val Lys Pro Cys Val Asp Val Arg Arg Phe Leu Ser Asp Asn
385                 390                 395                 400

Ser Thr Val Leu Pro Ser Thr Ser Ala Ser Asp Pro Ser Ser Arg Glu
            405                 410                 415

Leu Trp Thr Gln Tyr Val Cys Glu Ala Cys Gly Asn Arg Val Leu Arg
            420                 425                 430

Gly Ala His Glu Trp Glu Gln His Arg Gln Gly Arg Gly His Arg Lys
            435                 440                 445

Arg Val Gln Arg Leu Lys Gln Lys Ser Leu Arg Pro Trp Pro Ser Leu
        450                 455                 460

Leu Pro Gln Asp Arg Ser
465                 470

<210> SEQ ID NO 256
<211> LENGTH: 359
<212> TYPE: PRT
<213> ORGANISM: Zea mays

<400> SEQUENCE: 256

Met Glu Glu Ile Thr Gln His Phe Gly Val Gly Ala Ser Ser His Gly
1               5                   10                  15

His Gly His Gly Gln His His His His His His His His Pro Trp
            20                  25                  30

Ala Ser Ser Leu Ser Ala Val Val Ala Pro Leu Pro Pro Gln Pro Pro
        35                  40                  45

```
Ser Ala Gly Leu Pro Leu Thr Leu Asn Thr Val Ala Ala Thr Gly Asn
 50                  55                  60

Ser Gly Gly Ser Gly Asn Pro Val Leu Gln Leu Ala Asn Gly Gly Gly
 65                  70                  75                  80

Leu Leu Asp Ala Cys Val Lys Ala Lys Glu Pro Ser Ser Ser Ser Pro
                 85                  90                  95

Tyr Ala Gly Asp Val Glu Ala Ile Lys Ala Lys Ile Ile Ser His Pro
                100                 105                 110

His Tyr Tyr Ser Leu Leu Thr Ala Tyr Leu Glu Cys Asn Lys Val Gly
            115                 120                 125

Ala Pro Pro Glu Val Ser Ala Arg Leu Thr Glu Ile Ala Gln Glu Val
        130                 135                 140

Glu Ala Arg Gln Arg Thr Ala Leu Gly Gly Leu Ala Ala Ala Thr Glu
145                 150                 155                 160

Pro Glu Leu Asp Gln Phe Met Glu Ala Tyr His Glu Met Leu Val Lys
                165                 170                 175

Phe Arg Glu Glu Leu Thr Arg Pro Leu Gln Glu Ala Met Glu Phe Met
                180                 185                 190

Arg Arg Val Glu Ser Gln Leu Asn Ser Leu Ser Ile Ser Gly Arg Ser
            195                 200                 205

Leu Arg Asn Ile Leu Ser Ser Gly Ser Ser Glu Glu Asp Gln Glu Gly
        210                 215                 220

Ser Gly Gly Glu Thr Glu Leu Pro Glu Val Asp Ala His Gly Val Asp
225                 230                 235                 240

Gln Glu Leu Lys His His Leu Leu Lys Lys Tyr Ser Gly Tyr Leu Ser
                245                 250                 255

Ser Leu Lys Gln Glu Leu Ser Lys Lys Lys Lys Gly Lys Leu Pro
                260                 265                 270

Lys Glu Ala Arg Gln Gln Leu Leu Ser Trp Trp Asp Gln His Tyr Lys
            275                 280                 285

Trp Pro Tyr Pro Ser Glu Thr Gln Lys Val Ala Leu Ala Glu Ser Thr
        290                 295                 300

Gly Leu Asp Leu Lys Gln Ile Asn Asn Trp Phe Ile Asn Gln Arg Lys
305                 310                 315                 320

Arg His Trp Lys Pro Ser Glu Glu Met His His Leu Met Met Asp Gly
                325                 330                 335

Tyr His Thr Thr Asn Ala Phe Tyr Met Asp Gly His Phe Ile Asn Asp
                340                 345                 350

Gly Gly Leu Tyr Arg Leu Gly
            355

<210> SEQ ID NO 257
<211> LENGTH: 311
<212> TYPE: PRT
<213> ORGANISM: Zea mays

<400> SEQUENCE: 257

Met Thr Gly Leu Asp Glu Ala Leu Met Leu Pro Phe Thr Asp Ile Asp
  1               5                  10                  15

Leu Glu Ala Phe Asp Asn Ala Glu Glu Gln Lys Pro Pro Val Asp Gln
                 20                  25                  30

Met Val Met Pro Pro Thr Val Glu His Pro Ala Ala Ala Gly Thr
             35                  40                  45
```

```
Arg Ala Pro Ile Ile Ile Asp Gly Thr Ala Thr Val Gly Gln Asn Val
     50                  55                  60

Gly Gly Gly Val Val His Ala His Gln Lys Ala Ala Met Thr Thr Ile
 65              70                  75                  80

Glu Asp Ser Ser Cys Phe Arg Arg Gly Ala Ser Cys Val Asp Asp Asp
                 85                  90                  95

Met Ala Val Val Ile His His Val Glu Arg Arg Gln Ala Gly Ser
            100                 105                 110

Thr Ala Val Ala Leu Leu Pro Pro Pro Gln Pro Ser Leu Pro Arg Pro
            115                 120                 125

Arg Ala Arg Ala Ser Gly Gly Ala Gly Glu Arg Ser Ala Pro Ala Ala
        130                 135                 140

Ala Gly Lys Thr Arg Met Asp His Ile Gly Phe Asp Glu Leu Arg Lys
145                 150                 155                 160

Tyr Phe Tyr Met Pro Ile Thr Arg Ala Ala Arg Glu Met Asn Val Gly
                165                 170                 175

Leu Thr Val Leu Lys Lys Arg Cys Arg Glu Leu Gly Val Ala Arg Trp
                180                 185                 190

Pro His Arg Lys Met Lys Ser Leu Lys Ser Leu Met Ala Asn Val Gln
            195                 200                 205

Glu Met Gly Asn Gly Met Ser Pro Val Ala Val Gln His Glu Leu Ala
210                 215                 220

Ala Leu Glu Thr Tyr Cys Ala Leu Met Glu Glu Asn Pro Trp Ile Glu
225                 230                 235                 240

Leu Thr Asp Arg Thr Lys Arg Leu Arg Gln Ala Cys Phe Lys Glu Ser
                245                 250                 255

Tyr Lys Arg Arg Lys Ala Ala Ala Gly Asn Ala Ile Glu Thr Asp His
                260                 265                 270

Ile Val Tyr Ser Phe Gly Gln His Arg Arg Tyr Lys Gln Gln Leu Leu
            275                 280                 285

Pro Pro Pro Thr Ala Gly Ser Thr Ser Ala Asp Asp Arg His Gly Gln
        290                 295                 300

Ser Ser Arg Phe Phe Cys Tyr
305                 310

<210> SEQ ID NO 258
<211> LENGTH: 391
<212> TYPE: PRT
<213> ORGANISM: Zea mays

<400> SEQUENCE: 258

Met Ala Met Val Pro Cys Gly Gly Asp Asp Ala Glu Trp Cys Asn Met
  1               5                  10                  15

Met Glu Ala Ile Asn His Leu Met Met Ser Ser Met Ser Ser Pro His
             20                  25                  30

Val Ala Met Gly Ala Ser Ser Cys Arg Glu Glu Asp Asp Asp Ser Leu
         35                  40                  45

Tyr Leu Pro Met Tyr Tyr Ser Ser Ala Pro Pro Ala Val Val Ser
     50                  55                  60

Asp Gln Tyr Cys Pro Glu Gln Leu Pro Pro Leu Pro Ala Ala Gly Ala
 65                  70                  75                  80

Met Thr Gly Leu Asp Glu Ala Leu Met Leu Pro Phe Thr Asp Ile Asp
                 85                  90                  95
```

```
Leu Glu Ala Phe Asp Asn Ala Glu Glu Gln Lys Pro Pro Val Asp Gln
                100                 105                 110
Met Val Met Met Pro Thr Val Glu His Pro Ala Ala Ala Gly Thr
            115                 120                 125
Arg Ala Pro Ile Ile Ile Asp Gly Thr Ala Thr Val Gly Gln Asn Val
        130                 135                 140
Gly Gly Gly Val Val His Ala His Gln Lys Ala Ala Met Thr Thr Ile
145                 150                 155                 160
Glu Asp Ser Ser Cys Phe Arg Arg Gly Ala Ser Cys Val Asp Asp Asp
                165                 170                 175
Met Ala Val Val Ile His His Val Glu Arg Arg Gln Ala Gly Ser
            180                 185                 190
Thr Ala Val Ala Leu Leu Pro Pro Gln Pro Ser Leu Pro Arg Pro
        195                 200                 205
Arg Ala Arg Ala Ser Gly Gly Ala Gly Glu Arg Ser Ala Pro Ala Ala
        210                 215                 220
Ala Gly Lys Thr Arg Met Asp His Ile Gly Phe Asp Glu Leu Arg Lys
225                 230                 235                 240
Tyr Phe Tyr Met Pro Ile Thr Arg Ala Ala Arg Glu Met Asn Val Gly
                245                 250                 255
Leu Thr Val Leu Lys Lys Arg Cys Arg Glu Leu Gly Val Ala Arg Trp
            260                 265                 270
Pro His Arg Lys Met Lys Ser Leu Lys Ser Leu Met Ala Asn Val Gln
        275                 280                 285
Glu Met Gly Asn Gly Met Ser Pro Val Ala Val Gln His Glu Leu Ala
        290                 295                 300
Ala Leu Glu Thr Tyr Cys Ala Leu Met Glu Glu Asn Pro Trp Ile Glu
305                 310                 315                 320
Leu Thr Asp Arg Thr Lys Arg Leu Arg Gln Ala Cys Phe Lys Glu Ser
                325                 330                 335
Tyr Lys Arg Arg Lys Ala Ala Ala Gly Asn Ala Ile Glu Thr Asp His
            340                 345                 350
Ile Val Tyr Ser Phe Gly Gln His Arg Arg Tyr Lys Gln Gln Leu Leu
        355                 360                 365
Pro Pro Pro Thr Ala Gly Ser Thr Ser Ala Asp Asp Arg His Gly Gln
        370                 375                 380
Ser Ser Arg Phe Phe Cys Tyr
385                 390

<210> SEQ ID NO 259
<211> LENGTH: 33
<212> TYPE: DNA
<213> ORGANISM: herpes simplex virus

<400> SEQUENCE: 259
gacgctttgg acgacttcga cttggacatg ttg                          33

<210> SEQ ID NO 260
<211> LENGTH: 183
<212> TYPE: DNA
<213> ORGANISM: herpes simplex virus

<400> SEQUENCE: 260
gaagcctctg gatctggcag agccgatgcc ctggatgatt ttgatctgga tatgctggga    60
agcgacgccc tggatgattt cgatctggat atgctgggat ctgacgccct ggatgatttc   120
```

```
gatctggata tgctgggatc tgacgccctg gatgatttcg atctggacat gctgatcaac    180
agc                                                                  183

<210> SEQ ID NO 261
<211> LENGTH: 1569
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: tripartite effector VPR (VP64, p65, and Rta)

<400> SEQUENCE: 261
gacgcattgg acgattttga tctggatatg ctgggaagtg acgccctcga tgattttgac    60
cttgacatgc ttggttcgga tgcccttgat gactttgacc tcgacatgct cggcagtgac   120
gcccttgatg atttcgacct ggacatgctg attaactcta gaagttccgg atctccgaaa   180
aagaaacgca agttggtag ccagtacctg cccgacaccg acgaccggca ccggatcgag    240
gaaaagcgga agcggaccta cgagacattc aagagcatca tgaagaagtc ccccttcagc   300
ggccccaccg accctagacc tccacctaga gaatcgccg tgcccagcag atccagcgcc    360
agcgtgccaa aacctgcccc ccagccttac cccttcacca gcagcctgag caccatcaac   420
tacgacgagt ccctaccat ggtgttcccc agcggccaga tctctcaggc ctctgctctg    480
gctccagccc ctcctcaggt gctgcctcag gctcctgctc ctgcaccagc tccagccatg   540
gtgtctgcac tggctcaggc accagcaccc gtgcctgtgc tggctcctgg acctccacag   600
gctgtggctc caccagcccc taaacctaca caggccggcg agggcacact gtctgaagct   660
ctgctgcagc tgcagttcga cgacgaggat ctgggagccc tgctgggaaa cagcaccgat   720
cctgccgtgt tcaccgacct ggccagcgtg gacaacagcg agttccagca gctgctgaac   780
cagggcatcc ctgtggcccc tcacaccacc gagcccatgc tgatggaata ccccgaggcc   840
atcacccggc tcgtgacagg cgctcagagg cctcctgatc cagctcctgc ccctctggga   900
gcaccaggcc tgcctaatgg actgctgtct ggcgacgagg acttcagctc tatcgccgac   960
atggacttct ccgcactgct gggtagcgga tcgggatctc gggattccag ggaagggatg  1020
tttttgccga gcctgaggc cggctccgct attagtgacg tgtttgaggg ccgcgaggtg  1080
tgccagccaa aacgaatccg gccattcat cctccaggaa gtccatgggc aaccgcccca    1140
ctccccgcca gcctcgcacc aacaccaacc ggtccagtac atgagccagt cgggtcactg  1200
accccggcac cagtccctca gccactggat ccagcgcccg cagtgactcc cgaggccagt   1260
cacctgttgg aggatcccga tgaagagacg agccaggctg tcaaagccct tcgggagatg  1320
gccgatactg tgattcccca gaaggaagag gctgcaatct gtggccaaat ggacctttcc  1380
catccgcccc aaggggcca tctggatgag ctgacaacca cacttgagtc catgaccgag  1440
gatctgaacc tggactcacc cctgacccg gaattgaacg agattctgga taccttcctg    1500
aacgacgagt gcctcttgca tgccatgcat atcagcacag gactgtccat cttcgacaca   1560
tctctgttt                                                          1569

<210> SEQ ID NO 262
<211> LENGTH: 136
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<223> OTHER INFORMATION: SAM Part I (modification to the gRNA adding two
      ms2 hairpin extensions)

<400> SEQUENCE: 262
gttttagagc taggccaaca tgaggatcac ccatgtctgc agggcctagc aagttaaaat      60
aaggctagtc cgttatcaac ttggccaaca tgaggatcac ccatgtctgc agggccaagt     120
ggcaccgagt cggtgc                                                     136

<210> SEQ ID NO 263
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: MCP domain

<400> SEQUENCE: 263
gcggccgctg actacaagga tgacgacgat aaatctagaa tggcttctaa ctttactcag      60
ttcgttctcg tcgacaatgg cggaactggc gacgtgactg tcgccccaag caacttcgct     120
aacgggatcg ctgaatggat cagctctaac tcgcgttcac aggcttacaa agtaacctgt     180
agcgttcgtc agagctctgc gcagaatcgc aaatacacca tcaaagtcga ggtgcctaaa     240
ggcgcctggc gttcgtactt aaatatggaa ctaaccattc aatttcgc cacgaattcc       300 gactgcgagc ttattgttaa ggcaatgcaa ggtctcctaa aagatggaaa cccgattccc     360
tcagcaatcg cagcaaactc cggcatctac gaggccagc                            399

<210> SEQ ID NO 264
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Scaffold Part I (modification to the gRNA)

<400> SEQUENCE: 264
gggagcacat gaggatcacc catgtgcgac tcccacagtc actggggagt cttccc          56

<210> SEQ ID NO 265
<211> LENGTH: 353
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: MCP domain

<400> SEQUENCE: 265
agaatggctt ctaactttac tcagttcgtt ctcgtcgaca atggcggaac tggcgacgtg      60
actgtcgccc caagcaactt cgctaacggg atcgctgaat ggatcagctc taactcgcgt    120
tcacaggctt acaaagtaac ctgtagcgtt cgtcagagct ctgcgcagaa tcgcaaatac    180
```

```
accatcaaag tcgaggtgcc taaaggcgcc tggcgttcgt acttaaatat ggaactaacc    240
attccaattt tcgccacgaa ttccgactgc gagcttattg ttaaggcaat gcaaggtctc    300
ctaaaagatg gaaacccgat tccctcagca atcgcagcaa actccggcat cta           353

<210> SEQ ID NO 266
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Suntag Part I (10xGCN4_v4)

<400> SEQUENCE: 266
gaagaacttt tgagcaagaa ttatcatctt gagaacgaag tggctcgtct taagaaaggt     60
tctggcagtg gagaagaact gctttcaaag aattaccacc tggaaaatga ggtagctaga    120
ctgaaaaagg ggagcggaag tggggaggag ttgctgagca aaaattatca tttggagaac    180
gaagtagcac gactaaagaa agggtccgga tcgggtgagg agttactctc gaaaaattat    240
catctcgaaa acgaagtggc tcggctaaaa aagggcagtg gttctggaga agagctatta    300
tctaaaaact accacctcga aaatgaggtg gcacgcttaa aaagggaagt ggcagtggt     360 gaagagctac tatccaagaa ttatcatctt gagaacgagt agcgcgtttt gaagaaggggt    420 tccggctcag gagaggaact gctctcgaag aactatcatc ttgaaaatga ggtcgctcga    480
ttaaaaaagg gatcgggcag tggtgaggaa ctactttcaa agaattacca cctcgaaaac    540
gaagtagctc gattaaagaa aggttcaggg tcgggtgaag aattactgag taaaaattat    600
catctggaaa atgaggtagc gagactaaaa aaggggagtg gttctggcga ggaattgcta    660
tcgaaaaatt atcatcttga aacgaagtt gctaggctca aaaag                     705

<210> SEQ ID NO 267
<211> LENGTH: 831
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Suntag Part II (ScFv_GCN4)

<400> SEQUENCE: 267
atgggccccg acatcgtgat gacccagagc cccagcagcc tgagcgccag cgtgggcgac     60
cgcgtgacca tcacctgccg cagcagcacc ggcgccgtga ccaccagcaa ctacgccagc    120
tgggtgcagg agaagcccgg caagctgttc aaggcctga tcggcggcac caacaaccgc    180 gccccggcg tgcccagccg cttcagcggc agcctgatcg gcgacaaggc caccctgacc    240
atcagcagcc tgcagcccga ggacttcgcc acctacttct gcgccctgtg gtacagcaac    300
cactgggtgt tcggccaggg caccaaggtg gagctgaagc gcggcggcgg cggcagcggc    360
ggcggcggca gcggcggcgg cggcagcagc ggcggcggca gcgaggtgaa gctgctggag    420
agcggcggcg gcctggtgca gcccggcggc agcctgaagc tgagctgcgc cgtgagcggc    480
ttcagcctga ccgactacgg cgtgaactgg gtgcgccagg cccccggccg cggcctggag    540
tggatcggcg tgatctgggg cgacggcatc accgactaca cagcgccct gaaggaccgc    600 ttcatcatca gcaaggacaa cggcaagaac accgtgtacc tgcagatgag caaggtgcgc    660
```

| | |
|---|---|
| agcgacgaca ccgccctgta ctactgcgtg accggcctgt tcgactactg gggccagggc | 720 |
| accctggtga ccgtgagcag ctacccatac gatgttccag attacgctgg tggaggcgga | 780 |
| ggttctgggg gaggaggtag tggcggtggt ggttcaggag gcggcggaag c | 831 |

<210> SEQ ID NO 268
<211> LENGTH: 1851
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: P300

<400> SEQUENCE: 268

| | |
|---|---|
| attttcaaac cagaagaact acgacaggca ctgatgccaa ctttggaggc actttaccgt | 60 |
| caggatccag aatcccttcc ctttcgtcaa cctgtggacc ctcagctttt aggaatccct | 120 |
| gattactttg atattgtgaa gagccccatg gatctttcta ccattaagag gaagttagac | 180 |
| actggacagt atcaggagcc ctggcagtat gtcgatgata tttggcttat gttcaataat | 240 |
| gcctggttat ataaccggaa aacatcacgg gtatacaaat actgctccaa gctctctgag | 300 |
| gtctttgaac aagaaattga cccagtgatg caaagccttg gatactgttg tggcagaaag | 360 |
| ttggagttct ctccacagac actgtgttgc tacggcaaac agttgtgcac aatacctcgt | 420 |
| gatgccactt attacagtta ccagaacagg tatcatttct gtgagaagtg tttcaatgag | 480 |
| atccaagggg agagcgtttc tttgggggat gacccttccc agcctcaaac tacaataaat | 540 |
| aaagaacaat tttccaagag aaaaaatgac acactggatc ctgaactgtt tgttgaatgt | 600 |
| acagagtgcg gaagaaagat gcatcagatc tgtgtccttc accatgagat catctggcct | 660 |
| gctggattcg tctgtgatgg ctgtttaaag aaaagtgcac gaactaggaa agaaaataag | 720 |
| ttttctgcta aaaggttgcc atctaccaga cttggcacct ttctagagaa tcgtgtgaat | 780 |
| gactttctga ggcgacagaa tcaccctgag tcaggagagg tcactgttag agtagttcat | 840 |
| gcttctgaca aaaccgtgga agtaaaacca ggcatgaaag caggtttgt ggacagtgga | 900 |
| gagatggcag aatcctttcc ataccgaacc aaagccctct tgcctttga gaaattgat | 960 |
| ggtgttgacc tgtgcttctt tggcatgcat gttcaagagt atggctctga ctgccctcca | 1020 |
| cccaaccaga ggagagtata catatcttac ctcgatagtg ttcatttctt ccgtcctaaa | 1080 |
| tgcttgagga ctgcagtcta tcatgaaatc ctaattggat atttagaata tgtcaagaaa | 1140 |
| ttaggttaca caacagggca tatttgggca tgtccaccaa gtgagggaga tgattatatc | 1200 |
| ttccattgcc atcctcctga ccagaagata cccaagccca gcgactgca ggaatggtac | 1260 |
| aaaaaaatgc ttgacaaggc tgtatcagag cgtattgtcc atgactacaa ggatatttt | 1320 |
| aaacaagcta ctgaagatag attaacaagt gcaaggaat tgccttattt cgagggtgat | 1380 |
| ttctggccca tgttctgga agaaagcatt aaggaactgg aacaggagga agaagagaga | 1440 |
| aaacgagagg aaaacaccag caatgaaagc acagatgtga ccaagggaga cagcaaaaat | 1500 |
| gctaaaaaga gaataataa gaaaaccagc aaaaataaga gcagcctgag taggggcaac | 1560 |
| aagaagaaac ccgggatgcc caatgtatct aacgacctct cacagaaact atatgccacc | 1620 |
| atggagaagc ataagaggt cttctttgtg atccgcctca ttgctggccc tgctgccaac | 1680 |
| tccctgcctc ccattgttga tcctgatcct ctcatccctg gcgatctgat ggatggtcgg | 1740 |

```
gatgcgtttc tcacgctggc aagggacaag cacctggagt tctcttcact ccgaagagcc      1800
cagtggtcca ccatgtgcat gctggtggag ctgcacacgc agagccagga c               1851

<210> SEQ ID NO 269
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VP160

<400> SEQUENCE: 269
gacgcgctgg acgatttcga tctcgacatg ctgggttctg atgccctcga tgactttgac       60
ctggatatgt tgggaagcga cgcattggat gactttgatc tggacatgct cggctccgat      120
gctctggacg atttcgatct cgatatgtta gggtcagacg cactggatga tttcgacctt      180
gatatgttgg gaagcgatgc ccttgatgat ttcgacctgg acatgctcgg cagcgacgcc      240
ctggacgatt tcgatctgga catgctgggg tccgatgcct ggatgatttt gacttggat       300 atgctgggga gtgatgccct ggacgacttt gacctggaca tgctgggctc cgatgcgctc      360
gatgacttcg atttggatat gttg                                             384

<210> SEQ ID NO 270
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: BBM target sequence

<400> SEQUENCE: 270
tggagtgtac cagttgtata aatat                                             25

<210> SEQ ID NO 271
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: BBM target sequence

<400> SEQUENCE: 271
tcctcgaatc attctaagaa gaaac                                             25

<210> SEQ ID NO 272
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: BBM target sequence

<400> SEQUENCE: 272
tggccgtgac aacgtatact attat                                             25

<210> SEQ ID NO 273
```

```
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of ZmPLT7

<400> SEQUENCE: 273
atggacatgg acatgagctc agcttatccc caccattggc tctccttctc cctctccaac     60
aactaccacc atggcctact cgaagccttc tctaactcct ccggtactcc tcttggagac    120
gagcagggcg cagtggagga gtccccgagg acggtggagg acttcctcgg cggcgtcggt    180
ggcgccggcg ccccgccgca gccggcggcg gctgcagatc aggatcacca gcttgtgtgc    240
ggcgagctgg gcagcatcac agccaggttc ttgcgccact accggcggc gccagctggg    300 acgacggtgg agaaccccgg cgcggtgacc gtggcggcca tgtcgtcgac ggacgtggcc    360
ggggcggagt ccgaccaggc gaggcggccc gccgagacgt tcggccagcg cacatccatc    420
taccgtggcg tcaccaggca ccggtggacg gggagatatg aggcgcacct gtgggacaac    480
agctgccgcc gggagggcca aagccgcaaa ggacggcaag gaggctatga caaggaggag    540
aaggcggcta gagcttacga cctcgccgcg ctcaagtact gggggcctac aaccacgacc    600 aacttccccgg tgtccaacta cgagaaggag ctggaggaga tgaagtccat gacgcggcag    660
gagttcatcg cgtcgttgcg caggaagagc agcggcttct cacgaggcgc ctccatctac    720
agaggagtca caaggcatca tcagcacggc cggtggcagg cgaggatcgg cagggtggcc    780
ggaaacaagg acctgtactt gggcactttc agtactcagg aagaggcggc ggaggcgtac    840
gacatcgctg cgatcaagtt ccgcgggctc aacgccgtca ccaactttga catgagccgc    900
tacgacgtgg agagcatcct cagcagcgac ctccccgtcg ggggcggagc tagcggtcgc    960 gccccccgcca agttcccgtt ggactcgctg cagccgggga cgctgccgc catgatgctc   1020 gccggggctg ctgccgcttc gcaggccacc atgccgccgt ccgagaagga ctactggtct   1080
ctgctcgccc tgcactacca gcagcagcag gagcaggagc ggcagttccc ggcttctgct   1140
tacgaggctt acggctccgg cggcgtgaac gtggacttca cgatgggcac cagtagcggc   1200
aacaacaaca caacaccgg cagcggcgtc atgtggggcg ccaccactgg tgcagtagta   1260
gtgggacagc aagacagcag cggcaagcag ggcaacggct atgccagcaa cattccttat   1320
gctgctgctg ctatggtttc tggatctgct ggctacgagg gctccaccgg cgacaatgga   1380
acctgggtta ctacgactac cagcagcaac accggcacgg ctcccactac ctacaactat   1440
ctcttcggga tggagtag                                                 1458

<210> SEQ ID NO 274
<211> LENGTH: 485
<212> TYPE: PRT
<213> ORGANISM: Zea mays

<400> SEQUENCE: 274

Met Asp Met Asp Met Ser Ser Ala Tyr Pro His His Trp Leu Ser Phe
1               5                   10                  15

Ser Leu Ser Asn Asn Tyr His His Gly Leu Leu Glu Ala Phe Ser Asn
            20                  25                  30

Ser Ser Gly Thr Pro Leu Gly Asp Glu Gln Gly Ala Val Glu Glu Ser
        35                  40                  45
```

```
Pro Arg Thr Val Glu Asp Phe Leu Gly Gly Val Gly Ala Gly Ala
 50                  55                  60

Pro Pro Gln Pro Ala Ala Ala Asp Gln Asp His Gln Leu Val Cys
 65                  70                  75                  80

Gly Glu Leu Gly Ser Ile Thr Ala Arg Phe Leu Arg His Tyr Pro Ala
                 85                  90                  95

Ala Pro Ala Gly Thr Thr Val Glu Asn Pro Gly Ala Val Thr Val Ala
                100                 105                 110

Ala Met Ser Ser Thr Asp Val Ala Gly Ala Glu Ser Asp Gln Ala Arg
            115                 120                 125

Arg Pro Ala Glu Thr Phe Gly Gln Arg Thr Ser Ile Tyr Arg Gly Val
130                 135                 140

Thr Arg His Arg Trp Thr Gly Arg Tyr Glu Ala His Leu Trp Asp Asn
145                 150                 155                 160

Ser Cys Arg Arg Glu Gly Gln Ser Arg Lys Gly Arg Gln Gly Gly Tyr
                165                 170                 175

Asp Lys Glu Glu Lys Ala Ala Arg Ala Tyr Asp Leu Ala Ala Leu Lys
            180                 185                 190

Tyr Trp Gly Pro Thr Thr Thr Asn Phe Pro Val Ser Asn Tyr Glu
            195                 200                 205

Lys Glu Leu Glu Glu Met Lys Ser Met Thr Arg Gln Glu Phe Ile Ala
210                 215                 220

Ser Leu Arg Arg Lys Ser Ser Gly Phe Ser Arg Gly Ala Ser Ile Tyr
225                 230                 235                 240

Arg Gly Val Thr Arg His His Gln His Gly Arg Trp Gln Ala Arg Ile
                245                 250                 255

Gly Arg Val Ala Gly Asn Lys Asp Leu Tyr Leu Gly Thr Phe Ser Thr
            260                 265                 270

Gln Glu Glu Ala Ala Glu Ala Tyr Asp Ile Ala Ala Ile Lys Phe Arg
        275                 280                 285

Gly Leu Asn Ala Val Thr Asn Phe Asp Met Ser Arg Tyr Asp Val Glu
        290                 295                 300

Ser Ile Leu Ser Ser Asp Leu Pro Val Gly Gly Ala Ser Gly Arg
305                 310                 315                 320

Ala Pro Ala Lys Phe Pro Leu Asp Ser Leu Gln Pro Gly Ser Ala Ala
                325                 330                 335

Ala Met Met Leu Ala Gly Ala Ala Ala Ser Gln Ala Thr Met Pro
            340                 345                 350

Pro Ser Glu Lys Asp Tyr Trp Ser Leu Leu Ala Leu His Tyr Gln Gln
            355                 360                 365

Gln Gln Glu Gln Glu Arg Gln Phe Pro Ala Ser Ala Tyr Glu Ala Tyr
            370                 375                 380

Gly Ser Gly Gly Val Asn Val Asp Phe Thr Met Gly Thr Ser Ser Gly
385                 390                 395                 400

Asn Asn Asn Asn Asn Thr Gly Ser Gly Val Met Trp Gly Ala Thr Thr
                405                 410                 415

Gly Ala Val Val Val Gly Gln Gln Asp Ser Ser Gly Lys Gln Gly Asn
            420                 425                 430

Gly Tyr Ala Ser Asn Ile Pro Tyr Ala Ala Ala Met Val Ser Gly
            435                 440                 445

Ser Ala Gly Tyr Glu Gly Ser Thr Gly Asp Asn Gly Thr Trp Val Thr
450                 455                 460
```

Thr Thr Thr Ser Ser Asn Thr Gly Thr Ala Pro His Tyr Tyr Asn Tyr
465                 470                 475                 480

Leu Phe Gly Met Glu
                485

<210> SEQ ID NO 275
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 275

Xaa Cys Xaa Cys Xaa His Xaa His
1               5

<210> SEQ ID NO 276
<211> LENGTH: 9
<212> TYPE: PRT
<213> ORGANISM: Unknown
<220> FEATURE:
<223> OTHER INFORMATION: Description of Unknown:
      "LAGLIDADG" family peptide motif sequence

<400> SEQUENCE: 276

Leu Ala Gly Leu Ile Asp Ala Asp Gly
1               5

<210> SEQ ID NO 277
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 277
cgaccggatg ccgcagccgt agtagagctc cttcagcatc ctgatctgct ccggcgtcgg      60
cgtccaccgc gagccgctgg ggcggcacac cgccggcgca gccacgctgc cgctgcctcc     120
tcccgctcca ccgccgcccg cattggccgc catgcctcta tctcagcggc cttcctgagc     180
gctcctgtga cctagctctc cggtgtccgg tctatggcaa gagaggcgaa ggagggttcc     240
ttgtttataa ggagggagtg cattggacct agaggctaga tagctagaag gtagctagca     300
tgcagagagc gagagcggga gaagagagcg tagctgcgct aggtgatata ggttggggct     360

<210> SEQ ID NO 278
<211> LENGTH: 900
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 278

```
taatcgttct tgacagcaac ctgccagtca aatggccgtg acaacgtata ctattatcga      60
gtaaaaggtc gccactttag tagtacatgt acatgcatgc gcagatacat catcaggtac     120
tcatatatgg gcacacatat agacatgttt tgaggaaaat gagacaaagt atagtggaga     180
cttccctaga aagcagaaga aaaagaagtg gtttatgttc cgttaaatca tactacaact     240
tttttttatt atactctcca ttttgtcatc attaggtact catatatggg cacacatata     300
gtactgccaa tttttcttgc taaaaaaagt tccactatat atatgtatgt atgcacaaat     360
aaactaattt tcttagaaaa gaaaaccggt gtaatacata ctaagggcta gtttgggaac     420
cctggtttcc taaggaattt tatttttcca aaaaaaatag tttattttc cttcggaaat      480 taggaatctc ttataaaatt cgagttccca aactattcct aatatatata tcatactctc     540
catcagtcta tatatagatt acatatagta agtatagagt atctcgctat cacatagtgc     600
cactaatctt ctggagtgta ccagttgtat aaatatctat cagtatcagc actactgttt     660
gctgaatacc ccaaaactct ctgcttgact tctcttccct aacctttgca ctgtccaaaa     720
tggcttcctg atcccctcac ttcctcgaat cattctaaga agaaactcaa gccgctacca     780
ttaggggcag attaattgct gcactttcag ataatctacc atggccactg tgaacaactg     840
gctcgctttc tccctctccc cgcaggagct gccgccctcc cagacgacgg actccacgct     900
```